US011274140B2

(12) United States Patent
Dillon et al.

(10) Patent No.: US 11,274,140 B2
(45) Date of Patent: Mar. 15, 2022

(54) APRIL AND BAFF INHIBITORY IMMUNOMODULATORY PROTEINS AND METHODS OF USE THEREOF

(71) Applicant: Alpine Immune Sciences, Inc., Seattle, WA (US)

(72) Inventors: Stacey Dillon, Seattle, WA (US); Mark Rixon, Seattle, WA (US); Lawrence Evans, Seattle, CA (US); Daniel William Demonte, Seattle, WA (US); Joseph L. Kuijper, Seattle, WA (US); Stanford L. Peng, Seattle, WA (US)

(73) Assignee: Alpine Immune Sciences, Inc., Seattle, WA (US)

( * ) Notice: Subject to any disclaimer, the term of this patent is extended or adjusted under 35 U.S.C. 154(b) by 0 days.

(21) Appl. No.: 17/346,095

(22) Filed: Jun. 11, 2021

(65) Prior Publication Data
US 2021/0363223 A1 Nov. 25, 2021

Related U.S. Application Data

(63) Continuation of application No. 17/315,168, filed on May 7, 2021.

(60) Provisional application No. 63/080,643, filed on Sep. 18, 2020, provisional application No. 63/034,361, filed on Jun. 3, 2020, provisional application No. 63/022,373, filed on May 8, 2020.

(51) Int. Cl.
C07K 14/705 (2006.01)
C07K 14/715 (2006.01)
A61K 38/00 (2006.01)
A61K 39/00 (2006.01)

(52) U.S. Cl.
CPC .... C07K 14/70578 (2013.01); C07K 14/7151 (2013.01); A61K 38/00 (2013.01); A61K 2039/505 (2013.01); C07K 2317/76 (2013.01); C07K 2317/92 (2013.01); C07K 2319/30 (2013.01); C07K 2319/31 (2013.01)

(58) Field of Classification Search
CPC .................. C07K 14/70578; C07K 2319/30
USPC ..................................... 424/134.1
See application file for complete search history.

(56) References Cited

U.S. PATENT DOCUMENTS

| | | |
|---|---|---|
| 5,168,062 A | 12/1992 | Stinski |
| 5,283,173 A | 2/1994 | Fields et al. |
| 5,385,839 A | 1/1995 | Stinski |
| 5,443,964 A | 8/1995 | Pickup et al. |
| 5,457,035 A | 10/1995 | Baum et al. |
| 5,468,614 A | 11/1995 | Fields et al. |
| 5,500,362 A | 3/1996 | Robinson et al. |
| 5,624,821 A | 4/1997 | Winter et al. |
| 5,641,870 A | 6/1997 | Rinderknecht et al. |
| 5,648,260 A | 7/1997 | Winter et al. |
| 5,698,530 A | 12/1997 | Schlom et al. |
| 5,731,168 A | 3/1998 | Carter et al. |
| 5,821,337 A | 10/1998 | Carter et al. |
| 5,969,102 A | 10/1999 | Bram et al. |
| 6,143,290 A | 11/2000 | Zhang et al. |
| 6,194,551 B1 | 2/2001 | Idusogie et al. |
| 6,596,535 B1 | 7/2003 | Carter |
| 6,737,056 B1 | 5/2004 | Presta |
| 6,855,317 B2 | 2/2005 | Koelle et al. |
| 6,936,257 B1 | 8/2005 | Bennett |
| 6,998,252 B1 | 2/2006 | Moss et al. |
| 7,125,717 B2 | 10/2006 | Carter |
| 7,247,615 B2 | 7/2007 | Schlom et al. |
| 7,332,581 B2 | 2/2008 | Presta |
| 7,368,116 B2 | 5/2008 | Schlom et al. |
| 7,371,826 B2 | 5/2008 | Presta |
| 7,378,087 B2 | 5/2008 | Jefferies et al. |
| 7,501,497 B2 | 3/2009 | Rixon et al. |
| 7,550,296 B2 | 6/2009 | Hermiston et al. |
| 7,635,767 B2 | 12/2009 | Rixon et al. |
| 7,833,529 B1 | 11/2010 | Gross et al. |
| 7,862,814 B2 | 1/2011 | Rixon et al. |
| 7,951,919 B2 | 5/2011 | Rixon et al. |
| 7,964,711 B2 | 6/2011 | Rixon et al. |
| 8,193,316 B2 | 6/2012 | Fang et al. |
| 8,524,232 B2 | 9/2013 | Rixon et al. |
| 8,669,350 B2 | 3/2014 | Chou et al. |
| 8,815,238 B2 | 8/2014 | Rixon et al. |

(Continued)

FOREIGN PATENT DOCUMENTS

CA 2446734 A1 11/2002
CA 2453995 A1 2/2003

(Continued)

OTHER PUBLICATIONS

Alperovich et al., "New immunosuppresor strategies in the treatment of murine lupus nephritis," Lupus. (2007) 16(1): 18-24.
Andrews et al., "Spontaneous murine lupus-like syndromes. Clinical and immunopathological manifestations in several strains," J Exp Med. (1978) 148(5): 1198-1215.
Ansell et al., "Phase I clinical study of atacicept in patients with relapsed and refractory B-cell non-Hodgkin's lymphoma," Clin Cancer Res. (2008) 14(4): 1105-1110.
Bachmann et al., "The EVH2 Domain of the Vasodilator-stimulated Phosphoprotein Mediates Tetramerization, F-actin Binding, and Actin Bundle Formation," J Biol Chem. (1999) 274(33):23549-23557.

(Continued)

Primary Examiner — Gyan Chandra
(74) Attorney, Agent, or Firm — Morrison & Foerster LLP

(57) ABSTRACT

Provided herein are immunomodulatory proteins that exhibit neutralizing activity of BAFF and APRIL (or BAFF/APRIL heterotrimers). The immunomodulatory proteins provided herein include variant domains of Transmembrane Activator and CAML Interactor (TACI). Among provided immunodulatory proteins are TACI-Fc fusion proteins. Also provided are nucleic acid molecules encoding the immunomodulatory proteins. The immunomodulatory proteins provide therapeutic utility for a variety of immunological diseases, disorders or conditions. Also provided are compositions and methods for making and using such proteins.

30 Claims, 22 Drawing Sheets

Specification includes a Sequence Listing.

(56) References Cited

U.S. PATENT DOCUMENTS

| | | |
|---|---|---|
| 8,911,726 B2 | 12/2014 | Takahashi et al. |
| 9,290,582 B2 | 3/2016 | Yang et al. |
| 9,346,878 B2 | 5/2016 | Rixon et al. |
| 10,183,967 B2 | 1/2019 | Blum et al. |
| 10,562,954 B2 | 2/2020 | Cai et al. |
| 2004/0013674 A1 | 1/2004 | Ambrose et al. |
| 2005/0014934 A1 | 1/2005 | Hinton et al. |
| 2005/0163775 A1 | 7/2005 | Chan et al. |
| 2006/0024298 A1 | 2/2006 | Lazar et al. |
| 2006/0067933 A1 | 3/2006 | Gross et al. |
| 2007/0086979 A1 | 4/2007 | Chevrier et al. |
| 2009/0148462 A1 | 6/2009 | Chevrier et al. |
| 2009/0226440 A1 | 9/2009 | Grey |
| 2009/0291080 A1 | 11/2009 | Gottenberg et al. |
| 2010/0256337 A1 | 10/2010 | Eon-Duval |
| 2010/0297122 A1 | 11/2010 | Del Rio et al. |
| 2011/0110950 A1 | 5/2011 | Kalled et al. |
| 2011/0311548 A1 | 12/2011 | Wasserman et al. |
| 2016/0017041 A1 | 1/2016 | Violette et al. |
| 2019/0241633 A1 | 8/2019 | Fotin-Mleczek et al. |
| 2021/0087253 A1 | 3/2021 | Fang et al. |

FOREIGN PATENT DOCUMENTS

| | | |
|---|---|---|
| CA | 2492447 A1 | 2/2004 |
| CA | 2501459 A1 | 4/2004 |
| CA | 2585927 A1 | 5/2006 |
| CA | 2661872 A1 | 3/2008 |
| CA | 2674213 A1 | 7/2008 |
| CA | 2690119 A1 | 12/2008 |
| CA | 2701221 A1 | 4/2009 |
| CA | 2703545 A1 | 5/2009 |
| CA | 2705357 C | 5/2009 |
| CA | 2705435 A1 | 5/2009 |
| CA | 2763439 A1 | 12/2010 |
| CA | 2681728 C | 12/2015 |
| CA | 2661748 C | 2/2016 |
| CA | 2701329 C | 8/2017 |
| CA | 3019199 A1 | 10/2017 |
| CA | 3032120 A1 | 2/2018 |
| CA | 3040296 A1 | 4/2018 |
| CA | 3053804 A1 | 9/2018 |
| CA | 3053812 A1 | 9/2018 |
| CA | 3054068 A1 | 9/2018 |
| CA | 3070468 A1 | 3/2019 |
| CA | 3077509 A1 | 4/2019 |
| CA | 3078517 A1 | 4/2019 |
| CA | 3087149 A1 | 7/2019 |
| CA | 3091681 A1 | 9/2019 |
| CA | 3112578 A1 | 3/2020 |
| CA | 3117978 A1 | 5/2020 |
| CN | 102085368 B | 6/2013 |
| EP | 1746106 | 1/2007 |
| EP | 2116259 | 1/2012 |
| EP | 2431054 | 3/2012 |
| EP | 2161287 | 3/2015 |
| EP | 3299378 | 3/2018 |
| EP | 3415528 | 12/2018 |
| JP | 2003-533218 A | 11/2003 |
| JP | 2004-533997 A | 11/2004 |
| JP | 2006-517191 A | 7/2006 |
| JP | 2007-526220 A | 9/2007 |
| JP | 2009-504668 A | 2/2009 |
| JP | 2009-507777 A | 2/2009 |
| JP | 2009-537563 A | 10/2009 |
| JP | 2010-501622 | 1/2010 |
| JP | 2011-523037 | 8/2011 |
| JP | 2018-518974 A | 7/2018 |
| JP | 2019-521643 | 8/2019 |
| KR | 2013-0118315 A | 10/2013 |
| WO | WO-1993/010151 | 5/1993 |
| WO | WO-1994/029351 | 12/1994 |
| WO | WO-1998/018921 | 5/1998 |
| WO | WO-1998/050431 | 11/1998 |
| WO | WO-1999/051642 | 10/1999 |
| WO | WO-2000/067034 | 4/2000 |
| WO | WO-2000/040716 | 7/2000 |
| WO | WO-2000/042072 | 7/2000 |
| WO | WO-2001/060397 | 8/2001 |
| WO | WO-2001/081417 | 11/2001 |
| WO | WO-2001/087979 | 11/2001 |
| WO | WO-2002/066516 | 8/2002 |
| WO | WO-2002/094852 | 11/2002 |
| WO | WO-2004/056312 | 7/2004 |
| WO | WO-2004/060911 | 7/2004 |
| WO | WO-2005/005462 | 1/2005 |
| WO | WO-2005/063816 | 7/2005 |
| WO | WO-2005/100402 | 10/2005 |
| WO | WO-2006/019447 | 2/2006 |
| WO | WO-2006/029879 | 3/2006 |
| WO | WO-2007/019573 | 2/2007 |
| WO | WO-2007/019575 | 2/2007 |
| WO | WO-2007/134326 | 11/2007 |
| WO | WO-2008/025747 | 3/2008 |
| WO | WO-2008/154814 | 12/2008 |
| WO | WO-2009/076524 | 6/2009 |
| WO | WO-2009/132058 | 10/2009 |
| WO | WO-2009/134633 | 11/2009 |
| WO | WO-2010/003766 | 1/2010 |
| WO | WO-2011/109280 | 9/2011 |
| WO | WO 2012/032112 | 3/2012 |
| WO | WO-2012/125850 | 9/2012 |
| WO | WO-2012/141984 | 10/2012 |
| WO | WO-2013/130683 | 9/2013 |
| WO | WO-2015/107026 | 7/2015 |
| WO | WO-2016/011083 | 1/2016 |
| WO | WO-2017/011804 | 7/2016 |
| WO | WO-2016/210293 | 12/2016 |
| WO | WO-2017/222593 | 12/2016 |
| WO | WO-2017/181152 | 10/2017 |
| WO | WO-2018/022945 | 2/2018 |
| WO | WO-2018/236995 | 12/2018 |
| WO | WO-2019/110209 | 6/2019 |
| WO | WO-201 9/223581 | 11/2019 |
| WO | WO-2019/241758 | 12/2019 |
| WO | WO-2020/028572 | 2/2020 |
| WO | WO-2020/113141 | 6/2020 |
| WO | WO-2020/214867 | 10/2020 |
| WO | WO-2020/252421 | 12/2020 |
| WO | WO-2021/049606 | 3/2021 |
| WO | WO-2021/115321 | 6/2021 |
| WO | WO-2021/128027 | 7/2021 |

OTHER PUBLICATIONS

Baumgartner et al., "The role of the WSXWS equivalent motif in growth hormone receptor function," J Biol Chem. (1994) 269(46): 29094-101.

Benatuil et al., "An improved yeast transformation method for the generation of very large human antibody libraries," Protein Eng Des Sel. (2010) 23(4): 155-159.

Benoist et al., "In vivo sequence requirements of the SV40 early promotor region," Nature. (1981) 290(5804): 304-10.

Benson et al., "Cutting edge: the dependence of plasma cells and independence of memory B cells on BAFF and APRIL," J Immunol. (2008) 180(6): 3655-3659.

Bilsborough et al., "TACI-Ig prevents the development of airway hyperresponsiveness in a murine model of asthma," Clin Exp Allergy. (2008) 38(12): 1959-1968.

Brown et al., "Structure-based mutagenesis of the human immunodeficiency virus type 1 DNA attachment site: effects on integration and cDNA synthesis," J Virol. (1999) 73(11):9011-9020.

Bruggemann et al., "Comparison of the effector functions of human immunoglobulins using a matched set of chimeric antibodies," J Exp Med. (1987) 166(5):1351-1361.

Buchschacher et al., "Human immunodeficiency virus vectors for inducible expression of foreign genes," J Virol. (1992) 66(5):2731-2739.

Busch et al., "Dimers, leucine zippers and DNA-binding domains," Trends Genet. (1990) 6(2): 36-40.

Carbonatto et al., "Nonclinical safety, pharmacokinetics, and pharmacodynamics of atacicept," Toxicol Sci. (2008) 105(1): 200-210.

(56) References Cited

OTHER PUBLICATIONS

Chen et al., "Pharmacokinetics, pharmacodynamics, short term efficacy and safety of RCT-18, a novel BLyS/APRIL fusion protein, in patients with rheumatoid arthritis," Br J Clin Pharmacol. (2016) 82(1): 41-52.

Chen et al., "Pharmacokinetics, pharmacodynamics, and tolerability of single ascending doses of RCT-18 in Chinese patients with rheumatoid arthritis," Clin Pharmacokinet. (2014) 53(11): 1033-44.

Christadoss et al., "Immunotherapy for myasthenia gravis: a murine model," J Immunol. (1986) 136(7):2437-40.

Clynes et al., "Fc receptors are required in passive and active immunity to melanoma," Proc Natl Acad Sci U S A. (1998) 95(2):652-656.

Cornetta et al., "No retroviremia or pathology in long-term follow-up of monkeys exposed to a murine amphotropic retrovirus," Hum Gene Ther. (1991) Fall;2(3):215-9.

Cragg et al., "Antibody specificity controls in vivo effector mechanisms of anti-CD20 reagents," Blood. (2004) 103(7):2738-2743.

Cragg et al., "Complement-mediated lysis by anti-CD20 mAb correlates with segregation into lipid rafts," Blood. (2003) 101(3):1045-1052.

Daikh et al., "Long-term inhibition of murine lupus by brief simultaneous blockade of the B7/CD28 and CD40/gp39 costimulation pathways," J Immunol. (1997) 159(7): 3104-8.

Dall'Era et al., "Reduced B lymphocyte and immunoglobulin levels after atacicept treatment in patients with systemic lupus erythematosus: results of a multicenter, phase Ib, double-blind, placebo-controlled, dose-escalating trial," Arthritis Rheum. (2007) 56(12): 4142-4150.

De Wet et al., "Firefly luciferase gene: structure and expression in mammalian cells," Mol Cell Biol. (1987) 7(2): 725-37.

Deisenhofer et al., "Crystallographic refinement and atomic models of a human Fc fragment and its complex with fragment B of protein A from *Staphylococcus aureus* at 2.9- and 2.8-A resolution," Biochemistry. Apr. 28, 1981;20(9):2361-70.

Dillon et al., "B-lymphocyte stimulator/a proliferation-inducing ligand heterotrimers are elevated in the sera of patients with autoimmune disease and are neutralized by atacicept and B-cell maturation antigen-immunoglobulin," Arthritis Res Ther. (2010) 12(2): R48.

Ding et al., "Telitacicept Following Plasma Exchange in the Treatment of Subjects With Recurrent NMOSD: Study Protocol for a Single-Center, Single-Arm, Open-Label Study," Front Neurol. (2021) 12: 596791.

Duncan et al., "The binding site for C1q on IgG," Nature. (1988) 332(6166): 738-40.

Engelman et al., "Multiple effects of mutations in human immunodeficiency virus type 1 integrase on viral replication," J Virol. 1995 69(5):2729-2736.

Eslami et al., "Function, occurrence and inhibition of different forms of BAFF," Curr Opin Immunol. (2021) 71:75-80.

Foecking et al., "Powerful and versatile enhancer-promoter unit for mammalian expression vectors," Gene. (1986) 45(1): 101-105.

Furie et al., "A phase III, randomized, placebo-controlled study of belimumab, a monoclonal antibody that inhibits B lymphocyte stimulator, in patients with systemic lupus erythematosus," Arthritis Rheum. (2011) 63(12): 3918-3930.

Gazzano-Santoro et al., "A non-radioactive complement-dependent cytotoxicity assay for anti-CD20 monoclonal antibody," J Immunol Methods. Mar. 28, 1997;202(2):163-71.

Genovese et al., "Atacicept in patients with rheumatoid arthritis and an inadequate response to tumor necrosis factor antagonist therapy: results of a phase II, randomized, placebo-controlled, dose-finding trial," Arthritis Rheum. (2011) 63(7): 1793-803.

Gentz et al., "Parallel association of Fos and Jun leucine zippers juxtaposes DNA binding domains," Science. (1989) 243(4899): 1695-1699.

Gherardi et al., "Recombinant poxviruses as mucosal vaccine vectors," J Gen Virol. (2005) 86(Pt 11):2925-2936.

Ginzler et al., "Atacicept in combination with MMF and corticosteroids in lupus nephritis: results of a prematurely terminated trial," Arthritis Res Ther. (2012) 14(1): R33.

Glabinski et al., "Murine experimental autoimmune encephalomyelitis: a model of immune-mediated inflammation and multiple sclerosis," Methods Enzymol. (1997) 288: 182-190.

Gonzalez-Mendioroz et al., "Structural analysis of the inhibition of APRIL by TACI and BCMA through molecular dynamics simulations," J Mol Graph Model. (2013) 39:13-22.

Gordon et al., "Post Hoc Analysis of the Phase II/III APRIL-SLE Study: Association Between Response to Atacicept and Serum Biomarkers Including BLyS and APRIL," Arthritis Rheumatol. (2017) 69(1): 122-130.

Gorman et al., "The Rous sarcoma virus long terminal repeat is a strong promoter when introduced into a variety of eukaryotic cells by DNA-mediated transfection," Proc Natl Acad Sci U S A. (1982) 79(22): 6777-6781.

Gross et al., "TACI-Ig neutralizes molecules critical for B cell development and autoimmune disease. impaired B cell maturation in mice lacking BLyS," Immunity. (2001) 15(2): 289-302.

Gross et al., "TACI and BCMA are receptors for a TNF homologue implicated in B-cell autoimmune disease," Nature. (2000) 404(6781): 995-999.

Guerra et al., "Host response to the attenuated poxvirus vector NYVAC: upregulation of apoptotic genes and NF-kappaB-responsive genes in infected HeLa cells," J Virol. (2006) 80(2): 985-98.

Hahne et al., "APRIL, a new ligand of the tumor necrosis factor family, stimulates tumor cell growth," J Exp Med. (1998) 188(6): 1185-90.

Hamer et al., "Regulation in vivo of a cloned mammalian gene: cadmium induces the transcription of a mouse metallothionein gene in SV40 vectors," J Mol Appl Genet. (1982) 1(4): 273-288.

Haselmayer et al., "A mouse model of systemic lupus erythematosus responds better to soluble TACI than to soluble BAFFR, correlating with depletion of plasma cells," Eur J Immunol. (2017) 47(6): 1075-1085.

Hellstrom et al., "Antitumor effects of L6, an IgG2a antibody that reacts with most human carcinomas," Proc Natl Acad Sci U S A. (1986) 83(18):7059-7063.

Hellstrom et al., "Strong antitumor activities of IgG3 antibodies to a human melanoma-associated ganglioside," Proc Natl Acad Sci U S A. (1985) 82(5):1499-1502.

Hu et al., "Yaba-like disease virus: an alternative replicating poxvirus vector for cancer gene therapy," J Virol. (2001) 75(21):10300-10308.

Huard et al., "Selective APRIL blockade delays systemic lupus erythematosus in mouse," PLoS One. (2012) 7(2): e31837.

Hymowitz et al., "Structures of APRIL-receptor complexes: like BCMA, TACI employs only a single cysteine-rich domain for high affinity ligand binding," J Biol Chem. (2005) 280(8): 7218-7227.

Idusogie et al., "Mapping of the C1q binding site on rituxan, a chimeric antibody with a human IgG1 Fc," J Immunol. (2000) 164(8):4178-4184.

Isenberg et al., "Efficacy and safety of atacicept for prevention of flares in patients with moderate-to-severe systemic lupus erythematosus (SLE): 52-week data (APRIL-SLE randomised trial)," Ann Rheum Dis. (2015) 74(11): 2006-15.

Johann et al., "GLVR1, a receptor for gibbon ape leukemia virus, is homologous to a phosphate permease of Neurospora crassa and is expressed at high levels in the brain and thymus," J Virol. (1992) 66(3): 1635-1640.

Kabat et al., "Sequences of Proteins of Immunological Interest," Fifth Edition, U.S. Department of Health and Human Services, NIH Publication No. 91-3242 (1991), 83 pages.

Kaegi et al., "Systematic Review of Safety and Efficacy of Atacicept in Treating Immune-Mediated Disorders," Front Immunol. (2020) 11:433.

Kappos et al., "Atacicept in multiple sclerosis (ATAMS): a randomised, placebo-controlled, double-blind, phase 2 trial," Lancet Neurol. (2014) 13(4): 353-63.

(56) References Cited

OTHER PUBLICATIONS

Kaufman et al., "Improved vectors for stable expression of foreign genes in mammalian cells by use of the untranslated leader sequence from EMC virus," Nucleic Acids Res. (1991) 19(16): 4485-4490.
Kelkka et al., "Reactive oxygen species deficiency induces autoimmunity with type 1 interferon signature," Antioxid Redox Signal. (2014) 21(16): 2231-2245.
Kelly et al., "APRIL/TRDL-1, a tumor necrosis factor-like ligand, stimulates cell death" Cancer Res. (2000) 60(4): 1021-1027.
Kimberley et al., "The design and characterization of receptor-selective APRIL variants," J Biol Chem. (2012) 287(44): 37434-37446.
Klarquist et al., "The bm12 Inducible Model of Systemic Lupus Erythematosus (SLE) in C57BL/6 Mice," J Vis Exp. (2015) (105): e53319.
Kolberg, "Gene-transfer virus contaminant linked to monkey's cancer," J NIH Res. (1992) 4:43-44.
Kofler et al., "Phase 1b trial of atacicept, a recombinant protein binding BLyS and APRIL, in patients with chronic lymphocytic leukemia," Leukemia. (2012) 26(4): 841-844.
Labrijn et al., "Therapeutic IgG4 antibodies engage in Fab-arm exchange with endogenous human IgG4 in vivo," Nat Biotechnol. Aug. 2009;27(8):767-71.
Larsen et al., "Rational development of LEA29Y (belatacept), a high-affinity variant of CTLA4-Ig with potent immunosuppressive properties," Am J Transplant. Mar. 2005;5(3):443-53.
Lindstrom et al., "Production and Assay of Antibodies to Acetylcholine Receptors," Methods Enzymol. (1981) ;74 Pt C:432-60.
Linsley et al., "Human B7-1 (CD80) and B7-2 (CD86) bind with similar avidities but distinct kinetics to CD28 and CTLA-4 receptors," Immunity. (1994) 1(9): 793-801.
Mayr et al., "Passage history, properties, and applicability of the attenuated vaccinia virus strain MVA," Infection. (1975);3:6-14. (English translation of abstract provided).
McKnight et al., "Functional relationships between transcriptional control signals of the thymidine kinase gene of herpes simplex virus," Cell. (1982) 31(2): 355-365.
McWilliams et al., "Mutations in the 5' end of the human immunodeficiency virus type 1 polypurine tract affect RNase H cleavage specificity and virus titer," J Virol. (2003) 77(20):11150-11157.
Merchant et al., "An efficient route to human bispecific IgG," Nat Biotechnol. (1998) 16(7): 677-681.
Mercier et al., "A chimeric adenovirus vector encoding reovirus attachment protein sigma1 targets cells expressing junctional adhesion molecule 1," Proc Natl Acad Sci U S A. (2004) 101(16): 6188-6193.
Merrill et al., "Efficacy and Safety of Atacicept in Patients With Systemic Lupus Erythematosus: Results of a Twenty-Four-Week, Multicenter, Randomized, Double-Blind, Placebo-Controlled, Parallel-Arm, Phase IIb Study," Arthritis Rheumatol. (2018) 70(2): 266-276.
Merrill, J., Clinical Trials Report, "Biomarkers Relevant to Atacicept Effects in Systemic Lupus Erythrematosus Patients" Current Rheumatology Reports; 264.
Miller et al., "Construction and properties of retrovirus packaging cells based on gibbon ape leukemia virus," J Virol. (1991) 65(5):2220-2224.
Miller et al., "Gene transfer by retrovirus vectors occurs only in cells that are actively replicating at the time of infection," Mol Cell Biol. (1990) 10(8):4239-4242.
Miller, "Protein-protein recognition and the association of immunoglobulin constant domains," J Mol Biol. Dec. 20, 1990;216(4):965-73.
Miyoshi et al. "Development of a self-inactivating lentivirus vector," J Virol. (1998) 72(10):8150-8157.
Mohan et al., "Interaction between CD40 and its ligand gp39 in the development of murine lupus nephritis," J Immunol. (1995) 154(3): 1470-1480.
Molin et al., "Two novel adenovirus vector systems permitting regulated protein expression in gene transfer experiments," J Virol. (1998) 72(10):8358-8361.

Moore et al., "BLyS: member of the tumor necrosis factor family and B lymphocyte stimulator," Science. (1999) 285(5425): 260-263.
Mosmann, "Rapid colorimetric assay for cellular growth and survival: application to proliferation and cytotoxicity assays," J Immunol Methods. (1983) 65(1-2): 55-63.
Mujtaba et al., "IFN-t Suppresses Both the Autoreactive Humoral and Cellular Immune Responses and Induces Stable Remission in Mice with Chronic Experimental Allergic Encephalomyelitis," Cell Immunol. (1998) 186(2): 94-102.
Mukhopadhyay et al., "Identification and characterization of a novel cytokine, THANK, a TNF homologue that activates apoptosis, nuclear factor-kappaB, and c-Jun NH2-terminal kinase," J Biol Chem. (1999) 274(23): 15978-15981.
Munafo et al., "Safety, pharmacokinetics and pharmacodynamics of atacicept in healthy volunteers," Eur J Clin Pharmacol. (2007) 63(7): 647-656.
Myers et al., "Collagen-induced arthritis, an animal model of autoimmunity," Life Sci. (1997) 61(19): 1861-1878.
Narumi et al., "Adenovirus vector-mediated perforin expression driven by a glucocorticoid-inducible promoter inhibits tumor growth in vivo," Am J Respir Cell Mol Biol. (1998) 19(6):936-941.
Navarra et al., "Efficacy and safety of belimumab in patients with active systemic lupus erythematosus: a randomised, placebo-controlled, phase 3 trial," Lancet. (2011) 377(9767): 721-731.
Nestorov et al., "Pharmacokinetics and biological activity of atacicept in patients with rheumatoid arthritis," J Clin Pharmacol. (2008) 48(4): 406-417.
Nestorov et al., "Pharmacokinetics and immunoglobulin response of subcutaneous and intravenous atacicept in patients with systemic lupus erythematosus," J Pharm Sci. (2010) 99(1): 524-538.
Nightingale et al., "Transient gene expression by nonintegrating lentiviral vectors," Mol Ther. (2006) 13(6):1121-1132.
Pena-Rossi et al., "An exploratory dose-escalating study investigating the safety, tolerability, pharmacokinetics and pharmacodynamics of intravenous atacicept in patients with systemic lupus erythematosus," Lupus. (2009) 18(6): 547-555.
Perez-Melgosa et al., "Cutting edge: CD40 ligand is a limiting factor in the humoral response to T cell-dependent antigens," J Immunol. (1999) 163(3): 1123-1127.
Petkova et al., "Enhanced half-life of genetically engineered human IgG1 antibodies in a humanized FcRn mouse model: potential application in humorally mediated autoimmune disease," Int Immunol. (2006) 18(12):1759-1769.
Pfeifer et al., "Gene therapy: promises and problems," Annu Rev Genomics Hum Genet. (2001);2:1 77-211.
Philpott et al., "Use of nonintegrating lentiviral vectors for gene therapy," Hum Gene Ther. (2007) 18(6): 483-9.
Ponce, "Preclinical support for combination therapy in the treatment of autoimmunity with atacicept," Toxicol Pathol. (2009) 37(1): 89-99.
Powell et al., "Sequence and structural determinants required for priming of plus-strand DNA synthesis by the human immunodeficiency virus type 1 polypurine tract," J Virol. (1996) 70(8):5288-5296.
Putterman et al., "Murine Models of Spontaneous Systemic Lupus Erythematosus," Autoimmune Disease Models: A Guidebook, (1994) Chapter 14: 217-34.
Ramanujam et al., "Similarities and differences between selective and nonselective BAFF blockade in murine SLE," J Clin Invest. (2006) 116(3): 724-734.
Ravetch et al., "Fc receptors," Annu Rev Immunol. (1991) 9:457-492.
Ridgway et al., "'Knobs-into-holes' engineering of antibody CH3 domains for heavy chain heterodimerization," Protein Eng. Jul. 1996;9(7):617-21.
Rossi et al., "Atacicept in relapsed/refractory multiple myeloma or active Waldenstrom's macroglobulinemia: a phase I study," Br J Cancer. 2009 101(7): 1051-1058.
Scatchard et al., "The attractions of proteins for small molecules and ions," Ann. N.Y. Acad. Sci. (1949) 51:660.
Schenborn et al., "A new lysis buffer for luciferase, CAT and β-galactosidase reporter gene co-transfections," Promega Notes (1993) 41:11.

(56) References Cited

OTHER PUBLICATIONS

Schneider et al., "BAFF, a novel ligand of the tumor necrosis factor family, stimulates B cell growth," J Exp Med. (1999) 189(11): 1747-1756.
Sergott et al., "ATON: results from a Phase II randomized trial of the B-cell-targeting agent atacicept in patients with optic neuritis," J Neurol Sci. (2015) 351(1-2): 174-178.
Shaw et al., "The ability of a ternary complex to form over the serum response element correlates with serum inducibility of the human c-fos promoter," Cell. (1989) 56(4): 563-572.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. (2001) 276(9):6591-6604.
Shu et al., "TALL-1 is a novel member of the TNF family that is down-regulated by mitogens," J Leukoc Biol. (1999) 65(5): 680-683.
Sommerfelt et al., "Receptor interference groups of 20 retroviruses plating on human cells," Virology. (1990) 176(1): 58-69.
Tak et al., "Atacicept in patients with rheumatoid arthritis: results of a multicenter, phase Ib, double-blind, placebo-controlled, dose-escalating, single- and repeated-dose study," Arthritis Rheum. (2008) 58(1): 61-72.
Tartaglia et al., "Highly attenuated poxvirus vectors," AIDS Res Hum Retroviruses. K1992) 8(8):1445-1447.
Tejon et al., "A Spontaneous Mouse Model of Lupus: Physiology and Therapy," Book Chapter Within "Lupus: New Advances and Challenges" InTechOpen.com, Apr. 23, 2019. DOI: 10.5772/intechopen.85938.
Theofilopoulos et al., "Murine Models of Systemic Lupus Erythematosus," Adv Immunol. (1985) 37:269-390.
Urlaub et al., "Effect of gamma rays at the dihydrofolate reductase locus: deletions and inversions," Somat Cell Mol Genet. (1986) 12(6): 555-566.
Van Vollenhoven et al., "Atacicept in patients with rheumatoid arthritis and an inadequate response to methotrexate: results of a phase II, randomized, placebo-controlled trial," Arthritis Rheum. (2011) 63(7): 1782-1792.
Van Vollenhoven et al., "Safety and efficacy of atacicept in combination with rituximab for reducing the signs and symptoms of rheumatoid arthritis: a phase II, randomized, double-blind, placebo-controlled pilot trial," Arthritis Rheumatol. (2015) 67(11): 2828-2836.
Vigolo et al., "A loop region of BAFF controls B cell survival and regulates recognition by different inhibitors," Nat Commun. (2018) 9(1): 1199.
Voulgaraki et al., "Multivalent recombinant proteins for probing functions of leucocyte surface proteins such as the CD200 receptor," Immunology. (2005) 115(3): 337-346.
Wallace et al., "Safety and clinical activity of atacicept in the long-term extension of the Phase IIb ADDRESS II study in systemic lupus erythematosus," Rheumatology (Oxford). (2021) keab115.
Wang et al., "Identify the key amino acid of BAFF binding with TACI," Cell Immunol.(2013) 284(1-2): 84-90.
Wang et al., "Effect of rhTACI-Ig fusion protein on antigen-specific T cell responses from keyhole limpet haemocyanin challenged mice," Mol Immunol. (2011) 49(1-2): 380-386.
Wang et al., "Anti-C5 monoclonal antibody therapy prevents collagen-induced arthritis and ameliorates established disease," Proc Natl Acad Sci U S A. (1995) 92(19): 8955-8959.
Weinberg et al., "Blocking OX-40/OX-40 ligand interaction in vitro and in vivo leads to decreased T cell function and amelioration of experimental allergic encephalomyelitis," J Immunol. (1999) 162(3): 1818-1826.
Williams et al., "Anti-tumor necrosis factor ameliorates joint disease in murine collagen-induced arthritis," Proc Natl Acad Sci U S A. (1992) 89(20): 9784-9788.

Wilson et al., "Formation of infectious hybrid virions with gibbon ape leukemia virus and human T-cell leukemia virus retroviral envelope glycoproteins and the gag and pol proteins of Moloney murine leukemia virus," J Virol. (1989) 63(5):2374-2378.
Wilson et al., Analyzing biomolecular interactions, Science. (2002) 295(5562): 2103-2105.
Wolff et al., "Monoclonal Antibody Homodimers: Enhanced Anti-tumor Activity in Nude Mice," Cancer Res. (1993) 53(11): 2560-2565.
Wooley et al., "Animal models of rheumatoid arthritis," Curr. Opin. Rheum. (1999) 3:407-420.
Wu et al., "Experimental autoimmune myasthenia gravis in the mouse," Curr Protoc Immunol. (2001) Chapter 15: Unit 15.8.
Wu et al., "Telitacicept (RC18) in Patients with Systemic Lupus Erythematosus (SLE): Results of a Phase 2b, Randomized, Double Blind, Placebo Controlled Study," Oral Presentation.
Yaccoby et al., "Atacicept (TACI-Ig) inhibits growth of TACI(high) primary myeloma cells in SCID-hu mice and in coculture with osteoclasts," Leukemia. (2008) 22(2): 406-413.
Yao et al., "Pharmacokinetics analysis based on target-mediated drug distribution for RC18, a novel BLyS/APRIL fusion protein to treat systemic lupus erythematosus and rheumatoid arthritis," Eur J Pharm Sci. (2021) 159: 105704.
Zapata et al., "Engineering linear F(ab')2 fragments for efficient production in *Escherichia coli* and enhanced antiproliferative activity," Protein Eng. (1995) 8(10): 1057-62.
Zhao et al., "Pharmacokinetics, Pharmacodynamics, Safety, and Clinical Activity of Multiple Doses of RCT-18 in Chinese Patients With Systemic Lupus Erythematosus," J Clin Pharmacol. (2016) 56(8): 948-959.
Zhou et al., "Synthesis of functional mRNA in mammalian cells by bacteriophage T3 RNA polymerase," Mol Cell Biol. (1990) 10(9): 4529-4537.
Zhou et al., "Endogenous programmed death ligand-1 restrains the development and onset of Sjögren's syndrome in non-obese diabetic mice," Scientific Reports. (2016) vol. 6; Article No. 39105.
Zufferey et al., "Self-inactivating lentivirus vector for safe and efficient in vivo gene delivery," J Virol. (1998) 72(12):9873-9880.
"Database accession No. 014836" Retrieved from UNIPROT, https://www.uniprot.org/uniprot/014836, Retrieved on Oct. 26, 2021.
"Telitacicept", WHO Drug Information, (2018) vol. 32, No. 4; pp. 651-652.
Bossen et al., "Baff, April and their receptors: structure, function and signaling," Semin Immunol. (2006) 18(5): 263-275.
Dillon et al. "ALPN-303, an Enhanced, Potent Dual BAFF/APRIL Antagonist Engineered by Directed Evolution for the Treatment of Systemic Lupus Erythematosus (SLE) and Other B Cell-Related Autoimmune Diseases," Abstract OP0039 Eular Abstracts 2021.
Dillon et al., "B Cell Modulatory Variant TNF Receptor Domains (vTDs) Identified by Directed Evolution to Inhibit BAFF and APRIL, Alone or Combined with Variant Ig Domains (vIgD™) that Inhibit T Cell Costimulation, for the Treatment of Severe Autoimmune and/or Inflammatory Disease" Abstract THU0222; EULAR Abstracts 2020.
Dillon et al. "B Cell Modulatory Variant TNF Receptor Domains (vTDs) Identified by Directed Evolution to Inhibit BAFF and APRIL, Alone or Combined with Variant Ig Domains (vIgD™) that Inhibit T Cell Costimulation, for the Treatment of Severe Autoimmune and/or Inflammatory Disease," EULAR Abstracts 2020, Abstract No. L1545.
Schmidts et al., "Rational design of a trimeric APRIL-based CAR-binding domain enables efficient targeting of multiple myeloma," Blood Adv. (2019) 3(21): 3248-3260.
Wu et al., A Human Recombinant Fusion Protein Targeting B Lymphocyte Stimulator (BlyS) and a Proliferation-Inducing Ligand (APRIL), Telitacicept (RC18), in Systemic.
Lupus Erythematosus (SLE): Results of a Phase 2b Study, 2019 ACR/ARP Annual Meeting, Abstract L18.

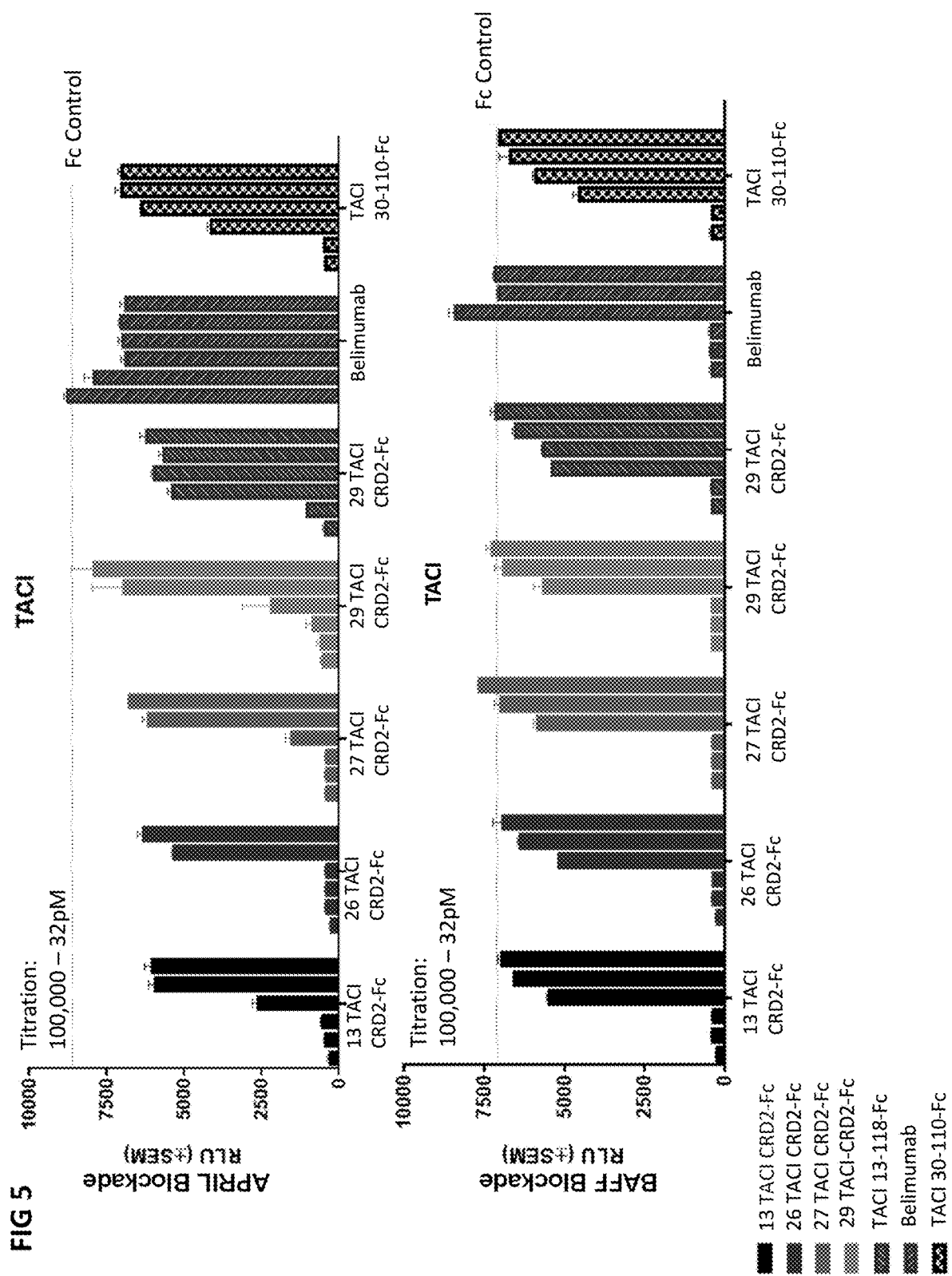

FIG. 9

```
TACI   122  MSGLGRSRRGGRSRVDQEERFPQGLWTGVAMRSCPEEQYWDPLLGTCMSCKTICNHQSQR   60
TACI    13  ------------------------------------------------------------    0

TACI   122  TCAAFCRSLSCRKEQGKFYDHLLRDCISCASICGQHPKQCAYFCENKLRSPVNLPPELRR  120
TACI    13  ------SLSCRKEQGKFYDHLLRDCISCASICGQHPKQCAYFCENKLRS-----------   43
                  *******************************************

TACI   122  QRSGEVENNSDNSGRYQGLEHRGSEASPALPGLKLSADQVALVYST               166
TACI    13  ----------------------------------------------                43
```

1. Fc Control
2. TACI 30-110 – Fc
3. TACI 13-118 – Fc
4. 26 TACI CRD2-Fc
5. 27 TACI CRD2-Fc
6. 29 TACI CRD2-Fc
7. Naïve 1. Fc Control
2. TACI 30-110 – Fc
3. TACI 13-118 – Fc
4. 26 TACI CRD2-Fc
5. 27 TACI CRD2-Fc
6. 29 TACI CRD2-Fc
7. Naïve 1. Fc Control
2. TACI 30-110 – Fc
3. TACI 13-118 – Fc
4. 26 TACI CRD2-Fc
5. 27 TACI CRD2-Fc
6. 29 TACI CRD2-Fc
7. Naïve

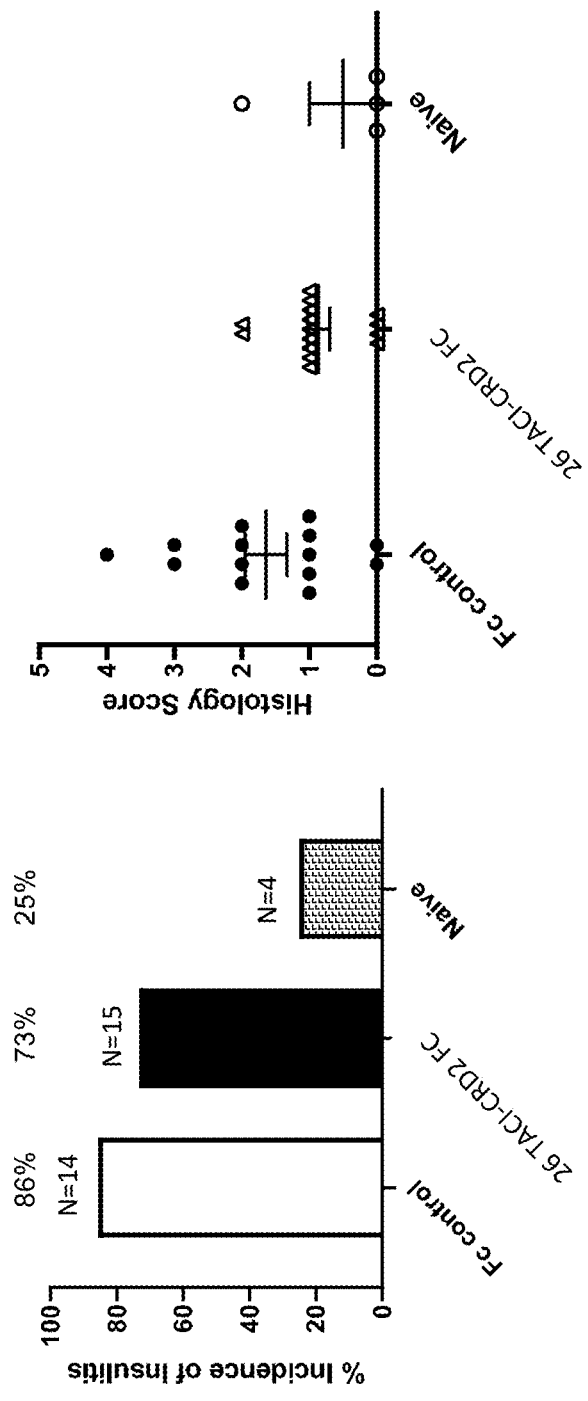

SEQUENCE LISTING

<160> NUMBER OF SEQ ID NOS: 239

<210> SEQ ID NO 1
<211> LENGTH: 82
<212> TYPE: PRT
<213> ORGANISM: ARTIFICIAL SEQUENCE
<220> FEATURE:

<223> OTHER INFORMATION: TACI WT ECD

<400> SEQUENCE: 1

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Arg Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 2
<211> LENGTH: 82
<212> TYPE: PRT
<213> ORGANISM: ARTIFICIAL SEQUENCE
<220> FEATURE:
<223> OTHER INFORMATION: TACI L82P ECD

<400> SEQUENCE: 2

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Pro Leu Arg Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 3
<211> LENGTH: 82
<212> TYPE: PRT
<213> ORGANISM: ARTIFICIAL SEQUENCE
<220> FEATURE:
<223> OTHER INFORMATION: TACI D85E, K98T ECD

<400> SEQUENCE: 3

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Arg Glu Cys Ile Ser Cys Ala Ser Ile
    50                  55                  60

Cys Gly Gln His Pro Thr Gln Cys Ala Tyr Phe Cys Glu Asn Lys Leu
65                  70                  75                  80

Arg Ser

<210> SEQ ID NO 4
<211> LENGTH: 82
<212> TYPE: PRT

<213> ORGANISM: ARTIFICIAL SEQUENCE
<220> FEATURE:
<223> OTHER INFORMATION: TACI I87L, K98T ECD

<400> SEQUENCE: 4

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Arg Asp Cys Leu Ser Cys Ala Ser Ile
    50                  55                  60

Cys Gly Gln His Pro Thr Gln Cys Ala Tyr Phe Cys Glu Asn Lys Leu
65                  70                  75                  80

Arg Ser

<210> SEQ ID NO 5
<211> LENGTH: 82
<212> TYPE: PRT
<213> ORGANISM: ARTIFICIAL SEQUENCE
<220> FEATURE:
<223> OTHER INFORMATION: TACI R60G, Q75E, L82P ECD

<400> SEQUENCE: 5

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Gly
            20                  25                  30

Thr Cys Ala Ala Phe Cys Arg Ser Leu Ser Cys Arg Lys Glu Glu Gly
        35                  40                  45

Lys Phe Tyr Asp His Pro Leu Arg Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 6
<211> LENGTH: 82
<212> TYPE: PRT
<213> ORGANISM: ARTIFICIAL SEQUENCE
<220> FEATURE:
<223> OTHER INFORMATION: TACI R60G, C86Y ECD

<400> SEQUENCE: 6

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Gly
            20                  25                  30

Thr Cys Ala Ala Phe Cys Arg Ser Leu Ser Cys Arg Lys Glu Gln Gly
        35                  40                  45

Lys Phe Tyr Asp His Leu Leu Arg Asp Tyr Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 7

```
<211> LENGTH: 82
<212> TYPE: PRT
<213> ORGANISM: ARTIFICIAL SEQUENCE
<220> FEATURE:
<223> OTHER INFORMATION: TACI A101D ECD

<400> SEQUENCE: 7
```

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Arg Asp Cys Ile Ser Cys Ala Ser Ile
    50                  55                  60

Cys Gly Gln His Pro Lys Gln Cys Asp Tyr Phe Cys Glu Asn Lys Leu
65                  70                  75                  80

Arg Ser

```
<210> SEQ ID NO 8
<211> LENGTH: 82
<212> TYPE: PRT
<213> ORGANISM: ARTIFICIAL SEQUENCE
<220> FEATURE:
<223> OTHER INFORMATION: TACI C86Y ECD

<400> SEQUENCE: 8
```

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Arg Asp Tyr Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

```
<210> SEQ ID NO 9
<211> LENGTH: 82
<212> TYPE: PRT
<213> ORGANISM: ARTIFICIAL SEQUENCE
<220> FEATURE:
<223> OTHER INFORMATION: TACI W40R, L82P, F103Y ECD

<400> SEQUENCE: 9
```

Val Ala Met Arg Ser Cys Pro Glu Glu Gln Tyr Arg Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Pro Leu Arg Asp Cys Ile Ser Cys Ala Ser Ile
    50                  55                  60

Cys Gly Gln His Pro Lys Gln Cys Ala Tyr Tyr Cys Glu Asn Lys Leu
65                  70                  75                  80

Arg Ser

<210> SEQ ID NO 10
<211> LENGTH: 82
<212> TYPE: PRT
<213> ORGANISM: ARTIFICIAL SEQUENCE
<220> FEATURE:
<223> OTHER INFORMATION: TACI W40R, Q59R, T61P, K98T ECD

<400> SEQUENCE: 10

```
Val Ala Met Arg Ser Cys Pro Glu Glu Gln Tyr Arg Asp Pro Leu Leu
1               5                   10                  15

Gly Thr Cys Met Ser Cys Lys Thr Ile Cys Asn His Gln Ser Arg Arg
                20                  25                  30

Pro Cys Ala Ala Phe Cys Arg Ser Leu Ser Cys Arg Lys Glu Gln Gly
            35                  40                  45

Lys Phe Tyr Asp His Leu Leu Arg Asp C

Arg Ser

```
<210> SEQ ID NO 13
<211> LENGTH: 43
<212> TYPE: PRT
<213> ORGANISM: ARTIFICIAL SEQUENCE
<220> FEATURE:
<223> OTHER INFORMATION: TACI WT ECD

<400> SEQUENCE: 13
```

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

```
<210> SEQ ID NO 14
<211> LENGTH: 43
<212> TYPE: PRT
<213> ORGANISM: ARTIFICIAL SEQUENCE
<220> FEATURE:
<223> OTHER INFORMATION: TACI D85V ECD

<400> SEQUENCE: 14
```

Ser Leu Ser Cys Arg Lys Glu Gln Gly Lys Phe Tyr Asp His Leu Leu
1               5                   10                  15

Arg Val Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

```
<210> SEQ ID NO 15
<211> LENGTH: 43
<212> TYPE: PRT
<213> ORGANISM: ARTIFICIAL SEQUENCE
<220> FEATURE:
<223> OTHER INFORMATION: TACI E74V ECD

<400> SEQUENCE: 15
```

Ser Leu Ser Cys Arg Lys Val Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

```
<210> SEQ ID NO 16
<211> LENGTH: 43
<212> TYPE: PRT
<213> ORGANISM: ARTIFICIAL SEQUENCE
<220> FEATURE:
<223> OTHER INFORMATION: TACI R84L ECD

<400> SEQUENCE: 16
```

Ser Leu Ser Cys Arg Lys Glu Gln Gly Lys Phe Tyr Asp His Leu Leu
1               5                   10                  15

Leu Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

```
<210> SEQ ID NO 17
<211> LENGTH: 43
<212> TYPE: PRT
<213> ORGANISM: ARTIFICIAL SEQUENCE
<220> FEATURE:
<223> OTHER INFORMATION: TACI K77E, R84L, F103Y ECD

<400> SEQUENCE: 17

Ser Leu Ser Cys Arg Lys Glu Gln Gly Glu Phe Tyr Asp His Leu Leu
1               5                   10                  15

Leu Asp Cys Ile Ser Cys Ala Ser Ile Cys Gly Gln His Pro Lys Gln
            20                  25                  30

Cys Ala Tyr Tyr Cys Glu Asn Lys Leu Arg Ser
        35                  40

<210> SEQ ID NO 18
<211> LENGTH: 43
<212> TYPE: PRT
<213> ORGANISM: ARTIFICIAL SEQUENCE
<220> FEATURE:
<223> OTHER INFORMATION: TACI Y79F, Q99E ECD

<400> SEQUENCE: 18

Ser Leu Ser Cys Arg Lys Glu Gln Gly Lys Phe Phe Asp His Leu Leu
1               5                   10                  15

Arg Asp Cys Ile Ser Cys Ala Ser Ile Cys Gly Gln His Pro Lys Glu
            20                  25                  30

Cys Ala Tyr Phe Cys Glu Asn Lys Leu Arg Ser
        35                  40

<210> SEQ ID NO 19
<211> LENGTH: 43
<212> TYPE: PRT
<213> ORGANISM: ARTIFICIAL SEQUENCE
<220> FEATURE:
<223> OTHER INFORMATION: TACI Y79F ECD

<400> SEQUENCE: 19

Ser Leu Ser Cys Arg Lys Glu Gln Gly Lys Phe Phe Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 20
<211> LENGTH: 43
<212> TYPE: PRT
<213> ORGANISM: ARTIFICIAL SEQUENCE
<220> FEATURE:
<223> OTHER INFORMATION: TACI R84G ECD

<400> SEQUENCE: 20

Ser Leu Ser Cys Arg Lys Glu Gln Gly Lys Phe Tyr Asp His Leu Leu
1               5                   10                  15

Gly Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 21
<211> LENGTH: 82
<212> TYPE: PRT
```

<213> ORGANISM: ARTIFICIAL SEQUENCE
<220> FEATURE:
<223> OTHER INFORMATION: TACI L83S, F103S ECD

<400> SEQUENCE: 21

| Val | Ala | Met | Arg | Ser | Cys | Pro | Glu | Glu | Gln | Tyr | Trp | Asp | Pro | Leu | Leu |
|---|---|---|---|---|---|---|---|---|---|---|---|---|---|---|---|
| 1 | | | | 5 | | | | | 10 | | | | | 15 | |
| Gly | Thr | Cys | Met | Ser | Cys | Lys | Thr | Ile | Cys | Asn | His | Gln | Ser | Gln | Arg |
| | | | 20 | | | | | 25 | | | | | 30 | | |
| Thr | Cys | Ala | Ala | Phe | Cys | Arg | Ser | Leu | Ser | Cys | Arg | Lys | Glu | Gln | Gly |
| | | | 35 | | | | | 40 | | | | | 45 | | |
| Lys | Phe | Tyr | Asp | His | Leu | Ser | Arg | Asp | Cys | Ile | Ser | Cys | Ala | Ser | Ile |
| | | | 50 | | | | | 55 | | | | | 60 | | |
| Cys | Gly | Gln | His | Pro | Lys | Gln | Cys | Ala | Tyr | Ser | Cys | Glu | Asn | Lys | Leu |
| 65 | | | | | 70 | | | | | 75 | | | | | 80 |
| Arg | Ser | | | | | | | | | | | | | | |

<210> SEQ ID NO 22
<211> LENGTH: 82
<212> TYPE: PRT
<213> ORGANISM: ARTIFICIAL SEQUENCE
<220> FEATURE:
<223> OTHER INFORMATION: TACI L82H ECD

<400> SEQUENCE: 22

| Val | Ala | Met | Arg | Ser | Cys | Pro | Glu | Glu | Gln | Tyr | Trp | Asp | Pro | Leu | Leu |
|---|---|---|---|---|---|---|---|---|---|---|---|---|---|---|---|
| 1 | | | | 5 | | | | | 10 | | | | | 15 | |
| Gly | Thr | Cys | Met | Ser | Cys | Lys | Thr | Ile | Cys | Asn | His | Gln | Ser | Gln | Arg |
| | | | 20 | | | | | 25 | | | | | 30 | | |
| Thr | Cys | Ala | Ala | Phe | Cys | Arg | Ser | Leu | Ser | Cys | Arg | Lys | Glu | Gln | Gly |
| | | | 35 | | | | | 40 | | | | | 45 | | |
| Lys | Phe | Tyr | Asp | His | His | Leu | Arg | Asp | Cys | Ile | Ser | Cys | Ala | Ser | Ile |
| | | | 50 | | | | | 55 | | | | | 60 | | |
| Cys | Gly | Gln | His | Pro | Lys | Gln | Cys | Ala | Tyr | Phe | Cys | Glu | Asn | Lys | Leu |
| 65 | | | | | 70 | | | | | 75 | | | | | 80 |
| Arg | Ser | | | | | | | | | | | | | | |

<210> SEQ ID NO 23
<211> LENGTH: 43
<212> TYPE: PRT
<213> ORGANISM: ARTIFICIAL SEQUENCE
<220> FEATURE:
<223> OTHER INFORMATION: TACI A101D ECD

<400> SEQUENCE: 23

| Ser | Leu | Ser | Cys | Arg | Lys | Glu | Gln | Gly | Lys | Phe | Tyr | Asp | His | Leu | Leu |
|---|---|---|---|---|---|---|---|---|---|---|---|---|---|---|---|
| 1 | | | | 5 | | | | | 10 | | | | | 15 | |
| Arg | Asp | Cys | Ile | Ser | Cys | Ala | Ser | Ile | Cys | Gly | Gln | His | Pro | Lys | Gln |
| | | | 20 | | | | | 25 | | | | | 30 | | |
| Cys | Asp | Tyr | Phe | Cys | Glu | Asn | Lys | Leu | Arg | Ser | | | | | |
| | | | 35 | | | | | 40 | | | | | | | |

<210> SEQ ID NO 24
<211> LENGTH: 43
<212> TYPE: PRT
<213> ORGANISM: ARTIFICIAL SEQUENCE
<220> FEATURE:
<223> OTHER INFORMATION: TACI K77E, R84Q ECD

<400> SEQUENCE: 24

```
Ser Leu Ser Cys Arg Lys Glu Gln Gly Glu Phe Tyr Asp His Leu Leu
1               5                   10                  15

Gln Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 25
<211> LENGTH: 43
<212> TYPE: PRT
<213> ORGANISM: ARTIFICIAL SEQUENCE
<220> FEATURE:
<223> OTHER INFORMATION: TACI K77E, A101D ECD

<400> SEQUENCE: 25

Ser Leu Ser Cys Arg Lys Glu Gln Gly Glu Phe Tyr Asp His Leu Leu
1               5                   10                  15

Arg Asp Cys Ile Ser Cys Ala Ser Ile Cys Gly Gln His Pro Lys Gln
            20                  25                  30

Cys Asp Tyr Phe Cys Glu Asn Lys Leu Arg Ser
        35                  40

<210> SEQ ID NO 26
<211> LENGTH: 43
<212> TYPE: PRT
<213> ORGANISM: ARTIFICIAL SEQUENCE
<220> FEATURE:
<223> OTHER INFORMATION: TACI K77E, F78Y, Y102D ECD

<400> SEQUENCE: 26

Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser
        35                  40

<210> SEQ ID NO 27
<211> LENGTH: 43
<212> TYPE: PRT
<213> ORGANISM: ARTIFICIAL SEQUENCE
<220> FEATURE:
<223> OTHER INFORMATION: TACI Q75E, R84Q ECD

<400> SEQUENCE: 27

Ser Leu Ser Cys Arg Lys Glu Glu Gly Lys Phe Tyr Asp His Leu Leu
1               5                   10                  15

Gln Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 28
<211> LENGTH: 43
<212> TYPE: PRT
<213> ORGANISM: ARTIFICIAL SEQUENCE
<220> FEATURE:
<223> OTHER INFORMATION: TACI Q75R, R84G, I92V ECD

<400> SEQUENCE: 28

Ser Leu Ser Cys Arg Lys Glu Arg Gly Lys Phe Tyr Asp His Leu Leu
1               5                   10                  15
```

-continued

```
Gly Asp Cys Ile Ser Cys Ala Ser Val Cys Gly Gln His Pro Lys Gln
                20                  25                  30

Cys Ala Tyr Phe Cys Glu Asn Lys Leu Arg Ser
            35                  40

<210> SEQ ID NO 29
<211> LENGTH: 43
<212> TYPE: PRT
<213> ORGANISM: ARTIFICIAL SEQUENCE
<220> FEATURE:
<223> OTHER INFORMATION: TACI K77E, A101D, Y102D ECD

<400> SEQUENCE: 29

Ser Leu Ser Cys Arg Lys Glu Gln Gly Glu Phe Tyr Asp His Leu Leu
1               5                   10                  15

Arg Asp Cys Ile Ser Cys Ala Ser Ile Cys Gly Gln His Pro Lys Gln
                20                  25                  30

Cys Asp Asp Phe Cys Glu Asn Lys Leu Arg Ser
            35                  40

<210> SEQ ID NO 30
<211> LENGTH: 43
<212> TYPE: PRT
<213> ORGANISM: ARTIFICIAL SEQUENCE
<220> FEATURE:
<223> OTHER INFORMATION: TACI R84Q ECD

<400> SEQUENCE: 30

Ser Leu Ser Cys Arg Lys Glu Gln Gly Lys Phe Tyr Asp His Leu Leu
1               5                   10                  15

Gln Asp Cys Ile Ser Cys Ala Ser Ile Cys Gly Gln His Pro Lys Gln
                20                  25                  30

Cys Ala Tyr Phe Cys Glu Asn Lys Leu Arg Ser
            35                  40

<210> SEQ ID NO 31
<211> LENGTH: 43
<212> TYPE: PRT
<213> ORGANISM: ARTIFICIAL SEQUENCE
<220> FEATURE:
<223> OTHER INFORMATION: TACI R84Q, S88N, A101D ECD

<400> SEQUENCE: 31

Ser Leu Ser Cys Arg Lys Glu Gln Gly Lys Phe Tyr Asp His Leu Leu
1               5                   10                  15

Gln Asp Cys Ile Asn Cys Ala Ser Ile Cys Gly Gln His Pro Lys Gln
                20                  25                  30

Cys Asp Tyr Phe Cys Glu Asn Lys Leu Arg Ser
            35                  40

<210> SEQ ID NO 32
<211> LENGTH: 43
<212> TYPE: PRT
<213> ORGANISM: ARTIFICIAL SEQUENCE
<220> FEATURE:
<223> OTHER INFORMATION: TACI K77E ECD

<400> SEQUENCE: 32

Ser Leu Ser Cys Arg Lys Glu Gln Gly Glu Phe Tyr Asp His Leu Leu
1               5                   10                  15

Arg Asp Cys Ile Ser Cys Ala Ser Ile Cys Gly Gln His Pro Lys Gln
                20                  25                  30
```

Cys Ala Tyr Phe Cys Glu Asn Lys Leu Arg Ser
            35                  40

<210> SEQ ID NO 33
<211> LENGTH: 43
<212> TYPE: PRT
<213> ORGANISM: ARTIFICIAL SEQUENCE
<220> FEATURE:
<223> OTHER INFORMATION: TACI R84Q, F103V ECD

<400> SEQUENCE: 33

Ser Leu Ser Cys Arg Lys Glu Gln Gly Lys Phe Tyr Asp His Leu Leu
1               5                   10                  15

Gln Asp Cys Ile Ser Cys Ala Ser Ile Cys Gly Gln His Pro Lys Gln
            20                  25                  30

Cys Ala Tyr Val Cys Glu Asn Lys Leu Arg Ser
            35                  40

<210> SEQ ID NO 34
<211> LENGTH: 43
<212> TYPE: PRT
<213> ORGANISM: ARTIFICIAL SEQUENCE
<220> FEATURE:
<223> OTHER INFORMATION: TACI K77E, Q95R, A101D ECD

<400> SEQUENCE: 34

Ser Leu Ser Cys Arg Lys Glu Gln Gly Glu Phe Tyr Asp His Leu Leu
1               5                   10                  15

Arg Asp Cys Ile Ser Cys Ala Ser Ile Cys Gly Arg His Pro Lys Gln
            20                  25                  30

Cys Asp Tyr Phe Cys Glu Asn Lys Leu Arg Ser
            35                  40

<210> SEQ ID NO 35
<211> LENGTH: 43
<212> TYPE: PRT
<213> ORGANISM: ARTIFICIAL SEQUENCE
<220> FEATURE:
<223> OTHER INFORMATION: TACI I87M, A101D ECD

<400> SEQUENCE: 35

Ser Leu Ser Cys Arg Lys Glu Gln Gly Lys Phe Tyr Asp His Leu Leu
1               5                   10                  15

Arg Asp Cys Met Ser Cys Ala Ser Ile Cys Gly Gln His Pro Lys Gln
            20                  25                  30

Cys Asp Tyr Phe Cys Glu Asn Lys Leu Arg Ser
            35                  40

<210> SEQ ID NO 36
<211> LENGTH: 246
<212> TYPE: DNA
<213> ORGANISM: ARTIFICIAL SEQUENCE
<220> FEATURE:
<223> OTHER INFORMATION: TACI WT ECD

<400> SEQUENCE: 36
gtggcaatgc gctcatgccc agaggaacaa tattgggatc cgcttcttgg gacgtgtatg      60
agctgcaaga ccatctgtaa tcatcaatcc caaaggacat gcgcagcttt ctgcaggagt     120
ctctcttgca ggaaagagca aggcaaattt tacgaccatc ttttgcgaga ctgtataagc     180
tgtgcgtcta tttgtggaca acaccctaaa caatgtgctt atttctgtga aaataagctt     240
cgatct                                                                246

<210> SEQ ID NO 37
<211> LENGTH: 246
<212> TYPE: DNA
<213> ORGANISM: ARTIFICIAL SEQUENCE
<220> FEATURE:
<223> OTHER INFORMATION: TACI L82P ECD

<400> SEQUENCE: 37

```
gtggcaatgc gctcatgccc agaggaacaa tattgggatc cgcttcttgg gacgtgtatg    60
agctgcaaga ccatctgtaa tcatcaatcc caaaggacat gcgcagcttt ctgcaggagt   120
ctctcttgca ggaaagagca aggcaaattt tacgaccatc ctttgcgaga ctgtataagc   180
tgtgcgtcta tttgtggaca acaccctaaa caatgtgctt atttctgtga aaataagctt   240
cgatct                                                              246
```

<210> SEQ ID NO 38
<211> LENGTH: 246
<212> TYPE: DNA
<213> ORGANISM: ARTIFICIAL SEQUENCE
<220> FEATURE:
<223> OTHER INFORMATION: TACI D85E, K98T ECD

<400> SEQUENCE: 38

```
gtggcaatgc gctcatgccc agaggaacaa tattgggatc cgcttcttgg gacgtgtatg    60
agctgcaaga ccatctgtaa tcatcaatcc caaaggacat gcgcagcttt ctgcaggagt   120
ctctcttgca ggaaagagca aggcaaattt tacgaccatc ttttgcgaga atgtataagc   180
tgtgcgtcta tttgtggaca acaccctaca caatgtgctt atttctgtga aaataagctt   240
cgatct                                                              246
```

<210> SEQ ID NO 39
<211> LENGTH: 246
<212> TYPE: DNA
<213> ORGANISM: ARTIFICIAL SEQUENCE
<220> FEATURE:
<223> OTHER INFORMATION: TACI I87L, K98T ECD

<400> SEQUENCE: 39

```
gtggcaatgc gctcatgccc agaggaacaa tattgggatc cgcttcttgg gacgtgtatg    60
agctgcaaga ccatctgtaa tcatcaatcc caaaggacat gcgcagcttt ctgcaggagt   120
ctctcttgca ggaaagagca aggcaaattt tacgaccatc ttttgcgaga ctgtttaagc   180
tgtgcgtcta tttgtggaca acaccctaca caatgtgctt atttctgtga aaataagctt   240
cgatct                                                              246
```

<210> SEQ ID NO 40
<211> LENGTH: 246
<212> TYPE: DNA
<213> ORGANISM: ARTIFICIAL SEQUENCE
<220> FEATURE:
<223> OTHER INFORMATION: TACI R60G, Q75E, L82P ECD

<400> SEQUENCE: 40

```
gtggcaatgc gctcatgccc agaggaacaa tattgggatc cgcttcttgg gacgtgtatg    60
agctgcaaga ccatctgtaa tcatcaatcc caaggacat gcgcagcttt ctgcaggagt    120
ctctcttgca ggaaagagga aggcaaattt tacgaccatc ctttgcgaga ctgtataagc   180
tgtgcgtcta tttgtggaca acaccctaaa caatgtgctt atttctgtga aaataagctt   240
```

```
cgatct                                                                  246
```

<210> SEQ ID NO 41
<211> LENGTH: 246
<212> TYPE: DNA
<213> ORGANISM: ARTIFICIAL SEQUENCE
<220> FEATURE:
<223> OTHER INFORMATION: TACI R60G, C86Y ECD

<400> SEQUENCE: 41

```
gtggcaatgc gctcatgccc agaggaacaa tattgggatc cgcttcttgg gacgtgtatg       60
agctgcaaga ccatctgtaa tcatcaatcc caagggacat gcgcagcttt ctgcaggagt      120
ctctcttgca ggaaagagca aggcaaattt tacgaccatc ttttgcgaga ctacataagc      180
tgtgcgtcta tttgtggaca acaccctaaa caatgtgctt atttctgtga aaataagctt      240
cgatct                                                                  246
```

<210> SEQ ID NO 42
<211> LENGTH: 246
<212> TYPE: DNA
<213> ORGANISM: ARTIFICIAL SEQUENCE
<220> FEATURE:
<223> OTHER INFORMATION: TACI A101D ECD

<400> SEQUENCE: 42

```
gtggcaatgc gctcatgccc agaggaacaa tattgggatc cgcttcttgg gacgtgtatg       60
agctgcaaga ccatctgtaa tcatcaatcc caaaggacat gcgcagcttt ctgcaggagt      120
ctctcttgca ggaaagagca aggcaaattt tacgaccatc ttttgcgaga ctgtataagc      180
tgtgcgtcta tttgtggaca acaccctaaa caatgtgatt atttctgtga aaataagctt      240
cgatct                                                                  246
```

<210> SEQ ID NO 43
<211> LENGTH: 246
<212> TYPE: DNA
<213> ORGANISM: ARTIFICIAL SEQUENCE
<220> FEATURE:
<223> OTHER INFORMATION: TACI C86Y ECD

<400> SEQUENCE: 43

```
gtggcaatgc gctcatgccc agaggaacaa tattgggatc cgcttcttgg gacgtgtatg       60
agctgcaaga ccatctgtaa tcatcaatcc caaaggacat gcgcagcttt ctgcaggagt      120
ctctcttgca ggaaagagca aggcaaattt tacgaccatc ttttgcgaga ctatataagc      180
tgtgcgtcta tttgtggaca acaccctaaa caatgtgctt atttctgtga aaataagctt      240
cgatct                                                                  246
```

<210> SEQ ID NO 44
<211> LENGTH: 246
<212> TYPE: DNA
<213> ORGANISM: ARTIFICIAL SEQUENCE
<220> FEATURE:
<223> OTHER INFORMATION: TACI W40R, L82P, F103Y ECD

<400> SEQUENCE: 44

```
gtggcaatgc gctcatgccc agaggaacaa tatcgggatc cgcttcttgg gacgtgtatg       60
agctgcaaga ccatctgtaa tcatcaatcc caaaggacat gcgcagcttt ctgcaggagt      120
ctctcttgca ggaaagagca aggcaaattt tacgaccatc ttttgcgaga ctgtataagc      180
tgtgcgtcta tttgtggtca acaccctaaa caatgtgctt attactgtga aaataagctt      240
```

```
cgatct                                                          246

<210> SEQ ID NO 45
<211> LENGTH: 246
<212> TYPE: DNA
<213> ORGANISM: ARTIFICIAL SEQUENCE
<220> FEATURE:
<223> OTHER INFORMATION: TACI W40R, Q59R, T61P, K98T ECD

<400> SEQUENCE: 45
gtggcaatgc gctcatgccc agaggaacaa tatcgggatc cgcttcttgg gacgtgtatg    60
agctgcaaga ccatctgtaa tcatcaatcc cgaaggccat gcgcagcatt ctgcaggagt   120
ctctcttgca ggaaagagca aggcaaattt tacgaccatc ttttgcgaga ctgtataagc   180
tgtgcgtcta tttgtggaca cacccctaca caatgtgctt atttctgtga aaataagctt   240
cgatct                                                              246

<210> SEQ ID NO 46
<211> LENGTH: 246
<212> TYPE: DNA
<213> ORGANISM: ARTIFICIAL SEQUENCE
<220> FEATURE:
<223> OTHER INFORMATION: TACI L82P, I87L ECD

<400> SEQUENCE: 46
gtggcaatgc gctcatgccc agaggaacaa tattgggatc cgcttcttgg gacgtgtatg    60
agctgcaaga ccatctgtaa tcatcaatcc caaaggacat gcgcagcttt ctgcaggagt   120
ctctcttgca ggaaagagca aggcaaattt tacgaccatc ttttgcgaga ctgtttaagc   180
tgtgcgtcta tttgtggaca cacccctaaa caatgtgctt atttctgtga aaataagctt   240
cgatct                                                              246

<210> SEQ ID NO 47
<211> LENGTH: 246
<212> TYPE: DNA
<213> ORGANISM: ARTIFICIAL SEQUENCE
<220> FEATURE:
<223> OTHER INFORMATION: TACI G76S, P97S ECD

<400> SEQUENCE: 47
gtggcaatgc gctcatgccc agaggaacaa tattgggatc cgcttcttgg gacgtgtatg    60
agctgcaaga ccatctgtaa tcatcaatcc caaaggacat gcgcagcttt ctgcaggagt   120
ctctcttgca ggaaagagca aagcaaattt tacgaccatc ttttgcgaga ctgtataagc   180
tgtgcgtcta tttgtggtca cactctaaa  caatgtgctt atttctgtga aaataagctt   240
cgatct                                                              246

<210> SEQ ID NO 48
<211> LENGTH: 129
<212> TYPE: DNA
<213> ORGANISM: ARTIFICIAL SEQUENCE
<220> FEATURE:
<223> OTHER INFORMATION: TACI WT ECD

<400> SEQUENCE: 48
agtctctctt gcaggaaaga gcaaggcaaa ttttacgacc atcttttgcg agactgtata    60
agctgtgcgt ctatttgtgg acaacaccct aaacaatgtg cttatttctg tgaaaataag   120
cttcgatct                                                          129
```

<210> SEQ ID NO 49
<211> LENGTH: 129
<212> TYPE: DNA
<213> ORGANISM: ARTIFICIAL SEQUENCE
<220> FEATURE:
<223> OTHER INFORMATION: TACI D85V ECD

<400> SEQUENCE: 49

```
agtctctctt gcaggaaaga gcaaggcaaa ttttacgacc atcttttgcg agtctgtata    60
agctgtgcgt ctatttgtgg acaacaccct aaacaatgtg cttatttctg tgaaaataag   120
cttcgatct                                                           129
```

<210> SEQ ID NO 50
<211> LENGTH: 129
<212> TYPE: DNA
<213> ORGANISM: ARTIFICIAL SEQUENCE
<220> FEATURE:
<223> OTHER INFORMATION: TACI E74V ECD

<400> SEQUENCE: 50

```
agtctctctt gcaggaaagt gcaaggcaaa ttttacgacc atcttttgcg agactgtata    60
agctgtgcgt ctatttgtgg acaacaccct aaacaatgtg cttatttctg tgaaaataag   120
cttcgatct                                                           129
```

<210> SEQ ID NO 51
<211> LENGTH: 129
<212> TYPE: DNA
<213> ORGANISM: ARTIFICIAL SEQUENCE
<220> FEATURE:
<223> OTHER INFORMATION: TACI R84L ECD

<400> SEQUENCE: 51

```
agtctctctt gcaggaaaga gcaaggcaaa ttttacgacc atcttttgct agactgtata    60
agctgtgcgt ctatttgtgg acaacaccct aaacaatgtg cttatttctg tgaaaataag   120
cttcgatct                                                           129
```

<210> SEQ ID NO 52
<211> LENGTH: 129
<212> TYPE: DNA
<213> ORGANISM: ARTIFICIAL SEQUENCE
<220> FEATURE:
<223> OTHER INFORMATION: TACI K77E, R84L, F103Y ECD

<400> SEQUENCE: 52

```
agtctctctt gcaggaaaga gcaaggcgaa ttttacgacc atcttttgct agactgtata    60
agctgtgcgt ctatttgtgg acaacaccct aaacaatgtg cttattactg tgaaaataag   120
cttcgatct                                                           129
```

<210> SEQ ID NO 53
<211> LENGTH: 129
<212> TYPE: DNA
<213> ORGANISM: ARTIFICIAL SEQUENCE
<220> FEATURE:
<223> OTHER INFORMATION: TACI Y79F, Q99E ECD

<400> SEQUENCE: 53

```
agtctctctt gcaggaaaga gcaaggcaaa ttttncgacc atcttttgcg agactgtata    60
agctgtgcgt ctatttgtgg acaacaccct aaagaatgtg cttatttctg tgaaaataag   120
cttcgatct                                                           129
```

<210> SEQ ID NO 54
<211> LENGTH: 129
<212> TYPE: DNA
<213> ORGANISM: ARTIFICIAL SEQUENCE
<220> FEATURE:
<223> OTHER INFORMATION: TACI Y79F ECD

<400> SEQUENCE: 54

```
agtctctctt gcaggaaaga gcaaggcaaa ttttcgacc atcttttgcg agactgtata    60
agctgtgcgt ctatttgtgg acaacaccct aaacaatgtg cttatttctg tgaaaataag   120
cttcgatct                                                          129
```

<210> SEQ ID NO 55
<211> LENGTH: 129
<212> TYPE: DNA
<213> ORGANISM: ARTIFICIAL SEQUENCE
<220> FEATURE:
<223> OTHER INFORMATION: TACI R84G ECD

<400> SEQUENCE: 55

```
agtctctctt gcaggaaaga gcaaggcaaa ttttacgacc atcttttggg agactgtata    60
agctgtgcgt ctatttgtgg acaacaccct aaacaatgtg cttatttctg tgaaaataag   120
cttcgatct                                                          129
```

<210> SEQ ID NO 56
<211> LENGTH: 246
<212> TYPE: DNA
<213> ORGANISM: ARTIFICIAL SEQUENCE
<220> FEATURE:
<223> OTHER INFORMATION: TACI L83S, F103S ECD

<400> SEQUENCE: 56

```
gtggcaatgc gctcatgccc agaggaacaa tattgggatc cgcttcttgg gacgtgtatg    60
agctgcaaga ccatctgtaa tcatcaatcc caaaggacat gcgcagcttt ctgcaggagt   120
ctctcttgca ggaaagagca aggcaaattt tacgaccatc tttcgcgaga ctgtataagc   180
tgtgcgtcta tttgtggaca acaccctaaa caatgtgctt attcctgtga aaataagctt   240
cgatct                                                              246
```

<210> SEQ ID NO 57
<211> LENGTH: 246
<212> TYPE: DNA
<213> ORGANISM: ARTIFICIAL SEQUENCE
<220> FEATURE:
<223> OTHER INFORMATION: TACI L82H ECD

<400> SEQUENCE: 57

```
gtggcaatgc gctcatgccc agaggaacaa tattgggatc cgcttcttgg gacgtgtatg    60
agctgcaaga ccatctgtaa tcatcaatcc caaaggacat gcgcagcttt ctgcaggagt   120
ctctcttgca ggaaagagca aggcaaattt tacgaccatc atttgcgaga ctgtataagc   180
tgtgcgtcta tctgtggaca acaccctaaa caatgtgctt atttctgtga aaataagctt   240
cgatct                                                              246
```

<210> SEQ ID NO 58
<211> LENGTH: 129
<212> TYPE: DNA
<213> ORGANISM: ARTIFICIAL SEQUENCE
<220> FEATURE:

<223> OTHER INFORMATION: TACI A101D ECD

<400> SEQUENCE: 58
agtctctctt gcaggaaaga gcaaggcaaa ttttacgacc atcttttgcg agactgtata    60
agctgtgcgt ctatttgtgg acaacaccct aaacaatgtg attatttctg tgaaaataag   120
cttcgatct                                                           129

<210> SEQ ID NO 59
<211> LENGTH: 129
<212> TYPE: DNA
<213> ORGANISM: ARTIFICIAL SEQUENCE
<220> FEATURE:
<223> OTHER INFORMATION: TACI K77E, R84Q ECD

<400> SEQUENCE: 59
agtctctctt gcaggaaaga gcaaggcgaa ttttacgacc atcttttgca agactgtata    60
agctgtgcgt ctatttgtgg acaacaccct aaacaatgtg cttatttctg tgaaaataag   120
cttcgatct                                                           129

<210> SEQ ID NO 60
<211> LENGTH: 129
<212> TYPE: DNA
<213> ORGANISM: ARTIFICIAL SEQUENCE
<220> FEATURE:
<223> OTHER INFORMATION: TACI K77E, A101D ECD

<400> SEQUENCE: 60
agtctctctt gcaggaaaga gcaaggcgaa ttttacgacc atcttttgcg agactgtata    60
agctgtgcgt ctatttgtgg acaacaccct aaacaatgtg attatttctg tgaaaataag   120
cttcgatct                                                           129

<210> SEQ ID NO 61
<211> LENGTH: 129
<212> TYPE: DNA
<213> ORGANISM: ARTIFICIAL SEQUENCE
<220> FEATURE:
<223> OTHER INFORMATION: TACI K77E, F78Y, Y102D ECD

<400> SEQUENCE: 61
agtctctctt gcaggaaaga gcaaggcgaa tattacgacc atcttttgcg agactgtata    60
agctgtgcgt ctatttgtgg acaacaccct aaacaatgtg ctgatttctg tgaaaataag   120
cttcgatct                                                           129

<210> SEQ ID NO 62
<211> LENGTH: 129
<212> TYPE: DNA
<213> ORGANISM: ARTIFICIAL SEQUENCE
<220> FEATURE:
<223> OTHER INFORMATION: TACI Q75E, R84Q ECD

<400> SEQUENCE: 62
agtctctctt gcaggaaaga ggaaggcaaa ttttacgacc atcttttgca agactgtata    60
agctgtgcgt ctatttgtgg acaacaccct aaacaatgtg cttatttctg tgaaaataag   120
cttcgatct                                                           129

<210> SEQ ID NO 63
<211> LENGTH: 129
<212> TYPE: DNA
<213> ORGANISM: ARTIFICIAL SEQUENCE

```
<220> FEATURE:
<223> OTHER INFORMATION: TACI Q75R, R84G, I92V ECD

<400> SEQUENCE: 63
agtctctctt gcaggaaaga gcgaggcaaa ttttacgacc atcttttggg agactgtata      60
agctgtgcgt ctgtttgtgg acaacaccct aaacaatgtg cttatttctg tgaaaataag     120
cttcgatct                                                             129

<210> SEQ ID NO 64
<211> LENGTH: 129
<212> TYPE: DNA
<213> ORGANISM: ARTIFICIAL SEQUENCE
<220> FEATURE:
<223> OTHER INFORMATION: TACI K77E, A101D, Y102D ECD

<400> SEQUENCE: 64
agtctctctt gcaggaaaga gcaaggcgaa ttttacgacc atcttttgcg agactgtata      60
agctgtgcgt ctatttgtgg acaacaccct aaacaatgtg atgatttctg tgaaaataag     120
cttcgatct                                                             129

<210> SEQ ID NO 65
<211> LENGTH: 129
<212> TYPE: DNA
<213> ORGANISM: ARTIFICIAL SEQUENCE
<220> FEATURE:
<223> OTHER INFORMATION: TACI R84Q ECD

<400> SEQUENCE: 65
agtctctctt gcaggaaaga gcaaggcaaa ttttatgacc atcttttgca agactgtata      60
agctgtgcgt ctatttgtgg acaacaccct aaacaatgtg cttatttctg tgaaaataag     120
cttcgatct                                                             129

<210> SEQ ID NO 66
<211> LENGTH: 129
<212> TYPE: DNA
<213> ORGANISM: ARTIFICIAL SEQUENCE
<220> FEATURE:
<223> OTHER INFORMATION: TACI R84Q, S88N, A101D ECD

<400> SEQUENCE: 66
agtctctctt gcaggaaaga gcaaggcaaa ttttacgacc atcttttgca agactgtata      60
aactgtgcgt ctatatgtgg acaacaccct aaacaatgtg attatttctg tgaaaataag     120
cttcgatct                                                             129

<210> SEQ ID NO 67
<211> LENGTH: 129
<212> TYPE: DNA
<213> ORGANISM: ARTIFICIAL SEQUENCE
<220> FEATURE:
<223> OTHER INFORMATION: TACI K77E ECD

<400> SEQUENCE: 67
agtctctctt gcaggaaaga gcaaggcgaa ttttacgacc atcttttgcg agactgtata      60
agctgtgcgt ctatttgtgg acaacaccct aaacaatgtg cttatttctg tgaaaataag     120
cttcgatct                                                             129

<210> SEQ ID NO 68
<211> LENGTH: 129
<212> TYPE: DNA
```

<213> ORGANISM: ARTIFICIAL SEQUENCE
<220> FEATURE:
<223> OTHER INFORMATION: TACI R84Q, F103V ECD

<400> SEQUENCE: 68
agtctctctt gcaggaaaga gcaaggcaaa ttttacgacc atctttttgca agactgtata    60 agctgtgcgt ctatttgtgg acaacaccct aaacaatgtg cttatgtctg tgaaaataag   120
cttcgatct                                                           129

<210> SEQ ID NO 69
<211> LENGTH: 129
<212> TYPE: DNA
<213> ORGANISM: ARTIFICIAL SEQUENCE
<220> FEATURE:
<223> OTHER INFORMATION: TACI K77E, Q95R, A101D ECD

<400> SEQUENCE: 69
agtctctctt gcaggaaaga gcaaggcgaa ttttacgacc atctttttgcg agactgtata    60 agctgtgcgt ctatttgtgg acgacaccct aaacaatgtg attatttctg tgaaaataag   120
cttcgatct                                                           129

<210> SEQ ID NO 70
<211> LENGTH: 129
<212> TYPE: DNA
<213> ORGANISM: ARTIFICIAL SEQUENCE
<220> FEATURE:
<223> OTHER INFORMATION: TACI I87M, A101D ECD

<400> SEQUENCE: 70
agtctctctt gcaggaaaga gcaaggcaaa ttttacgacc atctttttgcg agactgtatg    60 agctgtgcgt caatttgtgg acaacaccct aaacaatgtg attatttctg tgaaaataag   120
cttcgatct                                                           129

<210> SEQ ID NO 71
<211> LENGTH: 232
<212> TYPE: PRT
<213> ORGANISM: ARTIFICIAL SEQUENCE
<220> FEATURE:
<223> OTHER INFORMATION: IgG1 Fc

<400> SEQUENCE: 71

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr

```
            130                 135                 140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 72
<211> LENGTH: 8
<212> TYPE: PRT
<213> ORGANISM: ARTIFICIAL SEQUENCE
<220> FEATURE:
<223> OTHER INFORMATION: FLAG-tag

<400> SEQUENCE: 72

Asp Tyr Lys Asp Asp Asp Asp Lys
1               5

<210> SEQ ID NO 73
<211> LENGTH: 231
<212> TYPE: PRT
<213> ORGANISM: ARTIFICIAL SEQUENCE
<220> FEATURE:
<223> OTHER INFORMATION: Fc C220S/L234A/L235E/G237A/K447del

<400> SEQUENCE: 73

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly
225                 230

<210> SEQ ID NO 74
<211> LENGTH: 7
<212> TYPE: PRT
<213> ORGANISM: ARTIFICIAL SEQUENCE
<220> FEATURE:
<223> OTHER INFORMATION: Linker

<400> SEQUENCE: 74

Gly Ser Gly Gly Gly Gly Ser
1               5

<210> SEQ ID NO 75
<211> LENGTH: 232
<212> TYPE: PRT
<213> ORGANISM: ARTIFICIAL SEQUENCE
<220> FEATURE:
<223> OTHER INFORMATION: Fc C220S/L234A/L235E/G237A/E356D/M358L

<400> SEQUENCE: 75

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 76
```

```
<211> LENGTH: 5
<212> TYPE: PRT
<213> ORGANISM: ARTIFICIAL SEQUENCE
<220> FEATURE:
<223> OTHER INFORMATION: Linker

<400> SEQUENCE: 76

Gly Ser Gly Gly Ser
1               5

<210> SEQ ID NO 77
<211> LENGTH: 5
<212> TYPE: PRT
<213> ORGANISM: ARTIFICIAL SEQUENCE
<220> FEATURE:
<223> OTHER INFORMATION: LINKER

<400> SEQUENCE: 77

Gly Gly Gly Gly Ser
1               5

<210> SEQ ID NO 78
<211> LENGTH: 10
<212> TYPE: PRT
<213> ORGANISM: ARTIFICIAL SEQUENCE
<220> FEATURE:
<223> OTHER INFORMATION: LINKER

<400> SEQUENCE: 78

Gly Gly Gly Gly Ser Gly Gly Gly Gly Ser
1               5                   10

<210> SEQ ID NO 79
<211> LENGTH: 15
<212> TYPE: PRT
<213> ORGANISM: ARTIFICIAL SEQUENCE
<220> FEATURE:
<223> OTHER INFORMATION: LINKER

<400> SEQUENCE: 79

Gly Gly Gly Gly Ser Gly Gly Gly Gly Ser Gly Gly Gly Gly Ser
1               5                   10                  15

<210> SEQ ID NO 80
<211> LENGTH: 7
<212> TYPE: PRT
<213> ORGANISM: ARTIFICIAL SEQUENCE
<220> FEATURE:
<223> OTHER INFORMATION: LINKER

<400> SEQUENCE: 80

Gly Gly Gly Gly Ser Ser Ala
1               5

<210> SEQ ID NO 81
<211> LENGTH: 231
<212> TYPE: PRT
<213> ORGANISM: ARTIFICIAL SEQUENCE
<220> FEATURE:
<223> OTHER INFORMATION: Fc (E356D and M358L)

<400> SEQUENCE: 81

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

```
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 82
<211> LENGTH: 232
<212> TYPE: PRT
<213> ORGANISM: ARTIFICIAL SEQUENCE
<220> FEATURE:
<223> OTHER INFORMATION: Fc (C5S (C220S), R77C, (R292C), N82G (N297G),
      V87C (V302C))

<400> SEQUENCE: 82

Glu Pro Lys Ser Ser Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Cys Glu Glu Gln
 65                  70                  75                  80

Tyr Gly Ser Thr Tyr Arg Cys Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160
```

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 83
<211> LENGTH: 232
<212> TYPE: PRT
<213> ORGANISM: ARTIFICIAL SEQUENCE
<220> FEATURE:
<223> OTHER INFORMATION: Fc with C220S/L234A/L235E/G237A

<400> SEQUENCE: 83

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 84
<211> LENGTH: 20
<212> TYPE: PRT
<213> ORGANISM: ARTIFICIAL SEQUENCE
<220> FEATURE:
<223> OTHER INFORMATION: LINKER

```
<400> SEQUENCE: 84

Gly Gly Gly Gly Ser Gly Gly Gly Ser Gly Gly Gly Ser Gly
1               5                   10                  15

Gly Gly Gly Ser
            20

<210> SEQ ID NO 85
<211> LENGTH: 323
<212> TYPE: PRT
<213> ORGANISM: ARTIFICIAL SEQUENCE
<220> FEATURE:
<223> OTHER INFORMATION: Fc (G4S)2 TACI (516)

<400> SEQUENCE: 85

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Gly Gly Gly Gly
225                 230                 235                 240

Ser Val Ala Met Arg Ser Cys Pro Glu Glu Gln Tyr Trp Asp Pro Leu
                245                 250                 255

Leu Gly Thr Cys Met Ser Cys Lys Thr Ile Cys Asn His Gln Ser Gln
            260                 265                 270

Arg Thr Cys Ala Ala Phe Cys Arg Ser Leu Ser Cys Arg Lys Glu Gln
        275                 280                 285

Gly Lys Phe Tyr Asp His Leu Leu Arg Asp Cys Ile Ser Cys Ala Ser
    290                 295                 300

Ile Cys Gly Gln His Pro Lys Gln Cys Ala Tyr Phe Cys Glu Asn Lys
305                 310                 315                 320

Leu Arg Ser
```

<210> SEQ ID NO 86
<211> LENGTH: 294
<212> TYPE: PRT
<213> ORGANISM: ARTIFICIAL SEQUENCE
<220> FEATURE:
<223> OTHER INFORMATION: Fc (G4S)4 TACI (541)

<400> SEQUENCE: 86

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Gly Gly Gly Gly
225                 230                 235                 240

Ser Gly Gly Gly Gly Ser Gly Gly Gly Ser Ser Leu Ser Cys Arg
                245                 250                 255

Lys Glu Gln Gly Glu Tyr Tyr Asp His Leu Leu Arg Asp Cys Ile Ser
            260                 265                 270

Cys Ala Ser Ile Cys Gly Gln His Pro Lys Gln Cys Ala Asp Phe Cys
        275                 280                 285

Glu Asn Lys Leu Arg Ser
    290

<210> SEQ ID NO 87
<211> LENGTH: 30
<212> TYPE: PRT
<213> ORGANISM: ARTIFICIAL SEQUENCE
<220> FEATURE:
<223> OTHER INFORMATION: LINKER

<400> SEQUENCE: 87

Glu Ala Ala Ala Lys Glu Ala Ala Ala Lys Glu Ala Ala Ala Lys Glu

<210> SEQ ID NO 88
<211> LENGTH: 293
<212> TYPE: PRT
<213> ORGANISM: ARTIFICIAL SEQUENCE
<220> FEATURE:
<223> OTHER INFORMATION: FULL LENGTH TACI

<400> SEQUENCE: 88

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
                20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
                100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
        130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290

<210> SEQ ID NO 89
<211> LENGTH: 230
<212> TYPE: PRT
<213> ORGANISM: ARTIFICIAL SEQUENCE
<220> FEATURE:
<223> OTHER INFORMATION: Fc K S139C, D141E, L143M, T151W

<400> SEQUENCE: 89

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Glu Glu Met Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro
225                 230

<210> SEQ ID NO 90
<211> LENGTH: 230
<212> TYPE: PRT
<213> ORGANISM: ARTIFICIAL SEQUENCE
<220> FEATURE:
<223> OTHER INFORMATION: Fc H Y134C, D141E, L143M, T151S, L153A

<400> SEQUENCE: 90

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

-continued

```
Leu Pro Ala Pro Ile Glu Lys Thr Ile Ser Lys Ala Lys Gly Gln Pro
            115                 120                 125
Arg Glu Pro Gln Val Cys Thr Leu Pro Pro Ser Arg Glu Glu Met Thr
        130                 135                 140
Lys Asn Gln Val Ser Leu Ser Cys Ala Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Val
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro
225                 230

<210> SEQ ID NO 91
<211> LENGTH: 25
<212> TYPE: PRT
<213> ORGANISM: ARTIFICIAL SEQUENCE
<220> FEATURE:
<223> OTHER INFORMATION: LINKER

<400> SEQUENCE: 91

Gly Gly Gly Gly Ser Gly Gly Gly Ser Gly Gly Gly Ser Gly
1               5                   10                  15
Gly Gly Gly Ser Gly Gly Gly Gly Ser
            20                  25

<210> SEQ ID NO 92
<211> LENGTH: 43
<212> TYPE: PRT
<213> ORGANISM: ARTIFICIAL SEQUENCE
<220> FEATURE:
<223> OTHER INFORMATION: TACI L82P ECD

<400> SEQUENCE: 92

Ser Leu Ser Cys Arg Lys Glu Gln Gly Lys Phe Tyr Asp His Pro Leu
1               5                   10                  15
Arg Asp Cys Ile Ser Cys Ala Ser Ile Cys Gly Gln His Pro Lys Gln
            20                  25                  30
Cys Ala Tyr Phe Cys Glu Asn Lys Leu Arg Ser
        35                  40

<210> SEQ ID NO 93
<211> LENGTH: 43
<212> TYPE: PRT
<213> ORGANISM: ARTIFICIAL SEQUENCE
<220> FEATURE:
<223> OTHER INFORMATION: TACI D85E, K98T ECD

<400> SEQUENCE: 93

Ser Leu Ser Cys Arg Lys Glu Gln Gly Lys Phe Tyr Asp His Leu Leu
1               5                   10                  15
Arg Glu Cys Ile Ser Cys Ala Ser Ile Cys Gly Gln His Pro Thr Gln
            20                  25                  30
Cys Ala Tyr Phe Cys Glu Asn Lys Leu Arg Ser
        35                  40
```

```
<210> SEQ ID NO 94
<211> LENGTH: 43
<212> TYPE: PRT
<213> ORGANISM: ARTIFICIAL SEQUENCE
<220> FEATURE:
<223> OTHER INFORMATION: TACI I87L, K98T ECD

<400> SEQUENCE: 94

Ser Leu Ser Cys Arg Lys Glu Gln Gly Lys Phe Tyr Asp His Leu Leu
1               5                   10                  15

Arg Asp Cys Leu Ser Cys Ala Ser Ile Cys Gly Gln His Pro Thr Gln
            20                  25                  30

Cys Ala Tyr Phe Cys Glu Asn Lys Leu Arg Ser
        35                  40

<210> SEQ ID NO 95
<211> LENGTH: 43
<212> TYPE: PRT
<213> ORGANISM: ARTIFICIAL SEQUENCE
<220> FEATURE:
<223> OTHER INFORMATION: TACI A101D ECD

<400> SEQUENCE: 95

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Asp Tyr Phe Cys Glu Asn Lys Leu Arg Ser
        35                  40

<210> SEQ ID NO 96
<211> LENGTH: 43
<212> TYPE: PRT
<213> ORGANISM: ARTIFICIAL SEQUENCE
<220> FEATURE:
<223> OTHER INFORMATION: TACI C86Y ECD

<400> SEQUENCE: 96

Ser Leu Ser Cys Arg Lys Glu Gln Gly Lys Phe Tyr Asp His Leu Leu
1               5                   10                  15

Arg Asp Tyr Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 97
<211> LENGTH: 43
<212> TYPE: PRT
<213> ORGANISM: ARTIFICIAL SEQUENCE
<220> FEATURE:
<223> OTHER INFORMATION: TACI L82P, I87L ECD

<400> SEQUENCE: 97

Ser Leu Ser Cys Arg Lys Glu Gln Gly Lys Phe Tyr Asp His Pro Leu
1               5                   10                  15

Arg Asp Cys Leu Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 98
<211> LENGTH: 43
<212> TYPE: PRT
```

<213> ORGANISM: ARTIFICIAL SEQUENCE
<220> FEATURE:
<223> OTHER INFORMATION: TACI G76S, P97S ECD

<400> SEQUENCE: 98

Ser Leu Ser Cys Arg Lys Glu Gln Ser Lys Phe Tyr Asp His Leu Leu
1               5                   10                  15

Arg Asp Cys Ile Ser Cys Ala Ser Ile Cys Gly Gln His Ser Lys Gln
            20                  25                  30

Cys Ala Tyr Phe Cys Glu Asn Lys Leu Arg Ser
        35                  40

<210> SEQ ID NO 99
<211> LENGTH: 43
<212> TYPE: PRT
<213> ORGANISM: ARTIFICIAL SEQUENCE
<220> FEATURE:
<223> OTHER INFORMATION: TACI L83S, F103S ECD

<400> SEQUENCE: 99

Ser Leu Ser Cys Arg Lys Glu Gln Gly Lys Phe Tyr Asp His Leu Ser
1               5                   10                  15

Arg Asp Cys Ile Ser Cys Ala Ser Ile Cys Gly Gln His Pro Lys Gln
            20                  25                  30

Cys Ala Tyr Ser Cys Glu Asn Lys Leu Arg Ser
        35                  40

<210> SEQ ID NO 100
<211> LENGTH: 43
<212> TYPE: PRT
<213> ORGANISM: ARTIFICIAL SEQUENCE
<220> FEATURE:
<223> OTHER INFORMATION: TACI L82H ECD

<400> SEQUENCE: 100

Ser Leu Ser Cys Arg Lys Glu Gln Gly Lys Phe Tyr Asp His His Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 101
<211> LENGTH: 82
<212> TYPE: PRT
<213> ORGANISM: ARTIFICIAL SEQUENCE
<220> FEATURE:
<223> OTHER INFORMATION: TACI D85V ECD

<400> SEQUENCE: 101

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Arg Val Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 102
<211> LENGTH: 82
<212> TYPE: PRT
<213> ORGANISM: ARTIFICIAL SEQUENCE
<220> FEATURE:
<223> OTHER INFORMATION: TACI E74V ECD

<400> SEQUENCE: 102

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Val Gln Gly
        35                  40                  45

Lys Phe Tyr Asp His Leu Leu Arg Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 103
<211> LENGTH: 82
<212> TYPE: PRT
<213> ORGANISM: ARTIFICIAL SEQUENCE
<220> FEATURE:
<223> OTHER INFORMATION: TACI R84L ECD

<400> SEQUENCE: 103

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Leu Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 104
<211> LENGTH: 82
<212> TYPE: PRT
<213> ORGANISM: ARTIFICIAL SEQUENCE
<220> FEATURE:
<223> OTHER INFORMATION: TACI K77E, R84L, F103Y ECD

<400> SEQUENCE: 104

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Glu Phe Tyr Asp His Leu Leu Leu Asp Cys Ile Ser Cys Ala Ser Ile
    50                  55                  60

Cys Gly Gln His Pro Lys Gln Cys Ala Tyr Tyr Cys Glu Asn Lys Leu
65                  70                  75                  80

Arg Ser

<210> SEQ ID NO 105
<211> LENGTH: 82
<212> TYPE: PRT
<213> ORGANISM: ARTIFICIAL SEQUENCE
<220> FEATURE:
<223> OTHER INFORMATION: TACI Y79F, Q99E ECD

<400> SEQUENCE: 105

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Phe Asp His Leu Leu Arg Asp Cys Ile Ser Cys Ala Ser Ile
    50                  55                  60

Cys Gly Gln His Pro Lys Glu Cys Ala Tyr Phe Cys Glu Asn Lys Leu
65                  70                  75                  80

Arg Ser

<210> SEQ ID NO 106
<211> LENGTH: 82
<212> TYPE: PRT
<213> ORGANISM: ARTIFICIAL SEQUENCE
<220> FEATURE:
<223> OTHER INFORMATION: TACI Y79F ECD

<400> SEQUENCE: 106

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Phe Asp His Leu Leu Arg Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 107
<211> LENGTH: 82
<212> TYPE: PRT
<213> ORGANISM: ARTIFICIAL SEQUENCE
<220> FEATURE:
<223> OTHER INFORMATION: TACI R84G ECD

<400> SEQUENCE: 107

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Gly Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 108
<211> LENGTH: 82
<212> TYPE: PRT
<213> ORGANISM: ARTIFICIAL SEQUENCE
<220> FEATURE:
<223> OTHER INFORMATION: TACI A101D ECD

<400> SEQUENCE: 108

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
                20                  25                  30

Thr Cys Ala Ala Phe Cys Arg Ser Leu Ser Cys Arg Lys Glu Gln Gly
            35                  40                  45

Lys Phe Tyr Asp His Leu Leu Arg Asp Cys Ile Ser Cys Ala Ser Ile
    50                  55                  60

Cys Gly Gln His Pro Lys Gln Cys Asp Tyr Phe Cys Glu Asn Lys Leu
65                  70                  75                  80

Arg Ser

<210> SEQ ID NO 109
<211> LENGTH: 82
<212> TYPE: PRT
<213> ORGANISM: ARTIFICIAL SEQUENCE
<220> FEATURE:
<223> OTHER INFORMATION: TACI K77E, R84Q ECD

<400> SEQUENCE: 109

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
                20                  25                  30

Thr Cys Ala Ala Phe Cys Arg Ser Leu Ser Cys Arg Lys Glu Gln Gly
            35                  40                  45

Glu Phe Tyr Asp His Leu Leu Gln Asp Cys Ile Ser Cys Ala Ser Ile
    50                  55                  60

Cys Gly Gln His Pro Lys Gln Cys Ala Tyr Phe Cys Glu Asn Lys Leu
65                  70                  75                  80

Arg Ser

<210> SEQ ID NO 110
<211> LENGTH: 82
<212> TYPE: PRT
<213> ORGANISM: ARTIFICIAL SEQUENCE
<220> FEATURE:
<223> OTHER INFORMATION: TACI K77E, A101D ECD

<400> SEQUENCE: 110

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
                20                  25                  30

Thr Cys Ala Ala Phe Cys Arg Ser Leu Ser Cys Arg Lys Glu Gln Gly
            35                  40                  45

Glu Phe Tyr Asp His Leu Leu Arg Asp Cys Ile Ser Cys Ala Ser Ile

```
                50                  55                  60
Cys Gly Gln His Pro Lys Gln Cys Asp Tyr Phe Cys Glu Asn Lys Leu
 65                  70                  75                  80

Arg Ser

<210> SEQ ID NO 111
<211> LENGTH: 82
<212> TYPE: PRT
<213> ORGANISM: ARTIFICIAL SEQUENCE
<220> FEATURE:
<223> OTHER INFORMATION: TACI K77E, F78Y, Y102D ECD

<400> SEQUENCE: 111

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
                20                  25                  30

Thr Cys Ala Ala Phe Cys Arg Ser Leu Ser Cys Arg Lys Glu Gln Gly
            35                  40                  45

Glu Tyr Tyr Asp His Leu Leu Arg Asp Cys Ile Ser Cys Ala Ser Ile
        50                  55                  60

Cys Gly Gln His Pro Lys Gln Cys Ala Asp Phe Cys Glu Asn Lys Leu
 65                  70                  75                  80

Arg Ser

<210> SEQ ID NO 112
<211> LENGTH: 82
<212> TYPE: PRT
<213> ORGANISM: ARTIFICIAL SEQUENCE
<220> FEATURE:
<223> OTHER INFORMATION: TACI Q75E, R84Q ECD

<400> SEQUENCE: 112

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
                20                  25                  30

Thr Cys Ala Ala Phe Cys Arg Ser Leu Ser Cys Arg Lys Glu Glu Gly
            35                  40                  45

Lys Phe Tyr Asp His Leu Leu Gln Asp Cys Ile Ser Cys Ala Ser Ile
        50                  55                  60

Cys Gly Gln His Pro Lys Gln Cys Ala Tyr Phe Cys Glu Asn Lys Leu
 65                  70                  75                  80

Arg Ser

<210> SEQ ID NO 113
<211> LENGTH: 82
<212> TYPE: PRT
<213> ORGANISM: ARTIFICIAL SEQUENCE
<220> FEATURE:
<223> OTHER INFORMATION: TACI Q75R, R84G, I92V ECD

<400> SEQUENCE: 113

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
                20                  25                  30

Thr Cys Ala Ala Phe Cys Arg Ser Leu Ser Cys Arg Lys Glu Arg Gly
            35                  40                  45
```

Lys Phe Tyr Asp His Leu Leu Gly Asp Cys Ile Ser Cys Ala Ser Val
            50                  55                  60

Cys Gly Gln His Pro Lys Gln Cys Ala Tyr Phe Cys Glu Asn Lys Leu
 65                  70                  75                  80

Arg Ser

<210> SEQ ID NO 114
<211> LENGTH: 82
<212> TYPE: PRT
<213> ORGANISM: ARTIFICIAL SEQUENCE
<220> FEATURE:
<223> OTHER INFORMATION: TACI K77E, A101D, Y102D ECD

<400> SEQUENCE: 114

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Glu Phe Tyr Asp His Leu Leu Arg Asp Cys Ile Ser Cys Ala Ser Ile
            50                  55                  60

Cys Gly Gln His Pro Lys Gln Cys Asp Asp Phe Cys Glu Asn Lys Leu
 65                  70                  75                  80

Arg Ser

<210> SEQ ID NO 115
<211> LENGTH: 82
<212> TYPE: PRT
<213> ORGANISM: ARTIFICIAL SEQUENCE
<220> FEATURE:
<223> OTHER INFORMATION: TACI R84Q ECD

<400> SEQUENCE: 115

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
        35                  40                  45

Lys Phe Tyr Asp His Leu Leu Gln Asp Cys Ile Ser Cys Ala Ser Ile
            50                  55                  60

Cys Gly Gln His Pro Lys Gln Cys Ala Tyr Phe Cys Glu Asn Lys Leu
 65                  70                  75                  80

Arg Ser

<210> SEQ ID NO 116
<211> LENGTH: 82
<212> TYPE: PRT
<213> ORGANISM: ARTIFICIAL SEQUENCE
<220> FEATURE:
<223> OTHER INFORMATION: TACI R84Q, S88N, A101D ECD

<400> SEQUENCE: 116

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
            20                  25                  30

```
Thr Cys Ala Ala Phe Cys Arg Ser Leu Ser Cys Arg Lys Glu Gln Gly
        35                  40                  45

Lys Phe Tyr Asp His Leu Leu Gln Asp Cys Ile Asn Cys Ala Ser Ile
 50                  55                  60

Cys Gly Gln His Pro Lys Gln Cys Asp Tyr Phe Cys Glu Asn Lys Leu
 65                  70                  75                  80

Arg Ser

<210> SEQ ID NO 117
<211> LENGTH: 82
<212> TYPE: PRT
<213> ORGANISM: ARTIFICIAL SEQUENCE
<220> FEATURE:
<223> OTHER INFORMATION: TACI K77E ECD

<400> SEQUENCE: 117

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
             20                  25                  30

Thr Cys Ala Ala Phe Cys Arg Ser Leu Ser Cys Arg Lys Glu Gln Gly
        35                  40                  45

Glu Phe Tyr Asp His Leu Leu Arg Asp Cys Ile Ser Cys Ala Ser Ile
 50                  55                  60

Cys Gly Gln His Pro Lys Gln Cys Ala Tyr Phe Cys Glu Asn Lys Leu
 65                  70                  75                  80

Arg Ser

<210> SEQ ID NO 118
<211> LENGTH: 82
<212> TYPE: PRT
<213> ORGANISM: ARTIFICIAL SEQUENCE
<220> FEATURE:
<223> OTHER INFORMATION: TACI R84Q, F103V ECD

<400> SEQUENCE: 118

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
             20                  25                  30

Thr Cys Ala Ala Phe Cys Arg Ser Leu Ser Cys Arg Lys Glu Gln Gly
        35                  40                  45

Lys Phe Tyr Asp His Leu Leu Gln Asp Cys Ile Ser Cys Ala Ser Ile
 50                  55                  60

Cys Gly Gln His Pro Lys Gln Cys Ala Tyr Val Cys Glu Asn Lys Leu
 65                  70                  75                  80

Arg Ser

<210> SEQ ID NO 119
<211> LENGTH: 82
<212> TYPE: PRT
<213> ORGANISM: ARTIFICIAL SEQUENCE
<220> FEATURE:
<223> OTHER INFORMATION: TACI K77E, Q95R, A101D ECD

<400> SEQUENCE: 119

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
```

```
                 20                  25                  30

Thr Cys Ala Ala Phe Cys Arg Ser Leu Ser Cys Arg Lys Glu Gln Gly
             35                  40                  45

Glu Phe Tyr Asp His Leu Leu Arg Asp Cys Ile Ser Cys Ala Ser Ile
         50                  55                  60

Cys Gly Arg His Pro Lys Gln Cys Asp Tyr Phe Cys Glu Asn Lys Leu
 65                  70                  75                  80

Arg Ser

<210> SEQ ID NO 120
<211> LENGTH: 82
<212> TYPE: PRT
<213> ORGANISM: ARTIFICIAL SEQUENCE
<220> FEATURE:
<223> OTHER INFORMATION: TACI I87M, A101D ECD

<400> SEQUENCE: 120

Val Ala Met Arg Ser Cys Pro Glu Glu Gln Tyr Trp Asp Pro Leu Leu
 1               5                  10                  15

Gly Thr Cys Met Ser Cys Lys Thr Ile Cys Asn His Gln Ser Gln Arg
             20                  25                  30

Thr Cys Ala Ala Phe Cys Arg Ser Leu Ser Cys Arg Lys Glu Gln Gly
         35                  40                  45

Lys Phe Tyr Asp His Leu Leu Arg Asp Cys Met Ser Cys Ala Ser Ile
     50                  55                  60

Cys Gly Gln His Pro Lys Gln Cys Asp Tyr Phe Cys Glu Asn Lys Leu
 65                  70                  75                  80

Arg Ser

<210> SEQ ID NO 121
<211> LENGTH: 660
<212> TYPE: PRT
<213> ORGANISM: ARTIFICIAL SEQUENCE
<220> FEATURE:
<223> OTHER INFORMATION: CTLA4 113 GSG4S Fc K/ BCMA 357 GSG4S Fc H

<400> SEQUENCE: 121

Lys Ala Met His Val Ala Gln Pro Ala Val Val Phe Ala Ser Ser His
 1               5                  10                  15

Gly Ile Ala Ser Phe Val Cys Glu Tyr Ala Ser Pro Trp Lys Ala Thr
             20                  25                  30

Glu Val Arg Val Thr Val Leu Arg Gln Ala Asp Ser Gln Val Thr Glu
         35                  40                  45

Val Cys Ala Ala Thr Tyr Met Thr Gly Asn Glu Leu Thr Phe Leu Asp
     50                  55                  60

Asp Ser Ile Cys Thr Gly Thr Ser Ser Gly Asn Gln Val Asn Leu Thr
 65                  70                  75                  80

Ile Gln Gly Leu Arg Ala Met Asp Thr Gly Leu Tyr Ile Cys Lys Val
             85                  90                  95

Glu Gln Met Tyr Pro Pro Pro Tyr Leu Leu Gly Ile Gly Asn Gly Thr
            100                 105                 110

Gln Ile Tyr Val Ile Asp Pro Glu Pro Cys Pro Asp Ser Asp Gly Ser
        115                 120                 125

Gly Gly Gly Gly Ser Glu Pro Lys Ser Ser Asp Lys Thr His Thr Cys
    130                 135                 140

Pro Pro Cys Pro Ala Pro Glu Ala Glu Gly Ala Pro Ser Val Phe Leu
145                 150                 155                 160
```

-continued

```
Phe Pro Pro Lys Pro Lys Asp Thr Leu Met Ile Ser Arg Thr Pro Glu
            165                 170                 175
Val Thr Cys Val Val Asp Val Ser His Glu Asp Pro Glu Val Lys
        180                 185                 190
Phe Asn Trp Tyr Val Asp Gly Val Glu Val His Asn Ala Lys Thr Lys
        195                 200                 205
Pro Arg Glu Glu Gln Tyr Asn Ser Thr Tyr Arg Val Val Ser Val Leu
        210                 215                 220
Thr Val Leu His Gln Asp Trp Leu Asn Gly Lys Glu Tyr Lys Cys Lys
225                 230                 235                 240
Val Ser Asn Lys Ala Leu Pro Ala Pro Ile Glu Lys Thr Ile Ser Lys
                245                 250                 255
Ala Lys Gly Gln Pro Arg Glu Pro Gln Val Tyr Thr Leu Pro Pro Cys
                260                 265                 270
Arg Glu Glu Met Thr Lys Asn Gln Val Ser Leu Trp Cys Leu Val Lys
                275                 280                 285
Gly Phe Tyr Pro Ser Asp Ile Ala Val Glu Trp Glu Ser Asn Gly Gln
            290                 295                 300
Pro Glu Asn Asn Tyr Lys Thr Thr Pro Pro Val Leu Asp Ser Asp Gly
305                 310                 315                 320
Ser Phe Phe Leu Tyr Ser Lys Leu Thr Val Asp Lys Ser Arg Trp Gln
                325                 330                 335
Gln Gly Asn Val Phe Ser Cys Ser Val Met His Glu Ala Leu His Asn
                340                 345                 350
His Tyr Thr Gln Lys Ser Leu Ser Leu Ser Pro Gly Leu Gln Met Ala
            355                 360                 365
Gly Gln Cys Ser Gln Asn Glu Tyr Phe Asp Ser Leu Leu Tyr Ala Cys
            370                 375                 380
Ile Pro Cys Gln Leu Arg Cys Ser Ser Asn Thr Pro Pro Leu Thr Cys
385                 390                 395                 400
Gln Arg Tyr Cys Asn Ala Ser Val Thr Asn Ser Val Lys Gly Thr Asn
                405                 410                 415
Ala Gly Ser Gly Gly Ser Gly Gly Ser Gly Ser Gly Ser Glu Pro
                420                 425                 430
Lys Ser Ser Asp Lys Thr His Thr Cys Pro Pro Cys Pro Ala Pro Glu
            435                 440                 445
Ala Glu Gly Ala Pro Ser Val Phe Leu Phe Pro Pro Lys Pro Lys Asp
450                 455                 460
Thr Leu Met Ile Ser Arg Thr Pro Glu Val Thr Cys Val Val Val Asp
465                 470                 475                 480
Val Ser His Glu Asp Pro Glu Val Lys Phe Asn Trp Tyr Val Asp Gly
                485                 490                 495
Val Glu Val His Asn Ala Lys Thr Lys Pro Arg Glu Glu Gln Tyr Asn
            500                 505                 510
Ser Thr Tyr Arg Val Val Ser Val Leu Thr Val Leu His Gln Asp Trp
            515                 520                 525
Leu Asn Gly Lys Glu Tyr Lys Cys Lys Val Ser Asn Lys Ala Leu Pro
530                 535                 540
Ala Pro Ile Glu Lys Thr Ile Ser Lys Ala Lys Gly Gln Pro Arg Glu
545                 550                 555                 560
Pro Gln Val Cys Thr Leu Pro Pro Ser Arg Glu Glu Met Thr Lys Asn
                565                 570                 575
```

-continued

```
Gln Val Ser Leu Ser Cys Ala Val Lys Gly Phe Tyr Pro Ser Asp Ile
            580                 585                 590

Ala Val Glu Trp Glu Ser Asn Gly Gln Pro Glu Asn Asn Tyr Lys Thr
        595                 600                 605

Thr Pro Pro Val Leu Asp Ser Asp Gly Ser Phe Phe Leu Val Ser Lys
    610                 615                 620

Leu Thr Val Asp Lys Ser Arg Trp Gln Gln Gly Asn Val Phe Ser Cys
625                 630                 635                 640

Ser Val Met His Glu Ala Leu His Asn His Tyr Thr Gln Lys Ser Leu
                645                 650                 655

Ser Leu Ser Pro
            660
```

<210> SEQ ID NO 122
<211> LENGTH: 166
<212> TYPE: PRT
<213> ORGANISM: artificial sequence
<220> FEATURE:
<223> OTHER INFORMATION: TACI ECD (1-166)

<400> SEQUENCE: 122

```
Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr
                165
```

<210> SEQ ID NO 123
<211> LENGTH: 5
<212> TYPE: PRT
<213> ORGANISM: artificial sequence
<220> FEATURE:
<223> OTHER INFORMATION: 1xEAAAK

<400> SEQUENCE: 123

```
Glu Ala Ala Ala Lys
1               5
```

<210> SEQ ID NO 124
<211> LENGTH: 10
<212> TYPE: PRT
<213> ORGANISM: artificial sequence

```
<220> FEATURE:
<223> OTHER INFORMATION: 2xEAAAK

<400> SEQUENCE: 124

Glu Ala Ala Ala Lys Glu Ala Ala Ala Lys
1               5                   10

<210> SEQ ID NO 125
<211> LENGTH: 15
<212> TYPE: PRT
<213> ORGANISM: artificial sequence
<220> FEATURE:
<223> OTHER INFORMATION: 3xEAAAK

<400> SEQUENCE: 125

Glu Ala Ala Ala Lys Glu Ala Ala Ala Lys Glu Ala Ala Ala Lys
1               5                   10                  15

<210> SEQ ID NO 126
<211> LENGTH: 20
<212> TYPE: PRT
<213> ORGANISM: artificial sequence
<220> FEATURE:
<223> OTHER INFORMATION: 4xEAAAK

<400> SEQUENCE: 126

Glu Ala Ala Ala Lys Glu Ala Ala Ala Lys Glu Ala Ala Ala Lys Glu
1               5                   10                  15

Ala Ala Ala Lys
            20

<210> SEQ ID NO 127
<211> LENGTH: 25
<212> TYPE: PRT
<213> ORGANISM: artificial sequence
<220> FEATURE:
<223> OTHER INFORMATION: 5xEAAAK

<400> SEQUENCE: 127

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 128
<211> LENGTH: 232
<212> TYPE: PRT
<213> ORGANISM: artificial sequence
<220> FEATURE:
<223> OTHER INFORMATION: knob Fc

<400> SEQUENCE: 128

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
```

```
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
            115                 120                 125
Arg Glu Pro Gln Val Tyr Thr Leu Pro Pro Cys Arg Glu Glu Met Thr
        130                 135                 140
Lys Asn Gln Val Ser Leu Trp Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
            195                 200                 205
Ser Cys Ser Val Met His Glu Ala Leu His Asn His Tyr Thr Gln Lys
        210                 215                 220
Ser Leu Ser Leu Ser Pro Gly Lys
225                 230

<210> SEQ ID NO 129
<211> LENGTH: 232
<212> TYPE: PRT
<213> ORGANISM: artificial sequence
<220> FEATURE:
<223> OTHER INFORMATION: hole Fc

<400> SEQUENCE: 129

Glu Pro Lys Ser Ser Asp Lys Thr His Thr Cys Pro Pro Cys Pro Ala
1               5                   10                  15
Pro Glu Ala Glu Gly Ala Pro Ser Val Phe Leu Phe Pro Pro Lys Pro
            20                  25                  30
Lys Asp Thr Leu Met Ile Ser Arg Thr Pro Glu Val Thr Cys Val Val
            35                  40                  45
Val Asp Val Ser His Glu Asp Pro Glu Val Lys Phe Asn Trp Tyr Val
50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
            115                 120                 125
Arg Glu Pro Gln Val Cys Thr Leu Pro Pro Ser Arg Glu Glu Met Thr
        130                 135                 140
Lys Asn Gln Val Ser Leu Ser Cys Ala Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Val
            180                 185                 190
Ser Lys Leu Thr Val Asp Lys Ser Arg Trp Gln Gln Gly Asn Val Phe
            195                 200                 205
Ser Cys Ser Val Met His Glu Ala Leu His Asn His Tyr Thr Gln Lys
```

```
                 210                 215                 220

Ser Leu Ser Leu Ser Pro Gly Lys
225                 230

<210> SEQ ID NO 130
<211> LENGTH: 81
<212> TYPE: PRT
<213> ORGANISM: artificial sequence
<220> FEATURE:
<223> OTHER INFORMATION: atacicept (TACI portion, 30-110)

<400> SEQUENCE: 130

Ala Met Arg Ser Cys Pro Glu Glu Gln Tyr Trp Asp Pro Leu Leu Gly
1               5                   10                  15

Thr Cys Met Ser Cys Lys Thr Ile Cys Asn His Gln Ser Gln Arg Thr
            20                  25                  30

Cys Ala Ala Phe Cys Arg Ser Leu Ser Cys Arg Lys Glu Gln Gly Lys
        35                  40                  45

Phe Tyr Asp His Leu Leu Arg Asp Cys Ile Ser Cys Ala Ser Ile Cys
    50                  55                  60

Gly Gln His Pro Lys Gln Cys Ala Tyr Phe Cys Glu Asn Lys Leu Arg
65                  70                  75                  80

Ser

<210> SEQ ID NO 131
<211> LENGTH: 106
<212> TYPE: PRT
<213> ORGANISM: artificial sequence
<220> FEATURE:
<223> OTHER INFORMATION: telitacicept (TACI portion, 13-118)

<400> SEQUENCE: 131

Ser Arg Val Asp Gln Glu Glu Arg Phe Pro Gln Gly Leu Trp Thr Gly
1               5                   10                  15

Val Ala Met Arg Ser Cys Pro Glu Glu Gln Tyr Trp Asp Pro Leu Leu
            20                  25                  30

Gly Thr Cys Met Ser Cys Lys Thr Ile Cys Asn His Gln Ser Gln Arg
        35                  40                  45

Thr Cys Ala Ala Phe Cys Arg Ser Leu Ser Cys Arg Lys Glu Gln Gly
    50                  55                  60

Lys Phe Tyr Asp His Leu Leu Arg Asp Cys Ile Ser Cys Ala Ser Ile
65                  70                  75                  80

Cys Gly Gln His Pro Lys Gln Cys Ala Tyr Phe Cys Glu Asn Lys Leu
                85                  90                  95

Arg Ser Pro Val Asn Leu Pro Pro Glu Leu
            100                 105

<210> SEQ ID NO 132
<211> LENGTH: 313
<212> TYPE: PRT
<213> ORGANISM: artificial sequence
<220> FEATURE:
<223> OTHER INFORMATION: atacicept

<400> SEQUENCE: 132

Ala Met Arg Ser Cys Pro Glu Glu Gln Tyr Trp Asp Pro Leu Leu Gly
1               5                   10                  15

Thr Cys Met Ser Cys Lys Thr Ile Cys Asn His Gln Ser Gln Arg Thr
            20                  25                  30
```

```
Cys Ala Ala Phe Cys Arg Ser Leu Ser Cys Arg Lys Glu Gln Gly Lys
            35                  40                  45

Phe Tyr Asp His Leu Leu Arg Asp Cys Ile Ser Cys Ala Ser Ile Cys
 50                  55                  60

Gly Gln His Pro Lys Gln Cys Ala Tyr Phe Cys Glu Asn Lys Leu Arg
 65                  70                  75                  80

Ser Glu Pro Lys Ser Ser Asp Lys Thr His Thr Cys Pro Pro Cys Pro
                 85                  90                  95

Ala Pro Glu Ala Glu Gly Ala Pro Ser Val Phe Leu Phe Pro Pro Lys
            100                 105                 110

Pro Lys Asp Thr Leu Met Ile Ser Arg Thr Pro Glu Val Thr Cys Val
            115                 120                 125

Val Val Asp Val Ser His Glu Asp Pro Glu Val Lys Phe Asn Trp Tyr
130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ser Ser Ile Glu Lys Thr Ile Ser Lys Ala Lys Gly Gln
        195                 200                 205

Pro Arg Glu Pro Gln Val Tyr Thr Leu Pro Pro Ser Arg Asp Glu Leu
210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270

Tyr Ser Lys Leu Thr Val Asp Lys Ser Arg Trp Gln Gln Gly Asn Val
        275                 280                 285

Phe Ser Cys Ser Val Met His Glu Ala Leu His Asn His Tyr Thr Gln
290                 295                 300

Lys Ser Leu Ser Leu Ser Pro Gly Lys
305                 310

<210> SEQ ID NO 133
<211> LENGTH: 13
<212> TYPE: PRT
<213> ORGANISM: artificial sequence
<220> FEATURE:
<223> OTHER INFORMATION: linker

<400> SEQUENCE: 133

Gly Gly Gly Gly Ser Gly Gly Gly Gly Ser Ala Ala Ala
1               5                   10

<210> SEQ ID NO 134
<211> LENGTH: 231
<212> TYPE: PRT
<213> ORGANISM: artificial sequence
<220> FEATURE:
<223> OTHER INFORMATION: Fc with C220S/E233P/L234V/L235A/G236del/S267K

<400> SEQUENCE: 134

Glu Pro Lys Ser Ser Asp Lys Thr His Thr Cys Pro Pro Cys Pro Ala
1               5                   10                  15
```

Pro Pro Val Ala Gly Pro Ser Val Phe Leu Phe Pro Pro Lys Pro Lys
                    20                  25                  30

Asp Thr Leu Met Ile Ser Arg Thr Pro Glu Val Thr Cys Val Val Val
                35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 135
<211> LENGTH: 231
<212> TYPE: PRT
<213> ORGANISM: artificial sequence
<220> FEATURE:
<223> OTHER INFORMATION: Fc (C5S (C220S), R77C, (R292C), N82G (N297G),
      V87C (V302C), L232del (K447del))

<400> SEQUENCE: 135

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Cys Glu Glu Gln
65                  70                  75                  80

Tyr Gly Ser Thr Tyr Arg Cys Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr

```
                130               135               140
Lys Asn Gln Val Ser Leu Thr Cys Leu Val Lys Gly Phe Tyr Pro Ser
145                 150               155               160

Asp Ile Ala Val Glu Trp Glu Ser Asn Gly Gln Pro Glu Asn Asn Tyr
                165               170               175

Lys Thr Thr Pro Pro Val Leu Asp Ser Asp Gly Ser Phe Phe Leu Tyr
                180               185               190

Ser Lys Leu Thr Val Asp Lys Ser Arg Trp Gln Gln Gly Asn Val Phe
            195               200               205

Ser Cys Ser Val Met His Glu Ala Leu His Asn His Tyr Thr Gln Lys
            210               215               220

Ser Leu Ser Leu Ser Pro Gly
225                 230

<210> SEQ ID NO 136
<211> LENGTH: 231
<212> TYPE: PRT
<213> ORGANISM: artificial sequence
<220> FEATURE:
<223> OTHER INFORMATION: Fc with C220S/L234A/L235E/G237A/K447del

<400> SEQUENCE: 136

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150               155               160

Asp Ile Ala Val Glu Trp Glu Ser Asn Gly Gln Pro Glu Asn Asn Tyr
                165               170               175

Lys Thr Thr Pro Pro Val Leu Asp Ser Asp Gly Ser Phe Phe Leu Tyr
                180               185               190

Ser Lys Leu Thr Val Asp Lys Ser Arg Trp Gln Gln Gly Asn Val Phe
            195               200               205

Ser Cys Ser Val Met His Glu Ala Leu His Asn His Tyr Thr Gln Lys
            210               215               220

Ser Leu Ser Leu Ser Pro Gly
225                 230

<210> SEQ ID NO 137
<211> LENGTH: 230
<212> TYPE: PRT
```

<213> ORGANISM: artificial sequence
<220> FEATURE:
<223> OTHER INFORMATION: Fc with C220S/E233P/L234V/L235A/G236del/S267K/
      K447del

<400> SEQUENCE: 137

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Lys His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly
225                 230

<210> SEQ ID NO 138
<211> LENGTH: 235
<212> TYPE: PRT
<213> ORGANISM: artificial sequence
<220> FEATURE:
<223> OTHER INFORMATION: IgG2 Fc

<400> SEQUENCE: 138

Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
            115                 120                 125

Gly Gln Pro Arg Glu Pro Gln Val Tyr Thr Leu Pro Pro Ser Arg Glu
130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

<210> SEQ ID NO 139
<211> LENGTH: 229
<212> TYPE: PRT
<213> ORGANISM: artificial sequence
<220> FEATURE:
<223> OTHER INFORMATION: IgG4 Fc

<400> SEQUENCE: 139

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 140
<211> LENGTH: 229
<212> TYPE: PRT
<213> ORGANISM: artificial sequence
<220> FEATURE:
<223> OTHER INFORMATION: IgG4 Fc S228P

<400> SEQUENCE: 140

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 141
<211> LENGTH: 231
<212> TYPE: PRT
<213> ORGANISM: artificial sequence
<220> FEATURE:
<223> OTHER INFORMATION: Fc K chain

<400> SEQUENCE: 141

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val

```
            50                  55                  60
Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Lys Lys Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 142
<211> LENGTH: 231
<212> TYPE: PRT
<213> ORGANISM: artificial sequence
<220> FEATURE:
<223> OTHER INFORMATION: Fc D chain

<400> SEQUENCE: 142

Glu Pro Lys Ser Ser Asp Lys Thr His Thr Cys Pro Pro Cys Pro Ala
 1               5                  10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Asp Gly Phe Tyr Pro Ser
145                 150                 155                 160

Asp Ile Ala Val Glu Trp Glu Ser Asn Gly Gln Pro Glu Asn Asn Tyr
                165                 170                 175

Asp Thr Thr Pro Pro Val Leu Asp Ser Asp Gly Ser Phe Phe Leu Tyr
```

```
            180                 185                 190
Ser Asp Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly
225                 230
```

<210> SEQ ID NO 143
<211> LENGTH: 237
<212> TYPE: PRT
<213> ORGANISM: artificial sequence
<220> FEATURE:
<223> OTHER INFORMATION: Green Fluorescent protein

<400> SEQUENCE: 143

```
Ser Lys Gly Glu Glu Leu Phe Thr Gly Val Val Pro Ile Leu Val Glu
1               5                   10                  15

Leu Asp Gly Asp Val Asn Gly His Lys Phe Ser Val Ser Gly Glu Gly
            20                  25                  30

Glu Gly Asp Ala Thr Tyr Gly Lys Leu Thr Leu Lys Phe Ile Cys Thr
            35                  40                  45

Thr Gly Lys Leu Pro Val Pro Trp Pro Thr Leu Val Thr Thr Phe Ser
50                  55                  60

Tyr Gly Val Gln Cys Phe Ser Arg Tyr Pro Asp His Met Lys Gln His
65                  70                  75                  80

Asp Phe Phe Lys Ser Ala Met Pro Glu Gly Tyr Val Gln Glu Arg Thr
            85                  90                  95

Ile Phe Phe Lys Asp Asp Gly Asn Tyr Lys Thr Arg Ala Glu Val Lys
            100                 105                 110

Phe Glu Gly Asp Thr Leu Val Asn Arg Ile Glu Leu Lys Gly Ile Asp
            115                 120                 125

Phe Lys Glu Asp Gly Asn Ile Leu Gly His Lys Leu Glu Tyr Asn Tyr
            130                 135                 140

Asn Ser His Asn Val Tyr Ile Met Ala Asp Lys Gln Lys Asn Gly Ile
145                 150                 155                 160

Lys Val Asn Phe Lys Ile Arg His Asn Ile Glu Asp Gly Ser Val Gln
            165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Ala Leu Ser Lys
            195                 200                 205

Asp Pro Asn Glu Lys Arg Asp His Met Val Leu Leu Glu Phe Val Thr
            210                 215                 220

Ala Ala Gly Ile Thr His Gly Met Asp Glu Leu Tyr Lys
225                 230                 235
```

<210> SEQ ID NO 144
<211> LENGTH: 237
<212> TYPE: PRT
<213> ORGANISM: artificial sequence
<220> FEATURE:
<223> OTHER INFORMATION: eGFP

<400> SEQUENCE: 144

```
Ser Lys Gly Glu Glu Leu Phe Thr Gly Val Val Pro Ile Leu Val Glu
1               5                   10                  15
```

Leu Asp Gly Asp Val Asn Gly His Lys Phe Ser Val Ser Gly Glu Gly
            20                  25                  30

Glu Gly Asp Ala Thr Tyr Gly Lys Leu Thr Leu Lys Phe Ile Cys Thr
        35                  40                  45

Thr Gly Lys Leu Pro Val Pro Trp Pro Thr Leu Val Thr Thr Leu Thr
50                  55                  60

Tyr Gly Val Gln Cys Phe Ser Arg Tyr Pro Asp His Met Lys Gln His
65                  70                  75                  80

Asp Phe Phe Lys Ser Ala Met Pro Glu Gly Tyr Val Gln Glu Arg Thr
                85                  90                  95

Ile Phe Phe Lys Asp Asp Gly Asn Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Tyr
    130                 135                 140

Asn Ser His Asn Val Tyr Ile Met Ala Asp Lys Gln Lys Asn Gly Ile
145                 150                 155                 160

Lys Val Asn Phe Lys Ile Arg His Asn Ile Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Ala Leu Ser Lys
        195                 200                 205

Asp Pro Asn Glu Lys Arg Asp His Met Val Leu Leu Glu Phe Val Thr
    210                 215                 220

Ala Ala Gly Ile Thr His Gly Met Asp Glu Leu Tyr Lys
225                 230                 235

<210> SEQ ID NO 145
<211> LENGTH: 239
<212> TYPE: PRT
<213> ORGANISM: artificial sequence
<220> FEATURE:
<223> OTHER INFORMATION: eGFP

<400> SEQUENCE: 145

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 146
<211> LENGTH: 45
<212> TYPE: PRT
<213> ORGANISM: artificial sequence
<220> FEATURE:
<223> OTHER INFORMATION: Moiety: COMP

<400> SEQUENCE: 146

Asp Leu Gly Pro Gln Met Leu Arg Glu Leu Gln Glu Thr Asn Ala Ala
1               5                   10                  15

Leu Gln Asp Val Arg Glu Leu Leu Arg Gln Gln Val Arg Glu Ile Thr
            20                  25                  30

Phe Leu Lys Asn Thr Val Met Glu Cys Asp Ala Cys Gly
        35                  40                  45

<210> SEQ ID NO 147
<211> LENGTH: 33
<212> TYPE: PRT
<213> ORGANISM: artificial sequence
<220> FEATURE:
<223> OTHER INFORMATION: Moiety: VASP

<400> SEQUENCE: 147

Asp Leu Gln Arg Val Lys Gln Glu Leu Leu Glu Glu Val Lys Lys Glu
1               5                   10                  15

Leu Gln Lys Val Lys Glu Glu Ile Ile Glu Ala Phe Val Gln Glu Leu
            20                  25                  30

Arg

<210> SEQ ID NO 148
<211> LENGTH: 40
<212> TYPE: PRT
<213> ORGANISM: artificial sequence
<220> FEATURE:
<223> OTHER INFORMATION: Moiety: ZZ12.6

<400> SEQUENCE: 148

Asp Val Gln Ala Ile Ser Ser Thr Ile Gln Asp Leu Gln Asp Gln Val
1               5                   10                  15

Asp Ser Leu Ala Glu Val Val Leu Gln Asn Arg Arg Gly Leu Asp Leu
            20                  25                  30

Leu Thr Arg Ser Gly Gly Gly Ser
        35                  40

<210> SEQ ID NO 149
<211> LENGTH: 18
<212> TYPE: PRT
<213> ORGANISM: artificial sequence

```
<220> FEATURE:
<223> OTHER INFORMATION: HSA signal peptide

<400> SEQUENCE: 149

Met Lys Trp Val Thr Phe Ile Ser Leu Leu Phe Leu Phe Ser Ser Ala
1               5                   10                  15

Tyr Ser

<210> SEQ ID NO 150
<211> LENGTH: 22
<212> TYPE: PRT
<213> ORGANISM: artificial sequence
<220> FEATURE:
<223> OTHER INFORMATION: Ig kappa light chain

<400> SEQUENCE: 150

Met Asp Met Arg Ala Pro Ala Gly Ile Phe Gly Phe Leu Leu Val Leu
1               5                   10                  15

Phe Pro Gly Tyr Arg Ser
            20

<210> SEQ ID NO 151
<211> LENGTH: 19
<212> TYPE: PRT
<213> ORGANISM: artificial sequence
<220> FEATURE:
<223> OTHER INFORMATION: human azurocidin preprotein signal sequence

<400> SEQUENCE: 151

Met Thr Arg Leu Thr Val Leu Ala Leu Leu Ala Gly Leu Leu Ala Ser
1               5                   10                  15

Ser Arg Ala

<210> SEQ ID NO 152
<211> LENGTH: 19
<212> TYPE: PRT
<213> ORGANISM: artificial sequence
<220> FEATURE:
<223> OTHER INFORMATION: IgG heavy chain signal peptide

<400> SEQUENCE: 152

Met Glu Leu Gly Leu Ser Trp Ile Phe Leu Leu Ala Ile Leu Lys Gly
1               5                   10                  15

Val Gln Cys

<210> SEQ ID NO 153
<211> LENGTH: 19
<212> TYPE: PRT
<213> ORGANISM: artificial sequence
<220> FEATURE:
<223> OTHER INFORMATION: IgG heavy chain signal peptide

<400> SEQUENCE: 153

Met Glu Leu Gly Leu Arg Trp Val Phe Leu Val Ala Ile Leu Glu Gly
1               5                   10                  15

Val Gln Cys

<210> SEQ ID NO 154
<211> LENGTH: 19
<212> TYPE: PRT
<213> ORGANISM: artificial sequence
<220> FEATURE:
<223> OTHER INFORMATION: IgG heavy chain signal peptide
```

```
<400> SEQUENCE: 154

Met Lys His Leu Trp Phe Phe Leu Leu Leu Val Ala Ala Pro Arg Trp
1               5                   10                  15

Val Leu Ser

<210> SEQ ID NO 155
<211> LENGTH: 19
<212> TYPE: PRT
<213> ORGANISM: artificial sequence
<220> FEATURE:
<223> OTHER INFORMATION: IgG heavy chain signal peptide

<400> SEQUENCE: 155

Met Asp Trp Thr Trp Arg Ile Leu Phe Leu Val Ala Ala Ala Thr Gly
1               5                   10                  15

Ala His Ser

<210> SEQ ID NO 156
<211> LENGTH: 19
<212> TYPE: PRT
<213> ORGANISM: artificial sequence
<220> FEATURE:
<223> OTHER INFORMATION: IgG heavy chain signal peptide

<400> SEQUENCE: 156

Met Asp Trp Thr Trp Arg Phe Leu Phe Val Val Ala Ala Ala Thr Gly
1               5                   10                  15

Val Gln Ser

<210> SEQ ID NO 157
<211> LENGTH: 19
<212> TYPE: PRT
<213> ORGANISM: artificial sequence
<220> FEATURE:
<223> OTHER INFORMATION: IgG heavy chain signal peptide

<400> SEQUENCE: 157

Met Glu Phe Gly Leu Ser Trp Leu Phe Leu Val Ala Ile Leu Lys Gly
1               5                   10                  15

Val Gln Cys

<210> SEQ ID NO 158
<211> LENGTH: 19
<212> TYPE: PRT
<213> ORGANISM: artificial sequence
<220> FEATURE:
<223> OTHER INFORMATION: IgG heavy chain signal peptide

<400> SEQUENCE: 158

Met Glu Phe Gly Leu Ser Trp Val Phe Leu Val Ala Leu Phe Arg Gly
1               5                   10                  15

Val Gln Cys

<210> SEQ ID NO 159
<211> LENGTH: 26
<212> TYPE: PRT
<213> ORGANISM: artificial sequence
<220> FEATURE:
<223> OTHER INFORMATION: IgG heavy chain signal peptide

<400> SEQUENCE: 159

Met Asp Leu Leu His Lys Asn Met Lys His Leu Trp Phe Phe Leu Leu
1               5                   10                  15
```

```
Leu Val Ala Ala Pro Arg Trp Val Leu Ser
         20                  25

<210> SEQ ID NO 160
<211> LENGTH: 22
<212> TYPE: PRT
<213> ORGANISM: artificial sequence
<220> FEATURE:
<223> OTHER INFORMATION: IgG Kappa light chain signal sequence

<400> SEQUENCE: 160

Met Asp Met Arg Val Pro Ala Gln Leu Leu Gly Leu Leu Leu Leu Trp
1               5                   10                  15

Leu Ser Gly Ala Arg Cys
         20

<210> SEQ ID NO 161
<211> LENGTH: 22
<212> TYPE: PRT
<213> ORGANISM: artificial sequence
<220> FEATURE:
<223> OTHER INFORMATION: IgG Kappa light chain signal sequence

<400> SEQUENCE: 161

Met Lys Tyr Leu Leu Pro Thr Ala Ala Ala Gly Leu Leu Leu Leu Ala
1               5                   10                  15

Ala Gln Pro Ala Met Ala
         20

<210> SEQ ID NO 162
<211> LENGTH: 17
<212> TYPE: PRT
<213> ORGANISM: artificial sequence
<220> FEATURE:
<223> OTHER INFORMATION: Gaussia luciferase

<400> SEQUENCE: 162

Met Gly Val Lys Val Leu Phe Ala Leu Ile Cys Ile Ala Val Ala Glu
1               5                   10                  15

Ala

<210> SEQ ID NO 163
<211> LENGTH: 18
<212> TYPE: PRT
<213> ORGANISM: homo sapiens
<220> FEATURE:
<221> NAME/KEY: MISC_FEATURE
<223> OTHER INFORMATION: Human albumin

<400> SEQUENCE: 163

Met Lys Trp Val Thr Phe Ile Ser Leu Leu Phe Leu Phe Ser Ser Ala
1               5                   10                  15

Tyr Ser

<210> SEQ ID NO 164
<211> LENGTH: 18
<212> TYPE: PRT
<213> ORGANISM: homo sapiens
<220> FEATURE:
<221> NAME/KEY: MISC_FEATURE
<223> OTHER INFORMATION: Human chymotrypsinogen

<400> SEQUENCE: 164

Met Ala Phe Leu Trp Leu Leu Ser Cys Trp Ala Leu Leu Gly Thr Thr
```

Phe Gly

<210> SEQ ID NO 165
<211> LENGTH: 14
<212> TYPE: PRT
<213> ORGANISM: homo sapiens
<220> FEATURE:
<221> NAME/KEY: MISC_FEATURE
<223> OTHER INFORMATION: Human interleukin-2

<400> SEQUENCE: 165

Met Gln Leu Leu Ser Cys Ile Ala Leu Ile Leu Ala Leu Val
1               5                   10

<210> SEQ ID NO 166
<211> LENGTH: 15
<212> TYPE: PRT
<213> ORGANISM: homo sapiens
<220> FEATURE:
<221> NAME/KEY: MISC_FEATURE
<223> OTHER INFORMATION: Human trypsinogen-2

<400> SEQUENCE: 166

Met Asn Leu Leu Leu Ile Leu Thr Phe Val Ala Ala Val Ala
1               5                   10                  15

<210> SEQ ID NO 167
<211> LENGTH: 281
<212> TYPE: PRT
<213> ORGANISM: artificial sequence
<220> FEATURE:
<223> OTHER INFORMATION: TACI Fc

<400> SEQUENCE: 167

Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr

```
            195                 200                 205
Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly
            275                 280

<210> SEQ ID NO 168
<211> LENGTH: 281
<212> TYPE: PRT
<213> ORGANISM: artificial sequence
<220> FEATURE:
<223> OTHER INFORMATION: TACI Fc

<400> SEQUENCE: 168

Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
                20                  25                  30

Cys Ala Asp Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly
```

<210> SEQ ID NO 169
<211> LENGTH: 281
<212> TYPE: PRT
<213> ORGANISM: artificial sequence
<220> FEATURE:
<223> OTHER INFORMATION: TACI Fc

<400> SEQUENCE: 169

```
Ser Leu Ser Cys Arg Lys Glu Glu Gly Lys Phe Tyr Asp His Leu Leu
1               5                   10                  15

Gln Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280
```

<210> SEQ ID NO 170
<211> LENGTH: 281
<212> TYPE: PRT
<213> ORGANISM: artificial sequence
<220> FEATURE:
<223> OTHER INFORMATION: TACI Fc

<400> SEQUENCE: 170

```
Ser Leu Ser Cys Arg Lys Glu Glu Gly Lys Phe Tyr Asp His Leu Leu
1               5                   10                  15
```

Gln Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
            85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
            165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
            260                 265                 270

Gln Lys Ser Leu Ser Leu Ser Pro Gly
            275                 280

<210> SEQ ID NO 171
<211> LENGTH: 281
<212> TYPE: PRT
<213> ORGANISM: artificial sequence
<220> FEATURE:
<223> OTHER INFORMATION: TACI Fc

<400> SEQUENCE: 171

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
            85                  90                  95

```
Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 172
<211> LENGTH: 281
<212> TYPE: PRT
<213> ORGANISM: artificial sequence
<220> FEATURE:
<223> OTHER INFORMATION: TACI Fc

<400> SEQUENCE: 172

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175
```

```
Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 173
<211> LENGTH: 227
<212> TYPE: PRT
<213> ORGANISM: artificial sequence
<220> FEATURE:
<223> OTHER INFORMATION: Fc

<400> SEQUENCE: 173

Asp Lys Pro His Thr Cys Pro Leu Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Ala Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 174
<211> LENGTH: 232
```

```
<212> TYPE: PRT
<213> ORGANISM: artificial sequence
<220> FEATURE:
<223> OTHER INFORMATION: Fc

<400> SEQUENCE: 174

Asp Pro Lys Ser Cys Asp Lys Pro His Thr Cys Pro Leu Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Ala Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 175
<211> LENGTH: 227
<212> TYPE: PRT
<213> ORGANISM: artificial sequence
<220> FEATURE:
<223> OTHER INFORMATION: Fc variant

<400> SEQUENCE: 175

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

-continued

Lys Glu Tyr Lys Cys Lys Val Ser Asn Lys Ala Leu Pro Ser Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 176
<211> LENGTH: 232
<212> TYPE: PRT
<213> ORGANISM: artificial sequence
<220> FEATURE:
<223> OTHER INFORMATION: Fc variant

<400> SEQUENCE: 176

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 177
<211> LENGTH: 43
<212> TYPE: PRT
<213> ORGANISM: artificial sequence
<220> FEATURE:
<223> OTHER INFORMATION: TACI variant

<400> SEQUENCE: 177

Ser Leu Ser Cys Arg Lys Glu Glu Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 178
<211> LENGTH: 43
<212> TYPE: PRT
<213> ORGANISM: artificial sequence
<220> FEATURE:
<223> OTHER INFORMATION: TACI variant

<400> SEQUENCE: 178

Ser Leu Ser Cys Arg Lys Glu Glu Gly Glu Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 179
<211> LENGTH: 43
<212> TYPE: PRT
<213> ORGANISM: artificial sequence
<220> FEATURE:
<223> OTHER INFORMATION: TACI variant

<400> SEQUENCE: 179

Ser Leu Ser Cys Arg Lys Glu Glu Gly Lys Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 180
<211> LENGTH: 43
<212> TYPE: PRT
<213> ORGANISM: artificial sequence
<220> FEATURE:
<223> OTHER INFORMATION: TACI variant

<400> SEQUENCE: 180

Ser Leu Ser Cys Arg Lys Glu Glu Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Asp Tyr Phe Cys Glu Asn Lys Leu Arg Ser
        35                  40

<210> SEQ ID NO 181
<211> LENGTH: 43
<212> TYPE: PRT
<213> ORGANISM: artificial sequence
<220> FEATURE:
<223> OTHER INFORMATION: TACI variant

<400> SEQUENCE: 181

Ser Leu Ser Cys Arg Lys Glu Glu Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser
        35                  40

<210> SEQ ID NO 182
<211> LENGTH: 43
<212> TYPE: PRT
<213> ORGANISM: artificial sequence
<220> FEATURE:
<223> OTHER INFORMATION: TACI variant

<400> SEQUENCE: 182

Ser Leu Ser Cys Arg Lys Glu Gln Gly Glu Tyr Tyr Asp His Leu Leu
1               5                   10                  15

Gln Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 183
<211> LENGTH: 43
<212> TYPE: PRT
<213> ORGANISM: artificial sequence
<220> FEATURE:
<223> OTHER INFORMATION: TACI variant

<400> SEQUENCE: 183

Ser Leu Ser Cys Arg Lys Glu Gln Gly Lys Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 184
<211> LENGTH: 43
<212> TYPE: PRT
<213> ORGANISM: artificial sequence
<220> FEATURE:
<223> OTHER INFORMATION: TACI variant

<400> SEQUENCE: 184

Ser Leu Ser Cys Arg Lys Glu Gln Gly Lys Tyr Tyr Asp His Leu Leu
1               5                   10                  15

Gln Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 185

<211> LENGTH: 43
<212> TYPE: PRT
<213> ORGANISM: artificial sequence
<220> FEATURE:
<223> OTHER INFORMATION: TACI variant

<400> SEQUENCE: 185

Ser Leu Ser Cys Arg Lys Glu Gln Gly Lys Tyr Tyr Asp His Leu Leu
1               5                   10                  15

Arg Asp Cys Ile Ser Cys Ala Ser Ile Cys Gly Gln His Pro Lys Gln
            20                  25                  30

Cys Asp Tyr Phe Cys Glu Asn Lys Leu Arg Ser
        35                  40

<210> SEQ ID NO 186
<211> LENGTH: 43
<212> TYPE: PRT
<213> ORGANISM: artificial sequence
<220> FEATURE:
<223> OTHER INFORMATION: TACI variant

<400> SEQUENCE: 186

Ser Leu Ser Cys Arg Lys Glu Gln Gly Lys Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser
        35                  40

<210> SEQ ID NO 187
<211> LENGTH: 43
<212> TYPE: PRT
<213> ORGANISM: artificial sequence
<220> FEATURE:
<223> OTHER INFORMATION: TACI variant

<400> SEQUENCE: 187

Ser Leu Ser Cys Arg Lys Glu Gln Gly Lys Phe Tyr Asp His Leu Leu
1               5                   10                  15

Gln Asp Cys Ile Ser Cys Ala Ser Ile Cys Gly Gln His Pro Lys Gln
            20                  25                  30

Cys Asp Tyr Phe Cys Glu Asn Lys Leu Arg Ser
        35                  40

<210> SEQ ID NO 188
<211> LENGTH: 43
<212> TYPE: PRT
<213> ORGANISM: artificial sequence
<220> FEATURE:
<223> OTHER INFORMATION: TACI variant

<400> SEQUENCE: 188

Ser Leu Ser Cys Arg Lys Glu Gln Gly Lys Phe Tyr Asp His Leu Leu
1               5                   10                  15

Gln Asp Cys Ile Ser Cys Ala Ser Ile Cys Gly Gln His Pro Lys Gln
            20                  25                  30

Cys Ala Asp Phe Cys Glu Asn Lys Leu Arg Ser
        35                  40

<210> SEQ ID NO 189
<211> LENGTH: 43
<212> TYPE: PRT
<213> ORGANISM: artificial sequence

```
<220> FEATURE:
<223> OTHER INFORMATION: TACI variant

<400> SEQUENCE: 189

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Asp Asp Phe Cys Glu Asn Lys Leu Arg Ser
        35                  40

<210> SEQ ID NO 190
<211> LENGTH: 43
<212> TYPE: PRT
<213> ORGANISM: artificial sequence
<220> FEATURE:
<223> OTHER INFORMATION: TACI variant

<400> SEQUENCE: 190

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser
        35                  40

<210> SEQ ID NO 191
<211> LENGTH: 43
<212> TYPE: PRT
<213> ORGANISM: artificial sequence
<220> FEATURE:
<223> OTHER INFORMATION: TACI variant

<400> SEQUENCE: 191

Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser
        35                  40

<210> SEQ ID NO 192
<211> LENGTH: 43
<212> TYPE: PRT
<213> ORGANISM: artificial sequence
<220> FEATURE:
<223> OTHER INFORMATION: TACI variant

<400> SEQUENCE: 192

Ser Leu Ser Cys Arg Lys Glu Gln Gly Glu Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser
        35                  40

<210> SEQ ID NO 193
<211> LENGTH: 227
<212> TYPE: PRT
<213> ORGANISM: artificial sequence
<220> FEATURE:
<223> OTHER INFORMATION: Fc variant
```

<400> SEQUENCE: 193

Asp Lys Pro His Thr Cys Pro Leu Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Ala Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 194
<211> LENGTH: 12
<212> TYPE: PRT
<213> ORGANISM: artificial sequence
<220> FEATURE:
<223> OTHER INFORMATION: linker

<400> SEQUENCE: 194

Gly Ser Gly Gly Gly Gly Ser Gly Gly Gly Gly Ser
1               5                   10

<210> SEQ ID NO 195
<211> LENGTH: 65
<212> TYPE: PRT
<213> ORGANISM: artificial sequence
<220> FEATURE:
<223> OTHER INFORMATION: linker

<400> SEQUENCE: 195

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Gly Ser Gly Gly Gly Ser Gly Gly Gly
            50                  55                  60

Ser
65

<210> SEQ ID NO 196
<211> LENGTH: 577
<212> TYPE: PRT
<213> ORGANISM: artificial sequence
<220> FEATURE:
<223> OTHER INFORMATION: TACI FC

<400> SEQUENCE: 196

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Gly Gly Gly Gly Ser Glu Pro Lys Ser Ser Asp Lys Thr His
    50                  55                  60

Thr Cys Pro Pro Cys Pro Ala Pro Glu Ala Glu Gly Ala Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Asp Glu Leu Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Gly Gly
        275                 280                 285

Gly Gly Ser Gly Gly Gly Gly Ser Gly Gly Gly Gly Ser Gly Gly Gly
    290                 295                 300

Gly Ser Gly Gly Gly Gly Ser Gly Gly Gly Gly Ser Gly Gly Gly Gly
305                 310                 315                 320

Ser Gly Gly Gly Gly Ser Gly Gly Gly Ser Gly Gly Gly Gly Ser
                325                 330                 335

-continued

```
Gly Gly Gly Gly Ser Gly Gly Gly Ser Glu Pro Lys Ser Ser Asp
            340                 345                 350
Lys Thr His Thr Cys Pro Pro Cys Pro Ala Pro Glu Ala Glu Gly Ala
        355                 360                 365
Pro Ser Val Phe Leu Phe Pro Pro Lys Pro Lys Asp Thr Leu Met Ile
    370                 375                 380
Ser Arg Thr Pro Glu Val Thr Cys Val Val Val Asp Val Ser His Glu
385                 390                 395                 400
Asp Pro Glu Val Lys Phe Asn Trp Tyr Val Asp Gly Val Glu Val His
                405                 410                 415
Asn Ala Lys Thr Lys Pro Arg Glu Glu Gln Tyr Asn Ser Thr Tyr Arg
            420                 425                 430
Val Val Ser Val Leu Thr Val Leu His Gln Asp Trp Leu Asn Gly Lys
        435                 440                 445
Glu Tyr Lys Cys Lys Val Ser Asn Lys Ala Leu Pro Ala Pro Ile Glu
    450                 455                 460
Lys Thr Ile Ser Lys Ala Lys Gly Gln Pro Arg Glu Pro Gln Val Tyr
465                 470                 475                 480
Thr Leu Pro Pro Ser Arg Asp Glu Leu Thr Lys Asn Gln Val Ser Leu
                485                 490                 495
Thr Cys Leu Val Lys Gly Phe Tyr Pro Ser Asp Ile Ala Val Glu Trp
            500                 505                 510
Glu Ser Asn Gly Gln Pro Glu Asn Asn Tyr Lys Thr Thr Pro Pro Val
        515                 520                 525
Leu Asp Ser Asp Gly Ser Phe Phe Leu Tyr Ser Lys Leu Thr Val Asp
    530                 535                 540
Lys Ser Arg Trp Gln Gln Gly Asn Val Phe Ser Cys Ser Val Met His
545                 550                 555                 560
Glu Ala Leu His Asn His Tyr Thr Gln Lys Ser Leu Ser Leu Ser Pro
                565                 570                 575
Gly
```

<210> SEQ ID NO 197
<211> LENGTH: 281
<212> TYPE: PRT
<213> ORGANISM: artificial sequence
<220> FEATURE:
<223> OTHER INFORMATION: TACI FC

<400> SEQUENCE: 197

```
Ser Leu Ser Cys Arg Lys Glu Gln Gly Lys Phe Tyr Asp His Leu Leu
1               5                   10                  15
Arg Asp Cys Ile Ser Cys Ala Ser Ile Cys Gly Gln His Pro Lys Gln
            20                  25                  30
Cys Ala Tyr Phe Cys Glu Asn Lys Leu Arg Ser Gly Ser Gly Gly Gly
        35                  40                  45
Gly Ser Glu Pro Lys Ser Ser Asp Lys Thr His Thr Cys Pro Pro Cys
    50                  55                  60
Pro Ala Pro Glu Ala Glu Gly Ala Pro Ser Val Phe Leu Phe Pro Pro
65                  70                  75                  80
Lys Pro Lys Asp Thr Leu Met Ile Ser Arg Thr Pro Glu Val Thr Cys
                85                  90                  95
Val Val Val Asp Val Ser His Glu Asp Pro Glu Val Lys Phe Asn Trp
            100                 105                 110
Tyr Val Asp Gly Val Glu Val His Asn Ala Lys Thr Lys Pro Arg Glu
```

```
            115                 120                 125
Glu Gln Tyr Asn Ser Thr Tyr Arg Val Val Ser Val Leu Thr Val Leu
            130                 135                 140
His Gln Asp Trp Leu Asn Gly Lys Glu Tyr Lys Cys Lys Val Ser Asn
145                 150                 155                 160
Lys Ala Leu Pro Ala Pro Ile Glu Lys Thr Ile Ser Lys Ala Lys Gly
                165                 170                 175
Gln Pro Arg Glu Pro Gln Val Tyr Thr Leu Pro Pro Ser Arg Asp Glu
            180                 185                 190
Leu Thr Lys Asn Gln Val Ser Leu Thr Cys Leu Val Lys Gly Phe Tyr
            195                 200                 205
Pro Ser Asp Ile Ala Val Glu Trp Glu Ser Asn Gly Gln Pro Glu Asn
            210                 215                 220
Asn Tyr Lys Thr Thr Pro Pro Val Leu Asp Ser Asp Gly Ser Phe Phe
225                 230                 235                 240
Leu Tyr Ser Lys Leu Thr Val Asp Lys Ser Arg Trp Gln Gln Gly Asn
                245                 250                 255
Val Phe Ser Cys Ser Val Met His Glu Ala Leu His Asn His Tyr Thr
                260                 265                 270
Gln Lys Ser Leu Ser Leu Ser Pro Gly
            275                 280

<210> SEQ ID NO 198
<211> LENGTH: 344
<212> TYPE: PRT
<213> ORGANISM: ARTIFICIAL SEQUENCE
<220> FEATURE:
<223> OTHER INFORMATION: TACI FC

<400> SEQUENCE: 198

Ser Leu Ser Cys Arg Lys Glu Gln Gly Lys Phe Tyr Asp His Leu Leu
1               5                   10                  15
Arg Asp Cys Ile Ser Cys Ala Ser Ile Cys Gly Gln His Pro Lys Gln
                20                  25                  30
Cys Ala Tyr Phe Cys Glu Asn Lys Leu Arg Ser Gly Gly Gly Gly Ser
            35                  40                  45
Gly Gly Gly Gly Ser Gly Gly Gly Ser Gly Gly Gly Ser Ser
        50                  55                  60
Leu Ser Cys Arg Lys Glu Gln Gly Lys Phe Tyr Asp His Leu Leu Arg
65                  70                  75                  80
Asp Cys Ile Ser Cys Ala Ser Ile Cys Gly Gln His Pro Lys Gln Cys
                85                  90                  95
Ala Tyr Phe Cys Glu Asn Lys Leu Arg Ser Gly Ser Gly Gly Gly Gly
                100                 105                 110
Ser Glu Pro Lys Ser Ser Asp Lys Thr His Thr Cys Pro Pro Cys Pro
        115                 120                 125
Ala Pro Glu Ala Glu Gly Ala Pro Ser Val Phe Leu Phe Pro Pro Lys
        130                 135                 140
Pro Lys Asp Thr Leu Met Ile Ser Arg Thr Pro Glu Val Thr Cys Val
145                 150                 155                 160
Val Val Asp Val Ser His Glu Asp Pro Glu Val Lys Phe Asn Trp Tyr
                165                 170                 175
Val Asp Gly Val Glu Val His Asn Ala Lys Thr Lys Pro Arg Glu Glu
            180                 185                 190
Gln Tyr Asn Ser Thr Tyr Arg Val Val Ser Val Leu Thr Val Leu His
```

-continued

```
                195                 200                 205
Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly
                340

<210> SEQ ID NO 199
<211> LENGTH: 577
<212> TYPE: PRT
<213> ORGANISM: ARTIFICIAL SEQUENCE
<220> FEATURE:
<223> OTHER INFORMATION: TACI FC

<400> SEQUENCE: 199

Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
        35                  40                  45

Gly Ser Gly Gly Gly Gly Ser Glu Pro Lys Ser Ser Asp Lys Thr His
50                  55                  60

Thr Cys Pro Pro Cys Pro Ala Pro Glu Ala Glu Gly Ala Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Asp Glu Leu Thr Lys Asn Gln Val Ser Leu Thr Cys Leu
        195                 200                 205

Val Lys Gly Phe Tyr Pro Ser Asp Ile Ala Val Glu Trp Glu Ser Asn
```

```
            210                 215                 220
Gly Gln Pro Glu Asn Asn Tyr Lys Thr Thr Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Gly Gly
        275                 280                 285

Gly Gly Ser Gly Gly Gly Ser Gly Gly Gly Ser Gly Gly Gly
    290                 295                 300

Gly Ser Gly Gly Gly Ser Gly Gly Gly Ser Gly Gly Gly
305                 310                 315                 320

Ser Gly Gly Gly Ser Gly Gly Gly Ser Gly Gly Gly Ser
            325                 330                 335

Gly Gly Gly Gly Ser Gly Gly Gly Ser Glu Pro Lys Ser Ser Asp
        340                 345                 350

Lys Thr His Thr Cys Pro Pro Cys Pro Ala Pro Glu Ala Glu Gly Ala
                355                 360                 365

Pro Ser Val Phe Leu Phe Pro Pro Lys Pro Lys Asp Thr Leu Met Ile
370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
        435                 440                 445

Glu Tyr Lys Cys Lys Val Ser Asn Lys Ala Leu Pro Ala Pro Ile Glu
    450                 455                 460

Lys Thr Ile Ser Lys Ala Lys Gly Gln Pro Arg Glu Pro Gln Val Tyr
465                 470                 475                 480

Thr Leu Pro Pro Ser Arg Asp Glu Leu Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
        515                 520                 525

Leu Asp Ser Asp Gly Ser Phe Phe Leu Tyr Ser Lys Leu Thr Val Asp
    530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly
```

<210> SEQ ID NO 200
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 200

Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 201
<211> LENGTH: 344
<212> TYPE: PRT
<213> ORGANISM: ARTIFICIAL SEQUENCE
<220> FEATURE:
<223> OTHER INFORMATION: TACI FC

<400> SEQUENCE: 201

Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
50                  55                  60

Pro Ala Pro Glu Ala Glu Gly Ala Pro Ser Val Phe Leu Phe Pro Pro
65                  70                  75                  80

-continued

```
Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Gly Gly Gly Ser Gly Gly Gly
        275                 280                 285

Gly Ser Gly Gly Gly Gly Ser Gly Gly Gly Ser Ser Leu Ser
    290                 295                 300

Cys Arg Lys Glu Gln Gly Glu Tyr Tyr Asp His Leu Leu Arg Asp Cys
305                 310                 315                 320

Ile Ser Cys Ala Ser Ile Cys Gly Gln His Pro Lys Gln Cys Ala Asp
                325                 330                 335

Phe Cys Glu Asn Lys Leu Arg Ser
            340
```

<210> SEQ ID NO 202
<211> LENGTH: 344
<212> TYPE: PRT
<213> ORGANISM: ARTIFICIAL SEQUENCE
<220> FEATURE:
<223> OTHER INFORMATION: TACI FC

<400> SEQUENCE: 202

```
Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95
```

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Gly Gly Gly Ser Gly Gly
            275                 280                 285

Gly Gly Ser Gly Gly Gly Ser Gly Gly Gly Gly Ser Ser Leu Ser
            290                 295                 300

Cys Arg Lys Glu Gln Gly Lys Phe Tyr Asp His Leu Leu Arg Asp Cys
305                 310                 315                 320

Ile Ser Cys Ala Ser Ile Cys Gly Gln His Pro Lys Gln Cys Ala Tyr
                325                 330                 335

Phe Cys Glu Asn Lys Leu Arg Ser
            340

<210> SEQ ID NO 203
<211> LENGTH: 616
<212> TYPE: PRT
<213> ORGANISM: ARTIFICIAL SEQUENCE
<220> FEATURE:
<223> OTHER INFORMATION: TACI FC

<400> SEQUENCE: 203

Val Ala Met Arg Ser Cys Pro Glu Glu Gln Tyr Trp Asp Pro Leu Leu
1               5                   10                  15

Gly Thr Cys Met Ser Cys Lys Thr Ile Cys Asn His Gln Ser Gln Arg
            20                  25                  30

Thr Cys Ala Ala Phe Cys Arg Ser Leu Ser Cys Arg Lys Glu Gln Gly
            35                  40                  45

Lys Phe Tyr Asp His Leu Leu Arg Asp Cys Ile Ser Cys Ala Ser Ile
        50                  55                  60

Cys Gly Gln His Pro Lys Gln Cys Ala Tyr Phe Cys Glu Asn Lys Leu
65                  70                  75                  80

Arg Ser Gly Ser Gly Gly Gly Gly Ser Gly Gly Gly Gly Ser Glu Pro
                85                  90                  95

Lys Ser Ser Asp Lys Thr His Thr Cys Pro Pro Cys Pro Ala Pro Glu
            100                 105                 110

```
Ala Glu Gly Ala Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Gly Gly Gly Ser Gly Gly Gly Gly Ser Gly
                325                 330                 335

Gly Gly Gly Ser Gly Gly Gly Gly Ser Gly Gly Gly Gly Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Gly Gly Gly Gly
        370                 375                 380

Ser Glu Pro Lys Ser Ser Asp Lys Thr His Thr Cys Pro Pro Cys Pro
385                 390                 395                 400

Ala Pro Glu Ala Glu Gly Ala Pro Ser Val Phe Leu Phe Pro Pro Lys
            405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Asp Glu Leu
            515                 520                 525
```

```
Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
        580                 585                 590

Phe Ser Cys Ser Val Met His Glu Ala Leu His Asn His Tyr Thr Gln
        595                 600                 605

Lys Ser Leu Ser Leu Ser Pro Gly
610                 615
```

<210> SEQ ID NO 204
<211> LENGTH: 313
<212> TYPE: PRT
<213> ORGANISM: ARTIFICIAL SEQUENCE
<220> FEATURE:
<223> OTHER INFORMATION: TACI FC

<400> SEQUENCE: 204

```
Ala Met Arg Ser Cys Pro Glu Glu Gln Tyr Trp Asp Pro Leu Leu Gly
1               5                   10                  15

Thr Cys Met Ser Cys Lys Thr Ile Cys Asn His Gln Ser Gln Arg Thr
            20                  25                  30

Cys Ala Ala Phe Cys Arg Ser Leu Ser Cys Arg Lys Glu Gln Gly Lys
        35                  40                  45

Phe Tyr Asp His Leu Leu Arg Asp Cys Ile Ser Cys Ala Ser Ile Cys
    50                  55                  60

Gly Gln His Pro Lys Gln Cys Ala Tyr Phe Cys Glu Asn Lys Leu Arg
65                  70                  75                  80

Ser Glu Pro Lys Ser Ser Asp Lys Thr His Thr Cys Pro Pro Cys Pro
                85                  90                  95

Ala Pro Glu Ala Glu Gly Ala Pro Ser Val Phe Leu Phe Pro Pro Lys
            100                 105                 110

Pro Lys Asp Thr Leu Met Ile Ser Arg Thr Pro Glu Val Thr Cys Val
        115                 120                 125

Val Val Asp Val Ser His Glu Asp Pro Glu Val Lys Phe Asn Trp Tyr
    130                 135                 140

Val Asp Gly Val Glu Val His Asn Ala Lys Thr Lys Pro Arg Glu Glu
145                 150                 155                 160

Gln Tyr Asn Ser Thr Tyr Arg Val Val Ser Val Leu Thr Val Leu His
                165                 170                 175

Gln Asp Trp Leu Asn Gly Lys Glu Tyr Lys Cys Lys Val Ser Asn Lys
            180                 185                 190

Ala Leu Pro Ser Ser Ile Glu Lys Thr Ile Ser Lys Ala Lys Gly Gln
        195                 200                 205

Pro Arg Glu Pro Gln Val Tyr Thr Leu Pro Pro Ser Arg Asp Glu Leu
    210                 215                 220

Thr Lys Asn Gln Val Ser Leu Thr Cys Leu Val Lys Gly Phe Tyr Pro
225                 230                 235                 240

Ser Asp Ile Ala Val Glu Trp Glu Ser Asn Gly Gln Pro Glu Asn Asn
                245                 250                 255

Tyr Lys Thr Thr Pro Pro Val Leu Asp Ser Asp Gly Ser Phe Phe Leu
            260                 265                 270
```

```
Tyr Ser Lys Leu Thr Val Asp Lys Ser Arg Trp Gln Gln Gly Asn Val
            275                 280                 285

Phe Ser Cys Ser Val Met His Glu Ala Leu His Asn His Tyr Thr Gln
            290                 295                 300

Lys Ser Leu Ser Leu Ser Pro Gly Lys
305                 310

<210> SEQ ID NO 205
<211> LENGTH: 640
<212> TYPE: PRT
<213> ORGANISM: ARTIFICIAL SEQUENCE
<220> FEATURE:
<223> OTHER INFORMATION: TACI FC

<400> SEQUENCE: 205

Ser Arg Val Asp Gln Glu Glu Arg Phe Pro Gln Gly Leu Trp Thr Gly
1               5                   10                  15

Val Ala Met Arg Ser Cys Pro Glu Glu Gln Tyr Trp Asp Pro Leu Leu
            20                  25                  30

Gly Thr Cys Met Ser Cys Lys Thr Ile Cys Asn His Gln Ser Gln Arg
            35                  40                  45

Thr Cys Ala Ala Phe Cys Arg Ser Leu Ser Cys Arg Lys Glu Gln Gly
        50                  55                  60

Lys Phe Tyr Asp His Leu Leu Arg Asp Cys Ile Ser Cys Ala Ser Ile
65                  70                  75                  80

Cys Gly Gln His Pro Lys Gln Cys Ala Tyr Phe Cys Glu Asn Lys Leu
                85                  90                  95

Arg Ser Pro Val Asn Leu Pro Pro Glu Leu Gly Ser Gly Gly Gly Gly
            100                 105                 110

Ser Gly Gly Gly Gly Ser Glu Pro Lys Ser Ser Asp Lys Thr His Thr
            115                 120                 125

Cys Pro Pro Cys Pro Ala Pro Glu Ala Glu Gly Ala Pro Ser Val Phe
        130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
            195                 200                 205

Leu Thr Val Leu His Gln Asp Trp Leu Asn Gly Lys Glu Tyr Lys Cys
        210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
        290                 295                 300

Gly Ser Phe Phe Leu Tyr Ser Lys Leu Thr Val Asp Lys Ser Arg Trp
305                 310                 315                 320
```

```
Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Gly Gly Gly
            340                 345                 350

Gly Ser Gly Gly Gly Ser Gly Gly Gly Ser Gly Gly Gly Gly
        355                 360                 365

Ser Gly Gly Gly Gly Ser Gly Gly Gly Ser Gly Gly Gly Ser
370                 375                 380

Gly Gly Gly Gly Ser Gly Gly Gly Ser Gly Gly Gly Ser Gly
385                 390                 395                 400

Gly Gly Gly Ser Gly Gly Gly Ser Glu Pro Lys Ser Ser Asp Lys
            405                 410                 415

Thr His Thr Cys Pro Pro Cys Pro Ala Pro Glu Ala Glu Gly Ala Pro
            420                 425                 430

Ser Val Phe Leu Phe Pro Pro Lys Pro Lys Asp Thr Leu Met Ile Ser
            435                 440                 445

Arg Thr Pro Glu Val Thr Cys Val Val Val Asp Val Ser His Glu Asp
450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
            485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Pro Ile Glu Lys
            515                 520                 525

Thr Ile Ser Lys Ala Lys Gly Gln Pro Arg Glu Pro Gln Val Tyr Thr
            530                 535                 540

Leu Pro Pro Ser Arg Asp Glu Leu Thr Lys Asn Gln Val Ser Leu Thr
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Tyr Ser Lys Leu Thr Val Asp Lys
            595                 600                 605

Ser Arg Trp Gln Gln Gly Asn Val Phe Ser Cys Ser Val Met His Glu
            610                 615                 620

Ala Leu His Asn His Tyr Thr Gln Lys Ser Leu Ser Leu Ser Pro Gly
625                 630                 635                 640

<210> SEQ ID NO 206
<211> LENGTH: 333
<212> TYPE: PRT
<213> ORGANISM: ARTIFICIAL SEQUENCE
<220> FEATURE:
<223> OTHER INFORMATION: TACI FC

<400> SEQUENCE: 206

Ser Arg Val Asp Gln Glu Glu Arg Phe Pro Gln Gly Leu Trp Thr Gly
1               5                   10                  15

Val Ala Met Arg Ser Cys Pro Glu Glu Gln Tyr Trp Asp Pro Leu Leu
                20                  25                  30

Gly Thr Cys Met Ser Cys Lys Thr Ile Cys Asn His Gln Ser Gln Arg
            35                  40                  45
```

```
Thr Cys Ala Ala Phe Cys Arg Ser Leu Ser Cys Arg Lys Glu Gln Gly
     50                  55                  60

Lys Phe Tyr Asp His Leu Leu Arg Asp Cys Ile Ser Cys Ala Ser Ile
 65                  70                  75                  80

Cys Gly Gln His Pro Lys Gln Cys Ala Tyr Phe Cys Glu Asn Lys Leu
                 85                  90                  95

Arg Ser Pro Val Asn Leu Pro Pro Glu Leu Asp Lys Thr His Thr Cys
                100                 105                 110

Pro Pro Cys Pro Ala Pro Glu Ala Glu Gly Ala Pro Ser Val Phe Leu
            115                 120                 125

Phe Pro Pro Lys Pro Lys Asp Thr Leu Met Ile Ser Arg Thr Pro Glu
130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
                180                 185                 190

Thr Val Leu His Gln Asp Trp Leu Asn Gly Lys Glu Tyr Lys Cys Lys
                195                 200                 205

Val Ser Asn Lys Ala Leu Pro Ser Ser Ile Glu Lys Thr Ile Ser Lys
210                 215                 220

Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
                260                 265                 270

Pro Glu Asn Asn Tyr Lys Thr Thr Pro Pro Val Leu Asp Ser Asp Gly
                275                 280                 285

Ser Phe Phe Leu Tyr Ser Lys Leu Thr Val Asp Lys Ser Arg Trp Gln
290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330

<210> SEQ ID NO 207
<211> LENGTH: 1731
<212> TYPE: DNA
<213> ORGANISM: ARTIFICIAL SEQUENCE
<220> FEATURE:
<223> OTHER INFORMATION: TACI FC

<400> SEQUENCE: 207
agtctctctt gcaggaaaga gcaaggcaaa ttttacgacc atctttttgcg agactgtata      60 agctgtgcgt ctatttgtgg acaacaccct aaacaatgtg cttatttctg tgaaaataag     120
cttcgatctg gatccggtgg tggcgggtca gggggaggtg gaagcgagcc aagtcctca     180 gataagactc atacttgccc ccctgtcccg ccccctgagg ccgaaggcgc accgtcagtg     240
tttttgttcc caccaaagcc taaggacaca ctgatgataa gcagaacacc tgaggtaacc     300
tgtgttgttg tggatgtaag ccacgaagat ccggaggtta agtttaactg gtacgtggac     360
ggtgtagaag tccataatgc taagacgaag ccgagggagg aacaatacaa ctccacgtat     420
agagtggtct ccgtcttgac cgtactccat caagactggc tcaacgggaa agagtacaag     480
```

```
tgtaaagtct ctaacaaagc tcttcctgca ccgattgaga aaaccatatc taaagccaag    540
ggacaaccga gagaaccaca ggtttacacg ctcccccca  gtagagacga acttacaaaa    600
aaccaggtca gtcttacctg cctcgtcaaa ggcttctacc cctctgacat cgctgttgag    660
tgggaatcta acgccaacc  tgagaacaat tacaaaacaa ccccgcctgt ccttgactca    720
gacggttcct tttttcttta cagcaagctg accgtcgaca aatcacggtg caacaaggc    780 aatgtgtttt cctgttccgt gatgcacgag gcactgcaca accactacac tcaaaaatcc    840
ctttcccttt ccccaggggg aggtggaggg agcggtggag gtggtagcgg gggtggaggc    900
tcaggtggtg ggggttccgg cggtggcgga agtggaggcg gtggctctgg tggtggcgga    960
tctggcggag gaggcagcgg cggaggtggg tctgggggtg gaggctccgg aggcggggga   1020
agcggtggag gagggtcaga gcccaaaagc tccgacaaga ctcacacatg ccccccttgt   1080
ccagcgcctg aagctgaggg tgcgccctct gtcttccttt tccccctaa  gccgaaagat   1140 accctgatga tctcccgcac tcccgaagtc acatgtgttg ttgtcgacgt atctcatgaa   1200
gatcctgagg tgaaattcaa ctggtatgta gacggggtcg aagttcataa tgctaagact   1260
aagccacgag aagagcaata caactcaacg tatcgggtgg tgagcgttct gacggttctg   1320
caccaagatt ggcttaatgg aaaagagtat aagtgcaagg tgtccaacaa ggctcttccg   1380
gcacccatcg aaaagacgat ttccaaagcg aaaggccaac ctagggaacc gcaagtttac   1440
actttgcccc cgtcaagaga cgaacttacc aagaatcaag tttccctgac gtgccttgtg   1500
aagggcttct accctagcga tatagcagtt gagtgggaat ctaacggcca gcccgaaaat   1560
aattataaga ctactccgcc cgtgctggac agtgatggtt cattttcct  gtattcaaaa   1620 ctcactgtgg acaaatctag atggcagcag ggtaatgtgt tctcttgttc agttatgcac   1680
gaggcattgc acaatcacta tacgcaaaaa agtttgtctc tctctccggg g            1731
```

<210> SEQ ID NO 208
<211> LENGTH: 843
<212> TYPE: DNA
<213> ORGANISM: ARTIFICIAL SEQUENCE
<220> FEATURE:
<223> OTHER INFORMATION: TACI FC

<400> SEQUENCE: 208

```
agtctctctt gcaggaaaga gcaaggcaaa ttttacgacc atcttttgcg agactgtata     60
agctgtgcgt ctatttgtgg acaacaccct aaacaatgtg cttatttctg tgaaaataag    120
cttcgatctg gatccggtgg aggagggtca gagcccaaaa gctccgacaa gactcacaca    180 tgccccccctt gtccagcgcc tgaagctgag ggtgcgccct ctgtcttcct tttccccct    240 aagccgaaag ataccctgat gatctcccgc actcccgaag tcacatgtgt tgttgtcgac    300
gtatctcatg aagatcctga ggtgaaattc aactggtatg tagacggggt cgaagttcat    360
aatgctaaga ctaagccacg agaagagcaa tacaactcaa cgtatcgggt ggtgagcgtt    420
ctgacggttc tgcaccaaga ttggcttaat ggaaaagagt ataagtgcaa ggtgtccaac    480
aaggctcttc cggcacccat cgaaaagacg atttccaaag cgaaaggcca acctagggaa    540
ccgcaagttt acactttgcc cccgtcaaga gacgaactta ccaagaatca gtttccctg    600 acgtgccttg tgaagggctt ctaccctagc gatatagcag ttgagtggga atctaacggc    660
cagcccgaaa ataattataa gactactccg cccgtgctgg acagtgatgg ttcattttc    720 ctgtattcaa aactcactgt ggacaaatct agatggcagc agggtaatgt gttctcttgt    780
```

| | |
|---|---|
| tcagttatgc acgaggcatt gcacaatcac tatacgcaaa aaagtttgtc tctctctccg | 840 |
| ggg | 843 |

<210> SEQ ID NO 209
<211> LENGTH: 1032
<212> TYPE: DNA
<213> ORGANISM: ARTIFICIAL SEQUENCE
<220> FEATURE:
<223> OTHER INFORMATION: TACI FC

<400> SEQUENCE: 209

| | |
|---|---|
| agtctctctt gcaggaaaga gcaaggcaaa ttttacgacc atcttttgcg agactgtata | 60 |
| agctgtgcgt ctatttgtgg acaacaccct aaacaatgtg cttatttctg tgaaaataag | 120 |
| cttcgatctg ggggtggcgg atcaggaggt ggcggttcag gcggaggagg ttctgggggt | 180 |
| gggggttctt cattgtcctg cagaaaggaa caggggaaat tttacgatca cttgcttaga | 240 |
| gattgtataa gctgcgcgag catttgcggg caacaccccta aacagtgtgc gtatttctgc | 300 |
| gagaataaac tccggtctgg atccggtgga ggagggtcag agcccaaaag ctccgacaag | 360 |
| actcacacat gccccccttg tccagcgcct gaagctgagg gtgcgccctc tgtcttcctt | 420 |
| ttccccccta agccgaaaga taccctgatg atctcccgca ctcccgaagt cacatgtgtt | 480 |
| gttgtcgacg tatctcatga agatcctgag gtgaaattca actggtatgt agacggggtc | 540 |
| gaagttcata atgctaagac taagccacga gaagagcaat acaactcaac gtatcgggtg | 600 |
| gtgagcgttc tgacggttct gcaccaagat tggcttaatg gaaagagta agtgcaag | 660 |
| gtgtccaaca aggctcttcc ggcacccatc gaaaagacga tttccaaagc gaaaggccaa | 720 |
| cctagggaac cgcaagttta cactttgccc ccgtcaagag acgaacttac caagaatcaa | 780 |
| gtttccctga cgtgccttgt gaagggcttc tacccctagcg atatagcagt tgagtgggaa | 840 |
| tctaacggcc agcccgaaaa taattataag actactccgc ccgtgctgga cagtgatggt | 900 |
| tcattttttcc tgtattcaaa actcactgtg gacaaatcta gatggcagca gggtaatgtg | 960 |
| ttctcttgtt cagttatgca cgaggcattg cacaatcact atacgcaaaa aagtttgtct | 1020 |
| ctctctccgg gg | 1032 |

<210> SEQ ID NO 210
<211> LENGTH: 1731
<212> TYPE: DNA
<213> ORGANISM: ARTIFICIAL SEQUENCE
<220> FEATURE:
<223> OTHER INFORMATION: TACI FC

<400> SEQUENCE: 210

| | |
|---|---|
| agtctctctt gcaggaaaga gcaaggcgaa tattacgacc atcttttgcg agactgtata | 60 |
| agctgtgcgt ctatttgtgg acaacaccct aaacaatgtg ctgatttctg tgaaaataag | 120 |
| cttcgatctg gatccggtgg tggcgggtca gggggaggtg gaagcgagcc caagtcctca | 180 |
| gataagactc atacttgccc ccctgtcccg cccctgagg ccgaaggcgc accgtcagtg | 240 |
| tttttgttcc caccaaagcc taaggacaca ctgatgataa gcagaacacc tgaggtaacc | 300 |
| tgtgttgttg tggatgtaag ccacgaagat ccggaggtta gtttaactg gtacgtggac | 360 |
| ggtgtagaag tccataatgc taagacgaag ccgagggagg aacaatacaa ctccacgtat | 420 |
| agagtggtct ccgtcttgac cgtactccat caagactggc tcaacgggaa agagtacaag | 480 |
| tgtaaagtct ctaacaaagc tcttcctgca ccgattgaga aaaccatatc taaagccaag | 540 |
| ggacaaccga gagaaccaca ggtttacacg ctccccccca gtagagacga acttacaaaa | 600 |

```
aaccaggtca gtcttacctg cctcgtcaaa ggcttctacc cctctgacat cgctgttgag      660
tgggaatcta acggccaacc tgagaacaat tacaaaacaa ccccgcctgt ccttgactca      720
gacggttcct tttttcttta cagcaagctg accgtcgaca aatcacggtg caacaaggc       780 aatgtgtttt cctgttccgt gatgcacgag gcactgcaca accactacac tcaaaaatcc      840
ctttcccttt ccccaggggg aggtggaggg agcggtggag gtggtagcgg gggtggaggc      900
tcaggtggtg ggggttccgg cggtggcgga agtggaggcg gtggctctgg tggtggcgga      960
tctggcggag gaggcagcgg cggaggtggg tctgggggtg gaggctccgg aggcggggga     1020
agcggtggag gagggtcaga gcccaaaagc tccgacaaga ctcacacatg ccccccttgt     1080
ccagcgcctg aagctgaggg tgcgccctct gtcttccttt tccccctaa gccgaaagat      1140 accctgatga tctcccgcac tcccgaagtc acatgtgttg ttgtcgacgt atctcatgaa     1200
gatcctgagg tgaaattcaa ctggtatgta gacggggtcg aagttcataa tgctaagact     1260
aagccacgag aagagcaata caactcaacg tatcgggtgg tgagcgttct gacggttctg     1320
caccaagatt ggcttaatgg aaaagagtat aagtgcaagg tgtccaacaa ggctcttccg     1380
gcacccatcg aaaagacgat ttccaaagcg aaaggccaac ctagggaacc gcaagtttac     1440
actttgcccc cgtcaagaga cgaacttacc aagaatcaag tttccctgac gtgccttgtg     1500
aagggcttct accctagcga tatagcagtt gagtgggaat ctaacggcca gcccgaaaat     1560
aattataaga ctactccgcc cgtgctggac agtgatggtt cattttcct gtattcaaaa      1620 ctcactgtgg acaaatctag atggcagcag ggtaatgtgt tctcttgttc agttatgcac     1680
gaggcattgc acaatcacta tacgcaaaaa agtttgtctc tctctccggg g              1731

<210> SEQ ID NO 211
<211> LENGTH: 843
<212> TYPE: DNA
<213> ORGANISM: ARTIFICIAL SEQUENCE
<220> FEATURE:
<223> OTHER INFORMATION: TACI FC

<400> SEQUENCE: 211
agtctctctt gcaggaaaga gcaaggcgaa tattacgacc atcttttgcg agactgtata       60
agctgtgcgt ctatttgtgg acaacaccct aaacaatgtg ctgatttctg tgaaaataag      120
cttcgatctg gatccggtgg aggagggtca gagcccaaaa gctccgacaa gactcacaca      180
tgcccccctt gtccagcgcc tgaagctgag ggtgcgccct ctgtcttcct ttttccccct      240
aagccgaaag ataccctgat gatctcccgc actcccgaag tcacatgtgt tgttgtcgac      300
gtatctcatg aagatcctga ggtgaaattc aactggtatg tagacggggt cgaagttcat      360
aatgctaaga ctaagccacg agaagagcaa tacaactcaa cgtatcgggt ggtgagcgtt      420
ctgacggttc tgcaccaaga ttggcttaat ggaaaagagt ataagtgcaa ggtgtccaac      480
aaggctcttc cggcacccat cgaaaagacg atttccaaag cgaaaggcca acctagggaa      540
ccgcaagttt acactttgcc cccgtcaaga gacgaactta ccaagaatca gtttccctg      600 acgtgccttg tgaagggctt ctaccctagc gatatagcag ttgagtggga atctaacggc      660
cagcccgaaa ataattataa gactactccg cccgtgctgg acagtgatgg ttcattttc       720 ctgtattcaa aactcactgt ggacaaatct agatggcagc agggtaatgt gttctcttgt      780
tcagttatgc acgaggcatt gcacaatcac tatacgcaaa aaagtttgtc tctctctccg      840
ggg                                                                    843
```

<210> SEQ ID NO 212
<211> LENGTH: 1032
<212> TYPE: DNA
<213> ORGANISM: ARTIFICIAL SEQUENCE
<220> FEATURE:
<223> OTHER INFORMATION: TACI FC

<400> SEQUENCE: 212

| | | | | | |
|---|---|---|---|---|---|
| agtctctctt | gcaggaaaga | gcaaggcgaa | tattacgacc | atcttttgcg | agactgtata | 60 |
| agctgtgcgt | ctatttgtgg | acaacaccct | aaacaatgtg | ctgatttctg | tgaaaataag | 120 |
| cttcgatctg | gatccggtgg | aggagggtca | gagcccaaaa | gctccgacaa | gactcacaca | 180 |
| tgccccccct | gtccagcgcc | tgaagctgag | ggtgcgccct | ctgtcttcct | tttcccccct | 240 |
| aagccgaaag | ataccctgat | gatctcccgc | actcccgaag | tcacatgtgt | tgttgtcgac | 300 |
| gtatctcatg | aagatcctga | ggtgaaattc | aactggtatg | tagacggggt | cgaagttcat | 360 |
| aatgctaaga | ctaagccacg | agaagagcaa | tacaactcaa | cgtatcgggt | ggtgagcgtt | 420 |
| ctgacggttc | tgcaccaaga | ttggcttaat | ggaaaagagt | ataagtgcaa | ggtgtccaac | 480 |
| aaggctcttc | cggcacccat | cgaaaagacg | atttccaaag | cgaaaggcca | acctagggaa | 540 |
| ccgcaagttt | acactttgcc | cccgtcaaga | gacgaactta | ccaagaatca | gtttccctg | 600 |
| acgtgccttg | tgaagggctt | ctaccctagc | gatatagcag | ttgagtggga | atctaacggc | 660 |
| cagcccgaaa | ataattataa | gactactccg | cccgtgctgg | acagtgatgg | ttcattttc | 720 |
| ctgtattcaa | aactcactgt | ggacaaatct | agatggcagc | agggtaatgt | gttctcttgt | 780 |
| tcagttatgc | acgaggcatt | gcacaatcac | tatacgcaaa | aaagtttgtc | tctctctccg | 840 |
| ggggggggtg | gcggatcagg | aggtggcggt | tcaggcggag | gaggttctgg | gggtggggt | 900 |
| tcttcattgt | cctgcagaaa | ggaacagggg | gagtattacg | atcacttgct | tagagattgt | 960 |
| ataagctgcg | cgagcatttg | cgggcaacac | cctaaacagt | gtgcggattt | ctgcgagaat | 1020 |
| aaactccggt | ct | | | | | 1032 |

<210> SEQ ID NO 213
<211> LENGTH: 1032
<212> TYPE: DNA
<213> ORGANISM: ARTIFICIAL SEQUENCE
<220> FEATURE:
<223> OTHER INFORMATION: TACI FC

<400> SEQUENCE: 213

| | | | | | |
|---|---|---|---|---|---|
| agtctctctt | gcaggaaaga | gcaaggcaaa | ttttacgacc | atcttttgcg | agactgtata | 60 |
| agctgtgcgt | ctatttgtgg | acaacaccct | aaacaatgtg | cttatttctg | tgaaaataag | 120 |
| cttcgatctg | gatccggtgg | aggagggtca | gagcccaaaa | gctccgacaa | gactcacaca | 180 |
| tgccccccct | gtccagcgcc | tgaagctgag | ggtgcgccct | ctgtcttcct | tttcccccct | 240 |
| aagccgaaag | ataccctgat | gatctcccgc | actcccgaag | tcacatgtgt | tgttgtcgac | 300 |
| gtatctcatg | aagatcctga | ggtgaaattc | aactggtatg | tagacggggt | cgaagttcat | 360 |
| aatgctaaga | ctaagccacg | agaagagcaa | tacaactcaa | cgtatcgggt | ggtgagcgtt | 420 |
| ctgacggttc | tgcaccaaga | ttggcttaat | ggaaaagagt | ataagtgcaa | ggtgtccaac | 480 |
| aaggctcttc | cggcacccat | cgaaaagacg | atttccaaag | cgaaaggcca | acctagggaa | 540 |
| ccgcaagttt | acactttgcc | cccgtcaaga | gacgaactta | ccaagaatca | gtttccctg | 600 |
| acgtgccttg | tgaagggctt | ctaccctagc | gatatagcag | ttgagtggga | atctaacggc | 660 |
| cagcccgaaa | ataattataa | gactactccg | cccgtgctgg | acagtgatgg | ttcattttc | 720 |

```
ctgtattcaa aactcactgt ggacaaatct agatggcagc agggtaatgt gttctcttgt      780
tcagttatgc acgaggcatt gcacaatcac tatacgcaaa aaagtttgtc tctctctccg      840
ggggggggtg gcggatcagg aggtggcggt tcaggcggag gaggttctgg gggtggggt       900 tcttcattgt cctgcagaaa ggaacagggg aaattttacg atcacttgct tagagattgt      960
ataagctgcg cgagcatttg cgggcaacac cctaaacagt gtgcgtattt ctgcgagaat     1020
aaactccggt ct                                                          1032

<210> SEQ ID NO 214
<211> LENGTH: 1848
<212> TYPE: DNA
<213> ORGANISM: ARTIFICIAL SEQUENCE
<220> FEATURE:
<223> OTHER INFORMATION: TACI FC

<400> SEQUENCE: 214
gtggcaatgc gctcatgccc agaggaacaa tattgggatc cgcttcttgg gacgtgtatg       60
agctgcaaga ccatctgtaa tcatcaatcc caaaggacat gcgcagcttt ctgcaggagt      120
ctctcttgca ggaaagagca aggcaaattt tacgaccatc ttttgcgaga ctgtataagc      180
tgtgcgtcta tttgtggaca acaccctaaa caatgtgctt atttctgtga aaataagctt      240
cgatctggat ccggtggtgg cgggtcaggg ggaggtggaa gcgagcccaa gtcctcagat      300
aagactcata cttgccccc ctgtcccgcc cctgaggccg aaggcgcacc gtcagtgttt       360
ttgttcccac caaagcctaa ggacacactg atgataagca gaacacctga ggtaacctgt      420
gttgttgtgg atgtaagcca cgaagatccg gaggttaagt ttaactggta cgtggacggt      480
gtagaagtcc ataatgctaa gacgaagccg agggaggaac aatacaactc cacgtataga      540
gtggtctccg tcttgaccgt actccatcaa gactggctca cgggaaagga gtacaagtgt      600
aaagtctcta caaagctct tcctgcaccg attgagaaaa ccatatctaa agccaaggga      660
caaccgagag aaccacaggt ttacacgctc ccccccagta gagacgaact tacaaaaaac      720
caggtcagtc ttacctgcct cgtcaaaggc ttctaccct ctgacatcgc tgttgagtgg      780
gaatctaacg gccaacctga gaacaattac aaaacaaccc cgcctgtcct tgactcagac      840
ggttcctttt ttctttacag caagctgacc gtcgacaaat cacggtggca acaaggcaat      900
gtgttttcct gttccgtgat gcacgaggca ctgcacaacc actacactca aaaatccctt      960 tcccttttccc cagggggagg tggagggagc ggtggaggtg gtagcggggg tggaggctca     1020
ggtggtgggg gttccggcgg tggcggaagt ggaggcggtg gctctggtgg tggcggatct     1080
ggcggaggag gcagcggcgg aggtgggtct ggggtggag ctccggagg cggggaagc       1140 ggtggaggag ggtcagagcc caaaagctcc gacaagactc acacatgcc ccccttgtcca      1200 gcgcctgaag ctgagggtgc gccctctgtc ttcctttttc cccctaagcc gaaagatacc     1260
ctgatgatct cccgcactcc cgaagtcaca tgtgttgttg tcgacgtatc tcatgaagat     1320
cctgaggtga aattcaactg gtatgtagac ggggtcgaag ttcataatgc taagactaag     1380
ccacgagaag agcaatacaa ctcaacgtat cgggtggtga cgttctgac ggttctgcac     1440 caagattggc ttaatggaaa agagtataag tgcaaggtgt ccaacaaggc tcttccggca     1500
cccatcgaaa agacgatttc caaagcgaaa ggccaaccta gggaaccgca agtttacact     1560 tgcccccgt caagagacga acttaccaag aatcaagttt ccctgacgtg ccttgtgaag     1620
ggcttctacc ctagcgatat agcagttgag tgggaatcta acggccagcc cgaaaataat     1680
```

```
tataagacta ctccgcccgt gctggacagt gatggttcat ttttcctgta ttcaaaactc    1740
actgtggaca aatctagatg gcagcagggt aatgtgttct cttgttcagt tatgcacgag    1800
gcattgcaca atcactatac gcaaaaaagt ttgtctctct ctccgggg                1848

<210> SEQ ID NO 215
<211> LENGTH: 939
<212> TYPE: DNA
<213> ORGANISM: ARTIFICIAL SEQUENCE
<220> FEATURE:
<223> OTHER INFORMATION: TACI FC

<400> SEQUENCE: 215
gcaatgcgct catgcccaga ggaacaatat tgggatccgc ttcttgggac gtgtatgagc      60
tgcaagacca tctgtaatca tcaatcccaa aggacatgcg cagcttttctg caggagtctc    120 tcttgcagga aagagcaagg caaattttac gaccatcttt gcgagactg tataagctgt    180 gcgtctattt gtggacaaca ccctaaacaa tgtgcttatt tctgtgaaaa taagcttcga    240
tctgagccca aaagctccga caagactcac acatgccccc cttgtccagc gcctgaagct    300
gagggtgcgc cctctgtctt ccttttcccc cctaagccga agataccct gatgatctcc    360 cgcactcccg aagtcacatg tgttgttgtc gacgtatctc atgaagatcc tgaggtgaaa    420
ttcaactggt atgtagacgg ggtcgaagtt cataatgcta agactaagcc acgagaagag    480
caatacaact caacgtatcg ggtggtgagc gttctgacgg ttctgcacca agattggctt    540
aatggaaaag agtataagtg caaggtgtcc aacaaggctc ttccgagctc catcgaaaag    600
acgatttcca aagcgaaagg ccaacctagg gaaccgcaag tttacacttt gccccccgtca    660 agagacgaac ttaccaagaa tcaagttttcc ctgacgtgcc ttgtgaaggg cttctaccct    720
agcgatatag cagttgagtg ggaatctaac ggccagcccg aaaataatta taagactact    780
ccgcccgtgc tggacagtga tggttcattt ttcctgtatt caaaactcac tgtggacaaa    840
tctagatggc agcagggtaa tgtgttctct tgttcagtta tgcacgaggc attgcacaat    900
cactatacgc aaaaaagttt gtctctctct ccggggaag                             939

<210> SEQ ID NO 216
<211> LENGTH: 1920
<212> TYPE: DNA
<213> ORGANISM: ARTIFICIAL SEQUENCE
<220> FEATURE:
<223> OTHER INFORMATION: TACI FC

<400> SEQUENCE: 216
agccgtgtgg accaggagga gcgctttcca cagggcctgt ggacgggggt ggcaatgcgc      60
tcatgcccag aggaacaata tgggatccg cttcttggga cgtgtatgag ctgcaagacc    120
atctgtaatc atcaatccca aaggacatgc gcagctttct gcaggagtct ctcttgcagg    180
aaagagcaag gcaaattttta cgaccatctt tgcgagact gtataagctg tgcgtctatt    240
tgtggacaac accctaaaca atgtgcttat ttctgtgaaa ataagcttcg atctcccgtg    300
aacctgccac ccgagctggg atccggtggt ggcgggtcag ggggaggtgg aagcgagccc    360
aagtcctcag ataagactca tacttgcccc cctgtcccg cccctgaggc cgaaggcgca    420
ccgtcagtgt ttttgttccc accaaagcct aaggacacac tgatgataag cagaacacct    480
gaggtaacct gtgttgttgt ggatgtaagc cacgaagatc cggaggttaa gtttaactgg    540
tacgtggacg gtgtagaagt ccataatgct aagacgaagc cgaggaggga acaatacaac    600
tccacgtata gagtggtctc cgtcttgacc gtactccatc aagactggct caacgggaaa    660
```

| gagtacaagt gtaaagtctc taacaaagct cttcctgcac cgattgagaa aaccatatct | 720 |
| aaagccaagg gacaaccgag agaaccacag gtttacacgc tcccccccag tagagacgaa | 780 |
| cttacaaaaa accaggtcag tcttacctgc ctcgtcaaag gcttctaccc ctctgacatc | 840 |
| gctgttgagt gggaatctaa cggccaacct gagaacaatt acaaaacaac cccgcctgtc | 900 |
| cttgactcag acggttcctt ttttctttac agcaagctga ccgtcgacaa atcacggtgg | 960 |
| caacaaggca atgtgttttc ctgttccgtg atgcacgagg cactgcacaa ccactacact | 1020 |
| caaaaatccc tttcccttc cccagggga ggtggaggga gcggtggagg tggtagcggg | 1080 |
| ggtggaggct caggtggtgg gggttccggc ggtggcggaa gtggaggcgg tggctctggt | 1140 |
| ggtggcggat ctggcggagg aggcagcggc ggaggtgggt ctggggtgg aggctccgga | 1200 |
| ggcggggaa gcgtggagg agggtcagag cccaaaagct ccgacaagac tcacacatgc | 1260 |
| cccccttgtc cagcgcctga agctgagggt gcgccctctg tcttccttttt cccccctaag | 1320 |
| ccgaaagata ccctgatgat ctcccgcact cccgaagtca catgtgttgt tgtcgacgta | 1380 |
| tctcatgaag atcctgaggt gaaattcaac tggtatgtag acggggtcga agttcataat | 1440 |
| gctaagacta agccacgaga agagcaatac aactcaacgt atcgggtggt gagcgttctg | 1500 |
| acggttctgc accaagattg gcttaatgga aaagagtata agtgcaaggt gtccaacaag | 1560 |
| gctcttccgg cacccatcga aaagacgatt ccaaagcga aaggcaaacc tagggaaccg | 1620 |
| caagtttaca ctttgccccc gtcaagagac gaacttacca agaatcaagt ttccctgacg | 1680 |
| tgccttgtga agggcttcta ccctagcgat atagcagttg agtgggaatc taacggccag | 1740 |
| cccgaaaata attataagac tactccgccc gtgctggaca gtgatggttc attttttcctg | 1800 |
| tattcaaaac tcactgtgga caaatctaga tggcagcagg gtaatgtgtt ctcttgttca | 1860 |
| gttatgcacg aggcattgca caatcactat acgcaaaaaa gtttgtctct ctctccgggg | 1920 |

<210> SEQ ID NO 217
<211> LENGTH: 999
<212> TYPE: DNA
<213> ORGANISM: ARTIFICIAL SEQUENCE
<220> FEATURE:
<223> OTHER INFORMATION: TACI FC

<400> SEQUENCE: 217

| agccgtgtgg accaggagga gcgctttcca cagggcctgt ggacgggggt ggcaatgcgc | 60 |
| tcatgcccag aggaacaata ttgggatccg cttcttggga cgtgtatgag ctgcaagacc | 120 |
| atctgtaatc atcaatccca aaggacatgc gcagctttct gcaggagtct ctcttgcagg | 180 |
| aaagagcaag gcaaattta cgaccatctt ttgcgagact gtataagctg tgcgtctatt | 240 |
| tgtggacaac accctaaaca atgtgcttat ttctgtgaaa ataagcttcg atctcccgtg | 300 |
| aacctgccac ccgagctgga caagactcac acatgccccc cttgtccagc gcctgaagct | 360 |
| gagggtgcgc cctctgtctt ccttttcccc cctaagccga agatacccct gatgatctcc | 420 |
| cgcactcccg aagtcacatg tgttgttgtc gacgtatctc atgaagatcc tgaggtgaaa | 480 |
| ttcaactggt atgtagacgg ggtcgaagtt cataatgcta agactaagcc acgagaagag | 540 |
| caatacaact caacgtatcg ggtggtgagc gttctgacgg ttctgcacca agattggctt | 600 |
| aatggaaaag agtataagtg caaggtgtcc aacaaggctc ttccgagctc catcgaaaag | 660 |
| acgatttcca aagcgaaagg ccaacctagg gaaccgcaag tttacacttt gccccgtca | 720 |
| agagacgaac ttaccaagaa tcaagtttcc ctgacgtgcc ttgtgaaggg cttctaccct | 780 |

-continued

```
agcgatatag cagttgagtg ggaatctaac ggccagcccg aaaataatta taagactact    840
ccgcccgtgc tggacagtga tggttcattt ttcctgtatt caaaactcac tgtggacaaa    900
tctagatggc agcagggtaa tgtgttctct tgttcagtta tgcacgaggc attgcacaat    960
cactatacgc aaaaagttt gtctctctct ccggggaag                            999
```

<210> SEQ ID NO 218
<211> LENGTH: 522
<212> TYPE: PRT
<213> ORGANISM: ARTIFICIAL SEQUENCE
<220> FEATURE:
<223> OTHER INFORMATION: FC VARIANT

<400> SEQUENCE: 218

```
Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Ser Gly Gly Gly Gly
225                 230                 235                 240

Ser Gly Gly Gly Gly Ser Gly Gly Gly Gly Ser Gly Gly Gly Gly Ser
                245                 250                 255

Gly Gly Gly Gly Ser Gly Gly Gly Ser Gly Gly Gly Gly Ser Gly
            260                 265                 270

Gly Gly Gly Ser Gly Gly Gly Ser Gly Gly Gly Gly Ser Gly Gly
        275                 280                 285

Gly Gly Ser Glu Pro Lys Ser Ser Asp Lys Thr His Thr Cys Pro Pro
    290                 295                 300

Cys Pro Ala Pro Glu Ala Glu Gly Ala Pro Ser Val Phe Leu Phe Pro
305                 310                 315                 320

Pro Lys Pro Lys Asp Thr Leu Met Ile Ser Arg Thr Pro Glu Val Thr
```

|  |  |  |  | 325 |  |  |  | 330 |  |  |  | 335 |  |  |
|--|--|--|--|--|--|--|--|--|--|--|--|--|--|--|

Cys Val Val Asp Val Ser His Glu Asp Pro Glu Val Lys Phe Asn
         340                 345                 350

Trp Tyr Val Asp Gly Val Glu Val His Asn Ala Lys Thr Lys Pro Arg
         355                 360                 365

Glu Glu Gln Tyr Asn Ser Thr Tyr Arg Val Val Ser Val Leu Thr Val
    370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
                405                 410                 415

Gly Gln Pro Arg Glu Pro Gln Val Tyr Thr Leu Pro Pro Ser Arg Asp
         420                 425                 430

Glu Leu Thr Lys Asn Gln Val Ser Leu Thr Cys Leu Val Lys Gly Phe
         435                 440                 445

Tyr Pro Ser Asp Ile Ala Val Glu Trp Glu Ser Asn Gly Gln Pro Glu
    450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
         500                 505                 510

Thr Gln Lys Ser Leu Ser Leu Ser Pro Gly
         515                 520

<210> SEQ ID NO 219
<211> LENGTH: 222
<212> TYPE: PRT
<213> ORGANISM: ARTIFICIAL SEQUENCE
<220> FEATURE:
<223> OTHER INFORMATION: FC VARIANT

<400> SEQUENCE: 219

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Asp Val Ser His Glu Asp Pro Glu
         35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
         115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ser Val Glu Trp Glu Ser Asn
145                 150                 155                 160

Gly Gln Pro Glu Asn Asn Tyr Lys Thr Thr Pro Pro Met Leu Asp Ser

```
                    165                 170                 175
Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly
            210                 215                 220

<210> SEQ ID NO 220
<211> LENGTH: 228
<212> TYPE: PRT
<213> ORGANISM: ARTIFICIAL SEQUENCE
<220> FEATURE:
<223> OTHER INFORMATION: FC VARIANT

<400> SEQUENCE: 220

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 221
<211> LENGTH: 226
<212> TYPE: PRT
<213> ORGANISM: ARTIFICIAL SEQUENCE
<220> FEATURE:
<223> OTHER INFORMATION: FC VARIANT

<400> SEQUENCE: 221

Asp Lys Thr His Thr Cys Pro Pro Cys Pro Ala Pro Glu Ala Glu Gly
1               5                   10                  15
```

```
Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly
225

<210> SEQ ID NO 222
<211> LENGTH: 281
<212> TYPE: PRT
<213> ORGANISM: ARTIFICIAL SEQUENCE
<220> FEATURE:
<223> OTHER INFORMATION: TACI VARIANT

<400> SEQUENCE: 222

Ser Leu Ser Cys Arg Lys Glu Glu Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
 50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140
```

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 223
<211> LENGTH: 281
<212> TYPE: PRT
<213> ORGANISM: ARTIFICIAL SEQUENCE
<220> FEATURE:
<223> OTHER INFORMATION: TACI VARIANT

<400> SEQUENCE: 223

Ser Leu Ser Cys Arg Lys Glu Glu Gly Glu Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

-continued

```
Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
        260                 265                 270

Gln Lys Ser Leu Ser Leu Ser Pro Gly
    275                 280
```

<210> SEQ ID NO 224
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 224

```
Ser Leu Ser Cys Arg Lys Glu Glu Gly Lys Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280
```

<210> SEQ ID NO 225
<211> LENGTH: 281

```
<212> TYPE: PRT
<213> ORGANISM: ARTIFICIAL SEQUENCE
<220> FEATURE:
<223> OTHER INFORMATION: TACI FC

<400> SEQUENCE: 225

Ser Leu Ser Cys Arg Lys Glu Glu Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Asp Tyr Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
            275                 280

<210> SEQ ID NO 226
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 226

Ser Leu Ser Cys Arg Lys Glu Glu Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
            35                  40                  45
```

```
Gly Ser Glu Pro Lys Ser Ser Asp Lys Thr His Thr Cys Pro Pro Cys
        50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly
        275                 280

<210> SEQ ID NO 227
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 227

Ser Leu Ser Cys Arg Lys Glu Gln Gly Glu Tyr Tyr Asp His Leu Leu
1               5                   10                  15

Gln Asp Cys Ile Ser Cys Ala Ser Ile Cys Gly Gln His Pro Lys Gln
                20                  25                  30

Cys Ala Tyr Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
        50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125
```

```
Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 228
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 228

Ser Leu Ser Cys Arg Lys Glu Gln Gly Lys Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205
```

```
Pro Ser Asp Ile Ala Val Glu Trp Glu Ser Asn Gly Gln Pro Glu Asn
        210                 215                 220

Asn Tyr Lys Thr Thr Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly
                275                 280

<210> SEQ ID NO 229
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 229

Ser Leu Ser Cys Arg Lys Glu Gln Gly Lys Tyr Tyr Asp His Leu Leu
1               5                   10                  15

Gln Asp Cys Ile Ser Cys Ala Ser Ile Cys Gly Gln His Pro Lys Gln
                20                  25                  30

Cys Ala Tyr Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
        50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
        210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly
                275                 280
```

```
<210> SEQ ID NO 230
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 230

Ser Leu Ser Cys Arg Lys Glu Gln Gly Lys Tyr Tyr Asp His Leu Leu
1               5                   10                  15

Arg Asp Cys Ile Ser Cys Ala Ser Ile Cys Gly Gln His Pro Lys Gln
            20                  25                  30

Cys Asp Tyr Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 231
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 231

Ser Leu Ser Cys Arg Lys Glu Gln Gly Lys Tyr Tyr Asp His Leu Leu
1               5                   10                  15

Arg Asp Cys Ile Ser Cys Ala Ser Ile Cys Gly Gln His Pro Lys Gln
```

```
            20                  25                  30
Cys Ala Asp Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
        50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 232
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 232

Ser Leu Ser Cys Arg Lys Glu Gln Gly Lys Phe Tyr Asp His Leu Leu
1               5                   10                  15

Gln Asp Cys Ile Ser Cys Ala Ser Ile Cys Gly Gln His Pro Lys Gln
            20                  25                  30

Cys Asp Tyr Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
        50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
```

```
            100                 105                 110
Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
            165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
            260                 265                 270

Gln Lys Ser Leu Ser Leu Ser Pro Gly
            275                 280

<210> SEQ ID NO 233
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 233

Ser Leu Ser Cys Arg Lys Glu Gln Gly Lys Phe Tyr Asp His Leu Leu
1               5                   10                  15

Gln Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
        50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
            165                 170                 175

Gln Pro Arg Glu Pro Gln Val Tyr Thr Leu Pro Pro Ser Arg Asp Glu
```

```
                180                 185                 190
Leu Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
            260                 265                 270

Gln Lys Ser Leu Ser Leu Ser Pro Gly
            275                 280

<210> SEQ ID NO 234
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 234

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Asp Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
            165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
```

Gln Lys Ser Leu Ser Leu Ser Pro Gly
        275                 280

<210> SEQ ID NO 235
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 235

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
        35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 236
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 236

```
Ser Leu Ser Cys Arg Lys Glu Gln Gly Glu Tyr Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
            260                 265                 270

Gln Lys Ser Leu Ser Leu Ser Pro Gly
        275                 280

<210> SEQ ID NO 237
<211> LENGTH: 281
<212> TYPE: PRT
<213> ORGANISM: ARTIFICIAL SEQUENCE
<220> FEATURE:
<223> OTHER INFORMATION: TACI FC

<400> SEQUENCE: 237

Ser Leu Ser Cys Arg Lys Glu Gln Gly Glu Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Asp Phe Cys Glu Asn Lys Leu Arg Ser Gly Ser Gly Gly Gly
            35                  40                  45

Gly Ser Glu Pro Lys Ser Ser Asp Lys Thr His Thr Cys Pro Pro Cys
    50                  55                  60

Pro Ala Pro Glu Ala Glu Gly Ala Pro Ser Val Phe Leu Phe Pro Pro
65                  70                  75                  80
```

-continued

```
Lys Pro Lys Asp Thr Leu Met Ile Ser Arg Thr Pro Glu Val Thr Cys
            85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
            130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
            180                 185                 190

Leu Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly
            275                 280

<210> SEQ ID NO 238
<211> LENGTH: 5
<212> TYPE: PRT
<213> ORGANISM: ARTIFICIAL SEQUENCE
<220> FEATURE:
<223> OTHER INFORMATION: Hinge

<400> SEQUENCE: 238

Glu Pro Lys Ser Ser
1               5

<210> SEQ ID NO 239
<211> LENGTH: 5
<212> TYPE: PRT
<213> ORGANISM: artificial sequence
<220> FEATURE:
<223> OTHER INFORMATION: hinge

<400> SEQUENCE: 239

Glu Pro Lys Ser Cys
1               5
```

APRIL AND BAFF INHIBITORY IMMUNOMODULATORY PROTEINS AND METHODS OF USE THEREOF

CROSS REFERENCE TO RELATED APPLICATIONS

This application is a continuation of U.S. patent application Ser. No. 17/315,168, filed May 7, 2021, which claims priority to U.S. provisional application 63/022,373 entitled "APRIL AND BAFF INHIBITORY IMMUNOMODULATORY PROTEINS WITH AND WITHOUT A T CELL INHIBITORY PROTEIN AND METHODS OF USE THEREOF", filed May 8, 2020, to U.S. provisional application 63/034,361, entitled "APRIL AND BAFF INHIBITORY IMMUNOMODULATORY PROTEINS WITH AND WITHOUT A T CELL INHIBITORY PROTEIN AND METHODS OF USE THEREOF", filed Jun. 3, 2020, and to U.S. provisional application 63/080,643, entitled "APRIL AND BAFF INHIBITORY IMMUNOMODULATORY PROTEINS WITH AND WITHOUT A T CELL INHIBITORY PROTEIN AND METHODS OF USE THEREOF", filed Sep. 18, 2020, the contents of each of which are incorporated by reference in their entirety for all purposes.

INCORPORATION BY REFERENCE OF SEQUENCE LISTING

The present application is being filed along with a Sequence Listing in electronic format. The Sequence Listing is provided as a file 761612003801SubSeqList.TXT, created Jul. 21, 2021, which is 278,640 bytes in size. The information in the electronic format of the Sequence Listing is incorporated by reference in its entirety.

FIELD

The present disclosure provides immunomodulatory proteins that exhibit neutralizing activity of BAFF and APRIL (or BAFF/APRIL heterotrimers). The immunomodulatory proteins include variant domains of Transmembrane Activator and CAML Interactor (TACI). Among the provided immunomodulatory proteins are TACI-Fc fusion proteins. The present disclosure also provides nucleic acid molecules encoding the immunomodulatory proteins. The immunomodulatory proteins provide therapeutic utility for a variety of immunological diseases, disorders or conditions. Compositions and methods for making and using such proteins are provided.

BACKGROUND

Modulation of the immune response by intervening in processes involving interactions between soluble ligands and their receptors is of increasing medical interest. Currently, biologics used to enhance or suppress immune responses have generally been limited to antibodies (e.g., anti-PD-1 antibodies) or soluble receptors against a single cell surface molecule (e.g., Fc-CTLA-4). Improved therapeutic agents that can modulate the immune response, and particularly B cell immune responses, are needed. Provided are embodiments that meet such needs.

SUMMARY

Provided herein is an immunomodulatory protein containing at least one TACI polypeptide that is a truncated wild-type TACI extracellular domain or is a variant thereof, wherein the truncated wild-type TACI extracellular domain contains the cysteine rich domain 2 (CRD2) but lacks the entirety of the cysteine rich domain 1 (CRD1), wherein the variant TACI polypeptide comprises one or more amino acid substitutions in the truncated wild-type TACI extracellular domain.

Provided herein is an immunomodulatory protein containing at least one TACI polypeptide that is a truncated wild-type TACI extracellular domain or is a variant thereof, wherein the truncated wild-type TACI extracellular domain consists of a contiguous sequence contained within amino acid residues 67-118 that consists of amino acid residues 71-104, with reference to positions set forth in SEQ ID NO:122, wherein the variant TACI polypeptide comprises one or more amino acid substitutions in the truncated wild-type TACI extracellular domain. In some of any embodiments, the truncated wild-type TACI extracellular domain is 35, 36, 37, 38, 39, 40, 41, 42, 43, 44, 45, 46, 47, 48, 59, 50 or 51 amino acids in length. In some of any embodiments, the truncated wild-type TACI extracellular domain consists of amino acid residues 68-110 set forth in SEQ ID NO: 122. In some of any embodiments, the TACI polypeptide consists of the sequence of amino acid set forth in SEQ ID NO:13 or is a variant thereof containing one or more amino acid substitutions in the sequence set forth in SEQ ID NO: 13.

Provided herein is an immunomodulatory protein containing at least one TACI polypeptide that is a truncated TACI polypeptide consisting of the sequence of amino acid set forth in SEQ ID NO: 13 or a variant thereof containing one or more amino acid substitutions in the sequence set forth in SEQ ID NO: 13. In some of any embodiments, the truncated TACI polypeptide or the variant thereof binds to APRIL, BAFF, or a BAFF/APRIL heterotrimer. In some of any embodiments, the TACI polypeptide is a truncated wild-type TACI extracellular domain that consists of the sequence set forth in SEQ ID NO: 1. In some of any embodiments, the TACI polypeptide is a truncated wild-type TACI extracellular domain that consists of the sequence set forth in SEQ ID NO: 13.

Provided herein is an immunomodulatory protein containing a truncated TACI polypeptide consisting of the sequence set forth in SEQ ID NO: 13. In some of any embodiments, the TACI polypeptide is the variant TACI polypeptide, wherein the variant TACI polypeptide has increased binding affinity to one or both of APRIL and BAFF compared to the truncated TACI polypeptide. In some of any embodiments, the variant TACI polypeptide comprises one or more amino acid substitutions at positions selected from among 74, 75, 76, 77, 78, 79, 82, 83, 84, 85, 86, 87, 88, 92, 95, 97, 98, 99, 101, 102 and 103, corresponding to numbering set forth in SEQ ID NO: 122.

In some of any embodiments, the one or more amino acid substitutions are selected from E74V, Q75E, Q75R, G76S, K77E, F78Y, Y79F, L82H, L82P, L83S, R84G, R84L, R84Q, D85E, D85V, C86Y, I87L, I87M, S88N, I92V, Q95R, P97S, K98T, Q99E, A101D, Y102D, F103S, F103V, F103Y, or a conservative amino acid substitution thereof. In some of any embodiments, the one or more amino acid substitutions comprise at least one of E74V, K77E, Y79F, L82H, L82P, R84G, R84L, R84Q, D85V, or C86Y. In some of any embodiments, the one or more amino acid substitutions are D85E/K98T, I87L/K98T, L82P/I87L, G76S/P97S, K77E/R84L/F103Y, Y79F/Q99E, L83S/F103S, K77E/R84Q, K77E/A101D, K77E/F78Y/Y102D, Q75E/R84Q, Q75R/R84G/I92V, K77E/A101D/Y102D, R84Q/S88N/A101D, R84Q/F103V, K77E/Q95R/A101D or I87M/A101D. In some embodiments, the one or more amino acid substitutions are K77E/F78Y/Y102D. In some embodiments, the one or more amino acid substitutions are Q75E/R84Q. In some embodiments, the variant TACI polypeptide is set forth in SEQ ID NO: 26. In some embodiments, the variant TACI polypeptide is set forth in SEQ ID NO:27.

In some of any embodiments, the TACI polypeptide is a variant TACI polypeptide that comprises one or more amino acid substitutions in the extracellular domain (ECD) of a reference TACI polypeptide or a specific binding fragment thereof at positions selected from among 40, 59, 60, 61, 74, 75, 76, 77, 78, 79, 82, 83, 84, 85, 86, 87, 88, 92, 95, 97, 98, 99, 101, 102 and 103, corresponding to numbering of positions set forth in SEQ ID NO:122.

Provided herein is an immunomodulatory protein containing at least one variant TACI polypeptide, wherein the at least one variant TACI polypeptide comprises one or more amino acid substitutions in the extracellular domain (ECD) of a reference TACI polypeptide or a specific binding fragment thereof at positions selected from among 40, 59, 60, 61, 74, 75, 76, 77, 78, 79, 82, 83, 84, 85, 86, 87, 88, 92, 95, 97, 98, 99, 101, 102 and 103, corresponding to numbering of positions set forth in SEQ ID NO:122.

Provided herein is an immunomodulatory protein that is a variant TACI-Fc fusion protein containing a variant TACI polypeptide, an Fc region, and a linker between the TACI polypeptide and Fc region, wherein the variant TACI polypeptide comprises one or more amino acid substitutions in the extracellular domain (ECD) of a reference TACI polypeptide or a specific binding fragment thereof at positions selected from among 40, 59, 60, 61, 74, 75, 76, 77, 78, 79, 82, 83, 84, 85, 86, 87, 88, 92, 95, 97, 98, 99, 101, 102 and 103, corresponding to numbering of positions set forth in SEQ ID NO:122.

In some of any embodiments, the reference TACI polypeptide is a truncated polypeptide consisting of the extracellular domain of TACI or a specific binding portion thereof that binds to APRIL, BAFF, or a BAFF/APRIL heterotrimer.

In some of any embodiments, the reference TACI polypeptide comprises (i) the sequence of amino acids set forth in SEQ ID NO:122, (ii) a sequence of amino acids that has at least 95% sequence identity to SEQ ID NO:122; or (iii) a portion of (i) or (ii) containing one or both of a CRD1 domain and CRD2 domain that binds to APRIL, BAFF, or a BAFF/APRIL heterotrimer.

In some of any embodiments, the reference TACI polypeptide lacks an N-terminal methionine.

In some of any embodiments, the reference TACI polypeptide comprises the CRD1 domain and the CRD2 domain.

In some of any embodiments, the reference TACI polypeptide comprises the sequence set forth in SEQ ID NO:1. In some of any embodiments, the reference TACI polypeptide consists of the sequence set forth in SEQ ID NO:1.

In some of any embodiments, the reference TACI polypeptide consists essentially of the CRD2 domain.

In some of any embodiments, reference TACI polypeptide comprises the sequence set forth in SEQ ID NO:13. In some of any embodiments, the reference TACI polypeptide consists of the sequence set forth in SEQ ID NO:13.

In some of any embodiments, the one or more amino acid substitutions are selected from W40R, Q59R, R60G, T61P E74V, Q75E, Q75R, G76S, K77E, F78Y, Y79F, L82H, L82P, L83S, R84G, R84L, R84Q, D85E, D85V, C86Y, I87L, I87M, S88N, I92V, Q95R, P97S, K98T, Q99E, A101D, Y102D, F103S, F103V, F103Y, or a conservative amino acid substitution thereof.

In some of any embodiments, the one or more amino acid substitutions comprise at least one of E74V, K77E, Y79F, L82H, L82P, R84G, R84L, R84Q, D85V or C86Y.

In some of any embodiments, the one or more amino acid substitutions comprise an amino acid substitution selected from the group consisting of Q75E, K77E, F78Y, R84G, R84Q, A101D and Y102D, or any combination thereof.

In some of any embodiments, the one or more amino acid substitution comprises at least the amino acid substitution Q75E. In some of any embodiments, the one or more amino acid substitution comprises at least the amino acid substitution K77E. In some of any embodiments, the one or more amino acid substitution comprises at least the amino acid substitution F78Y. In some of any embodiments, the one or more amino acid substitution comprises at least the amino acid substitution R84G. In some of any embodiments, the one or more amino acid substitution comprises at least the amino acid substitution R84Q. In some of any embodiments, the one or more amino acid substitution comprises at least the amino acid substitution A101D.

In some of any embodiments, the one or more amino acid substitutions comprise Q75E/R84Q. In some of any embodiments, the one or more amino acid substitutions comprise Q75E/K77E. In some of any embodiments, the one or more amino acid substitutions comprise Q75E/F78Y. In some of any embodiments, the one or more amino acid substitutions comprise Q75E/A101D. In some of any embodiments, the one or more amino acid substitutions comprise Q75E/Y102D. In some of any embodiments, the one or more amino acid substitutions comprise F77E/F78Y. In some of any embodiments, the one or more amino acid substitutions comprise K77E/R84Q. In some of any embodiments, the one or more amino acid substitutions comprise K77E/A101D. In some of any embodiments, the one more amino acid substitutions comprise K77E/Y102D. In some of any embodiments, the one or more amino acid substitutions comprise F78Y/R84Q. In some of any embodiments, the one or more amino acid substitutions comprise F78Y/A101D. In some of any embodiments, the one or more amino acid substitutions comprise F78Y/Y102D. In some of any embodiments, the one or more amino acid substitutions comprise R84Q/A101D. In some of any embodiments, the one or more amino acid substitutions comprise R84Q/Y102D. In some of any embodiments, the one or more amino acid substitutions comprise A101D/Y102D.

In some of any embodiments, the one or more amino acid substitutions are D85E/K98T, I87L/K98T, R60G/Q75E/L82P, R60G/C86Y, W40R/L82P/F103Y, W40R/Q59R/T61P/K98T, L82P/I87L, G76S/P97S, K77E/R84L/F103Y, Y79F/Q99E, L83S/F103S, K77E/R84Q, K77E/A101D, K77E/F78Y/Y102D, Q75E/R84Q, Q75R/R84G/I92V, K77E/A101D/Y102D, R84Q/S88N/A101D, R84Q/F103V, K77E/Q95R/A101D or I87M/A101D.

In some of any embodiments, the one or more amino acid substitutions are R84G, A101D, K77E/R84Q, K77E/A101D, K77E/F78Y, K77E/F78Y/Y102D, Q75E/R84Q, K77E/A101D/Y102D, R84Q, K77E, A101D, Q75E, K77E/F78Y/R84Q, F78Y, F78Y/R84Q, F78Y/A101D, F78Y/Y102D, or K77E/Y102D.

In some of any embodiments, the one or more amino acid substitutions are K77E/F78Y/Y102D.

In some of any embodiments, the one or more amino acid substitutions are Q75E/R84Q.

In some of any embodiments, the one or more amino acid substitutions are K77E/A101D/Y102D.

In some of any embodiments, the variant TACI polypeptide has up to 10 amino acid modifications compared to the reference TACI polypeptide. In some of any embodiments, the variant TACI polypeptide has up to 5 amino acid modifications compared to the reference TACI polypeptide.

In some of any embodiments, the variant TACI polypeptide has at least 90% sequence identity to SEQ ID NO:122 or a specific binding fragment thereof comprising the CRD1 domain and/or CRD2 domain. In some embodiments, the variant TACI polypeptide has at least 95% sequence identity to SEQ ID NO:122 or a specific binding fragment thereof comprising the CRD1 domain and/or CRD2 domain. In some embodiments, the specific binding fragment is set forth in SEQ ID NO:1, SEQ ID NO:13, SEQ ID NO:130 or SEQ ID NO:131.

In some of any embodiments, the variant TACI polypeptide has at least 90% sequence identity to SEQ ID NO:13. In some of any embodiments, the variant TACI polypeptide has at least 95% sequence identity to SEQ ID NO:13.

In some of any embodiments, the variant TACI polypeptide has increased binding affinity to one or both of APRIL and BAFF compared to the reference TACI polypeptide. In some of any embodiments, the variant TACI polypeptide has increased binding affinity to APRIL. In some of any embodiments, the variant TACI polypeptide has increased binding affinity to BAFF. In some of any embodiments, the variant TACI polypeptide has increased binding affinity to APRIL and BAFF.

In some of any embodiments, the increased binding affinity for BAFF or APRIL is independently increased more than about 1.2-fold, about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold or about 60-fold.

In some of any embodiments, the variant TACI polypeptide comprises the sequence set forth in any one of SEQ ID NOS: 2-12, 21, 22, 101-120; or the variant TACI polypeptide comprises the sequence set forth in any one of SEQ ID NOS: 14-20, 23-35, 92-100 or 177-192.

In some of any embodiments, the variant TACI polypeptide consists or consists essentially of the sequence set forth in any one of SEQ ID NOS: 2-12, 21, 22, 101-120; or the variant TACI polypeptide consists or consists essentially of the sequence set forth in any one of SEQ ID NOS: 14-20, 23-35, 92-100 or 177-192.

In some of any embodiments, the variant TACI polypeptide consists or consists essentially of the sequence set forth in SEQ ID NO: 26. In some of any embodiments, the variant TACI polypeptide consists or consists essentially of the sequence set forth in SEQ ID NO:27. In some of any embodiments, the variant TACI polypeptide consists or consists essentially of the sequence set forth in SEQ ID NO:107. In some of any embodiments, the variant TACI polypeptide consists or consists essentially of the sequence set forth in SEQ ID NO:20.

In some of any embodiments, the linker comprises a peptide linker and the peptide linker is selected from GSGGS (SEQ ID NO: 76), GGGGS (G45; SEQ ID NO: 77), GSGGGGS (SEQ ID NO: 74), GGGGSGGGGS (2×GGGGS; SEQ ID NO: 78), GGGGSGGGGSGGGGS (3×GGGGS; SEQ ID NO: 79), GGGGSGGGGSGGGGSGGGGS (4×GGGGS, SEQ ID NO:84), GGGGSGGGGSGGGGSGGGGSGGGGS (5×GGGGS, SEQ ID NO: 91), GGGGSSA (SEQ ID NO: 80), or GSGGGGSGGGGS (SEQ ID NO:194) or combinations thereof.

In some of any embodiments, the immunomodulatory protein contains a heterologous moiety that is linked to the at least one TACI polypeptide. In some of any embodiments, the heterologous moiety is a half-life extending moiety, a multimerization domain, a targeting moiety that binds to a molecule on the surface of a cell, or a detectable label. In some of any embodiments, the half-life extending moiety comprises a multimerization domain, albumin, an albumin-binding polypeptide, Pro/Ala/Ser (PAS), a C-terminal peptide (CTP) of the beta subunit of human chorionic gonadotropin, polyethylene glycol (PEG), long unstructured hydrophilic sequences of amino acids (XTEN), hydroxyethyl starch (HES), an albumin-binding small molecule, or a combination thereof. In some of any embodiments, the at least one TACI polypeptide is linked to an Fc region of an immunoglobulin. In some embodiments, the immunomodulatory protein of any of the embodiments provided herein that is a TACI-Fc fusion protein includes at least one TACI polypeptide linked to an Fc region of an immunoglobulin.

In some embodiments, an immunomodulatory protein provided herein does not include a TACI polypeptide linked to another targeting moiety that binds to a molecule on the surface of a cell. In some embodiments, an immunomodulatory protein provided herein does not include a TACI polypeptide linked to a targeting moiety that is a binding partner of a T cell stimulatory receptor or a ligand of a T cell stimulatory receptor. In some embodiments, an immunomodulatory protein provided herein does not include a TACI polypeptide linked to a targeting moiety that is a binding partner of CD28 or a ligand of CD28 (e.g. CD80 or CD86). In some embodiments, an immunomodulatory protein provided herein does not include a TACI polypeptide linked to CTLA-4 polypeptide or an extracellular domain or binding portion of CTLA-4, or a variant thereof. For instance, in provided aspects, an immunomodulatory protein provided herein does not include a TACI polypeptide linked to a wild-type CTLA-4 polypeptide or an extracellular domain or binding portion thereof. In provided aspects, an immunomodulatory protein provided herein does not include a TACI polypeptide linked to a variant CTLA-4 polypeptide or an extracellular domain or binding portion thereof, such as a variant CTLA-4 or binding portion thereof containing one or more amino acid modifications (e.g. substitutions) in the extracellular domain of CTLA-4, e.g. to increase binding affinity to one or more cognate binding partner.

In some of any embodiments, the immunoglobulin Fc is an IgG4 Fc domain, or is a variant thereof. In some embodiments, the IgG4 Fc domain has the amino acid sequence set forth in SEQ ID NO:139. In some embodiments, the IgG4 Fc domain is a variant thereof containing the mutations S228P. In some embodiments, the IgG4 Fc domain has the amino acid sequence set forth in SEQ ID NO:140 or SEQ ID NO:220.

In some of any embodiments, the Fc fusion protein of a TACI-Fc is a dimer. In some of any embodiments, the immunoglobulin Fc region is a homodimeric Fc region.

In some of any embodiments, the immunoglobulin Fc is an IgG1 Fc domain, or is a variant Fc that exhibits reduced binding affinity to an Fc receptor and/or reduced effector function, optionally as compared to a wild-type IgG1 Fc domain. In some of any embodiments, the immunoglobulin Fc is set forth in SEQ ID NO:71. In some embodiments, the immunoglobulin Fc is an IgG1 Fc domain, and the Fc includes the amino acid sequence set forth in SEQ ID NO: 81. In some of any embodiments, the immunoglobulin Fc is a variant IgG1 Fc domain containing one or more amino acid substitutions selected from L234A, L234V, L235A, L235E, G237A, S267K, R292C, N297G, and V302C, by EU numbering. In some of any embodiments, the immunoglobulin Fc region contains the amino acid substitutions L234A, L235E an G237A by EU numbering or the amino acid substitutions R292C, N297G and V302C by EU numbering. In some embodiments, the Fc region comprises the amino acid substitutions L234A, L235E an G237A by EU numbering. In some embodiments, the Fc region the Fc region is set forth in SEQ ID NO: 73, 75, 83, 136 or 221. In some embodiments, the immunoglobulin Fc region further comprises the amino acid substitutions A330S and P331S. In some embodiments, the immunoglobuline Fc region is set forth in SEQ ID NO:175 or SEQ ID NO:176.

In some embodiments, the Fc is a variant Fc including the amino acid sequence set forth in SEQ ID NO:73.

In some of any embodiments, the immunomodulatory protein is a heterodimer, wherein each polypeptide of the dimer is linked to an immunoglobulin Fc domain individually containing one or more amino acid modifications in a wild-type Fc domain to effect heterodimer formation between the polypeptides. In some of any embodiments, the wild-type immunoglobulin Fc is an IgG1 Fc domain. In some of any embodiments, the one more amino acid modifications are selected from a knob-into-hole modification and a charge mutation to reduce or prevent self-association due to charge repulsion.

In some of any embodiments, the immunomodulatory protein contains one or more amino acid substitutions to reduced binding affinity to an Fc receptor and/or reduced effector function, optionally as compared to a wild-type IgG1 Fc domain. In some of any embodiments, the one or more amino acid substitutions are selected from L234A, L234V, L235A, L235E, G237A, S267K, R292C, N297G, and V302C, by EU numbering. In some of any embodiments, the immunoglobulin Fc region contains the amino acid substitutions L234A, L235E an G237A by EU numbering or the amino acid substitutions R292C, N297G and V302C by EU numbering.

In some of any embodiments, the TACI-Fc fusion protein comprises the structure: TACI polypeptide (TACI)-Linker-Fc region. In some embodiments, the TACI-Fc fusion protein is set forth in SEQ ID NO: 168. In some embodiments, the TACI-Fc fusion protein is set forth in SEQ ID NO:170. In some embodiments, the TACI-Fc fusion protein is set forth in SEQ ID NO: 167. In some embodiments, the TACI-Fc fusion protein is set forth in SEQ ID NO:169. In some embodiments, the immunomodularoy protein is a homodimer comprising two identical copies of the TACI-Fc fusion protein.

Provided herein is an immunomodulatory TACI-Fc fusion protein that is a homodimer comprising two identical copies of the TACI-Fc fusion protein set forth in SEQ ID NO:167 linked by a covalent disulfide bond.

Provided herein is an immunomodulatory TACI-Fc fusion protein that is a homodimer comprising two identical copies of the TACI-Fc fusion protein set forth in SEQ ID NO: 168 linked by a covalent disulfide bond.

Provided herein is an immunomodulatory TACI-Fc fusion protein that is a homodimer comprising two identical copies of the TACI-Fc fusion protein set forth in SEQ ID NO:169 linked by a covalent disulfide bond.

Provided herein is an immunomodulatory TACI-Fc fusion protein that is a homodimer comprising two identical copies of the TACI-Fc fusion protein set forth in SEQ ID NO:170 linked by a covalent disulfide bond.

In some of any embodiments, the TACI-Fc fusion protein comprises the structure: (TACI)-Linker-Fc region-Linker-(TACI). In some embodiments, the TACI-Fc fusion protein is set forth in SEQ ID NO: 201. In some embodiments, the TACI-Fc fusion protein is set forth in SEQ ID NO: 202. In some embodiments, the immunomodularoy protein is a homodimer comprising two identical copies of the TACI-Fc fusion protein.

In some of any embodiments, the TACI-Fc fusion protein comprises the structure: (TACI)-Linker-(TACI)-Linker-Fc region. In some embodiments, the TACI-Fc fusion protein is set forth in SEQ ID NO: 198. In some embodiments, the immunomodularoy protein is a homodimer comprising two identical copies of the TACI-Fc fusion protein.

In some of any embodiments, the immunomodulatory protein (e.g. Fc fusion protein) blocks binding of APRIL, BAFF, or an APRIL/BAFF heterotrimer to BCMA or TACI; and the immunomodulatory protein reduces the levels of circulating APRIL, BAFF, or an APRIL/BAFF in the blood following administration to a subject. In some of any embodiments, the immunomodulatory protein (e.g. Fc fusion protein) blocks binding of APRIL, BAFF, or an APRIL/BAFF heterotrimer to BCMA or TACI. In some of any embodiments, the immunomodulatory protein (e.g. Fc fusion protein) reduces the levels of circulating APRIL, BAFF, or an APRIL/BAFF in the blood following administration to a subject.

In some of any embodiments, the immunomodulatory protein (e.g. Fc fusion protein) reduces or inhibits B cell maturation, differentiation and proliferation. In some of any embodiments, the immunomodulatory protein reduces or inhibits B cell maturation, differentiation or proliferation.

In some embodiments, the Fc fusion protein neutralizes APRIL and BAFF. In some embodiments, the IC50 for neutralizing APRIL is less than 100 pM, less than 50 pM, less than 40 pM, less than 30 pM, less than 20 pM, less than 10 pM, less than 5 pM or less than 1 pM, or is any value between any of the foregoing; and/or the IC50 for neutralizing BAFF is less than 400 pM, less than 300 pM, less than 200 pM, less than 100 pM, less than 75 pM, less than 50 pM, less than 25 pm, or less than 10 pM, or is any value between any of the foregoing.

Provided herein is a nucleic acid molecule(s) encoding the immunomodulatory protein (e.g. Fc fusion protein) of any of the embodiments described herein. In some of any embodiments, the nucleic acid molecule is a synthetic nucleic acid. In some of any embodiments, the nucleic acid molecule is a cDNA.

Provided herein is a vector, containing the nucleic acid molecule of any of the embodiments described herein. In some of any embodiments, the vector is an expression vector. In some of any embodiments, the vector is a mammalian expression vector or a viral vector.

Provided herein is a cell, containing the nucleic acid of any of any of the embodiments described herein or the vector of any of any of embodiments described herein. In some of any embodiments, the cell is a mammalian cell. In some of any embodiments, the cell is a human cell.

Provided herein is a method of producing an immunomodulatory protein, containing introducing the nucleic acid molecule of any of any of the embodiments described herein or vector of any of any of the embodiments described herein into a host cell under conditions to express the protein in the cell. In some of any embodiments, the method includes isolating or purifying the immunomodulatory protein (e.g. Fc fusion protein) from the cell. Provided herein is a method of producing an Fc fusion protein, including introducing the nucleic acid molecule of any of the embodiments provided herein or vector of any of any of the embodiments provided herein into a host cell under conditions to express the protein in the cell.

Provided herein is an immunomodulatory protein (e.g. Fc fusion protein) produced by the method of any of the embodiments described herein. Provided herein is an Fc fusion protein produced by the method of any of the embodiments described herein.

Provided herein is a pharmaceutical composition, containing the immunomodulatory protein (e.g. Fc fusion protein) of any of the embodiments described herein. In some of any embodiments, the pharmaceutical composition contains a pharmaceutically acceptable excipient. In some of any embodiments, the pharmaceutical composition is sterile.

Provided herein is an article of manufacture including the pharmaceutical composition of any of the embodiments described herein in a vial or container. In some of any embodiments, the vial or container is sealed.

Provided herein is a kit containing the pharmaceutical composition of any of any of the embodiments provided herein and instructions for use. In some of any embodiments, the kit includes the article of manufacture of any of the embodiments described herein and instructions for use.

Provided herein is a method of reducing an immune response in a subject, containing administering the immunomodulatory protein of any of the embodiments described herein to a subject in need thereof.

Provided herein is a method of reducing an immune response in a subject, containing administering the Fc fusion protein of any of the embodiments described herein to a subject in need thereof.

Provided herein is a method of reducing an immune response in a subject, containing administering the pharmaceutical composition of any of any of the embodiments described herein to a subject in need thereof. In some of any embodiments, a B cell immune response is reduced in the subject, whereby B cell maturation, differentiation and/or proliferation is reduced or inhibited. In some of any embodiments, circulating levels of APRIL, BAFF or an APRIL/BAFF heterotrimer are reduced in the subject.

Provided herein is a method of reducing circulating levels of APRIL, BAFF or an APRIL/BAFF heterotrimer in a subject containing administering the pharmaceutical composition of any of any of the embodiments described herein to the subject. In some of any embodiments, a T cell immune response is reduced in the subject, whereby T cell co-stimulation is reduced or inhibited. In some of any embodiments, reducing the immune response treats a disease or condition in the subject.

Provided herein is a method of treating a disease, disorder or condition in a subject, containing administering the immunomodulatory protein of any of any of the embodiments described herein to a subject in need thereof.

Provided herein is a method of treating a disease, disorder or condition in a subject, containing administering the Fc fusion protein of any of any of the embodiments described herein to a subject in need thereof.

Provided herein is a method of treating a disease, disorder or condition in a subject, containing administering the pharmaceutical composition of any of any of the embodiments described herein to a subject in need thereof. In some of any embodiments, the disease, disorder or condition is an autoimmune disease, an inflammatory condition, a B cell cancer, an antibody-mediated pathology, a renal disease, a graft rejection, graft versus host disease, or a viral infection. In some of any embodiments, the disease, disorder or condition is selected from the group consisting of Systemic lupus erythematosus (SLE); Sjögren's syndrome, scleroderma, Multiple sclerosis, diabetes, polymyositis, primary biliary cirrhosis, IgA nephropathy, IgA vasculitis, optic neuritis, amyloidosis, antiphospholipid antibody syndrome (APS), autoimmune polyglandular syndrome type II (APS II), autoimmune thyroid disease (AITD), Graves' disease, autoimmune adrenalitis and pemphigus vulgaris. In some of any embodiments, the disease, disorder or condition is a B cell cancer and the cancer is myeloma.

Also provided herein is a pharmaceutical composition for use in reducing an immune response in a subject.

Also provided herein is the use of any of the provided immunomodulatory proteins (e.g. Fc fusion proteins) or any of the provided pharmaceutical compositions in the manufacture of a medicament for reducing an immune response in a subject.

In some embodiments of the pharmaceutical composition for use or the use provided herein, the immune response is a B cell immune response, wherein reducing the immune response reduces or inhibits B cell maturation, differentiation and/or proliferation. In some embodiments, reducing the immune response reduces circulating levels of APRIL, BAFF or an APRIL/BAFF heterotrimer in the subject. In some embodiments, reducing the immune response treats a disease, disorder or condition in the subject.

Also provided herein is a pharmaceutical composition for use in treating a disease, disorder or condition in a subject.

Also provided herein is the use of any of the provided immunomodulatory proteins or pharmaceutical compositions in the manufacture of a medicament for treating a disease, disorder or condition in a subject.

In some of any embodiments of the pharmaceutical composition for use or the uses provided herein, the disease, disorder or condition is an autoimmune disease, an inflammatory condition, a B cell cancer, an antibody-mediated pathology, a renal disease, a graft rejection, graft versus host disease, or a viral infection. In some embodiments, the disease, disorder or condition is selected from the group consisting of Systemic lupus erythematosus (SLE); Sjögren's syndrome, scleroderma, Multiple sclerosis, diabetes, polymyositis, primary biliary cirrhosis, IgA nephropathy, IgA vasculitis, optic neuritis, amyloidosis, antiphospholipid antibody syndrome (APS), autoimmune polyglandular syndrome type II (APS II), autoimmune thyroid disease (AITD), Graves' disease, autoimmune adrenalitis and pemphigus vulgaris. In some embodiments, the disease, disorder or condition is a B cell cancer and the cancer is myeloma. In some of any embodiments, the type of myeloma includes multiple myeloma, plasmacytoma, multiple solitary plasmacytoma, and/or extramedullary myeloma. In some of any embodiments, the type of myeloma includes light chain myeloma, nonsecretory myeloma, and/or IgD or IgE myeloma.

BRIEF DESCRIPTION OF THE DRAWINGS

FIG. 5 shows human TACI TD Fc fusion molecules for blockade of human APRIL (tope panel) and BAFF (bottom panel) mediated signaling relative to TACI 13-118-Fc, TACI 30-110-Fc, and belimumab.

FIG. 6I shows the histological score ±SEM.

FIG. 8A depicts an exemplary TACI-Fc fusion protein containing two cysteine-rich pseudo-repeats (CRD). FIG. 8B depicts an exemplary TACI-Fc fusion protein containing one cysteine-rich pseudo-repeat (CRD, e.g. CRD2).

FIG. 9 depicts exemplary sequence alignments to identify corresponding residues in a sequence compared to a reference sequence. The symbol "*" between two aligned amino acid indicates that the aligned amino acids are identical. The symbol "-" indicates a gap in the alignment. Exemplary, non-limiting positions for amino acid substitution described herein are indicated with bold text. Based on the alignment of two similar sequences having identical residues in common, a skilled artisan can identify "corresponding" positions in a sequence by comparison to a reference sequence using conserved and identical amino acid residues as guides. FIG. 9 provides an exemplary alignment of a reference TACI extracellular domain sequence set forth in SEQ ID NO:122 (containing the full extracellular domain with a CRD1 and CRD2 and an initiating methionine residue) with a TACI extracellular domain sequence set forth in SEQ ID NO:13 (containing only a single CRD, CRD2); aligning identical residues demonstrates, for example, that amino acid residue E7 in SEQ ID NO:13 corresponds to residue E74 in SEQ ID NO: 122, amino acid residue K10 in SEQ ID NO: 13 corresponds to residue K77 in SEQ ID NO:122, amino acid residue Y12 in SEQ ID NO: 13 corresponds to Y79 in SEQ ID NO:122, amino acid residue L15 in SEQ ID NO:13 corresponds to L82 in SEQ ID NO:122, amino acid residue R17 in SEQ ID NO: 13 corresponds to R84 in SEQ ID NO:122; and amino acid residue D16 in SEQ ID NO:13 correspond to D85 in SEQ ID NO:122. It is within the level of a skilled artisan to carry out similar alignments between two similar protein sequences to identify corresponding residues, including based on the exemplification and description herein.

FIGS. 16A-16B and FIGS. 17A-17B depict overall incidence and degree of sialadenitis (FIGS. 16A-16B) and insulitis (FIGS. 17A-17B) in diabetes-prone mice after treatment with the tested molecules.

DETAILED DESCRIPTION

Figure 1:
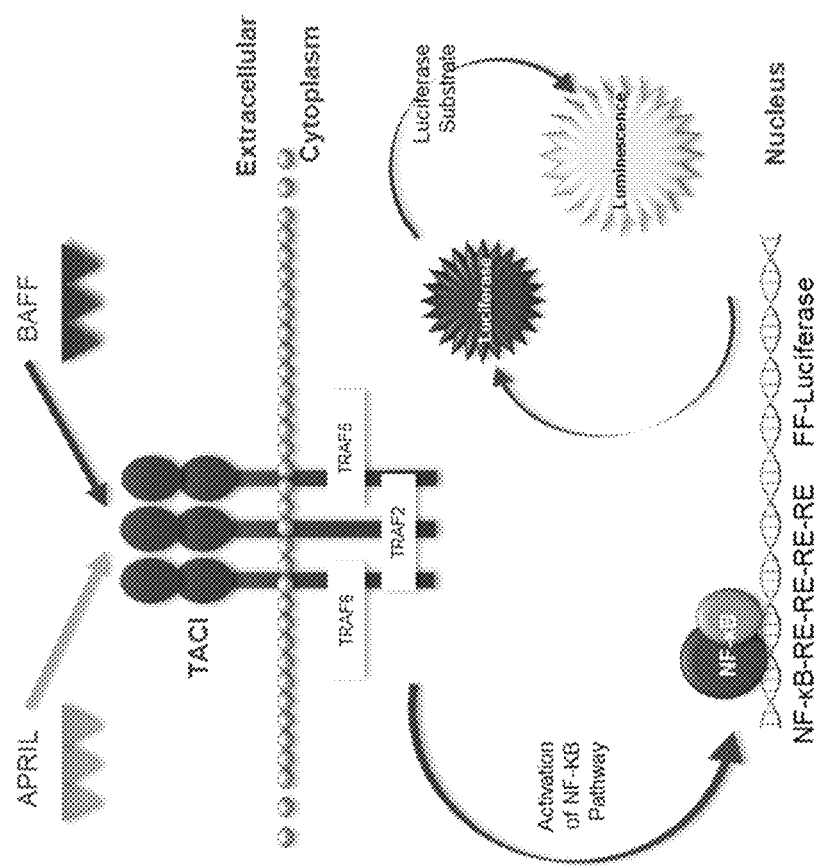
FIG. 1 shows a schematic representation of a functional inhibition assay involving recombinant APRIL and BAFF by TACI. In the assay, Jurkat cells transduced with a luciferase-based NF-κB reporter and to stably express mouse or human TACI on the cell-surface expression. Following activation by recombinant APRIL or BAFF, endogenous NF-κB transcription factors bind to the DNA response elements controlling transcription of a firefly luciferase gene. Luciferase expression can be monitored, such as by detection with Bio-Glo™ reagent and measurement using a Cytation 3 reader.

Provided herein are immunomodulatory proteins that engage with one or more ligand, e.g. produced as soluble factors, to suppress or reduce B cell responses or activity. Among the provided immunomodulatory proteins are proteins that bind to BAFF or APRIL ligands to neutralize their activity and block or antagonize the activity of B cell stimulatory receptors, such as TACI or BCMA. The provided immunomodulatory proteins may be fusion proteins of a TACI extracellular domain or binding portion thereof (hereinafter TACI ECD) and a multimerization domain, such as an immunoglobulin Fc. For example, provided herein are TACI-Fc fusion proteins. In some embodiments, the immunomodulatory proteins provided herein can be used for the treatment of diseases, disorders or conditions that are associated with a dysregulated immune response, such as associated with inflammatory or autoimmune symptoms including an inflammatory disease or an autoimmune disease.

The immune system relies on immune checkpoints to prevent autoimmunity (i.e., self-tolerance) and to protect tissues from excessive damage during an immune response, for example during an attack against a pathogenic infection. In some cases, however, the immune system can become dysregulated and an abnormal immune response can be mounted against a normal body part or tissue, resulting in an autoimmune disease or condition or autoimmune symptoms. In other cases, an unwanted immune response can be mounted to a foreign tissue, such as a transplant, resulting in transplant rejection.

In some aspects immunotherapy that alters immune cell activity, such as B cell activity, can treat certain diseases, disorders and conditions in which the immune response is dysregulated. In particular, inhibition or attenuation of an immune response, such as a B cell response, could be desirable to reduce or prevent unwanted inflammation, autoimmune symptoms and/or transplant rejection. Therapeutic approaches that seek to modulate interactions between ligands and their receptors that mediate an immune response, however, are not entirely satisfactory. In some cases, therapies to intervene and alter the immunomodulatory effects of immune cell, e.g. B cell, activation are constrained by the spatial orientation requirements as well as size limitations imposed by the confines of the immunological synapse. In some aspects existing therapeutic drugs, including antibody drugs, may not be able to interact simultaneously with the multiple target proteins involved in modulating these interactions. For example, soluble receptors and antibodies generally bind competitively (e.g., to no more than one target species at a time) and therefore lack the ability to simultaneously bind multiple targets. Additionally, pharmacokinetic differences between drugs that independently target one of these receptors can create difficulties in properly maintaining a desired blood concentration of a drug combination targeting two different targets throughout the course of treatment.

BAFF and APRIL are TNF superfamily members that bind both TACI and BCMA on B cells; BAFF also binds a $3^{rd}$ receptor, BAFF-R. Together, BAFF and APRIL support B cell development, differentiation, and survival, particularly for plasmablasts and plasma cells, and play a role in the pathogenesis of B cell-related autoimmune diseases. Their co-neutralization dramatically reduces B cell function, including antibody production, whereas inhibition of either BAFF or APRIL alone mediates relatively modest effects. Fc fusions of wild-type (WT) TACI (e.g. atacicept and telitacicept) target both BAFF and APRIL and have demonstrated promising clinical potential in e.g. systemic lupus erythematosus (SLE) and IgA nephropathy, but have not yet clearly exhibited long-term and/or complete disease remissions. While B cell targeting therapies have demonstrated promising therapeutic potential, they are not entirely satisfactory. For instance, soluble recombinant TACI demonstrates considerable promise as a therapeutic, but its usefulness appears hindered by low to moderate affinity to APRIL.

Among provided embodiments are those that provide for improved neutralizing activity and suppression or reduction of B cell responses. In some embodiments, the improved activity is mediated by increased or improved binding or interaction of the provided immunomodulatory proteins (e.g. TACI-Fc fusion protein) with BAFF and/or APRIL. The provided immunomodulatory proteins block or antagonize interactions of BAFF or APRIL, such as homotrimers of BAFF or APRIL, heterotrimers of BAFF/APRIL or BAFF 60mers, with a cognate B cell stimulatory receptor, and thereby neutralize activity of BAFF and/or APRIL ligands. In some embodiments, the provided immunomodulatory proteins reduce one or more B cell response or activity, including the ability of B cells to produce immunoglobulins. In some embodiments, the provided immunomodulatory proteins (e.g. TACI-Fc fusion protein), when administered to a subject, reduce circulating serum immunoglobulins. In some embodiments, the provided immunomodulatory proteins reduce one or more of B cell maturation, differentiation and proliferation. In provided aspects, such activity is improved or superior to that achieved by a WT TACI-Fc fusion protein (e.g. telitacicept or atacicept). In some embodiments, the provided immunomodulatory proteins (TACI-Fc fusion protein) are candidate therapeutics for the treatment of multiple autoimmune and inflammatory diseases, particularly B cell-related diseases, such as SLE, SjS, and other connective tissue diseases.

Provided embodiments relate to identification of variant TACI polypeptides engineered to have improved affinity towards APRIL and/or BAFF following random mutagenesis and directed evolution of the second cysteine rich domain (CRD2) of TACI, spanning residued 68-110. As shown herein, the affinity maturation included five selections alternating between APRIL and BAFF, with concurrent decreases in selection reagent concentration to maintain selection pressure. Results demonstrated variant TACI polypeptides that exhibit substantially enhanced affinity for BAFF and APRIL as compared to wild-type TACI. For example, provided herein are variant TACI polypeptides that contain one or more amino acid substitutions (replacement or mutations) that confer improved binding affinity of the protein for BAFF and/or APRIL. In particular, among provided embodiments are those that provide for improved, combined BAFF and APRIL inhibition. Thus, the provided immunomodulatory proteins provide effective and durable disease suppression in the treatment of autoimmune or inflammatory diseases, including in severe B cell-related autoimmune diseases like SLE.

For example, the provided embodiments are based on findings that directed evolution by affinity modification of TNFR domain (TD) of the ectodomain of TACI facilitated the development of molecules with improved affinity for APRIL and/or BAFF. Thus, the affinity modification produces a variant TACI that contains a variant TNFR domain (vTD). Fusion of such molecules with an immunoglobulin Fc results in immunomodulatory proteins that suppress B cell activity and response. For instance, reformatted as a soluble Fc fusion protein, the affinity-matured TACI variant outputs exhibited inhibition of APRIL and BAFF, as shown herein in a TACI-dependent reporter assay, and with lower IC50 values than wild-type TACI-Fc and belimumab comparators. Further, results in evaluated animal models demonstrate rapid and significantly reduced key lymphocyte subsets including plasma cells, germinal center B cells, a and follicular T helper cells. Further, tested variant molecules exhibited improved activities in mouse models, including significantly reduced autoantibodies and sialadenitis in the spontaneous SjS model, inhibited glomerular IgG deposition in the bm12-induced model of lupus, and potently suppressed anti-dsDNA autoAbs, blood urea nitrogen levels, proteinuria, sialadenitis, kidney lesions and renal immune complex deposition in the NZB/W lupus model. Further, as compared to wild-type TACI-Fc, tested TACI-Fc fusions exhibited significantly and persistently decreased titers of serum IgM, IgG, and IgA antibodies in mice. The findings herein demonstrate these immunomodulatory proteins consistently exhibit potent immunosuppressive activity and efficacy in vitro and in vivo, appearing superior to existing and/or approved immunomodulators like belimumab, abatacept, atacicept, or telitacicept. Such biologics may therefore be attractive development candidates for the treatment of serious autoimmune and/or inflammatory diseases, including B cell-related diseases such as SLE, Sjögren's syndrome, and other connective tissue diseases.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used in the specification and the appended claims, the singular forms "a," "an," and "the" include plural referents unless the context clearly indicates otherwise.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The term "affinity-modified" as used in the context of a domain of a protein means a mammalian protein having an altered amino acid sequence in an extracellular domain or a specific binding portion thereof (relative to the corresponding wild-type parental or unmodified domain) such that it has an increased or decreased binding activity, such as binding affinity, to at least one of its binding partners (alternatively "counter-structures") compared to the parental wild-type or unmodified (i.e., non-affinity modified domain) protein. In some embodiments, the affinity-modified domain can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions, in a wild-type or unmodified domain. An increase or decrease in binding activity, e.g. binding affinity, can be determined using well known binding assays, including flow cytometry. Larsen et al., American Journal of Transplantation, Vol 5: 443-453 (2005). See also, Linsley et al., Immunity, 1: 7930801 (1994). An increase in a protein's binding activity, e.g. affinity, to its binding partner(s) is to a value at least 10% greater than that of the wild-type control and in some embodiments, at least 20%, 30%, 40%, 50%, 100%, 200%, 300%, 500%, 1000%, 5000%, or 10000% greater than that of the wild-type control value. A decrease in a protein's binding activity, e.g. affinity, to at least one of its binding partner is to a value no greater than 90% of the control but no less than 10% of the wild-type control value, and in some embodiments no greater than 80%, 70% 60%, 50%, 40%, 30%, or 20% but no less than 10% of the wild-type control value. An affinity-modified protein is altered in primary amino acid sequence of the extracellular domain or a specific binding portion thereof by substitution, addition, or deletion of amino acid residues. The term "affinity-modified" is not be construed as imposing any condition for any particular starting composition or method by which the affinity-modified protein was created. Thus, an affinity-modified protein is not limited to wild-type protein domains that are then transformed to an affinity-modified domain by any particular process of affinity modification. An affinity-modified domain polypeptide can, for example, be generated starting from wild-type mammalian domain sequence information, then modeled in silico for binding to its binding partner, and finally recombinantly or chemically synthesized to yield the affinity-modified domain composition of matter. In but one alternative example, an affinity-modified domain can be created by site-directed mutagenesis of a wild-type domain. Thus, affinity modified TD domain denotes a product and not necessarily a product produced by any given process. A variety of techniques including recombinant methods, chemical synthesis, or combinations thereof, may be employed.

The term "affinity-modified TD domain" refers to an affinity-modified domain of a member of the tumor necrosis receptor superfamily (TNFRSF) protein or a TNF ligand thereof having an altered amino acid sequence of a TNFR domain or of a TNF domain therein, respectively. For example, an affinity-modified TD domain of a TNFRSF protein has an altered amino acid sequence of a TNFR domain composed of at least one cysteine rich domain (CRD) within the extracellular domain of the TNFRSF protein or a specific binding portion thereof (relative to the corresponding wild-type parental or unmodified domain) such that it has an increased or decreased binding activity, such as binding affinity, to at least one of its binding partners (alternatively "counter-structures") compared to the parental wild-type or unmodified protein containing the non-affinity modified or unmodified TD domain.

An "affinity-modified TACI (also referred to as a variant TACI) refers to a TACI protein molecule that antagonizes or blocks the activity of a B cell stimulatory receptor. For example, TACI binds to APRIL and/or BAFF, which are ligands of the B cell stimulatory receptors B cell maturation antigen (BCMA), B cell activation factor receptor (BAFF-R), and transmembrane activator and calcium modulator and cyclophilin ligand interactor (TACI). In particular embodiments, a BIM includes the extracellular domain of TACI, or a portion of the extracellular domain of TACI containing a TNF receptor family domain (e.g. TD, e.g. CRD) that binds to cognate ligands APRIL and/or BAFF, and heterotrimers of APRIL and BAFF. An affinity-modified variant of the extracellular domain or portion thereof of TACI can include one or more amino acid modifications (e.g. amino acid substitutions) in the TD that increase binding affinity for the cognate ligand (e.g. APRIL and/or BAFF, and heterotrimers of APRIL and BAFF).

As used herein, a "B cell stimulatory receptor" refers to one or more of B cell maturation antigen (BCMA), B cell activation factor receptor (BAFF-R), and transmembrane activator and calcium modulatory and cyclophilin ligand interactor (TACI), which are related tumor necrosis factor (TNFR) superfamily receptors expressed on B cells. Engagement or ligation of these related receptors by their cognate ligands, BAFF and/or APRIL, or heterotrimers of APRIL and BAFF, regulate B cell homeostasis, including B cell survival, B cell maturation and differentiation and immunoglobulin class switching. A B cell stimulatory receptor generally contains an extracellular portion, a transmembrane domain and cytoplasmic region, in which the cytoplasmic region contains one or more TNF receptor associated factor (TRAF) binding sites. Recruitment of various TRAF molecules to the cytoplasmic domain can activate various transcription factors, such as NF-κB (e.g. NF-κB1 or NF-κB2), to mediate B cell signaling pathways regulating B cell homeostasis.

As used herein, "bind," "bound" or grammatical variations thereof refers to the participation of a molecule in any attractive interaction with another molecule, resulting in a stable association in which the two molecules are in close proximity to one another. Binding includes, but is not limited to, non-covalent bonds, covalent bonds (such as reversible and irreversible covalent bonds), and includes interactions between molecules such as, but not limited to, proteins, nucleic acids, carbohydrates, lipids, and small molecules, such as chemical compounds including drugs.

As used herein, binding activity refer to characteristics of a molecule, e.g. a polypeptide, relating to whether or not, and how, it binds one or more binding partners. A binding activity can include any measure of binding of one molecule for a binding partner. Binding activities include the ability to bind the binding partner(s), the affinity with which it binds to the binding partner (e.g. high affinity), the avidity with which it binds to the binding partner, the strength of the bond with the binding partner and/or specificity or selectivity for binding with the binding partner.

The term "binding affinity" as used herein means the specific binding affinity of a protein for its binding partner (i.e., its counter-structure) under specific binding conditions. The binding affinity refers to the strength of the interaction between two or more molecules, such as binding partners, typically the strength of the noncovalent interactions between two binding partners. An increase or attenuation in binding affinity of an affinity-modified domain, or an immunomodulatory protein containing an affinity-modified domain, to a binding partner is determined relative to the binding affinity of the unmodified domain (e.g., the native or wild-type TD domain). Methods for determining binding affinity, or relative binding affinity, are known in art, solid-phase ELISA immunoassays, ForteBio Octet, Biacore measurements or flow cytometry. See, for example, Larsen et al., American Journal of Transplantation, vol. 5: 443-453 (2005); Linsley et al., Immunity, Vol 1 (9): 793-801 (1994). In some embodiments, binding affinity can be measured by flow cytometry, such as based on a Mean Fluorescence Intensity (MFI) in a flow binding assay.

The term "binding avidity" as used herein means the specific binding avidity, of a protein for its binding partner (i.e., its counter-structure) under specific binding conditions. In biochemical kinetics avidity refers to the accumulated strength of multiple affinities of individual non-covalent binding interactions, such as between a protein for its binding partner (i.e., its counter-structure). As such, avidity is distinct from affinity, which describes the strength of a single interaction.

The term "biological half-life" refers to the amount of time it takes for a substance, such as an immunomodulatory protein, to lose half of its pharmacologic or physiologic activity or concentration. Biological half-life can be affected by elimination, excretion, degradation (e.g., enzymatic degradation/digestion) of the substance, or absorption and concentration in certain organs or tissues of the body. In some embodiments, biological half-life can be assessed by determining the time it takes for the blood plasma concentration of the substance to reach half its steady state level ("plasma half-life"). Conjugates that can be used to derivatize and increase the biological half-life of a protein are known in the art and include, but are not limited to, multimerization domains (e.g. Fc immunoglobulin domain), polyethylene glycol (PEG), hydroxyethyl starch (HES), XTEN (extended recombinant peptides; see, WO2013130683), human serum albumin (HSA), bovine serum albumin (BSA), lipids (acylation), and poly-Pro-Ala-Ser (PAS), polyglutamic acid (glutamylation).

The term "cell surface counter-structure" (alternatively "cell surface binding partner") as used herein is a counter-structure (alternatively is a binding partner) expressed on a mammalian cell. Typically, the cell surface binding partner is a transmembrane protein. In some embodiments, the cell surface binding partner is a receptor.

The terms "binding partner" or "counter-structure" in reference to a protein, such as a receptor, soluble ligand, or to an extracellular domain or portion thereof or affinity-modified variant thereof, refers to at least one molecule (typically a native mammalian protein) to which the referenced protein specifically binds under specific binding conditions. In some aspects an affinity-modified domain, or an immunomodulatory protein containing an affinity-modified domain, specifically binds to the binding partner of the corresponding domain of the native or wild-type protein but with increased or attenuated affinity. A "cell surface binding partner" is a binding partner expressed on a mammalian cell. Typically, the cell surface binding partner is a transmembrane protein. In some embodiments, the cell surface binding partner is a receptor, or a ligand of a receptor expressed on and by cells, such as mammalian cells, forming the immunological synapse, for example immune cells.

The term "cis" with reference to binding to cell surface molecules refers to binding to two or more different cell surface molecules, each of which is present on the surface of the same cell. In some embodiments, cis means that the two or more cell surface molecules are exclusively on one or exclusively the other (but not both) of the two mammalian cells forming the IS.

The term "conservative amino acid substitution" as used herein means an amino acid substitution in which an amino acid residue is substituted by another amino acid residue having a side chain R group with similar chemical properties (e.g., charge or hydrophobicity). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

The term, "corresponding to" with reference to positions of a protein, such as recitation that nucleotides or amino acid positions "correspond to" nucleotides or amino acid positions in a disclosed sequence, such as set forth in the Sequence Listing, refers to nucleotides or amino acid positions identified upon alignment with the disclosed sequence based on structural sequence alignment or using a standard alignment algorithm, such as the GAP algorithm. By aligning the sequences, one skilled in the art can identify corresponding residues, for example, using conserved and identical amino acid residues as guides. FIG. 9 exemplifies identification of corresponding residues by aligning two sequences.

As used herein, "domain" (typically a sequence of three or more, generally 5 or 7 or more amino acids, such as 10 to 200 amino acid residues) refers to a portion of a molecule, such as a protein or encoding nucleic acid, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as binding activity. A protein can have one, or more than one, distinct domains. For example, a domain can be identified, defined or distinguished by homology of the primary sequence or structure to related family members, such as homology to motifs. In another example, a domain can be distinguished by its function, such as an ability to interact with a biomolecule, such as a cognate binding partner. A domain independently can exhibit a biological function or activity such that the domain independently or fused to another molecule can perform an activity, such as, for example binding. A domain can be a linear sequence of amino acids or a non-linear sequence of amino acids. Many polypeptides contain a plurality of domains. Such domains are known, and can be identified by those of skill in the art. For exemplification herein, definitions are provided, but it is understood that it is well within the skill in the art to recognize particular domains by name. If needed appropriate software can be employed to identify domains. It is understood that reference to amino acids, including to a specific sequence set forth as a SEQ ID NO used to describe domain organization (e.g. of a TD domain) are for illustrative purposes and are not meant to limit the scope of the embodiments provided. It is understood that polypeptides and the description of domains thereof are theoretically derived based on homology analysis and alignments with similar molecules. Also, in some cases, adjacent N- and/or C-terminal amino acids of a given domain (e.g. TD) also can be included in a sequence, such as to ensure proper folding of the domain when expressed. Thus, the exact locus can vary, and is not necessarily the same for each protein. For example, a specific TD domain, such as specific CRD domain, can be several amino acids (1-10, such as 1, 2, 3, 4, 5, 6, 7, 8, 9 or 10 amino acids) longer or shorter.

The term "ectodomain," "extracellular domain," or "ECD," which are used interchangeably herein, refers to a region of a membrane protein, such as a transmembrane protein, that lies outside the vesicular membrane (e.g., the space outside of a cell), when a full-length form of the membrane protein is expressed from a cell. For purposes herein, it is understood that reference to the ECD refers to sequences and domains that make up this region and do not require that a protein that contains an ECD is a membrane protein or that the domain is present outside a cell. For example, a soluble immunomodulatory protein can contain ECD sequences of a membrane protein fused to another moiety, such as a multimerization domain, for example an Fc region. Ectodomains often interact with specific ligands or specific cell surface receptors, such as via a binding domain that specifically binds to the ligand or cell surface receptor. Examples of binding domains include cysteine rich domains (CRDs). Ectodomains of members of the TNFR superfamily contain a TD domain (e.g. a CRD domain). Thus, reference to an ECD herein includes a full-length sequence of an ECD of a membrane protein as well as specific-binding fragments thereof containing a CRD that bind to a ligand or cognate binding partner.

The terms "effective amount" or "therapeutically effective amount" refer to a quantity and/or concentration of a therapeutic composition, such as containing an immunomodulatory protein or Fc fusion protein, that when administered ex vivo (by contact with a cell from a patient) or in vivo (by administration into a patient) either alone (i.e., as a monotherapy) or in combination with additional therapeutic agents, yields a statistically significant inhibition of disease progression as, for example, by ameliorating or eliminating symptoms and/or the cause of the disease. An effective amount for treating a disease, condition or disorder, such as an immune system disease, condition or disorder, may be an amount that relieves, lessens, or alleviates at least one symptom or biological response or effect associated with the disease, condition or disorder, prevents progression of the disease, condition or disorder, or improves physical functioning of the patient. In the case of cell therapy, the effective amount is an effective dose or number of cells administered to a patient. In some embodiments the patient is a human patient.

As used herein, a fusion protein refers to a polypeptide encoded by a nucleic acid sequence containing a coding sequence for two or more proteins, in some cases 2, 3, 4, 5 or more protein, in which the coding sequences are in the same reading frame such that when the fusion construct is transcribed and translated in a host cell, the protein is produced containing the two or more proteins. Each of the two or more proteins can be adjacent to another protein in the construct or separated by a linker polypeptide that contains, 1, 2, 3, or more, but typically fewer than 20, 15, 10, 9, 8, 7, or 6 amino acids. The protein product encoded by a fusion construct is referred to as a fusion polypeptide. An example of a fusion protein in accord with the provided embodiments is an Fc fusion protein containing an affinity-modified domain (e.g. a variant of a TACI extracellular domain or portion thereof containing a CRD) that is linked to an immunoglobulin Fc domain.

The term "half-life extending moiety" refers to a moiety of a polypeptide fusion or chemical conjugate that extends the half-life of a protein circulating in mammalian blood serum compared to the half-life of the protein that is not so conjugated to the moiety. In some embodiments, half-life is extended by greater than or about 1.2-fold, about 1.5-fold, about 2.0-fold, about 3.0-fold, about 4.0-fold, about 5.0-fold, or about 6.0-fold. In some embodiments, half-life is extended by more than 6 hours, more than 12 hours, more than 24 hours, more than 48 hours, more than 72 hours, more than 96 hours or more than 1 week after in vivo administration compared to the protein without the half-life extending moiety. The half-life refers to the amount of time it takes for the protein to lose half of its concentration, amount, or activity. Half-life can be determined for example, by using an ELISA assay or an activity assay. Exemplary half-life extending moieties include an Fc domain, a multimerization domain, polyethylene glycol (PEG), hydroxyethyl starch (HES), XTEN (extended recombinant peptides; see, WO2013130683), human serum albumin (HSA), bovine serum albumin (BSA), lipids (acylation), and poly-Pro-Ala-Ser (PAS), and polyglutamic acid (glutamylation).

An Fc (fragment crystallizable) region or domain of an immunoglobulin molecule (also termed an Fc polypeptide) corresponds largely to the constant region of the immunoglobulin heavy chain, and which, in some cases, is responsible for various functions, including the antibody's effector function(s). The Fc domain contains part or all of a hinge domain of an immunoglobulin molecule plus a CH2 and a CH3 domain. In some cases for inclusion in a provided fusion protein, all or a portion of the Fc hinge sequence may be deleted. The Fc domain can form a dimer of two polypeptide chains joined by one or more disulfide bonds. In some embodiments, the Fc is a variant Fc that exhibits reduced (e.g. reduced greater than about 30%, 40%, 50%, 60%, 70%, 80%, 90% or more) activity to facilitate an effector function. In some embodiments, reference to amino acid substitutions in an Fc region is by EU numbering system unless described with reference to a specific SEQ ID NO. EU numbering is known and is according to the most recently updated IMGT Scientific Chart (IMGT®, the international ImMunoGeneTics information System®, http://www.imgt.org/IMGTScientificChart/Numbering/Hu IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

An immunoglobulin Fc fusion ("Fc-fusion"), such as an immunomodulatory Fc fusion protein, is a molecule comprising one or more polypeptides operably linked to an Fc region of an immunoglobulin. An Fc-fusion may comprise, for example, an Fc region operably linked to a TACI extracellular domain or portion thereof containing a CRD, including any of the provided affinity-modified variants thereof. An immunoglobulin Fc region may be linked indirectly or directly to the one or more polypeptides. Various linkers are known in the art and can optionally be used to link an Fc to a fusion partner to generate an Fc-fusion. Fc-fusions of identical species can be dimerized to form Fc-fusion homodimers. Fc fusion of non-identical species (e.g. knob into hole engineering) may be used to form Fc-fusion heterodimers. In some embodiments, the Fc is a mammalian Fc such as a murine or human Fc.

The term "host cell" refers to any cell that can be used to express a protein encoded by a recombinant expression vector. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include Chinese hamster ovary (CHO) cells or their derivatives such as Veggie CHO and related cell lines which grow in serum-free media or CHO strain DX-B11, which is deficient in DHFR.

The term "immunological synapse" or "immune synapse" (abbreviated "IS") as used herein means the interface between a mammalian cell that expresses MHC I (major histocompatibility complex) or MHC II, such as an antigen-presenting cell or tumor cell, and a mammalian lymphocyte such as an effector T cell or Natural Killer (NK) cell.

The term "immunoglobulin" (abbreviated "Ig") as used herein is synonymous with the term "antibody" (abbreviated "Ab") and refers to a mammalian immunoglobulin protein including any of the five human classes: IgA (which includes subclasses IgA1 and IgA2), IgD, IgE, IgG (which includes subclasses IgG1, IgG2, IgG3, and IgG4), and IgM. The term is also inclusive of immunoglobulins that are less than full-length, whether wholly or partially synthetic (e.g., recombinant or chemical synthesis) or naturally produced, including any fragment thereof containing at least a portion of the variable heavy (VH) chain and/or variable light (VL) chain region of the immunoglobulin molecule that is sufficient to form an antigen binding site and, when assembled, to specifically bind antigen. The antibody also can include all or a portion of the constant region. Such fragments include antigen binding fragment (Fab), variable fragment (Fv) containing VH and VL, the single chain variable fragment (scFv) containing VH and VL linked together in one chain, as well as other antibody V region fragments, such as Fab', F(ab)2, F(ab')2, dsFv diabody, Fc, and Fd polypeptide fragments. Hence, it is understood that reference to an antibody herein includes full-length antibody and antigen-binding fragments. The term antibody also includes antibody compositions with polyepitopic specificity, multi-specific antibodies (e.g., bispecific antibodies), diabodies, and single-chain molecules. Bispecific antibodies, homobispecific and heterobispecific, are included within the meaning of the term. Antibodies include polyclonal antibodies or monoclonal antibodies. Antibody also includes synthetic antibodies or recombinantly produced antibodies. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6.

The terms "full-length antibody," "intact antibody" or "whole antibody" are used interchangeably to refer to an antibody in its substantially intact form, as opposed to an antibody fragment. A full-length antibody is an antibody typically having two full-length heavy chains (e.g., VH-CH1-CH2-CH3 or VH-CH1-CH2-CH3-CH4) and two full-length light chains (VL-CL) and hinge regions, such as antibodies produced from mammalian species (e.g. human, mouse, rat, rabbit, non-human primate, etc.) by antibody secreting B cells and antibodies with the same domains that are produced synthetically. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Antibody fragments, include, but are not limited to, Fab fragments, Fab' fragments, F(ab')$_2$ fragments, Fv fragments, disulfide-linked Fvs (dsFv), Fd fragments, Fd' fragments; diabodies; linear antibodies (see U.S. Pat. No. 5,641,870, Example 2; Zapata et al., *Protein Eng.* 8(10): 1057-1062 [1995]); single-chain antibody molecules, including single-chain Fvs (scFv) or single-chain Fabs (scFab); antigen-binding fragments of any of the above and multispecific antibodies from antibody fragments.

"Fv" is composed of one heavy- and one light-chain variable region domain linked by non-covalent association. From the folding of these two domains emanate six complementarity determining regions (CDR) (3 in each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although, in some cases, at a lower affinity than the entire binding site.

"dsFv" refers to an Fv with an engineered intermolecular disulfide bond, which stabilizes the $V_H$-$V_L$ pair.

An "Fd fragment" is a fragment of an antibody containing a variable domain ($V_H$) and one constant region domain ($C_H1$) of an antibody heavy chain.

A "Fab fragment" is an antibody fragment that results from digestion of a full-length immunoglobulin with papain, or a fragment having the same structure that is produced synthetically, e.g., by recombinant methods. A Fab fragment contains a light chain (containing a $V_L$ and $C_L$) and another chain containing a variable domain of a heavy chain ($V_H$) and one constant region domain of the heavy chain ($C_H1$).

A "F(ab')2 fragment" is an antibody fragment that results from digestion of an immunoglobulin with pepsin at pH 4.0-4.5, or a fragment having the same structure that is produced synthetically, e.g., by recombinant methods. The F(ab')2 fragment essentially contains two Fab fragments where each heavy chain portion contains an additional few amino acids including cysteine residues that form disulfide linkages joining the two fragments.

A "Fab' fragment" is a fragment containing one half (one heavy chain and one light chain) of the F(ab')$_2$ fragment.

An "Fd' fragment" is a fragment of an antibody containing one heavy chain portion of a F(ab')$_2$ fragment.

An "Fv' fragment" is a fragment containing only the $V_H$ and $V_L$ domains of an antibody molecule.

An "scFv fragment" refers to an antibody fragment that contains a variable light chain ($V_L$) and variable heavy chain ($V_H$), covalently connected by a polypeptide linker in any order. The linker is of a length such that the two variable domains are bridged without substantial interference. Exemplary linkers are (Gly-Ser)$_n$ residues with some Glu or Lys residues dispersed throughout to increase solubility.

"Diabodies" are dimeric scFv; diabodies typically have shorter peptide linkers than scFvs, and preferentially dimerize.

The term "immunological activity" as used herein refers to one or more activities of immune cells, such as T cells or B cells, including, for example, activation, cell survival, cell proliferation, cytokine production (e.g. interferon-gamma), cytotoxicity activity, or ability to activate NF-κB pathway or other signaling cascade leading to activation of a transcription factor in the immune cell. Assays to assess immunological activity of immunomodulatory proteins can be compared to control proteins with a known activity.

An "immunomodulatory protein" or "immunomodulatory polypeptide" is a protein that modulates immunological activity. By "modulation" or "modulating" an immune response is meant that immunological activity is either enhanced or suppressed. Such modulation includes any induction, or alteration in degree or extent, or suppression of immunological activity of an immune cell, such as a B cell or a T cell. For example, soluble Fc fusion proteins herein may suppress immunological activity of B cells. An immunomodulatory protein can be a single polypeptide chain or a multimer (dimers or higher order multimers) of at least two polypeptide chains covalently bonded to each other by, for example, interchain disulfide bonds. Thus, monomeric, dimeric, and higher order multimeric proteins are within the scope of the defined term. Multimeric proteins can be homomultimeric (of identical polypeptide chains) or heteromultimeric (of different polypeptide chains).

As used herein, modification is in reference to modification of a sequence of amino acids of a polypeptide or a sequence of nucleotides in a nucleic acid molecule and includes a change in amino acids or nucleotides, respectively, of the sequence. The amino acid modification or change may be a deletion, insertion, or replacement (substitution) of amino acids or nucleotides, respectively. Methods of modifying a polypeptide are routine to those of skill in the art, such as by using recombinant DNA methodologies.

The term, a "multimerization domain" refers to a sequence of amino acids that promotes the formation of a multimer of two or more polypeptides. A multimerization domain includes sequences that promote stable interaction of a polypeptide molecule with one or more additional polypeptide molecules, each containing a complementary multimerization domain (e.g. a first multimerization domain and a second multimerization domain), which can be the same or a different multimerization domain. The interactions between complementary multimerization domains, e.g. interaction between a first multimerization domain and a second multimerization domain, form a stable protein-protein interaction to produce a multimer of the polypeptide molecule with the additional polypeptide molecule. In some cases, the multimerization domain is the same and interacts with itself to form a stable protein-protein interaction between two polypeptide chains. Generally, a polypeptide is joined directly or indirectly to the multimerization domain. Exemplary multimerization domains include the immunoglobulin sequences or portions thereof, leucine zippers, hydrophobic regions, hydrophilic regions, and compatible protein-protein interaction domains. The multimerization domain, for example, can be an immunoglobulin constant region or domain, such as, for example, the Fc domain or portions thereof from IgG, including IgG1, IgG2, IgG3 or IgG4 subtypes, IgA, IgE, IgD and IgM and modified forms thereof.

The terms "nucleic acid" and "polynucleotide" are used interchangeably to refer to a polymer of nucleic acid residues (e.g., deoxyribonucleotides or ribonucleotides) in either single- or double-stranded form. Unless specifically limited, the terms encompass nucleic acids containing known analogues of natural nucleotides and that have similar binding properties to it and are metabolized in a manner similar to naturally-occurring nucleotides. Unless otherwise indicated, a particular nucleic acid sequence also implicitly encompasses conservatively modified variants thereof (e.g., degenerate codon substitutions) and complementary nucleotide sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid or polynucleotide encompasses cDNA or mRNA encoded by a gene.

The terms "in operable combination," "in operable order" and "operably linked" as used herein refer to the linkage of nucleic acid sequences in such a manner or orientation that the segments are arranged so that they function in concert for their intended purposes. In some embodiments, the term refers to linkage of nucleic acids to produce a nucleic acid molecule capable of directing the transcription of a given gene and/or to produce a desired protein molecule that is functional. For example, segments of a DNA sequence, e.g. a coding sequence and a regulatory sequence(s), are linked in such a way as to permit gene expression when the appropriate molecules (e.g. transcriptional activator proteins) are bound to the regulatory sequence.

The term "pharmaceutical composition" refers to a composition suitable for pharmaceutical use in a mammalian subject, often a human. A pharmaceutical composition typically comprises an effective amount of an active agent (e.g., an immunomodulatory protein) and a carrier, excipient, or diluent. The carrier, excipient, or diluent is typically a pharmaceutically acceptable carrier, excipient or diluent, respectively.

The terms "polypeptide" and "protein" are used interchangeably herein and refer to a molecular chain of two or more amino acids linked through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. The terms also include molecules in which one or more amino acid analogs or non-canonical or unnatural amino acids are included as can be synthesized, or expressed recombinantly using known protein engineering techniques. In addition, proteins can be derivatized as described herein by well-known organic chemistry techniques.

The term "purified" as applied to nucleic acids, such as encoding immunomodulatory proteins, or proteins (e.g. immunomodulatory proteins) generally denotes a nucleic acid or polypeptide that is substantially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or protein is at least about 50% pure, usually at least about 75%, 80%, 85%, 90%, 95%, 96%, 99% or more pure (e.g., percent by weight or on a molar basis).

The term "recombinant" indicates that the material (e.g., a nucleic acid or a polypeptide) has been artificially (i.e., non-naturally) altered by human intervention. The alteration can be performed on the material within, or removed from, its natural environment or state. For example, a "recombinant nucleic acid" is one that is made by recombining nucleic acids, e.g., during cloning, affinity modification, DNA shuffling or other well-known molecular biological procedures. A "recombinant DNA molecule," is comprised of segments of DNA joined together by means of such molecular biological techniques. The term "recombinant protein" or "recombinant polypeptide" as used herein refers to a protein molecule (e.g., an immunomodulatory protein) which is expressed using a recombinant DNA molecule. A "recombinant host cell" is a cell that contains and/or expresses a recombinant nucleic acid or that is otherwise altered by genetic engineering, such as by introducing into the cell a nucleic acid molecule encoding a recombinant protein, such as a immunomodulatory protein provided herein. Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest.

The term "recombinant expression vector" as used herein refers to a DNA molecule containing a desired coding sequence (e.g., encoding an immunomodulatory protein) and appropriate nucleic acid sequences necessary for the expression of an operably linked coding sequence in a particular cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the recombinant expression vector, operably linked to the coding sequence so that the expressed protein can be secreted by the recombinant host cell, such as for its expression as a secretable protein or for more facile isolation or purification of the immunomodulatory protein from the cell, if desired. The term includes the vector as a self-replicating nucleic acid structure as well as the vector incorporated into the genome of a host cell into which it has been introduced. Among the vectors are viral vectors, such as lentiviral vectors.

The term "sequence identity" as used herein refers to the sequence identity between genes or proteins at the nucleotide or amino acid level, respectively. "Sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. Methods for the alignment of sequences for comparison are well known in the art, such methods include GAP, BESTFIT, BLAST, BLAST-2, ALIGN or Megalign (DNASTAR) software, FASTA and TFASTA. The BLAST algorithm calculates percent sequence identity and performs a statistical analysis of the similarity between the two sequences. The software for performing BLAST analysis is publicly available through the National Center for Biotechnology Information (NCBI) website. In some cases, a percent sequence identity can be determined as the percentage of amino acid residues (or nucleotide residues) in a candidate sequence that are identical with the amino acid residues (or nucleotide residues) in a reference sequence, after aligning the sequences and introducing gaps, if necessary, to achieve the maximum percent sequence identity. Reference to sequence identity includes sequence identity across the full length of each of the sequences being compared. Those skilled in the art can determine appropriate parameters for aligning sequences, including any algorithms needed to achieve maximal alignment over the full length of the sequences being compared.

The term "soluble" as used herein in reference to proteins means that the protein is not a membrane protein or is not anchored in a cell membrane. A protein can be constructed as a soluble protein by inclusion of only an extracellular domain or a portion thereof and without a transmembrane domain. In some cases, solubility of a protein can be improved by linkage or attachment, directly or indirectly via a linker, to an Fc domain or other half-life extending molecule, which, in some cases, also can improve the stability and/or half-life of the protein. In some aspects, a soluble protein is an Fc fusion protein.

The term "specifically binds" as used herein means the ability of a protein, under specific binding conditions, to bind to a target protein such that its affinity or avidity is at least 10 times as great, but optionally 50, 100, 250 or 500 times as great, or even at least 1000 times as great as the average affinity or avidity of the same protein to a collection of random peptides or polypeptides of sufficient statistical size. A specifically binding protein need not bind exclusively to a single target molecule but may specifically bind to more than one target molecule. In some cases, a specifically binding protein may bind to a protein that has similarity in structural conformation with the target protein (e.g., paralogs or orthologs). Those of skill will recognize that specific binding to a molecule having the same function in a different species of animal (i.e., ortholog) or to a molecule having a substantially similar epitope as the target molecule (e.g., paralog) is possible and does not detract from the specificity of binding which is determined relative to a statistically valid collection of unique non-targets (e.g., random polypeptides). Thus, an immunomodulatory protein of the invention may specifically bind to more than one distinct species of target molecule due to cross-reactivity. Solid-phase ELISA immunoassays, ForteBio Octet or Biacore measurements can be used to determine specific binding between two proteins. Generally, interactions between two binding proteins have dissociation constants (Kd) less than about $1\times10^{-5}$ M, and often as low as about $1\times10^{-12}$ M. In certain aspects of the present disclosure, interactions between two binding proteins have dissociation constants of less than about $1\times10^{-6}$ M, $1\times10^{-7}$ M, $1\times10^{-8}$ M, $1\times10^{-9}$ M, $1\times10^{-10}$ M, or $1\times10^{-11}$ M or less.

The term "specific binding fragment" or "fragment" as used herein in reference to a protein means a polypeptide that is shorter than a full-length protein or a specific domain or region thereof and that specifically binds in vitro and/or in vivo to a binding partner of the full-length protein or of the specific domain or region. A specific finding fragment is in reference to a fragment of a full-length extracellular domain of a polypeptide or a binding domain of a polypeptide, but that still binds to a binding partner of the binding domain. For example, a specific binding fragment is in reference to a fragment of an extracellular domain of a full-length TNFR family member or a full-length TNFR domain (TD) thereof (e.g. CRD), but that still binds to a binding partner of the TNFR family member or of a CRD of an TNFR family member. In some embodiments, the specific binding fragment is at least about 20%, 30%, 40%, 50%, 60%, 70%, 75%, 80%, 85%, 90%, 95%, 96%, 97%, 98%, or 99% the sequence length of the full-length sequence of the extracellular domain or of a domain or region of the extracellular domain. In some embodiments, the specific binding fragment can have an amino acid length of at least 50 amino acids, such as at least 60, 70, 80, 90, 100, or 110 amino acids. In some embodiments, the specific binding fragment includes the CRD1 and/or CRD2 domain. In some embodiments, the specific binding fragment includes the CRD2 domain.

As used herein, a "subject" is a mammal, such as a human or other animal, and typically is human. The subject can be male or female and can be any suitable age, including infant, juvenile, adolescent, adult, and geriatric subjects.

As used herein, "synthetic," with reference to, for example, a synthetic nucleic acid molecule or a synthetic gene or a synthetic peptide refers to a nucleic acid molecule or polypeptide molecule that is produced by recombinant methods and/or by chemical synthesis methods.

The term "TNF receptor superfamily" or "TNFRSF" as used herein means the group of cell surface cytokine receptors that are all type I (N-terminus extracellular) transmembrane glycoproteins that contain one to six cysteine rich domains (CRD) in their extracellular domain. Molecules are categorized as members of this superfamily based on the shared structural features that include the one or more cysteine rich domain (CRD) present in their N-terminal extracellular region, which often play a role in protein binding of their cognate binding partner or ligand. A TNFRSF protein may have only one or several CRDs (e.g. CRD1, CRD2, etc.). Typically, ECD or ectodomain of TNFRSF members contain between 1 and 6 pseudorepeats of CRDs. For example, BAFF-receptor and BCMA each contain one CRD while TACI contains two CRDs (CRD1 and CRD2). TNFRSF members are usually trimeric or multimeric complexes that are stabilized by their intracysteine disulfide bonds. Binding of TNFRSF proteins to their ligands facilitates various biological activities in cells, such as the induction of apoptotic cell death or cell survival and proliferation.

The term "TD" refers to a structural domain or domains of TNFRSF proteins or of TNF family ligands. For example, a TD of a TNFRSF protein is a cysteine-rich domain (CRD) module of about 40 amino acids containing six (6) conserved cysteines. Hence, reference to CRD also can be used interchangeably with the term TD in reference to a TD of a TNFRSF protein. The six cysteines are involved in formation of intrachain disulphide bonds. The extracellular domain (ECD) of TNFRSF members contains one or more CRD domains; hence, the term TD is also used with reference to the ECD of such protein molecules. Reference to a variant TD (vTD) refers to a variant or modified sequence of a TD.

The term "trans" with reference to binding to cell surface molecules refers to binding to two different cell surface molecules, each of which is present on the surface of a different cell. In some embodiments, trans means that with respect to two different cell surface molecules, the first is exclusively present on one of the two mammalian cells forming the IS and the second is present exclusively on the second of the two mammalian cells forming the IS.

The term "transmembrane protein" as used herein means a membrane protein that substantially or completely spans a lipid bilayer such as those lipid bilayers found in a biological membrane such as a mammalian cell, or in an artificial construct such as a liposome. The transmembrane protein comprises a transmembrane domain ("transmembrane domain") by which it is integrated into the lipid bilayer and by which the integration is thermodynamically stable under physiological conditions. Transmembrane domains are generally predictable from their amino acid sequence via any number of commercially available bioinformatics software applications on the basis of their elevated hydrophobicity relative to regions of the protein that interact with aqueous environments (e.g., cytosol, extracellular fluid). A transmembrane domain is often a hydrophobic alpha helix that spans the membrane. A transmembrane protein can pass through both layers of the lipid bilayer once or multiple times.

The terms "treating," "treatment," or "therapy" of a disease, condition or disorder as used herein mean slowing, stopping or reversing the disease or disorders progression, as evidenced by decreasing, cessation or elimination of either clinical or diagnostic symptoms, by administration of an immunomodulatory protein or engineered cells of the present invention either alone or in combination with another compound as described herein. "Treating," "treatment," or "therapy" also means a decrease in the severity of symptoms in an acute or chronic disease, condition or disorder or a decrease in the relapse rate as for example in the case of a relapsing or remitting autoimmune disease course or inflammatory condition or a decrease in inflammation in the case of an inflammatory aspect of an autoimmune disease or inflammatory condition. "Preventing," "prophylaxis," or "prevention" of a disease, condition or disorder as used in the context of this invention refers to the administration of an immunomodulatory protein of the present invention, either alone or in combination with another compound, to prevent the occurrence or onset of a disease, condition or disorder or some or all of the symptoms of a disease, condition or disorder or to lessen the likelihood of the onset of a disease, condition or disorder.

The term "variant" (also "modified" or mutant," which can be used interchangeably) as used in reference to a variant protein or polypeptide means a protein, such as a mammalian (e.g., human or murine) protein created by human intervention. The variant is a polypeptide having an altered or modified amino acid sequence, such as by one or more amino acid substitutions, deletions, additions or combinations thereof, relative to an unmodified or wild-type protein or to a domain thereof. A variant polypeptide can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions. A variant polypeptide generally exhibits at least about 50%, 60%, 70%, 80%, 85%, 86%, 87%, 88%, 89%, 90%, 91%, 92%, 93%, 94%, 95%, 96%, 97%, 98%, 99% or more sequence identity to a corresponding form of a wild-type or unmodified protein, such as a mature sequence thereof (lacking the signal sequence) or a portion thereof containing the extracellular domain or an binding domain thereof. Non-naturally occurring amino acids as well as naturally occurring amino acids are included within the scope of permissible substitutions or additions. A variant protein is not limited to any particular method of making and includes, for example, chemical synthesis, recombinant DNA techniques, or combinations thereof. A variant protein of the invention specifically binds to at least one or more binding partners. In some embodiments, the altered amino acid sequence results in an altered (i.e., increased or decreased) binding activity, such as binding affinity or avidity, to the one or more binding partners. A variant protein may thus be an "affinity-modified" protein as described herein.

The term "wild-type" or "natural" or "native," which are used interchangeably, as used herein is used in connection with biological materials such as nucleic acid molecules, proteins, host cells, and the like, that are found in nature and not modified by human intervention.

II. TACI Immunomodulatory Proteins and Variant TACI Polypeptides

Provided herein are TACI immunomodulatory proteins that contain a portion of the extracellular domain (ECD) of the TACI receptor, or a variant thereof, that bind to at least one TACI cognate binding partner. Also provided herein are variant TACI polypeptides that exhibit altered (e.g. increased) binding activity or affinity for one or more of a TACI cognate binding partner. In some embodiments, the TACI cognate binding partner is one or more of BAFF or APRIL or is a BAFF/APRIL heterotrimer. The provided TACI immunomodulatory proteins and polypeptides include soluble fusion proteins thereof in which the TACI portion of the extracellular domain or variant thereof is linked to another moiety, such as an immunoglobulin Fc or other multimerization domain or half-life extending moiety. Thus, in some embodiments the immunomodulatory protein is a TACI-Fc fusion protein. In some embodiments, provided is a TACI-Fc fusion protein containing (1) a TACI polypeptide composed of the extracellular domain of the TACI receptor or a portion thereof, or a variant TACI polypeptide thereof, that binds to at least one TACI cognate binding partner, and (2) an Fc domain. The TACI polypeptide or variant TACI polypeptide can be linked directly or indirectly (e.g. via a peptide linker) to the Fc domain.

TACI is a tumor necrosis factor receptor family member characterized by having an extracellular domain (ECD) containing cysteine-rich pseudo-repeat domains (CRDs). TACI is a membrane bound receptor, which has an extracellular domain containing two cysteine-rich pseudo-repeats (CRD1 and CRD2), a transmembrane domain and a cytoplasmic domain that interacts with CAML (calcium-modulator and cyclophilin ligand), an integral membrane protein located at intracellular vesicles which is a co-inducer of NF-AT activation when overexpressed in Jurkat cells. TACI is associated with B cells and a subset of T cells. The TACI receptor binds two members of the tumor necrosis factor (TNF) ligand family. One ligand is designated BAFF (B cell Activating Factor of the TNF Family), and also is variously designated as ZTNF4, "neutrokine-α," "BLyS," "TALL-1," and "THANK" (Yu et al., international publication No. WO98/18921 (1998), Moore et al., Science 285:269 (1999); Mukhopadhyay et al., J. Biol. Chem. 274:15978 (1999); Schneider et al., J. Exp. Med. 189:1747 (1999); Shu et al., J. Leukoc. Biol. 65:680 (1999)). The other ligand has been designated as APRIL, and also is variously designated as "ZTNF2" and "TNRF death ligand-1" (Hahne et al., J. Exp. Med. 188:1185 (1998); Kelly et al., Cancer Res. 60:1021 (2000)). Both ligands are also bound by the B-cell maturation receptor (BCMA) (Gross et al., Nature 404:995 (2000)). Binding of TACI receptor to its ligands BAFF or APRIL stimulates B cell responses, including T cell-independent B cell antibody responses, isotype switching, and B cell homeostasis.

The amino acid sequence of full-length TACI is set forth in SEQ ID NO:88. The protein is a type III membrane protein and lacks a signal peptide; following expression in eukaryotic cells the N-terminal methionine is removed. In some embodiments, a mature TACI protein does not contain the N-terminal methionine as set forth in SEQ ID NO:88. The extracellular domain of TACI (amino acid residues 1-166 of SEQ ID NO:88; ECD set forth in SEQ ID NO:122) contains two cysteine rich domain (CRDs, hereinafter also called a tumor necrosis family receptor domain or TD), each of which exhibit affinity for binding to BAFF and APRIL. The first cysteine rich domain (CRD1) contains amino acid residues 34-66 of the sequence set forth in SEQ ID NO:122. The second cysteine rich domain (CRD2) corresponds to amino acids 71-104 of the sequence set forth in SEQ ID NO:122. TACI also contains a stalk region of about 60 amino acids following the second cysteine repeat in the extracellular domain, corresponding to amino acid residues 105-165 of the sequence set forth in SEQ ID NO:122.

In some embodiments, the variant TACI polypeptides provided herein contain one or more amino acid modifications, such as one or more substitutions (alternatively, "mutations" or "replacements"), deletions or additions in the extracellular domain of a reference TACI polypeptide, such as a wild-type or unmodified TACI polypeptide containing a CRD(s) (hereinafter also called TDs). Thus, a provided variant TACI polypeptide is or comprises a variant TD ("vTD") in which the one or more amino acid modifications (e.g. substitutions) is in a CRD. In some embodiments, the one or more amino acids modifications, such as one or more substitutions (alternatively, "mutations" or "replacements"), deletions or additions, is in the CRD1 region. In some embodiments, the one or more amino acids modifications, such as one or more substitutions (alternatively, "mutations" or "replacements"), deletions or additions, is in the CRD2 region. In some embodiments, the one or more amino acids modifications, such as one or more substitutions (alternatively, "mutations" or "replacements"), deletions or additions, is in amino acids within both the CRD1 and CRD2 regions.

In some embodiments, the reference (e.g. unmodified) TACI sequence is a wild-type TACI sequence or is a portion thereof that contains one or both CRDs. In some embodiments, the reference (e.g., unmodified) TACI is or comprises the extracellular domain (ECD) of TACI or a portion thereof containing one or both CRD domains. In some embodiments, the extracellular domain of a reference (e.g., unmodified) TACI polypeptide comprises a CRD1 and CRD2. However, the variant TACI polypeptide need not comprise both the CRD1 and the CRD2. In some embodiments, the variant TACI polypeptide comprises or consists essentially of the CRD1 or a specific binding fragment thereof. In some embodiments, the variant TACI polypeptide comprises or consists essentially of the CRD2 or specific binding fragments thereof. In some embodiments, the variant TACI is a soluble polypeptide and lacks a transmembrane domain. In some embodiments, the variant TACI polypeptide further comprises a transmembrane domain and, in some cases, also a cytoplasmic domain.

In some embodiments, the reference (e.g., unmodified) TACI sequence is a mammalian TACI sequence. In some embodiments, the reference (e.g., unmodified) TACI sequence can be a mammalian TACI that includes, but is not limited to, human, mouse, cynomolgus monkey, or rat. In some embodiments, the reference (e.g., unmodified) TACI sequence is human. The extracellular domain of an exemplary human TACI sequence is set forth in SEQ ID NO:122.

In some embodiments, the reference (e.g., unmodified) TACI sequence has (i) the sequence of amino acids set forth in SEQ ID NO:122 or a sequence thereof that lacks the N-terminal methionine, (ii) a sequence of amino acids that exhibits at least about 85%, 86%, 87%, 88%, 89%, 90%, 91%, 92%, 93%, 94%, 95%, 96%, 97%, 98%, 99% or more sequence identity to SEQ ID NO:122 and that binds to APRIL, BAFF or an APRIL/BAFF heterotrimer, or (iii) is a fragment or portion of (i) or (ii) containing a CRD1 and/or CRD2, in which the portion binds to APRIL, BAFF or an APRIL/BAFF heterotrimer. In some embodiments, the reference (e.g., unmodified) TACI sequence lacks the N-terminal methionine as set forth in SEQ ID NO: 122.

TACI Extracellular Domain (ECD): SEQ ID NO:122
MSGLGRSRRGGRSRVDQEERFPQGLWTG-VAMRSCPEEQYWDPLLGTCMSCKTIC NHQSQRTCAAFCRSLSCRKEQGKFYDHLLRD-CISCASICGQHPKQCAYFCENKLR SPVNLP-PELRRQRSGEVENNSDNSGRYQGLEH-RGSEASPALPGLKLSADQVALVY ST In some embodiments, the reference (e.g. unmodified) TACI sequence is an extracellular domain sequence of TACI that is a portion of the ECD that contains an N-terminal deletion relative to the sequence of amino acids set forth in SEQ ID NO:122. In some embodiments, the N-terminal deletion is deletion of N-terminal amino acid residues 1-28 corresponding to residues set forth in SEQ ID NO:122. In some embodiments, the N-terminal deletion is deletion of N-terminal amino acid residues 1-29 corresponding to residues set forth in SEQ ID NO:122. In some embodiments, the N-terminal deletion is deletion of N-terminal amino acid residues 1-30 corresponding to residues set forth in SEQ ID NO:122. In some embodiments, the N-terminal deletion is deletion of N-terminal amino acid residues 1-31 corresponding to residues set forth in SEQ ID NO:122. In some embodiments, the N-terminal deletion is deletion of N-terminal amino acid residues 1-32 corresponding to residues set forth in SEQ ID NO:122. In some embodiments, the N-terminal deletion is deletion of N-terminal amino acid residues 1-33 corresponding to residues set forth in SEQ ID NO:122.

In some of any of the provided embodiments, the reference (e.g. unmodified) TACI sequence is an ECD portion that contains deletion of one or more residues of the stalk portion of the TACI extracellular domain. In some embodiments, the reference (e.g. unmodified) TACI sequence is an ECD portion that lacks one or more contiguous C-terminal amino acid residues beginning at residue 105 and up to or including amino acid residue 166 corresponding to residues of the ECD sequence set forth in SEQ ID NO:122. In some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 or 62 of the ECD sequence is deleted.

In some embodiments, the reference (e.g. unmodified) TACI sequence contains an ECD portion having a contiguous sequence of amino acids that includes the CRD1 and/or CRD2 (e.g. CRD1 and CRD2 or CRD2 only) and only a segment or portion of the stalk sequence. Suitable stalk segments include one or more amino acids of amino acid residues 105 to 154 of SEQ ID NO:122. For example, the stalk segment can consist of the following with reference to SEQ ID NO:122: amino acid residue 105, amino acid residues 105 to 106, amino acid residues 105 to 107, amino acid residues 105 to 108, amino acid residues 105 to 109, amino acid residues 105 to 110, amino acid residues 105 to 111, amino acid residues 105 to 112, amino acid residues 105 to 113, amino acid residues 105 to 114, amino acid residues 105 to 115, amino acid residues 105 to 116, amino acid residues 105 to 117, amino acid residues 105 to 118, amino acid residues 105 to 119, amino acid residues 105 to 120, amino acid residues 105 to 121, amino acid residues 105 to 122, amino acid residues 105 to 123, amino acid residues 105 to 124, amino acid residues 105 to 125, amino acid residues 105 to 126, amino acid residues 105 to 127, amino acid residues 105 to 128, amino acid residues 105 to 129, amino acid residues 105 to 130, amino acid residues 105 to 131, amino acid residues 105 to 132, amino acid residues 105 to 133, amino acid residues 105 to 134, amino acid residues 105 to 135, amino acid residues 105 to 136, amino acid residues 105 to 137, amino acid residues 105 to 138, amino acid residues 105 to 139, amino acid residues 105 to 140, amino acid residues 105 to 141, amino acid residues 105 to 142, amino acid residues 105 to 143, amino acid residues 105 to 144, amino acid residues 105 to 145, amino acid residues 105 to 146, amino acid residues 105 to 147, amino acid residues 105 to 148, amino acid residues 105 to 149, amino acid residues 105 to 150, amino acid residues 105 to 151, amino acid residues 105 to 152, amino acid residues 105 to 153, and amino acid residues 105 to 154.

In some embodiments, the reference (e.g. unmodified) TACI sequence lacks or is mutated in one or more potential furin cleavage sites. In some cases, the reference (e.g. unmodified) TACI sequence is an ECD or portion that in which the arginine residue at position 119 is mutated, e.g. R119G. In some cases, the reference (e.g. unmodified) TACI sequence is an ECD or portion that in which the glutamine residue at position 121 is mutated, e.g. Q121P. In some cases, the reference (e.g. unmodified) TACI sequence is an ECD or portion that in which the arginine residue at position 122 is mutated, e.g. R122Q.

In some embodiments, the reference TACI sequence is a TACI ECD sequence as set forth in international PCT publication No. WO2000/067034, WO2002/094852 or WO2008/154814.

In some embodiments, the reference TACI sequence is a TACI ECD sequence that has or consists of the sequence set forth in SEQ ID NO:131.

TACI ECD (CRD1/CRD2): SEQ ID NO:131
SRVDQEER FPQGLWTGVA MRSCPEEQYW DPLLGTCMSCKTICNHQSQR TCAAFCRSLS CRKEQGKFYD HLLRDCISCA SICGQHPKQCAYFCENKLRS PVNLPPEL

In some embodiments, the reference TACI sequence is a TACI ECD sequence that has or consists of the sequence set forth in SEQ ID NO:130.

TACI ECD (CRD1/CRD2): SEQ ID NO:130
AMRSCPEEQYWDPLLGTCMSCKTICNHQSQRT-CAAFCRSLSCRKEQGKFYDHLL RDCISCA-SICGQHPKQCAYFCENKLRS

In some embodiments, the reference TACI sequence is a TACI ECD sequence that has or consists of the sequence set forth in SEQ ID NO:1 (encoded by the sequence of nucleotides set forth in SEQ ID NO:36).

TACI ECD (CRD1/CRD2): SEQ ID NO:1
VAMRSCPEEQYWDPLLGTCMSCKTICNHQSQRT-CAAFCRSLSCRKEQGKFYDHLLR DCISCA-SICGQHPKQCAYFCENKLRS

In some embodiments, the reference TACI sequence is an extracellular domain region of TACI that consists essentially of only the CRD2 sequence and that is deleted in or lacks the entirety of the sequence of the CRD1 and substantially all of the stalk region. Although previous studies have shown that residues in the stalk region may contain a protease cleavage site, it was believed that at least the CRD1 and CRD2 was required for sufficient expression and/or binding activity of TACI for its cognate ligands. For example, international PCT publication No. WO2002/094852 demonstrated that a TACI molecule containing a CRD1 and CRD2, but in which the whole amino terminal region and a partial sequence of the stalk region was deleted, exhibited reduced protein degradation when expressed. Other studies showed that at least a portion of the N-terminal region before the CRD1 was necessary for sufficient binding activity of TACI for its cognate ligands, see e.g. international publication No. WO2008/154814, in which residues 13-118 or 13-108 of the TACI extracellular region were determined to be necessary for biological activity while minimizing degradation of TACI during expression. Surprisingly, it is found herein (e.g. Example 3) that a TACI extracellular region that consists essentially only of the CRD2 with a small portion of the stalk region exhibits substantially improved cognate binding activity compared to a longer TACI molecule containing both the CRD1 and CRD2.

Provided herein is an immunomodulatory protein (e.g. TACI-Fc fusion protein) containing a TACI polypeptide that is a portion of the TACI extracellular domain (ECD) region that contains the CRD2, with a deletion of the N-terminal region and CRD1 and deletion of one or more residues of the stalk portion of the TACI extracellular domain, e.g. relative to the sequence of amino acids set forth in SEQ ID NO:122. In some embodiments, the portion of the TACI extracellular domain that contains the CRD2 includes amino acid residues 71-104 corresponding to residues set forth in SEQ ID NO:122. In provided embodiments, the TACI polypeptide of the immunomodulatory protein contains deletion of N-terminal amino acid residues 1-66 corresponding to residues set forth in SEQ ID NO:122. In provided embodiments, the TACI polypeptide of the immunomodulatory protein contains deletion of N-terminal amino acid residues 1-67 corresponding to residues set forth in SEQ ID NO:122. In provided embodiments, the TACI polypeptide of the immunomodulatory protein contains deletion of N-terminal amino acid residues 1-68 corresponding to residues set forth in SEQ ID NO:122. In provided embodiments, the TACI polypeptide of the immunomodulatory protein contains deletion of N-terminal amino acid residues 1-69 corresponding to residues set forth in SEQ ID NO:122. In provided embodiments, the TACI polypeptide of the immunomodulatory protein contains deletion of N-terminal amino acid residues 1-70 corresponding to residues set forth in SEQ ID NO:122. In some of any such embodiments, the TACI polypeptide of the immunomodulatory protein lacks one or more contiguous C-terminal amino acid residues beginning at residue 105 and up to or including amino acid residue 166 corresponding to residues of the ECD sequence set forth in SEQ ID NO:122. In some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61 or 62 of the ECD sequence is deleted.

In some embodiments, an immunomodulatory protein (e.g. TACI-Fc fusion protein) provided herein has a TACI polypeptide with a sequence that contains an ECD portion having a contiguous sequence of amino acids of a TACI ECD that includes the CRD2 (e.g. residues 71-104 with reference to SEQ ID NO:122), but with a deletion of the N-terminal region and CRD1 and deletion of one or more residues of the stalk portion of the TACI extracellular domain, e.g. relative to the sequence of amino acids set forth in SEQ ID NO:122. For example, the TACI ECD portion can consist of the following with reference to amino acid residues set forth in SEQ ID NO:122: amino acid residues 67 to 118, amino acid residues 67 to 117, amino acid residues 67 to 116, amino acid residues 67 to 115, amino acid residues 67 to 114, amino acid residues 67 to 113, amino acid residues 67 to 112, amino acid residues 67 to 111, amino acid residues 67 to 110, amino acid residues 67 to 109, amino acid residues 67 to 108, amino acid residues 67 to 107, amino acid residues 67 to 106, amino acid residues 67 to 105, or amino acid residues 67 to 104. In some examples, the TACI ECD portion can consist of the following with reference to residues set forth in SEQ ID NO: 122: amino acid residues 68 to 118, amino acid residues 68 to 117, amino acid residues 68 to 116, amino acid residues 68 to 115, amino acid residues 68 to 114, amino acid residues 68 to 113, amino acid residues 68 to 112, amino acid residues 68 to 111, amino acid residues 68 to 110, amino acid residues 68 to 109, amino acid residues 68 to 108, amino acid residues 68 to 107, amino acid residues 68 to 106, amino acid residues 68 to 105, or amino acid residues 68 to 104. In some examples, the TACI ECD portion can consist of the following with reference to residues set forth in SEQ ID NO: 122: amino acid residues 69 to 118, amino acid residues 69 to 117, amino acid residues 69 to 116, amino acid residues 69 to 115, amino acid residues 69 to 114, amino acid residues 69 to 113, amino acid residues 69 to 112, amino acid residues 69 to 111, amino acid residues 69 to 110, amino acid residues 69 to 109, amino acid residues 69 to 108, amino acid residues 69 to 107, amino acid residues 69 to 106, amino acid residues 69 to 105, or amino acid residues 69 to 104. In some examples, the TACI ECD portion can consist of the following with reference to residues set forth in SEQ ID NO: 122: amino acid residues 70 to 118, amino acid residues 70 to 117, amino acid residues 70 to 116, amino acid residues 70 to 115, amino acid residues 70 to 114, amino acid residues 70 to 113, amino acid residues 70 to 112, amino acid residues 70 to 111, amino acid residues 70 to 110, amino acid residues 70 to 109, amino acid residues 70 to 108, amino acid residues 70 to 107, amino acid residues 70 to 106, amino acid residues 70 to 105, or amino acid residues 70 to 104. In some examples, the TACI ECD portion can consist of the following with reference to residues set forth in SEQ ID NO: 122: amino acid residues 71 to 118, amino acid residues 71 to 117, amino acid residues 71 to 116, amino acid residues 71 to 115, amino acid residues 71 to 114, amino acid residues 71 to 113, amino acid residues 71 to 112, amino acid residues 71 to 111, amino acid residues 71 to 110, amino acid residues 71 to 109, amino acid residues 71 to 108, amino acid residues 71 to 107, amino acid residues 71 to 106, amino acid residues 71 to 105, or amino acid residues 71 to 104. Any of the above TACI ECD sequences also can be a TACI reference sequence in accord with the immunomodulatory proteins provided herein, in which such immunomodulatory proteins contain a variant TACI polypeptide that is modified by one or more amino acid modification (e.g. substitution) as described herein compared to such TACI reference sequence.

In particular, among TACI polypeptides provided herein is a TACI ECD sequence that has or consists of the sequence set forth in SEQ ID NO:13 (encoded by the sequence of nucleotides set forth in SEQ ID NO:48). In some embodiments, the reference TACI sequence has or consists of the sequence set forth in SEQ ID NO:13, in which a provided variant TACI polypeptide is modified by one or more amino acid modification (e.g. substitution) as described herein compared to such reference TACI sequence.

TACI ECD sequence (CRD2): SEQ ID NO:13
SLSCRKEQGKFYDHLLRDCISCASICGQHPKQCAYFCENKLRS Among provided TACI polypeptides are variant TACI polypeptides. Also provided are immunomodulatory proteins, such as TACI-Fc fusion proteins, that contain a provided variant TACI polypeptide. In some of any of the provided embodiments, the variant TACI sequence has the sequence of the reference (e.g. unmodified) TACI sequence, such as any described above, but additionally contains one more amino acid modifications, such as one or more amino acid substitutions. In particular, provided herein are variant TACI polypeptides containing at least one affinity-modified TD domain (e.g., CRD1 and/or CRD2) or a specific binding fragment thereof that contains one or more amino acid substitutions in a TD domain of a reference (e.g., unmodified or wild-type) TACI polypeptide, such that the variant TACI polypeptide exhibits altered (e.g. increased) binding activity or affinity for one or both of APRIL or BAFF compared to the reference (e.g., unmodified or wild-type) TACI polypeptide. In some embodiments, a variant TACI polypeptide has a binding affinity for APRIL and/or BAFF that differs from that of a reference (e.g., unmodified or wild-type) TACI polypeptide control sequence as determined by, for example, solid-phase ELISA immunoassays, flow cytometry or Biacore assays. Binding affinities for each of the cognate binding partners are independent; that is, in some embodiments, a variant TACI polypeptide has an increased binding affinity for one or both APRIL and BAFF, and a decreased or unchanged binding affinity for the other of APRIL or BAFF, relative to a reference (e.g., unmodified or wild-type) TACI polypeptide.

In some embodiments, the variant TACI polypeptide has an increased binding affinity for BAFF, relative to the reference (unmodified or wild-type) TACI polypeptide. In some embodiments, the variant TACI polypeptide has an increased binding affinity for APRIL relative to the reference (unmodified or wild-type) TACI polypeptide. In some embodiments, the variant TACI polypeptide has an increased binding affinity for APRIL and BAFF relative to the reference (unmodified or wild-type) TACI polypeptide.

The cognate ligands BAFF and/or APRIL can be a mammalian protein, such as a human protein or a murine protein. In some embodiments, the cognate ligands BAFF and/or APRIL are human. In some embodiments, a variant TACI polypeptide with increased or greater binding affinity to APRIL and/or BAFF will have an increase in binding affinity relative to the reference (e.g., unmodified or wild-type) TACI polypeptide control of at least about 5%, such as at least about 10%, 15%, 20%, 25%, 35%, or 50%. In some embodiments, the increase in binding affinity relative to the reference (e.g., unmodified or wild-type) TACI polypeptide is more than about 1.2-fold, about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold or about 50-fold. In any of the examples, the reference (e.g., unmodified or wild-type) TACI polypeptide has the same sequence as the variant TACI polypeptide except that it does not contain the one or more amino acid modifications (e.g., substitutions).

In some embodiments, the equilibrium dissociation constant ($K_d$) of any of the foregoing embodiments to BAFF can be less than $1\times10^{-5}$M, $1\times10^{-6}$ M, $1\times10^{-7}$M, $1\times10^{-8}$ M, $1\times10^{-9}$ M, $1\times10^{-10}$ M or $1\times10^{-11}$M, or $1\times10^{-12}$ M. In some embodiments, the $K_d$ of any of the foregoing embodiments to BAFF is less than at or about $1\times10^{-9}$ M, $1\times10^{-10}$ M or $1\times10^{-11}$M, or $1\times10^{-12}$ M. In some embodiments, the $K_d$ of any of the foregoing embodiments to BAFF is between $1\times10^{-9}$ M and at or about $1\times10^{-12}$M. In some embodiments, the $K_d$ of any of the foregoing embodiments to BAFF is at or about $1\times10^{-9}$M, at or about $2\times10^{-9}$ M, at or about $4\times10^{-9}$ M, at or about $6\times10^{-9}$M, at or about $8\times10^{-9}$ M, at or about $1\times10^{-10}$ M, at or about $2\times10^{-10}$ M, at or about $4\times10^{-10}$ M, at or about $6\times10^{-10}$ M, at or about $8\times10^{-10}$ M, at or about $1\times10^{-11}$ M, at or about $2\times10^{-11}$ M, at or about $4\times10^{-11}$M, at or about $6\times10^{-11}$M, at or about $8\times10^{-11}$M, or at or about $1\times10^{-12}$M, or any value between any of the foregoing. In some embodiments, a provided embodiment includes a variant TACI polypeptide as described above and the $K_d$ to BAFF is decreased (higher binding affinity) by greater than or greater than about 1.5-fold, such as greater than or about 2-fold, 3-fold, 4-fold, 5-fold, 6-fold, 7-fold, 8-fold, 9-fold, 10-fold or more.

In some embodiments, the equilibrium dissociation constant ($K_d$) of any of the foregoing embodiments to APRIL can be less than $1\times10^{-5}$M, $1\times10^{-6}$ M, $1\times10^{-7}$ M, $1\times10^{-8}$ M, $1\times10^{-9}$ M, $1\times10^{-10}$ M or $1\times10^{-11}$M, or $1\times10^{-12}$ M. In some embodiments, the $K_d$ of any of the foregoing embodiments to APRIL is less than at or about $1\times10^{-9}$ M, $1\times10^{-10}$ M or $1\times10^{-11}$M, or $1\times10^{-12}$ M. In some embodiments, the $K_d$ of any of the foregoing embodiments to APRIL is between $1\times10^{-9}$ M and at or about $1\times10^{-12}$M. In some embodiments, the $K_d$ of any of the foregoing embodiments to APRIL is at or about $1\times10^{-9}$ M, at or about $2\times10^{-9}$ M, at or about $4\times10^{-9}$ M, at or about $6\times10^{-9}$ M, at or about $8\times10^{-9}$ M, at or about $1\times10^{-10}$ M, at or about $2\times10^{-10}$ M, at or about $4\times10^{-10}$ M, at or about $6\times10^{-10}$ M, at or about $8\times10^{-10}$ M, at or about $1\times10^{-11}$ M, at or about $2\times10^{-11}$ M, at or about $4\times10^{-11}$ M, at or about $6\times10^{-11}$ M, at or about $8\times10^{-11}$ M, or at or about $1\times10^{-12}$M, or any value between any of the foregoing. In some embodiments, a provided embodiment includes a variant TACI polypeptide as described above and the $K_d$ to APRIL is decreased (higher binding affinity) by greater than or greater than about 1.5-fold, such as greater than or about 2-fold, 3-fold, 4-fold, 5-fold, 6-fold, 7-fold, 8-fold, 9-fold, 10-fold or more.

The reference (e.g., unmodified or wild-type) TACI sequence does not necessarily have to be used as a starting composition to generate variant TACI polypeptides described herein. Therefore, use of the term "modification", such as "substitution" does not imply that the present embodiments are limited to a particular method of making variant TACI polypeptides or immunomodulatory proteins containing the same. Variant TACI polypeptides can be made, for example, by de novo peptide synthesis and thus does not necessarily require a modification, such as a "substitution", in the sense of altering a codon to encode for the modification, e.g. substitution. This principle also extends to the terms "addition" and "deletion" of an amino acid residue which likewise do not imply a particular method of making. The means by which the variant TACI polypeptides are designed or created is not limited to any particular method. In some embodiments, however, a reference (e.g., unmodified or wild-type) TACI encoding nucleic acid is mutagenized from reference (e.g., unmodified or wild-type) TACI genetic material and screened for desired specific binding affinity or other functional activity. In some embodiments, a variant TACI polypeptide is synthesized de novo utilizing protein or nucleic acid sequences available at any number of publicly available databases and then subsequently screened. The National Center for Biotechnology Information provides such information, and its website is publicly accessible via the internet as is the UniProtKB database as discussed previously.

Unless stated otherwise, as indicated throughout the present disclosure, the amino acid modification(s) in a variant TACI polypeptide are designated by amino acid position number corresponding to the numbering of positions of the reference ECD sequence set forth in SEQ ID NO:122. It is within the level of a skilled artisan to identify the corresponding position of a modification, e.g. amino acid substitution, in an TACI polypeptide, including portion thereof containing TD (e.g. CRD1 and/or CRD2) thereof, such as by alignment of a reference sequence (e.g. SEQ ID NO:1 or 13) with SEQ ID NO:122. An alignment identifying corresponding residues is exemplified in FIG. 9. In the listing of modifications throughout this disclosure, the amino acid position is indicated in the middle, with the corresponding reference (e.g. unmodified or wild-type) amino acid listed before the number and the identified variant amino acid substitution listed after the number. If the modification is a deletion of the position a "del" is indicated and if the modification is an insertion at the position an "ins" is indicated. In some cases, an insertion is listed with the amino acid position indicated in the middle, with the corresponding reference amino acid listed before and after the number and the identified variant amino acid insertion listed after the unmodified (e.g. wild-type) amino acid.

In some embodiments, the variant TACI polypeptide has one or more amino acid modification, e.g. substitution in a reference (e.g., unmodified or wild-type) TACI sequence, such as any as described. The one or more amino acid modification, e.g. substitution, can be in the ectodomain (extracellular domain) of the reference (e.g., unmodified or wild-type) TACI sequence. In some embodiments, the one or more amino acid modification, e.g. substitution is in the CRD1 domain or specific binding fragment thereof. In some embodiments, the one or more amino acid modification, e.g. substitution is in the CRD2 domain or specific binding fragment thereof. In some embodiments of the variant TACI polypeptide, some of the one or more amino acid modification, e.g. substitution is in the CRD1 domain or a specific binding fragment thereof, and some of the one or more amino acid modification, e.g. substitution are in the CRD2 domain or a specific binding fragment thereof.

In some embodiments, the variant TACI polypeptide has up to 1, 2, 3, 4, 5, 6, 7, 8, 9, 10, 11, 12, 13, 14, 15, 16, 17, 18, 19, or 20 amino acid modification(s), e.g. substitution, in the reference TACI sequence. The modification, e.g. substitution can be in the CRD1 domain or the CRD2 domain. In some embodiments, the variant TACI polypeptide has up to 1, 2, 3, 4, 5, 6, 7, 8, 9, 10, 11, 12, 13, 14, 15, 16, 17, 18, 19, or 20 amino acid substitutions in the CRD1 domain or specific binding fragment thereof of the reference TACI sequence. In some embodiments, the variant TACI polypeptide has up to 1, 2, 3, 4, 5, 6, 7, 8, 9, 10, 11, 12, 13, 14, 15, 16, 17, 18, 19, or 20 amino acid substitutions in the CRD2 domain or specific binding fragment thereof of the reference TACI sequence.

In some embodiments, the variant TACI polypeptide containing the one or more amino acid modifications (e.g. amino acid substations) as described has at least about 85%, 86%, 86%, 88%, 89%, 90%, 91%, 92%, 93%, 94%, 95%, 96%, 97%, 98%, or 99% sequence identity with the reference (e.g., unmodified or wild-type) TACI polypeptide set forth in SEQ ID NO:122 or specific binding fragment thereof containing the CRD1 and/or CRD2 domain. In some embodiments, the specific binding fragment contains the CRD1 domain, e.g. the specific binding fragment contains the sequence set forth as amino acids 34-66 of SEQ ID NO:122. In some cases, the CRD1 domain is the only full CRD domain in the specific binding fragment. In some embodiments, the specific binding fragment is or contains the CRD2 domain, e.g. the specific binding fragment contains the sequence set forth as amino acids 71-104 of SEQ ID NO:122. In some cases, the CRD2 domain is the only full CRD domain in the specific binding fragment. In some embodiments, the specific binding fragment is or contains the CRD1 domain and the CRD2 domain, e.g. the specific binding fragment contains amino acids 34-104 of SEQ ID NO:122. In some embodiments, the specific binding fragment contains a contiguous portion of the stalk domain, e.g. the specific binding fragment contains a contiguous portion of amino acids 105-165 of SEQ ID NO:122. In some of any embodiments, the specific binding fragment of SEQ ID NO:122 is less than the full-length ECD set forth in SEQ ID NO:122. In some embodiments, the specific binding fragment is set forth in SEQ ID NO: 1. In some embodiments, the specific binding fragment is set forth in SEQ ID NO:13. In some embodiments, the specific binding fragment is set forth in SEQ ID NO: 130. In some embodiments, the specific binding fragment is set forth in SEQ ID NO:131.

In some embodiments, the variant TACI polypeptide containing the one or more amino acid modifications (e.g. amino acid substitutions) as described has at least about 85%, 86%, 86%, 88%, 89%, 90%, 91%, 92%, 93%, 94%, 95%, 96%, 97%, 98%, or 99% sequence identity with the reference (e.g., unmodified or wild-type) TACI polypeptide or specific binding fragment thereof, such as with the amino acid sequence of SEQ ID NO: 1, 13 or 122.

In some embodiments, the variant TACI polypeptide containing the one or more amino acid modifications (e.g. amino acid substitutions) as described has at least about 85%, 86%, 86%, 88%, 89%, 90%, 91%, 92%, 93%, 94%, 95%, 96%, 97%, 98%, or 99% sequence identity with the amino acid sequence of SEQ ID NO: 122.

In some embodiments, the variant TACI polypeptide containing the one or more amino acid modifications (e.g. amino acid substitutions) as described has at least about 85%, 86%, 86%, 88%, 89%, 90%, 91%, 92%, 93%, 94%, 95%, 96%, 97%, 98%, or 99% sequence identity with the amino acid sequence of SEQ ID NO: 1.

In some embodiments, the variant TACI polypeptide containing the one or more amino acid modifications (e.g. amino acid substitutions) as described has at least about 85%, 86%, 86%, 88%, 89%, 90%, 91%, 92%, 93%, 94%, 95%, 96%, 97%, 98%, or 99% sequence identity with the amino acid sequence of SEQ ID NO: 13.

In some embodiments, the variant TACI polypeptide containing the one or more amino acid modifications (e.g. amino acid substitutions) as described has at least about 85%, 86%, 86%, 88%, 89%, 90%, 91%, 92%, 93%, 94%, 95%, 96%, 97%, 98%, or 99% sequence identity with the amino acid sequence of SEQ ID NO: 130.

In some embodiments, the variant TACI polypeptide containing the one or more amino acid modifications (e.g. amino acid substitutions) as described has at least about 85%, 86%, 86%, 88%, 89%, 90%, 91%, 92%, 93%, 94%, 95%, 96%, 97%, 98%, or 99% sequence identity with the amino acid sequence of SEQ ID NO: 131.

In some embodiments, the variant TACI polypeptide has one or more amino acid modification, e.g. substitution in a reference TACI polypeptide or specific binding fragment there of corresponding to position(s) 40, 59, 60, 61, 74, 75, 76, 77, 78, 79, 82, 83, 84, 85, 86, 87, 88, 92, 95, 97, 98, 99, 101, 102 and 103 with reference to numbering of SEQ ID NO:122. In some embodiments, the variant TACI polypeptide has one or more amino acid modification, e.g. substitution selected from W40R, Q59R, R60G, T61P, E74V, Q75E, Q75R, G76S, K77E, F78Y, Y79F, L82H, L82P, L83S, R84G, R84L, R84Q, D85E, D85V, C86Y, I87L, I87M, S88N, I92V, Q95R, P97S, K98T, Q99E, A101D, Y102D, F103S, F103V, F103Y, or a conservative amino acid substitution thereof. In some embodiments, the reference TACI polypeptide includes the CRD1 domain or CRD2 domain, for example the reference TACI polypeptide is set forth in SEQ ID NO: 1 or SEQ ID NO:122.

In some embodiments, the amino acid substitutions are in the CRD2 domain only. In some embodiments, the variant TACI polypeptide has one or more amino acid modification, e.g. substitution in a reference TACI polypeptide or specific binding fragment there of corresponding to position(s) 74, 75, 76, 77, 78, 79, 82, 83, 84, 85, 86, 87, 88, 92, 95, 97, 98, 99, 101, 102 and 103 with reference to numbering of SEQ ID NO:122. In some embodiments, the variant TACI polypeptide has one or more amino acid modification, e.g. substitution selected from E74V, Q75E, Q75R, G76S, K77E, F78Y, Y79F, L82H, L82P, L83S, R84G, R84L, R84Q, D85E, D85V, C86Y, I87L, I87M, S88N, I92V, Q95R, P97S, K98T, Q99E, A101D, Y102D, F103S, F103V, F103Y, or a conservative amino acid substitution thereof. In some embodiments, among the CRD domains, the reference TACI polypeptide includes only the CRD2 domain but lacks the CRD1 domain, for example the reference TACI polypeptide is set forth in SEQ ID NO: 13. Accordingly, in some embodiments, the variant TACI polypeptide includes a portion of the ECD sequence of a TACI polypeptide that includes the CRD2 domain but lacks the CRD1 domain.

A conservative amino acid modification, e.g. substitution is any amino acid that falls in the same class of amino acids as the substituted amino acids, other than the reference (e.g., unmodified) or wild-type amino acid. The classes of amino acids are aliphatic (glycine, alanine, valine, leucine, and isoleucine), hydroxyl or sulfur-containing (serine, cysteine, threonine, and methionine), cyclic (proline), aromatic (phenylalanine, tyrosine, tryptophan), basic (histidine, lysine, and arginine), and acidic/amide (aspartate, glutamate, asparagine, and glutamine).

In some embodiments, the variant TACI polypeptide includes at least one amino acid substitution at position 75 with reference to numbering of SEQ ID NO:122. In some embodiments, the amino acid substitution at position 75 confers increased binding to BAFF or APRIL compared to the reference (e.g. wildtype or unmodified) TACI polypeptide not containing the amino acid substitution. In some embodiments, the substituted amino acid is an acidic amino acid or amide, such as to a different acidic amino acid or amide compared to the reference (e.g. wildtype or unmodified) TACI polypeptide. In some embodiments, the substituted amino acid at position 75 is a glutamic acid (Glu, E). In some embodiments, the substituted amino acid at position 75 is an aspartatic acid (Asp, D). In some embodiments, the substituted amino acid at position 75 is an asparagine (Asn, N). In some embodiments, the substituted amino acid at position 75 is a glutamine (Gln, Q).

In some embodiments, the variant TACI polypeptide includes at least one amino acid substitution at position 77 with reference to numbering of SEQ ID NO:122. In some embodiments, the amino acid substitution at position 77 confers increased binding to BAFF or APRIL compared to the reference (e.g. wildtype or unmodified) TACI polypeptide not containing the amino acid substitution. In some embodiments, the substituted amino acid at position 77 is an acidic amino acid or amide. In some embodiments, the substituted amino acid at position 77 is a glutamic acid (Glu, E). In some embodiments, the substituted amino acid at position 77 is an aspartatic acid (Asp, D). In some embodiments, the substituted amino acid at position 77 is an asparagine (Asn, N). In some embodiments, the substituted amino acid at position 77 is a glutamine (Gln, Q).

In some embodiments, the variant TACI polypeptide includes at least one amino acid substitution at position 78 with reference to numbering of SEQ ID NO:122. In some embodiments, the amino acid substitution at position 78 confers increased binding to BAFF or APRIL compared to the reference (e.g. wildtype or unmodified) TACI polypeptide not containing the amino acid substitution. In some embodiments, the substituted amino acid at position 78 is an aromatic amino acid, such as to a different aromatic amino acid compared to the reference (e.g. wildtype or unmodified) TACI polypeptide. In some embodiments, the substituted amino acid at position 78 is a phenyalanine (Phe, F). In some embodiments, the substituted amino acid at position 78 is a tyrosine (Tyr, Y). In some embodiments, the substituted amino acid at position 78 is a tryptophan (Trp, W).

In some embodiments, the variant TACI polypeptide includes at least one amino acid substitution at position 84 with reference to numbering of SEQ ID NO:122. In some embodiments, the amino acid substitution at position 84 confers increased binding to BAFF or APRIL compared to the reference (e.g. wildtype or unmodified) TACI polypeptide not containing the amino acid substitution. In some embodiments, the substituted amino acid at position 84 is an acidic amino acid or amide. In some embodiments, the substituted amino acid at position 84 is a glutamic acid (Glu, E). In some embodiments, the substituted amino acid at position 84 is an aspartic acid (Asp, D). In some embodiments, the substituted amino acid at position 84 is an asparagine (Asn, N). In some embodiments, the substituted amino acid at position 84 is a glutamine (Gln, Q).

In some embodiments, the variant TACI polypeptide includes at least one amino acid substitution at position 101 with reference to numbering of SEQ ID NO:122. In some embodiments, the amino acid substitution at position 101 confers increased binding to BAFF or APRIL compared to the reference (e.g. wildtype or unmodified) TACI polypeptide not containing the amino acid substitution. In some embodiments, the substituted amino acid at position 101 is an acidic amino acid or amide. In some embodiments, the substituted amino acid at position 101 is a glutamic acid (Glu, E). In some embodiments, the substituted amino acid at position 101 is an aspartatic acid (Asp, D). In some embodiments, the substituted amino acid at position 101 is an asparagine (Asn, N). In some embodiments, the substituted amino acid at position 101 is a glutamine (Gln, Q).

In some embodiments, the variant TACI polypeptide includes at least one amino acid substitution at position 102 with reference to numbering of SEQ ID NO:122. In some embodiments, the amino acid substitution at position 102 confers increased binding to BAFF or APRIL compared to the reference (e.g. wildtype or unmodified) TACI polypeptide not containing the amino acid substitution. In some embodiments, the substituted amino acid at position 102 is an acidic amino acid or amide. In some embodiments, the substituted amino acid at position 102 is a glutamic acid (Glu, E). In some embodiments, the substituted amino acid at position 102 is an aspartatic acid (Asp, D). In some embodiments, the substituted amino acid at position 102 is an asparagine (Asn, N). In some embodiments, the substituted amino acid at position 102 is a glutamine (Gln, Q).

In some embodiments, the variant TACI polypeptide includes at least one amino acid substitution E74V. In some embodiments, the variant TACI polypeptide includes at least one amino acid substitution Q75E. In some embodiments, the variant TACI polypeptide includes at least one amino acid substitution K77E. In some embodiments, the variant TACI polypeptide includes at least one amino acid substitution F78Y. In some embodiments, the variant TACI polypeptide includes at least one amino acid substitution Y79F. In some embodiments, the variant TACI polypeptide includes at least one amino acid substitution L82H. In some embodiments, the variant TACI polypeptide includes at least one amino acid substitution L82P. In some embodiments, the variant TACI polypeptide includes at least one amino acid substitution R84G. In some embodiments, the variant TACI polypeptide includes at least one amino acid substitution R84L. In some embodiments, the variant TACI polypeptide includes at least one amino acid substitution R84Q. In some embodiments, the variant TACI polypeptide includes at least one amino acid substitution D85V. In some embodiments, the variant TACI polypeptide includes at least one amino acid substitution C86Y. In some embodiments, the variant TACI polypeptide includes at least one amino acid substitution A101D. In some embodiments, the variant TACI polypeptide includes at least one amino acid substitution Y102D. In some embodiments, the variant TACI polypeptide contains two or more amino acid substitutions of any two or more of the foregoing. In some embodiments, the variant TACI polypeptide includes one or more amino acid substitution that is a conservative amino acid substitution of any of the foregoing. In provided embodiments, the variant TACI polypeptide includes the at least one amino acid substitution in any reference TACI polypeptide sequence as described. In some embodiments, the at least one amino acid substitution is in the reference TACI sequence set forth in SEQ ID NO: 1. In some embodiments, the at least one amino acid substitution is in the reference TACI sequence set forth in SEQ ID NO: 13. In some embodiments, the at least one amino acid substitution is in the reference TACI sequence set forth in SEQ ID NO: 130. In some embodiments, the at least one amino acid substitution is in the reference TACI sequence set forth in SEQ ID NO: 131.

In some embodiments, the variant TACI polypeptide includes the amino acid substitution E74V. In some embodiments, the variant TACI polypeptide includes the amino acid substitution Q75E. In some embodiments, the variant TACI polypeptide includes the amino acid substitution K77E. In some embodiments, the variant TACI polypeptide includes the amino acid substitution F78Y. In some embodiments, the variant TACI polypeptide includes the amino acid substitution Y79F. In some embodiments, the variant TACI polypeptide includes the amino acid substitution L82H. In some embodiments, the variant TACI polypeptide includes the amino acid substitution L82P. In some embodiments, the variant TACI polypeptide includes the amino acid substitution R84G. In some embodiments, the variant TACI polypeptide includes the amino acid substitution R84L. In some embodiments, the variant TACI polypeptide includes the amino acid substitution R84Q. In some embodiments, the variant TACI polypeptide includes the amino acid substitution D85V. In some embodiments, the variant TACI polypeptide includes the amino acid substitution C86Y. In some embodiments, the variant TACI polypeptide includes the amino acid substitution A102D. In some embodiments, the variant TACI polypeptide includes the amino acid substitution Y102D. In some embodiments, the variant TACI polypeptide contains two or more amino acid substitutions of any two or more of the foregoing. In some embodiments, the variant TACI polypeptide includes one or more of amino acid substitution that is a conservative amino acid substitution of any of the foregoing. In provided embodiments, the variant TACI polypeptide includes the amino acid substitution in any reference TACI polypeptide sequence as described. In some embodiments, the amino acid substitution is in the reference TACI sequence set forth in SEQ ID NO: 1. In some embodiments, the amino acid substitution is in the reference TACI sequence set forth in SEQ ID NO: 13. In some embodiments, the amino acid substitution is in the reference TACI sequence set forth in SEQ ID NO: 130. In some embodiments, the amino acid substitution is in the reference TACI sequence set forth in SEQ ID NO: 131.

In some embodiments, the amino acid substitutions are D85E/K98T. In some embodiments, the amino acid substitutions are I87L/K98T. In some embodiments, the amino acid substitutions are R60G/Q75E/L82P. In some embodiments, the amino acid substitutions are R60G/C86Y. In some embodiments, the amino acid substitutions are W40R/L82P/F103Y. In some embodiments, the amino acid substitutions are W40R/Q59R/T61P/K98T. In some embodiments, the amino acid substitutions are L82P/I87L. In some embodiments, the amino acid substitutions are G76S/P97S. In some embodiments, the amino acid substitutions are K77E/R84L/F103Y. In some embodiments, the amino acid substitutions are Y79F/Q99E. In some embodiments, the amino acid substitutions are L83S/F103S. In some embodiments, the amino acid substitutions are K77E/R84Q. In some embodiments, the amino acid substitutions are K77E/A101D. In some embodiments, the amino acid substitutions are K77E/F78Y/Y102D. In some embodiments, the amino acid substitutions are Q75E/R84Q. In some embodiments, the amino acid substitutions are Q75R/R84G/I92V. In some embodiments, the amino acid substitutions are K77E/A101D/Y102D. In some embodiments, the amino acid substitutions are R84Q/S88N/A101D. In some embodiments, the amino acid substitutions are R84Q/F103V. In some embodiments, the amino acid substitutions are K77E/Q95R/A101D. In some embodiments, the amino acid substitutions are I87M/A101D. In provided embodiments, the variant TACI polypeptide includes the amino acid substitutions in any reference TACI polypeptide sequence as described. In some embodiments, the amino acid substitution is in the reference TACI sequence set forth in SEQ ID NO: 1. In some embodiments, the amino acid substitution is in the reference TACI sequence set forth in SEQ ID NO: 13. In some embodiments, the amino acid substitution is in the reference TACI sequence set forth in SEQ ID NO: 130. In some embodiments, the amino acid substitution is in the reference TACI sequence set forth in SEQ ID NO: 131.

In some of any embodiments, the variant TACI polypeptide includes one or more amino acid substitutions from Q75E, K77E, F78Y, R84G, R84Q, A101D or Y102D, or any combination thereof. In some embodiments, the variant TACI polypeptide includes any 1, 2, 3, 4, 5 or 6 of the above amino acid substitutions. In some embodiments, the variant TACI polypeptide contains one of the above amino acid substitutions. In some embodiments, the variant TACI polypeptide contains two of the above amino acid substitutions. In some embodiments, the variant TACI polypeptide contains three of the above amino acid substitutions. In some embodiments, the variant TACI polypeptide contains four of the above amino acid substitutions. In some embodiments, the variant TACI polypeptide contains five of the above amino acid substitutions. In some embodiments, the variant TACI polypeptide contains six of the above amino acid substitutions.

In some of any embodiments, the one or more amino acid substitutions comprise Q75E/R84Q. In some of any embodiments, the one or more amino acid substitutions comprise Q75E/K77E. In some of any embodiments, the one or more amino acid substitutions comprise Q75E/F78Y. In some of any embodiments, the one or more amino acid substitutions comprise Q75E/A101D. In some of any embodiments, the one or more amino acid substitutions comprise Q75E/Y102D. In some of any embodiments, the one or more amino acid substitutions comprise F77E/F78Y. In some of any embodiments, the one or more amino acid substitutions comprise K77E/R84Q. In some of any embodiments, the one or more amino acid substitutions comprise K77E/A101D. In some of any embodiments, the one more amino acid substitutions comprise K77E/Y102D. In some of any embodiments, the one or more amino acid substitutions comprise F78Y/R84Q. In some of any embodiments, the one or more amino acid substitutions comprise F78Y/A101D. In some of any embodiments, the one or more amino acid substitutions comprise F78Y/Y102D. In some of any embodiments, the one or more amino acid substitutions comprise R84Q/A101D. In some of any embodiments, the one or more amino acid substitutions comprise R84Q/Y102D. In some of any embodiments, the one or more amino acid substitutions comprise A101D/Y102D. In provided embodiments, the variant TACI polypeptide includes the amino acid substitutions in any reference TACI polypeptide sequence as described, such as in the sequence set forth in SEQ ID NO:1, SEQ ID NO:13, SEQ ID NO:130 or SEQ ID NO: 131.

In some embodiments, the variant TACI polypeptides includes the amino acid substitution(s) R84G, A101D, K77E/R84Q, K77E/A101D, K77E/F78Y, K77E/F78Y/Y102D, Q75E/R84Q, K77E/A101D/Y102D, R84Q, K77E, A101D, Q75E, K77E/F78Y/R84Q, F78Y, F78Y/R84Q, F78Y/A101D, F78Y/Y102D, or K77E/Y102D. In provided embodiments, the variant TACI polypeptide includes the amino acid substitutions in any reference TACI polypeptide sequence as described, such as in the sequence set forth in SEQ ID NO:1, SEQ ID NO:13, SEQ ID NO:130 or SEQ ID NO: 131.

In some embodiments, the variant TACI polypeptide includes the amino acid substitutions K77E and F78Y (K77E/F78Y). In provided embodiments, the variant TACI polypeptide includes the amino acid substitutions in any reference TACI polypeptide sequence as described. In some embodiments, the amino acid substitution is in the reference TACI sequence set forth in SEQ ID NO: 1. In some embodiments, the amino acid substitution is in the reference TACI sequence set forth in SEQ ID NO: 13. In some embodiments, the amino acid substitution is in the reference TACI sequence set forth in SEQ ID NO: 130. In some embodiments, the amino acid substitution is in the reference TACI sequence set forth in SEQ ID NO: 131.

In some embodiments, the variant TACI polypeptide includes the amino acid substitutions K77E and Y102D (K77E/Y102D). In provided embodiments, the variant TACI polypeptide includes the amino acid substitutions in any reference TACI polypeptide sequence as described. In some embodiments, the amino acid substitution is in the reference TACI sequence set forth in SEQ ID NO: 1. In some embodiments, the amino acid substitution is in the reference TACI sequence set forth in SEQ ID NO: 13. In some embodiments, the amino acid substitution is in the reference TACI sequence set forth in SEQ ID NO: 130. In some embodiments, the amino acid substitution is in the reference TACI sequence set forth in SEQ ID NO: 131.

In some embodiments, the variant TACI polypeptide contains the amino acid substitutions F78Y and Y102D (F78Y/Y012D). In provided embodiments, the variant TACI polypeptide includes the amino acid substitutions in any reference TACI polypeptide sequence as described. In some embodiments, the amino acid substitution is in the reference TACI sequence set forth in SEQ ID NO: 1. In some embodiments, the amino acid substitution is in the reference TACI sequence set forth in SEQ ID NO: 13. In some embodiments, the amino acid substitution is in the reference TACI sequence set forth in SEQ ID NO: 130. In some embodiments, the amino acid substitution is in the reference TACI sequence set forth in SEQ ID NO: 131.

In some embodiments the variant TACI polypeptide contains the amino acid substitutions K77E, F78Y and Y102D (K77E/F78Y/Y102D). In provided embodiments, the variant TACI polypeptide includes the amino acid substitutions in any reference TACI polypeptide sequence as described. In some embodiments, the amino acid substitution is in the reference TACI sequence set forth in SEQ ID NO: 1. In some embodiments, the amino acid substitution is in the reference TACI sequence set forth in SEQ ID NO: 13. In some embodiments, the amino acid substitution is in the reference TACI sequence set forth in SEQ ID NO: 130. In some embodiments, the amino acid substitution is in the reference TACI sequence set forth in SEQ ID NO: 131.

In some embodiments, the variant TACI polypeptide contains the amino acid substitutions Q75E/R84Q. In provided embodiments, the variant TACI polypeptide includes the amino acid substitutions in any reference TACI polypeptide sequence as described. In some embodiments, the amino acid substitution is in the reference TACI sequence set forth in SEQ ID NO: 1. In some embodiments, the amino acid substitution is in the reference TACI sequence set forth in SEQ ID NO: 13. In some embodiments, the amino acid substitution is in the reference TACI sequence set forth in SEQ ID NO: 130. In some embodiments, the amino acid substitution is in the reference TACI sequence set forth in SEQ ID NO: 131.

In some embodiments, the variant TACI polypeptide comprises any of the mutations listed in Table 1. Table 1 also provides exemplary sequences by reference to SEQ ID NO of the reference (e.g., unmodified) TACI polypeptide, and exemplary variant TACI polypeptides. As indicated, the exact locus or residues corresponding to a given domain can vary, such as depending on the methods used to identify or classify the domain. Also, in some cases, adjacent N- and/or C-terminal amino acids of a given domain (e.g. CRD) also can be included in a sequence of a variant TACI polypeptide, such as to ensure proper folding of the domain when expressed. Thus, it is understood that the exemplification of the SEQ ID NOs in Table 1 is not to be construed as limiting. For example, the particular domain, such as the ECD domain or a portion thereof containing the CRD1/CRD2 or CRD2 only, of a variant TACI polypeptide can be several amino acids longer or shorter, such as 1-10, e.g., 1, 2, 3, 4, 5, 6 or 7 amino acids longer or shorter, than the sequence of amino acids set forth in the respective SEQ ID NO.

In some embodiments, the variant TACI polypeptide comprises any of the mutations (amino acid substitutions) listed in Table 1. In some examples, the mutations (amino acid substitutions) are made in a reference TACI containing the sequence of amino acids set forth in SEQ ID NO: 122. In some examples, the mutations (amino acid substitutions) are made a reference TACI that contains the CRD1 and CRD2 domain of TACI, for example as set forth in SEQ ID NO: 1. In some examples, the mutations (amino acid substitutions) are made in a reference TACI that is further truncated by deletion of N-terminal and C-terminal amino acid residues to retain the CRD2, for example as set forth in SEQ ID NO: 13.

The use of the term "modification", such as "substitution" or "mutation," does not imply that the present embodiments are limited to a particular method of making the immunomodulatory proteins. A variant TACI polypeptide can be made, for example, by de novo peptide synthesis and thus does not necessarily require a modification, such as a "substitution" in the sense of altering a codon to encode for the modification, e.g. substitution. This principle also extends to the terms "addition" and "deletion" of an amino acid residue which likewise do not imply a particular method of making. The means by which the vTDs are designed or created is not limited to any particular method. In some embodiments, however, a wild-type or unmodified TD encoding nucleic acid is mutagenized from wild-type or unmodified TD genetic material and screened for desired specific binding activity, e.g. binding affinity, and/or alteration of NF-κB modulation or other functional activity. In some embodiments, a vTD is synthesized de novo utilizing protein or nucleic acid sequences available at any number of publicly available databases and then subsequently screened. The National Center for Biotechnology Information provides such information and its website is publicly accessible via the internet as is the UniProtKB database.

In some embodiments, the variant TACI polypeptide comprises an extracellular domain (ECD) sequences containing a CRD1 and CRD2, such as a variant TACI polypeptide set forth in any one of SEQ ID NOS: 2-12, 21, 22, 101-120. In some embodiments, the variant TACI polypeptide comprises a polypeptide sequence that exhibits at least about 90% identity, at least about 91% identity, at least about 92% identity, at least about 93% identity, at least about 94% identity, at least about 95% identity, such as at least about 96% identity, 97% identity, 98% identity, or 99% identity to any one of SEQ ID NOS: 2-12, 21, 22, 101-120, and retains the amino acid modification(s), e.g. substitution(s) therein not present in the reference (e.g., unmodified or wild-type) TACI. In some embodiments, the variant TACI polypeptide comprises a specific binding fragment of any one of SEQ ID NOS: 2-12, 21, 22, 101-120, in which the specific binding fragment binds BAFF, APRIL or a BAFF/APRIL heterotrimer, and contains a contiguous sequence therein that contains the amino acid modification(s), e.g. substitution (s) therein not present in the reference (e.g., unmodified or wild-type) TACI.

In some embodiments, the variant TACI polypeptide consists or consists essentially of a variant TACI extracellular domain (ECD) sequences set forth in any one of SEQ ID NOS: 2-12, 21, 22, 101-120. In some embodiments, the variant TACI polypeptide consists or consists essentially of a polypeptide sequence that exhibits at least about 90% identity, at least about 91% identity, at least about 92% identity, at least about 93% identity, at least about 94% identity, at least about 95% identity, such as at least about 96% identity, 97% identity, 98% identity, or 99% identity to any one of SEQ ID NOS: 2-12, 21, 22, 101-120, and retains the amino acid modification(s), e.g. substitution(s) therein not present in the reference (e.g., unmodified or wild-type) TACI. In some embodiments, the variant TACI polypeptide consists or consists essentially of a specific binding fragment of any one of SEQ ID NOS: 2-12, 21, 22, 101-120, in which the specific binding fragment binds BAFF, APRIL or an APRIL/BAFF heterotrimer and contains a contiguous sequence therein that contains the amino acid modification (s), e.g. substitution (s) therein not present in the reference (e.g., unmodified or wild-type) TACI.

In some embodiments, the variant TACI polypeptide comprises an extracellular domain (ECD) sequences containing a CRD2 but lacking the CRD1 of a reference TACI polypeptide, such as a variant TACI polypeptide set forth in any one of SEQ ID NOS: 14-20, 23-35, 92-100, 177-192. In some embodiments, the variant TACI polypeptide comprises a polypeptide sequence that exhibits at least about 90% identity, at least about 91% identity, at least about 92% identity, at least about 93% identity, at least about 94% identity, at least about 95% identity, such as at least about 96% identity, 97% identity, 98% identity, or 99% identity to any one of SEQ ID NOS: 14-20, 23-35, 92-100, 177-192, and retains the amino acid modification(s), e.g. substitution (s) therein not present in the reference (e.g., unmodified or wild-type) TACI. In some embodiments, the variant TACI polypeptide comprises a specific binding fragment of any one of SEQ ID NOS: 14-20, 23-35, 92-100, 177-192, in which the specific binding fragment binds BAFF, APRIL or a BAFF/APRIL heterotrimer, and contains a contiguous sequence therein that contains the amino acid modification (s), e.g. substitution (s) therein not present in the reference (e.g., unmodified or wild-type) TACI.

In some embodiments, the variant TACI polypeptide consists or consists essentially of the sequence set forth in any one of SEQ ID NOS: 14-20, 23-35, 92-100, 177-192. In some embodiments, the variant TACI polypeptide consists or consists essentially of a polypeptide sequence that exhibits at least about 90% identity, at least about 91% identity, at least about 92% identity, at least about 93% identity, at least about 94% identity, at least about 95% identity, such as at least about 96% identity, 97% identity, 98% identity, or 99% identity to any one of SEQ ID NOS: 14-20, 23-35, 92-100, 177-192, and retains the amino acid modification(s), e.g. substitution(s) therein not present in the reference (e.g., unmodified or wild-type) TACI. In some embodiments, the variant TACI polypeptide consists or consists essentially of a specific binding fragment of any one of SEQ ID NOS: 14-20, 23-35, 92-100, 177-192, in which the specific binding fragment binds BAFF, APRIL or a BAFF/APRIL heterotrimer, and contains a contiguous sequence therein that contains the amino acid modification(s), e.g. substitution (s) therein not present in the reference (e.g., unmodified or wild-type) TACI.

In some embodiments, the variant TACI polypeptide comprises the sequence set forth in SEQ ID NO:20. In some embodiments, the variant TACI polypeptide consists essentially of the sequence set forth in SEQ ID NO:20. In some embodiments, the variant TACI polypeptide consists of the sequence set forth in SEQ ID NO:20.

In some embodiments, the variant TACI polypeptide comprises the sequence set forth in SEQ ID NO:26. In some embodiments, the variant TACI polypeptide consists essentially of the sequence set forth in SEQ ID NO:26. In some embodiments, the variant TACI polypeptide consists of the sequence set forth in SEQ ID NO:26.

In some embodiments, the variant TACI polypeptide comprises the sequence set forth in SEQ ID NO:27. In some embodiments, the variant TACI polypeptide consists essentially of the sequence set forth in SEQ ID NO:27. In some embodiments, the variant TACI polypeptide consists of the sequence set forth in SEQ ID NO:27.

In some embodiments, the variant TACI polypeptide comprises the sequence set forth in SEQ ID NO:107. In some embodiments, the variant TACI polypeptide consists essentially of the sequence set forth in SEQ ID NO:107. In some embodiments, the variant TACI polypeptide consists of the sequence set forth in SEQ ID NO:107.

In some embodiments, the variant TACI polypeptide is encoded by a sequence of nucleotides set forth in any of SEQ ID NOS: 37-47, 56 or 57. In some embodiments, the variant TACI polypeptide is encoded by a sequence of nucleotides that exhibits at least about 90% identity, at least about 91% identity, at least about 92% identity, at least about 93% identity, at least about 94% identity, at least about 95% identity, such as at least about 96% identity, 97% identity, 98% identity, or 99% identity to any one of SEQ ID NOS: 37-47, 56 or 57, and retains the amino acid modification(s), e.g. substitution(s) therein not present in the reference (e.g., unmodified or wild-type) TACI. Also provided herein is a nucleic acid containing the sequence set forth in any of SEQ ID NOS: 37-47, 56 or 57 or a sequence that exhibits at least 90% identity, at least 91% identity, at least 92% identity, at least 93% identity, at least 94% identity, at least 95% identity, such as at least 96% identity, 97% identity, 98% identity, or 99% identity to any one of SEQ ID NOS: 37-47, 56 or 57.

In some embodiments, the variant TACI polypeptide is encoded by a sequence of nucleotides set forth in any of SEQ ID NOS: 49-55 or 58-70. In some embodiments, the variant TACI polypeptide is encoded by a sequence of nucleotides that exhibits at least about 90% identity, at least about 91% identity, at least about 92% identity, at least about 93% identity, at least about 94% identity, at least about 95% identity, such as at least about 96% identity, 97% identity, 98% identity, or 99% identity to any one of SEQ ID NOS: 49-55 or 58-70, and retains the amino acid modification(s), e.g. substitution(s) therein not present in the reference (e.g., unmodified or wild-type) TACI. Also provided herein is a nucleic acid containing the sequence set forth in any of SEQ ID NOS: 49-55 or 58-70 or a sequence that exhibits at least 90% identity, at least 91% identity, at least 92% identity, at least 93% identity, at least 94% identity, at least 95% identity, such as at least 96% identity, 97% identity, 98% identity, or 99% identity to any one of SEQ ID NOS: 549-55 or 58-70.

TABLE 1

Exemplary variant TACI

| Name | Mutation(s) | ECD (CRD1/CRD2) | | ECD (CRD2) | |
|---|---|---|---|---|---|
| | | AA SEQ ID NO | NT SEQ ID NO | AA SEQ ID NO | NT SEQ ID NO |
| 1 (WT) TACI CRD1/CRD2 13 (WT) TACI CRD2 | Wild-type | 1 | 36 | 13 | 48 |
| 2 TACI CRD1/CRD2 92 TACI CRD2 | L82P | 2 | 37 | 92 | |
| 3 TACI CRD1/CRD2 93 TACI CRD2 | D85E, K98T | 3 | 38 | 93 | |
| 4 TACI CRD1/CRD2 94 TACI CRD2 | I87L, K98T | 4 | 39 | 94 | |
| 5 TACI CRD1/CRD2 | R60G, Q75E, L82P | 5 | 40 | | |
| 6 TACI CRD1/CRD2 | R60G, C86Y | 6 | 41 | | |
| 7 TACI CRD1/CRD2 95 TACI CRD2 | A101D | 7 | 42 | 95 | |
| 8 TACI CRD1/CRD2 96 TACI CRD2 | C86Y | 8 | 43 | 96 | |
| 9 TACI CRD1/CRD2 | W40R, L82P, F103Y | 9 | 44 | | |
| 10 TACI CRD1/CRD2 | W40R, Q59R, T61P, K98T | 10 | 45 | | |
| 11 TACI CRD1/CRD2 97 TACI CRD2 | L82P, I87L | 11 | 46 | 97 | |
| 12 TACI CRD1/CRD2 98 TACI CRD2 | G76S, P97S | 12 | 47 | 98 | |
| 101 TACI CRD1/CRD2 14 TACI CRD2 | D85V | 101 | | 14 | 49 |
| 102 TACI CRD1/CRD2 15 TACI CRD2 | E74V | 102 | | 15 | 50 |
| 103 TACI CRD1/CRD2 16 TACI CRD2 | R84L | 103 | | 16 | 51 |
| 104 TACI CRD1/CRD2 17 TACI CRD2 | K77E, R84L, F103Y | 104 | | 17 | 52 |
| 105 TACI CRD1/CRD2 18 TACI CRD2 | Y79F, Q99E | 105 | | 18 | 53 |

TABLE 1-continued

Exemplary variant TACI

| Name | Mutation(s) | ECD (CRD1/CRD2) AA SEQ ID NO | NT SEQ ID NO | ECD (CRD2) AA SEQ ID NO | NT SEQ ID NO |
|---|---|---|---|---|---|
| 106 TACI CRD1/CRD2 19TACI CRD2 | Y79F | 106 | | 19 | 54 |
| 107 TACI CRD1/CRD2 20 TACI CRD2 | R84G | 107 | | 20 | 55 |
| 21 TACI CRD1/CRD2 99 TACI CRD2 | L83S, F103S | 21 | 56 | 99 | |
| 22 TACI CRD1/CRD2 100 TACI CRD2 | L82H | 22 | 57 | 100 | |
| 108 TACI CRD1/CRD2 23 TACI CRD2 | A101D | 108 | | 23 | 58 |
| 109 TACI CRD1/CRD2 24 TACI CRD2 | K77E, R84Q | 109 | | 24 | 59 |
| 110 TACI CRD1/CRD2 25 TACI CRD2 | K77E, A101D | 110 | | 25 | 60 |
| 111 TACI CRD1/CRD2 26 TACI CRD2 | K77E, F78Y, Y102D | 111 | | 26 | 61 |
| 112 TACI CRD1/CRD2 27 TACI CRD2 | Q75E, R84Q | 112 | | 27 | 62 |
| 113 TACI CRD1/CRD2 28 TACI CRD2 | Q75R, R84G, I92V | 113 | | 28 | 63 |
| 114 TACI CRD1/CRD2 29 TACI CRD2 | K77E, A101D, Y102D | 114 | | 29 | 64 |
| 115 TACI CRD1/CRD2 30 TACI CRD2 | R84Q | 115 | | 30 | 65 |
| 116 TACI CRD1/CRD2 31 TACI CRD2 | R84Q, S88N, A101D | 116 | | 31 | 66 |
| 117 TACI CRD1/CRD2 32 TACI CRD2 | K77E | 117 | | 32 | 67 |
| 118 TACI CRD1/CRD2 33 TACI CRD2 | R84Q, F103V | 118 | | 33 | 68 |
| 119 TACI CRD1/CRD2 34 TACI CRD2 | K77E, Q95R, A101D | 119 | | 34 | 69 |
| 120 TACI CRD1/CRD2 35 TACI CRD2 | I87M, A101D | 120 | | 35 | 70 |
| 177 TACI CRD2 | Q75E | | | 177 | |
| 178 TACI CRD2 | Q75E, K77E | | | 178 | |
| 179 TACI CRD2 | Q75E, F78Y | | | 179 | |
| 180 TACI CRD2 | Q75E, A101D | | | 180 | |
| 181 TACI CRD2 | Q75E, Y102D | | | 181 | |
| 182 TACI CRD2 | K77E, F78Y, R84Q | | | 182 | |
| 183 TACI CRD2 | F78Y | | | 183 | |
| 184 TACI CRD2 | F78Y, R84Q | | | 184 | |
| 185 TACI CRD2 | F78Y, A101D | | | 185 | |
| 186 TACI CRD2 | F78Y, Y102D | | | 186 | |
| 187 TACI CRD2 | R84Q, A101D | | | 187 | |
| 188 TACI CRD2 | R84Q, Y102D | | | 188 | |
| 189 TACI CRD2 | A101D, Y102D | | | 189 | |
| 190 TACI CRD2 | Y102D | | | 190 | |
| 191 TACI CRD2 | K77E, F78Y | | | 191 | |
| 192 TACI CRD2 | K77E, Y102D | | | 192 | |

In some embodiments, also provided herein are TACI ECD fusion sequences in which any of the above TACI ECD sequence is linked or fused to a multimerization domain, such as any described herein.

Interaction of two or more polypeptides of the immunomodulatory proteins can be facilitated by their linkage, either directly or indirectly, to any moiety or other polypeptide that are themselves able to interact to form a stable structure. For example, separate encoded polypeptide chains can be joined by multimerization, whereby multimerization of the polypeptides is mediated by a multimerization domain. Typically, the multimerization domain provides for the formation of a stable protein-protein interaction between a first polypeptide and a second polypeptide.

In some embodiments, the two or more individual polypeptides of the immunomodulatory proteins can be joined by multimerization, such as joined as dimeric, trimeric, tetrameric, or pentameric molecules. In some cases, the individual polypeptides are the same. For example, a trimeric molecule can be formed from three copies of the same individual polypeptide. In other examples, a tetrameric molecule is generated from four copies of the same individual polypeptides. In further examples, a pentameric molecule is generated from five copies of the same individual polypeptides. The multimerization domain may be one that facilities dimerization, trimerization, tetramerization, or pentamerization of the polypeptide chains.

In some embodiments, the immunomodulatory protein forms a multimer, e.g., a dimer. In some embodiments, the dimer is a homodimer in which the two polypeptides of the immunomodulatory protein are the same. In some embodiments, the dimer is a heterodimer in which the two polypeptides of the immunomodulatory protein are different.

In some embodiments, a multimerization domain includes any capable of forming a stable protein-protein interaction. The multimerization domains can interact via an immunoglobulin sequence (e.g. Fc domain; see e.g., International Patent Pub. Nos. WO 93/10151 and WO 2005/063816 US; U.S. Pub. No. 2006/0024298; U.S. Pat. No. 5,457,035); leucine zipper (e.g. from nuclear transforming proteins fos and jun or the proto-oncogene c-myc or from General Control of Nitrogen (GCN4)) (ee e.g., Busch and Sassone-Corsi (1990) Trends Genetics, 6:36-40; Gentz et al., (1989) Science, 243:1695-1699); a hydrophobic region; a hydrophilic region; or a free thiol which forms an intermolecular disulfide bond between the chimeric molecules of a homo- or heteromultimer. In addition, a multimerization domain can include an amino acid sequence comprising a protuberance complementary to an amino acid sequence comprising a hole, such as is described, for example, in U.S. Pat. No. 5,731,168; International Patent Pub. Nos. WO 98/50431 and WO 2005/063816; Ridgway et al. (1996) Protein Engineering, 9:617-621. Such a multimerization region can be engineered such that steric interactions not only promote stable interaction, but further promote the formation of heterodimers over homodimers from a mixture of chimeric monomers. Generally, protuberances are constructed by replacing small amino acid side chains from the interface of the first polypeptide with larger side chains (e.g., tyrosine or tryptophan). Compensatory cavities of identical or similar size to the protuberances are optionally created on the interface of the second polypeptide by replacing large amino acid side chains with smaller ones (e.g., alanine or threonine). Exemplary multimerization domains are described below.

The TACI polypeptide sequence (e.g. variant TACI polypeptide sequence) can be joined anywhere, but typically via its N- or C-terminus, to the N- or C-terminus of a multimerization domain to form a chimeric polypeptide. The linkage can be direct or indirect via a linker. Also, the chimeric polypeptide can be a fusion protein or can be formed by chemical linkage, such as through covalent or non-covalent interactions. For example, when preparing a chimeric polypeptide containing a multimerization domain, nucleic acid encoding all or part of a TACI polypeptide sequence such as any described TACI ECD, including a variant TACI polypeptide sequence, can be operably linked to nucleic acid encoding the multimerization domain sequence, directly or indirectly or optionally via a linker domain. In some cases, the construct encodes a chimeric protein where the C-terminus of the TACI polypeptide sequence is joined to the N-terminus of the multimerization domain. In some instances, a construct can encode a chimeric protein where the N-terminus of the TACI polypeptide sequence is joined to the N- or C-terminus of the multimerization domain.

A polypeptide multimer contains two chimeric proteins created by linking, directly or indirectly, two of the same or different TACI polypeptide sequences (e.g. two of the same or different variant TACI polypeptide sequences) directly or indirectly to a multimerization domain. In some examples, where the multimerization domain is a polypeptide, a gene fusion encoding the TACI polypeptide sequence (e.g. variant TACI polypeptide sequence) and multimerization domain is inserted into an appropriate expression vector. The resulting chimeric or fusion protein can be expressed in host cells transformed with the recombinant expression vector, and allowed to assemble into multimers, where the multimerization domains interact to form multivalent polypeptides. Chemical linkage of multimerization domains to the TACI polypeptide (e.g. variant TACI polypeptide) can be effected using heterobifunctional linkers.

The resulting chimeric polypeptides, such as fusion proteins, and multimers formed therefrom, can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

In some embodiments, the multimerization domain is an Fc region of an immunoglobulin.

In some embodiments, the multimerization domain is an immunoglobulin (e.g. IgG1) Fc region, in which the fusion protein is a TACI-Fc containing (1) a TACI sequence containing or consisting of any of the provided TACI ECD sequences; and (2) an immunoglobulin Fc region. Thus, among provided embodiments are TACI-Fc fusion proteins containing (1) a TACI sequence containing or consisting of any of the above described TACI ECD polypeptide sequences, such as variant TACI polypeptide; and (2) an immunoglobulin Fc region.

In some embodiments, provided herein is a TACI-Fc fusion sequence that contains (1) a TACI ECD sequence that comprises the sequence set forth in SEQ ID NO:13, and (2) an immunoglobulin Fc region. In some embodiments, provided herein is a TACI-Fc fusion sequence that contains (1) a TACI ECD sequence that consists or consists essentially of the sequence set forth in SEQ ID NO:13, and (2) an immunoglobulin Fc region.

In some embodiments, the TACI-Fc fusion is a variant TACI-Fc fusion containing or consisting of any of the above described variant TACI polypeptides and an immunoglobulin Fc region.

In some embodiments, provided herein is a variant TACI-Fc fusion sequence that contains (1) a TACI ECD sequence containing a CRD1 and a CRD2, for example a TACI sequence that contains the sequence set forth in any one of SEQ ID NOS: 2-12, 21, 22, 101-120, and (2) an immunoglobulin Fc region. In some embodiments, provided herein is a variant TACI-Fc fusion sequence that contains (1) a TACI ECD sequence containing a CRD1 and a CRD2, for example a TACI sequence that consist or consists essentially of the sequence set forth in any one of SEQ ID NOS: 2-12, 21, 22, 101-120, and (2) an immunoglobulin Fc region.

In some embodiments, provided herein is a variant TACI-Fc fusion sequence that contains (1) a TACI ECD sequence containing the CRD2 but lacking the CRD1 domain, for example a TACI sequence that contains the sequence set forth in any one of SEQ ID NOS: 14-20, 23-35, 92-100, 177-192 and (2) an immunoglobulin Fc region. In some embodiments, provided herein is a variant TACI-Fc fusion sequence that contains (1) a TACI ECD sequence containing the CRD2 domain but lacking the CRD1 domain, for example a TACI sequence that consists or consists essentially of the sequence set forth in any one of SEQ ID NOS: 14-20, 23-35, 92-100, 177-192 and (2) an immunoglobulin Fc region.

In provided embodiments of a TACI-Fc, the immunoglobulin Fc region can be a wild-type Fc of an immunoglobulin, such as an IgG1 Fc. In some cases, the Fc region can be a variant Fc that lacks effector function (also called "effectorless Fc"). Exemplary Fc regions and variants thereof in provided TACI-Fc fusion proteins are described below.

In some embodiments, the Fc is murine or human Fc. In some embodiments, the Fc is a mammalian or human IgG1, IgG2, IgG3, or IgG4 Fc regions.

In some embodiments, the Fc region is or comprises the sequence set forth in any one of SEQ ID NOs: 71, 73, 75, 81, 82, 83, 134, 135, 136, 137, 138, 139, 140, 173, 174, 175, 176, 193, 218, 219, 220, or 221. In some embodiments, the Fc region is or is derived from an IgG1, such as set forth in any one of SEQ ID NOS: 71, 73, 75, 81, 82, 83, 134, 135, 136, 137, 139, 140, 173, 174, 175, 176, 193, 218, 220, or 221. In some embodiments, the Fc region is or is derived from an IgG2, such as any set forth in SEQ ID NO: 138 or 219. In some embodiments, the Fc region is or is derived from an IgG4, such as any set forth in SEQ ID NO: 139, 140 or 220. In some embodiments, an Fc region in Fc fusion proteins provided herein also can include an Fc region that exhibits at least about 85%, 86%, 87%, 88%, 89%, 90%, 91%, 92%, 93%, 94%, 95%, 96%, 97%, 98%, 99% to any of the above Fc regions.

In some embodiments, the Fc is derived from IgG1, such as human IgG1. In some embodiments, the Fc is an IgG1 Fc set forth in SEQ ID NO: 71 having an allotype containing residues Glu (E) and Met (M) at positions 356 and 358 by EU numbering. In some embodiments, the Fc comprises the amino acid sequence set forth in SEQ ID NO: 71 or a sequence of amino acids that exhibits at least about 85%, 86%, 87%, 88%, 89%, 90%, 91%, 92%, 93%, 94%, 95%, 96%, 97%, 98%, 99% or more sequence identity to SEQ ID NO: 71. In other embodiments, the Fc is an IgG1 Fc that contains amino acids of the human G1m1 allotype, such as residues containing Asp (D) and Leu (L) at positions 356 and 358, e.g. as set forth in SEQ ID NO:81. Thus, in some cases, an Fc provided herein can contain amino acid substitutions E356D and M358L to reconstitute residues of allotype G1 m1. In some embodiments, the Fc comprises the amino acid sequence set forth in SEQ ID NO: 81 or a sequence of amino acids that exhibits at least about 85%, 86%, 87%, 88%, 89%, 90%, 91%, 92%, 93%, 94%, 95%, 96%, 97%, 98%, 99% or more sequence identity to SEQ ID NO: 81.

In some embodiments, the Fc region has the amino acid sequence set forth in SEQ ID NO:81.

EPKSSDKTHTCPPCPA-
PELLGGPSVFLFPPKPKDTLMISRTPE-
VTCVVVDVSHEDPEVK
FNWYVDGVEVHNAKTKPREEQYN-
STYRVVSVLTVLHQDWLNGKEYKCKVSNKAL
PAPIEKTISKAKGQPREPQVYTLPPSRDELT-
KNQVSLTCLVKGFYPSDIAVEWESNGQ PEN-
NYKTTPPVLDSDGSFFLYSK-
LTVDKSRWQQGNVFSCSVMHEALHNHYTQK
SLS LSPG (SEQ ID NO:81)

In some embodiments, the variant Fc comprises the sequence set forth in SEQ ID NO: 173. In some embodiments, the variant Fc comprises the sequence set forth in SEQ ID NO:174. In some embodiments, an Fc region used in a construct provided herein can further lack a C-terminal lysine residue.

In some embodiments, the Fc is derived from IgG2, such as human IgG2. In some embodiments, the Fc comprises the amino acid sequence set forth in SEQ ID NO: 138 or a sequence of amino acids that exhibits at least about 85%, 86%, 87%, 88%, 89%, 90%, 91%, 92%, 93%, 94%, 95%, 96%, 97%, 98%, 99% or more sequence identity to SEQ ID NO: 138. In some embodiments, the Fc region is an IgG2 Fc region that has the sequence set forth in SEQ ID NO: 138. In some embodiments, the Fc region is an IgG2 Fc region that has the sequence set forth in SEQ ID NO: 219.

In some embodiments, the Fc is derived from IgG4, such as human IgG4. In some embodiments, the Fc comprises the amino acid sequence set forth in SEQ ID NO: 139 or a sequence of amino acids that exhibits at least about 85%, 86%, 87%, 88%, 89%, 90%, 91%, 92%, 93%, 94%, 95%, 96%, 97%, 98%, 99% or more sequence identity to SEQ ID NO: 139. In some embodiments, the IgG4 Fc is a stabilized Fc in which the CH3 domain of human IgG4 is substituted with the CH3 domain of human IgG1 and which exhibits inhibited aggregate formation, an antibody in which the CH3 and CH2 domains of human IgG4 are substituted with the CH3 and CH2 domains of human IgG1, respectively, or an antibody in which arginine at position 409 indicated in the EU index proposed by Kabat et al. of human IgG4 is substituted with lysine and which exhibits inhibited aggregate formation (see e.g. U.S. Pat. No. 8,911,726. In some embodiments, the Fc is an IgG4 containing the S228P mutation, which has been shown to prevent recombination between a therapeutic antibody and an endogenous IgG4 by Fab-arm exchange (see e.g. Labrijin et al. (2009) Nat. Biotechnol., 27(8): 767-71.) In some embodiments, the Fc comprises the amino acid sequence set forth in SEQ ID NO: 140 or a sequence of amino acids that exhibits at least about 85%, 86%, 87%, 88%, 89%, 90%, 91%, 92%, 93%, 94%, 95%, 96%, 97%, 98%, 99% or more sequence identity to SEQ ID NO: 140. In some embodiments, the Fc region is an IgG4 Fc region set forth in SEQ ID NO:140. In some embodiments, the Fc region is an IgG4 Fc region set forth in SEQ ID NO:220.

In some embodiments, the Fc region is a variant Fc region in which a wild-type Fc is modified by one or more amino acid substitutions to reduce effector activity or to render the Fc inert for Fc effector function. Exemplary effectorless or inert mutations include those described herein.

In some embodiments, the Fc region contains one more modifications that alter (e.g. reduce) one or more of its normal functions. In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments, such functions can be reduced or altered in an Fc for use with the provided Fc fusion proteins.

In some embodiments, one or more amino acid modifications may be introduced into the Fc region, thereby generating an Fc region variant. In some embodiments, the Fc region variant has decreased effector function. There are many examples of changes or mutations to Fc sequences that can alter effector function. For example, WO 00/42072, WO2006019447, WO2012125850, WO2015/107026, US2016/0017041 and Shields et al. *J Biol. Chem.* 9(2): 6591-6604 (2001) describe exemplary Fc variants with improved or diminished binding to FcRs. The contents of those publications are specifically incorporated herein by reference.

In some embodiments, the provided immunomodulatory proteins comprise an Fc region that exhibits reduced effector functions, which makes it a desirable candidate for applications in which the half-life of the immunomodulatory protein in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the immunomodulatory protein lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the immunomodulatory protein is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Immunomodulatory proteins with reduced effector function include those with substitution of one or more of Fc region residues 238, 265, 269, 270, 297, 327 and 329 by EU numbering (U.S. Pat. No. 6,737,056). Such Fc mutants include Fc mutants with substitutions at two or more of amino acid positions 265, 269, 270, 297 and 327 by EU numbering, including the so-called "DANA" Fc mutant with substitution of residues 265 and 297 to alanine (U.S. Pat. No. 7,332,581).

In some embodiments, the Fc region of immunomodulatory proteins has an Fc region in which any one or more of amino acids at positions 234, 235, 236, 237, 238, 239, 270, 297, 298, 325, and 329 (indicated by EU numbering) are substituted with different amino acids compared to the native Fc region. Such alterations of Fc region include, for example, alterations such as deglycosylated chains (N297A and N297Q), IgG1-N297G, IgG1-L234A/L235A, IgG1-L234A/L235E/G237A, IgG1-A325A/A330S/P331S, IgG1-C226S/C229S, IgG1-C226S/C229S/E233P/L234V/L235A, IgG1-E233P/L234V/L235A/G236del/S267K, IgG1-L234F/L235E/P331S, IgG1-S267E/L328F, IgG2-V234A/G237A, IgG2-H268Q/V309L/A330S/A331S, IgG4-L235A/G237A/E318A, and IgG4-L236E described in Current Opinion in Biotechnology (2009) 20 (6), 685-691; alterations such as G236R/L328R, L235G/G236R, N325A/L328R, and N325LL328R described in WO 2008/092117; amino acid insertions at positions 233, 234, 235, and 237 (indicated by EU numbering); and alterations at the sites described in WO 2000/042072.

Certain Fc variants with improved or diminished binding to FcRs are described. (See, e.g., U.S. Pat. No. 6,737,056; WO 2004/056312, WO2006019447 and Shields et al., *J. Biol. Chem.* 9(2): 6591-6604 (2001).)

In some embodiments, there is provided an immunomodulatory protein comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.) or WO2015107026. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434 by EU numbering, e.g., substitution of Fc region residue 434 (U.S. Pat. No. 7,371,826).

In some embodiments, the Fc region of the immunomodulatory protein comprises one or more amino acid substitutions C220S, C226S and/or C229S by EU numbering. In some embodiments, the Fc region of the immunomodulatory protein comprises one or more amino acid substitutions R292C and V302C. See also Duncan & Winter, *Nature* 322:738-40 (1988); U.S. Pat. Nos. 5,648,260; 5,624,821; and WO 94/29351 concerning other examples of Fc region variants.

In some embodiments, alterations are made in the Fc region that result in diminished C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, the variant Fc region comprising the one or more amino acid modifications (e.g amino acid substitutions) is derived from a wild-type IgG1, such as a wild-type human IgG1. In some embodiments, the wild-type IgG1 Fc can be the Fc set forth in SEQ ID NO: 71 having an allotype containing residues Glu (E) and Met (M) at positions 356 and 358 by EU numbering. In some embodiments, the variant Fc region is derived from the amino acid sequence set forth in SEQ ID NO: 71. In other embodiments, the wild-type IgG1 Fc contains amino acids of the human G1m1 allotype, such as residues containing Asp (D) and Leu (L) at positions 356 and 358, e.g. as set forth in SEQ ID NO:81. Thus, in some cases, the variant Fc is derived from the amino acid sequence set forth in SEQ ID NO:81.

In some embodiments, the Fc region lacks the C-terminal lysine corresponding to position 232 of the wild-type or unmodified Fc set forth in SEQ ID NO: 71 or 81 (corresponding to K447del by EU numbering).

In some embodiments, the variant Fc region comprises a C5S amino acid modification of the wild-type or unmodified Fc region by numbering of SEQ ID NO: 71 (corresponding to C220S by EU numbering).

In some embodiments, the Fc region is a variant Fc that contains at least one amino acid substitution that is N82G by numbering of SEQ ID NO: 71 (corresponding to N297G by EU numbering). In some embodiments, the Fc further contains at least one amino acid substitution that is R77C or V87C by numbering of SEQ ID NO: 71 (corresponding to R292C or V302C by EU numbering). In some embodiments, the variant Fc region further comprises a C5S amino acid modification by numbering of SEQ ID NO: 71 (corresponding to C220S by EU numbering). For example, in some embodiments, the variant Fc region comprises the following amino acid modifications: N297G and one or more of the following amino acid modifications C220S, R292C or V302C by EU numbering (corresponding to N82G and one or more of the following amino acid modifications C5S, R77C or V87C with reference to SEQ ID NO:71), e.g., the Fc region comprises the sequence set forth in SEQ ID NO:82.

In some embodiments, the variant Fc contains the amino acid substitutions L234A/L235E/G237A, by EU numbering. In some embodiments, the variant Fc contains the amino acid substitutions A330S/P331S, by EU numbering. In some embodiments, the variant Fc contains the amino acid substitutions L234A/L235E/G237A/A330S/P331S (Gross et al. (2001) Immunity 15:289). In some embodiments, the variant Fc comprises the sequence set forth in SEQ ID NO: 175. In some embodiments, the variant Fc comprises the sequence set forth in SEQ ID NO:176. In some embodiments, an Fc region used in a construct provided herein can further lack a C-terminal lysine residue.

In some embodiments, the Fc region is a variant Fc that includes mutations L234A, L235E and G237A by EU numbering. In some embodiments, a wild-type Fc is further modified by the removal of one or more cysteine residue, such as by replacement of the cysteine residues to a serine residue at position 220 (C220S) by EU numbering. Exemplary inert Fc regions having reduced effector function are set forth in SEQ ID NO: 83 and SEQ ID NO:75, which are based on allotypes set forth in SEQ ID NO:71 or SEQ ID NO: 81, respectively. In some embodiments, an Fc region can further lack a C-terminal lysine residue. In some embodiments, the variant Fc region comprises one or more of the amino acid modifications C220S, L234A, L235E or G237A, e.g. the Fc region comprises the sequence set forth in SEQ ID NO:73, 75, 83 or 136. In some embodiments, the variant Fc comprises has the sequence set forth in SEQ ID NO: 73. In some embodiments, the variant Fc comprises has the sequence set forth in SEQ ID NO: 75. In some embodiments, the variant Fc comprises has the sequence set forth in SEQ ID NO: 83. In some embodiments, the variant Fc comprises has the sequence set forth in SEQ ID NO: 136.

In some embodiments, the Fc region is a variant Fc that has the sequence set forth in SEQ ID NO:73.
EPKSSDKTHTCPPCPAPEAE-
GAPSVFLFPPKPKDTLMISRTPE-
VTCVVVDVSHEDPEV
KFNWYVDGVEVHNAKTKPREEQYN-
STYRVVSVLTVLHQDWLNGKEYKCKVSNKA
LPAPIEKTISKAKGQPREPQVYTLPPSRDELT-
KNQVSLTCLVKGFYPSDIAVEWESNG QPEN-
NYKTTPPVLDSDGSFFLYSK-
LTVDKSRWQQGNVFSCSVMHEALHNHYTQKSL
SLSPG (SEQ ID NO:73)

In some embodiments, the Fc region is an IgG1 Fc but does not contain a hinge sequence. In some embodiments, the IgG1 Fc region does not contain the hinge sequence EPKSC (SEQ ID NO:239). In some embodiments, the IgG1 Fc region does not contain a hinge sequence EPKSS (SEQ ID NO: 238).

In some embodiments, the Fc region is a variant Fc that has the sequence set forth in SEQ ID NO: 221.
DKTHTCPPCPAPEAEGAPSVFLFPPKPKDTLMISRT-
PEVTCVVVDVSHEDPEVKFNW
YVDGVEVHNAKTKPREEQYN-
STYRVVSVLTVLHQDWLNGKEYKCKVSNKAL-
PAPI EKTISKAKGQPREPQVYTLPPSRDELT-
KNQVSLTCLVKGFYPSDIAVEWESNGQPENN
YKTTPPVLDSDGSFFLYSK-
LTVDKSRWQQGNVFSCSVMHEALHN-
HYTQKSLSLSPG (SEQ ID NO:221)

In some embodiments, the Fc region is a variant Fc region that comprises one or more of the amino acid modifications C220S, L235P, L234V, L235A, G236del or S267K, e.g. the Fc region comprises the sequence set forth in SEQ ID NO:134. In some embodiments, the Fc region lacks the C-terminal lysine corresponding to position 232 of the wild-type or unmodified Fc set forth in SEQ ID NO: 71 (corresponding to K447del by EU numbering).

In some embodiments, the Fc region is a variant Fc region that comprises one or more of the amino acid modifications C220S, R292C, N297G, V302C. In some embodiments, the Fc region lacks the C-terminal lysine corresponding to position 232 of the wild-type or unmodified Fc set forth in SEQ ID NO: 71 (corresponding to K447del by EU numbering). An exemplary variant Fc region is set forth in SEQ ID NO: 135.

In some embodiments, the variant Fc region comprises one or more of the amino acid modifications C220S/E233P/L234V/L235A/G236del/S267K. In some embodiments, the Fc region lacks the C-terminal lysine corresponding to position 232 of the wild-type or unmodified Fc set forth in SEQ ID NO: 71 (corresponding to K447del by EU numbering). An exemplary variant Fc region is set forth in SEQ ID NO: 137.

Examples of such Fc regions for inclusion in an immunomodulatory polypeptide are set forth in Table 2.

TABLE 2

Exemplary IgG1 Fc Regions, wild-type or variant (effectorless)

| Fc mutations (EU numbering) | 356E/358M allotype SEQ ID NO | 356D/358L allotype SEQ ID NO |
|---|---|---|
| (wild-type) | 71 | 81 (with C220S, K447del) |
| C220S, R292C, N297G, V302C | 82 | |
| C220S, R292C, N297G, V302C, K447del | 135 | |
| C220S, L234A, L235E, G237A | 83 | 75 |
| C220S, L234A, L235E, G237A, K447del | 136 | 73 |
| L234A, L235E, G237A, K447del, with deletion of hinge | | 221 |
| C220S, L235P, L234V, L235A, G236del, S267K | 134 | |
| C220S/E233P/L234V/L235A/G236del/S267K/K447del | 137 | |
| L234A, L235E, G237A, A330S, P331S | | 176 |
| L234A, L235E, G237A, A330S, P331S, with deletion of hinge | | 175 |

In some embodiments, the Fc region is a variant Fc region containing any combination of the Fc mutations in Table 2. In some embodiments, the Fc region is a variant Fc region having the sequence set forth in any one of the SEQ ID NOs in Table 2.

For example, a variant Fc region may be an effectorless Fc that exhibits reduced effector activity compared to a wild-type IgG1 set forth in SEQ ID NO:71 or SEQ ID NO:81. In some embodiments, the variant Fc comprises the sequence of amino acids set forth in any of SEQ ID NOS:75, 82, 83, 134, 73, 135, 136, or 137 or a sequence of amino acids that exhibits at least about 85%, 86%, 87%, 88%, 89%, 90%, 91%, 92%, 93%, 94%, 95%, 96%, 97%, 98%, 99% or more sequence identity to any of SEQ ID NOS: 75, 82, 83, 134, 73, 135, 136, or 137. In some embodiments, the variant Fc has the sequence set forth in SEQ ID NO: 73. In embodiments, when produced and expressed from cells, the provided immunomodulatory protein (e.g. TACI-Fc fusion) is a homodimer containing two identical polypeptide chains.

In some embodiments, the immunomodulatory protein contains a first immunomodulatory Fc fusion polypeptide and a second immunomodulatory Fc fusion polypeptide in which the first and second polypeptide are different. In some embodiments, a first Fc polypeptide fusion contains an Fc region and one or more variant TACI polypeptide sequence and a second polypeptide fusion contains an Fc region and one or more TACI polypeptide sequence. In such embodiments, the Fc region can be a region that promotes or facilitates formation of heterodimers.

In some embodiments, the Fc domain of one or both of the first and second immunomodulatory Fc fusion polypeptides comprise a modification (e.g. substitution) such that the interface of the Fc molecule is modified to facilitate and/or promote heterodimerization. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. In some embodiments, the Fc region of the heterodimeric molecule additionally can contain one or more other Fc mutation, such as any described above. In some embodiments, the heterodimer molecule contains an Fc region with a mutation that reduces effector function. In some embodiments, such Fc regions contain mutations C220S, L234A, L235E and/or G237A by EU numbering. In some embodiments, any of the above mutations in an Fc backbone can be made in an allotype containing residues Glu (E) and Met (M) at positions 356 and 358 by EU numbering. In other embodiments, any of the above mutations in an Fc backbone can be made in an allotype containing residue Asp (D) and Leu (L) at positions 356 and 358 by EU numbering.

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first polypeptide that is modified to contain protuberance (knob) amino acids include replacement of a native or original amino acid with an amino acid that has at least one side chain which projects from the interface of the first polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 Å2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731, 168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

In some embodiments, the heterodimeric molecule contains a T366W mutation in the CH3 domain of the "knobs chain" and T366S, L368A, Y407V mutations in the CH3 domain of the "hole chain". In some cases, an additional interchain disulfide bridge between the CH3 domains can also be used (Merchant, A. M., et al., Nature Biotech. 16 (1998) 677-681) e.g. by introducing a Y349C mutation into the CH3 domain of the "knobs" or "hole" chain and a E356C mutation or a S354C mutation into the CH3 domain of the other chain. In some embodiments, the heterodimeric molecule contains S354C, T366W mutations in one of the two CH3 domains and Y349C, T366S, L368A, Y407V mutations in the other of the two CH3 domains. For example, the knob Fc may contain the sequence set forth in SEQ ID NO: 89, containing S354C and T366W, and a hole Fc set forth in SEQ ID NO: 90, containing mutations Y349C, T366S, L368A and Y407V). In some embodiments, the heterodimeric molecule comprises E356C, T366W mutations in one of the two CH3 domains and Y349C, T366S, L368A, Y407V mutations in the other of the two CH3 domains. In some embodiments, the heterodimeric molecule comprises Y349C, T366W mutations in one of the two CH3 domains and E356C, T366S, L368A, Y407V mutations in the other of the two CH3 domains. In some embodiments, the heterodimeric molecule comprises Y349C, T366W mutations in one of the two CH3 domains and S354C, T366S, L368A, Y407V mutations in the other of the two CH3 domains. Examples of other knobs-in-holes technologies are known in the art, e.g. as described by EP 1 870 459 A1.

In some embodiments, an Fc variant containing CH3 protuberance (knob) or cavity (hole) modifications can be joined to a multi-domain immunomodulatory polypeptide anywhere, but typically via its N- or C-terminus, to the N- or C-terminus of the one or more TACI polypeptide sequence (e.g. variant TACI polypeptide sequence), such as to form a fusion polypeptide. The linkage can be direct or indirect via a linker. Typically, a knob and hole molecule is generated by co-expression of a first immunomodulatory polypeptide linked to an Fc variant containing CH3 protuberance modification(s) with a second immunomodulatory polypeptide linked to an Fc variant containing CH3 cavity modification(s).

Exemplary sequences for knob and hole Fc polypeptides are set forth in SEQ ID NOs: 128, and 129, respectively. In some embodiments, the knob or hold Fc region lacks the C-terminal lysine corresponding to position 232 of the wild-type or unmodified Fc set forth in SEQ ID NO: 71 (corresponding to K447del by EU numbering). Exemplary sequences for knob and hole Fc polypeptides are set forth in SEQ ID NOs: 89 and 90, respectively.

In some embodiment, individual polypeptide of a multi-domain polypeptide or individual polypeptides of a single-domain polypeptide are linked to a multimerization domain that forms an immunomodulatory protein is a trimer, tetramer or pentamer. In some embodiments, the individual polypeptides of such a molecule are the same. In some embodiments, such a multimerization domain is a cartilage oligomeric matrix protein (COMP) assembly domain, a vasodilator-stimulated phosphoprotein (VASP) tetramerization domain or a ZymoZipper (ZZ) 12.6 domain.

In some embodiments, the multimerization domain is a portion of the cartilage oligomeric matrix protein (COMP) assembly domain (Voulgaraki et al., Immunology (2005) 115(3):337-346. In some examples, the COMP is or contains an amino acid sequence as set forth in SEQ ID NO: 146 (e.g. amino acids 29-72 of the full length COMP, Uniprot accession number P49747) or a sequence that has about 85%, 85%, 87%, 88%, 89%, 90%, 91%, 92%, 93%, 94%, 95%, 96%, 97%, 98%, 99% or more sequence identity to SEQ ID NO: 146.

In some embodiments, the multimerization domain is a vasodilator-stimulated phosphoprotein (VASP) tetramerization domain (Bachmann et al., J Biol Chem (1999) 274(33): 23549-23557). In some embodiments, the VASP is or contains an amino acid sequence as set forth in SEQ ID NO: 147 (e.g. amino acids 343-375 of the full length VASP; Uniprot accession number P50552) or a sequence that has about 85%, 85%, 87%, 88%, 89%, 90%, 91%, 92%, 93%, 94%, 95%, 96%, 97%, 98%, 99% or more sequence identity to SEQ ID NO: 147.

In some embodiments, a TACI polypeptide sequence (e.g. variant TACI polypeptide sequence) is joined to the multimerization domain (e.g. Fc region) via a linker, such as a peptide linker. In some embodiments, a peptide linker can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length.

In some embodiments, the linker is (in one-letter amino acid code): GGGGS ("4GS"; SEQ ID NO: 77) or multimers of the 4GS linker, such as repeats of 2, 3, 4, or 5 4GS linkers. In some embodiments, the peptide linker is the peptide linker is (GGGGS)2 (SEQ ID NO: 78), (GGGGS)3 (SEQ ID NO: 79), (GGGGS)4 (SEQ ID NO: 84) or (GGGGS)5 (SEQ ID NO: 91). In some embodiments, the linker also can include a series of alanine residues alone or in addition to another peptide linker (such as a 4GS linker or multimer thereof). In some embodiments, the linker (in one-letter amino acid code) is GSGGGGS (SEQ ID NO: 74) or GGGGSSA (SEQ ID NO: 80). In some examples, the linker is a 2×GGGGS followed by three alanines (GGGGSGGGGSAAA; SEQ ID NO:133). In some examples, the linker is set forth in SEQ ID NO: 194 or 195.

In some embodiments, the TACI polypeptide, such as the variant TACI polypeptide, is directly linked to the Fc sequence. In some embodiments, the TACI polypeptide, such as the variant TACI polypeptide, is indirectly linked to the Fc sequence, such as via a linker. In some embodiments, one or more "peptide linkers" link the TACI polypeptide (e.g. variant TACI polypeptide) and the Fc region. In some embodiments, a peptide linker can be a single amino acid residue or greater in length. In some embodiments, the peptide linker has at least one amino acid residue but is no more than 20, 19, 18, 17, 16, 15, 14, 13, 12, 11, 10, 9, 8, 7, 6, 5, 4, 3, 2, or 1 amino acid residues in length. Exemplary linkers include any linker as described herein.

In some embodiments, the TACI-Fc fusion protein has the structure TACI polypeptide (TACI)-Linker-Fc region. In some embodiments, the immunomodulatory protein is a homodimer of two identical copies of the TACI-Fc fusion protein. For instance, interactions between Fc regions of the two identical polypeptide fusions form covalent disulfide bonds to result in a dimeric molecule containing two TACI polypeptides (e.g. two variant TACI polypeptides).

In some embodiments, there is provided a TACI-Fc fusion protein containing in order a TACI polypeptide, e.g. any as described above, a linker and an Fc region. In some embodiments, each TACI polypeptide of the TACI Fc fusion is a truncated wild-type TACI polypeptide, such as any as described. In some embodiments, the TACI polypeptide of the TACI Fc fusion is set forth in SEQ ID NO: 13. The linker may be any as described. In some embodiments, the linker is GSGGGGS (SEQ ID NO: 74). In some embodiments, the linker is GS(G4S)$_2$ (SEQ ID NO: 194). The Fc region may be any Fc region as described. In some embodiments, the Fc region is a wild-type IgG1 Fc set forth in SEQ ID NO:81. In some embodiments, the Fc region is a variant Fc set forth in SEQ ID NO: 73.

In some embodiments, the TACI-Fc fusion protein has the sequence set forth in SEQ ID NO:171. In some embodiments, the TACI-Fc fusion protein has the sequence set forth in SEQ ID NO:197. In some embodiments, the TACI-Fc fusion is encoded by the sequence set forth in SEQ ID NO:208.

SLSCRKEQGKFYDHLLRDCISCASICGQHPKQCAY-FCENKLRSGSGGGGSEPKSSDKT HTCPPCPAPE-AEGAPSVFLFPPKPKDTLMISRTPE-VTCVVVDVSHEDPEVKFNWYVD GVEVHNAKTKPREEQYN-STYRVVSVLTVLHQDWLNGKEYKCKVSNKAL-PAPIEKTI SKAKGQPREPQVYTLPPSRDELT-KNQVSLTCLVKGFYPSDIAVEWESNGQPENNYKT TPPVLDSDGSFFLYSK-LTVDKSRWQQGNVFSCSVMHEALHN-HYTQKSLSLSPG (SEQ ID NO:171)

In some embodiments, the TACI-Fc fusion protein has the sequence set forth in SEQ ID NO:172.

SLSCRKEQGKFYDHLLRDCISCASICGQHPKQCAY-FCENKLRSGSGGGGSEPKSSDKT HTCPPCPA-PELLGGPSVFLFPPKPKDTLMISRTPE-VTCVVVDVSHEDPEVKFNWYVD GVEVHNAKTKPREEQYN-STYRVVSVLTVLHQDWLNGKEYKCKVSNKAL-PAPIEKTI SKAKGQPREPQVYTLPPSRDELT-KNQVSLTCLVKGFYPSDIAVEWESNGQPENNYKT TPPVLDSDGSFFLYSK-LTVDKSRWQQGNVFSCSVMHEALHN-HYTQKSLSLSPG (SEQ ID NO:172)

In some embodiments, the TACI-Fc fusion protein has the sequence set forth in SEQ ID NO: 196, and encoded the sequence set forth in SEQ ID NO:207.

In some embodiments, the TACI polypeptide is a variant TACI polypeptide. In some embodiments, there is provided a variant TACI-Fc fusion protein containing in order a variant TACI polypeptide, e.g. any as described above, a linker and an Fc region. In some embodiments, the TACI polypeptide of the TACI Fc fusion is a variant TACI polypeptide, such as any as described. In some embodiments, the variant TACI of the variant TACI Fc fusion is set forth in any one of SEQ ID NOS: 2-12, 21, 22, or 101-120. In some embodiments, the variant TACI of the variant TACI Fc fusion is set forth in any one of SEQ ID NOS: 14-20, 23-35, 92-100 or 177-192. In some embodiments, the linker is GSGGGGS (SEQ ID NO: 74). In some embodiments, the linker is GS(G4S)₂ (SEQ ID NO: 194). In some embodiments, the Fc region is a wild-type IgG1 Fc set forth in SEQ ID NO:81. In some embodiments, the Fc region is a variant Fc set forth in SEQ ID NO: 73.

In some embodiments, the TACI-Fc fusion protein has the sequence of amino acids set forth in any one of SEQ ID NOS: 167-170, 200, or 222-237.

In some embodiments, the TACI-Fc fusion protein has the sequence set forth in SEQ ID NO:167.
SLSCRKEQGEYYDHLLRDCISCASICGQHPKQCADFCENKLRSGSGGGGSEPKSSDKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO:167)

In some embodiments, the TACI-Fc fusion is encoded by the sequence set forth in SEQ ID NO:211.

In some embodiments, the TACI-Fc fusion protein has the sequence set forth in SEQ ID NO:168.
SLSCRKEQGEYYDHLLRDCISCASICGQHPKQCADFCENKLRSGSGGGGSEPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO:168)

In some embodiments, the TACI-Fc fusion protein has the sequence set forth in SEQ ID NO: 169.
SLSCRKEEGKFYDHLLQDCISCASICGQHPKQCAYFCENKLRSGSGGGGSEPKSSDKT HTCPPCPAPEAEGAPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNGQPENN YKT TPPVLDSDGSFFLYSKLTVDKSRWQQGNVFSCSVMHEALHNHYTQKSLSLSPG (SEQ ID NO:169)

In some embodiments, the TACI-Fc fusion protein has the sequence set forth in SEQ ID NO:170
SLSCRKEEGKFYDHLLQDCISCASICGQHPKQCAYFCENKLRSGSGGGGSEPKSSD KTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO:170)

In some embodiments, the TACI-Fc fusion protein contains multiple copies of a TACI polypeptide sequence (e.g. variant TACI-polypeptide sequence), such as 2, 3 or 4 TACI polypeptide sequences. In some embodiments, the TACI-Fc fusion proteins contains two TACI polypeptide sequences (e.g. two variant TACI polypeptide sequences). In some cases, the TACI polypeptide sequences may be linked directly or may be linked indirectly via a linker, such as a peptide linker including any as described. In such an example, one of the TACI polypeptide sequence is joined or linked to the Fc region, such as either to the N- or C-terminus of the Fc region. In other cases, the TACI polypeptide sequences may be separated from each other by the Fc region and each joined individually to the N- or C-terminus of the Fc region. The linkage to the Fc region may be direct or may be indirect via a linker, such as a peptide linker including any as described.

In some embodiments, the TACI polypeptide sequences (e.g. variant TACI polypeptide sequences) may be arranged in order in the fusion protein in tandem (hereinafter called a "tandem" Fc fusion construct). In some embodiments, the TACI-Fc fusion protein has the structure: (TACI)-Linker-(TACI)-Linker-Fc region. In some embodiments, the immunomodulatory protein is a tetravalent molecule that is a homodimer of two identical copies of the TACI-Fc fusion protein. For instance, interactions between Fc regions of the two identical polypeptide fusions form covalent disulfide bonds to result in a dimeric molecule containing four TACI polypeptides (e.g. four variant TACI polypeptides).

In some embodiments, there is provided a TACI-Fc fusion protein containing in order a TACI polypeptide, e.g. any as described above; a linker; another TACI polypeptide, e.g. any as described; and an Fc region. In some embodiments, each TACI polypeptide of the TACI Fc fusion is a truncated wild-type TACI polypeptide, such as any as described. In some embodiments, each TACI polypeptide of the TACI Fc fusion is set forth in SEQ ID NO: 13. In some embodiments, each TACI polypeptide of the TACI Fc fusion is a variant TACI polypeptide, such as any as described. In some embodiments, each TACI polypeptide of the TACI Fc fusion is a variant TACI set forth in any one of SEQ ID NOS: 2-12, 21, 22, or 101-120. In some embodiments, each TACI polypeptide of the TACI Fc fusion is a variant TACI set forth in any one of SEQ ID NOS: 14-20, 23-35, 92-100 or 177-192. The linkers may be any as described. In some embodiments, the linker is GSGGGGS (SEQ ID NO: 74). The Fc region may be any Fc region as described. In some embodiments, the Fc region is a wild-type IgG1 Fc set forth in SEQ ID NO:81. In some embodiments, the Fc region is a variant Fc set forth in SEQ ID NO: 73. In some embodiments, the TACI-Fc fusion protein has the sequence set forth in SEQ ID NO:198, and encoded by a sequence set forth in SEQ ID NO:209.

In some embodiments, the TACI polypeptide sequences (e.g. variant TACI polypeptide sequences) may be separated in the fusion protein by the Fc region in which the Fc region is positioned between the two TACI polypeptide sequences (hereinafter called a "barbell" Fc fusion construct). In some embodiments, the TACI-Fc fusion protein has the structure: (TACI)-Linker-Fc region-Linker-(TACI). In some embodiments, the linkers may be the same or different. In some embodiments, the immunomodulatory protein is a tetravalent molecule that is a homodimer of two identical copies of the TACI-Fc fusion protein. For instance, interactions between Fc regions of the two identical polypeptide fusions form covalent disulfide bonds to result in a dimeric molecule containing four TACI polypeptides (e.g. four variant TACI polypeptides).

In some embodiments, there is provided a TACI-Fc fusion protein containing in order a TACI polypeptide, e.g. any as described above; a linker; an Fc region; a linker; and another TACI polypeptide, e.g. any as described. In some embodiments, each TACI polypeptide of the TACI Fc fusion is a truncated wild-type TACI polypeptide, such as any as described. In some embodiments, each TACI polypeptide of the TACI Fc fusion is set forth in SEQ ID NO: 13. In some embodiments, each TACI polypeptide of the TACI Fc fusion is a variant TACI polypeptide, such as any as described. In some embodiments, each TACI polypeptide of the TACI Fc fusion is a variant TACI set forth in any one of SEQ ID NOS: 2-12, 21, 22, or 101-120. In some embodiments, each TACI polypeptide of the TACI Fc fusion is a variant TACI set forth in any one of SEQ ID NOS: 14-20, 23-35, 92-100 or 177-192. The linkers may be any as described, and may be the same or different. In some embodiments, the first linker is GSGGGGS (SEQ ID NO: 74) and the second linker is (GGGGS)$_4$ (SEQ ID NO: 84). The Fc region may be any Fc region as described. In some embodiments, the Fc region is a wild-type IgG1 Fc set forth in SEQ ID NO:81. In some embodiments, the Fc region is a variant Fc set forth in SEQ ID NO: 73. In some embodiments, the TACI-Fc fusion protein has the sequence set forth in SEQ ID NO:201, and encoded by a sequence set forth in SEQ ID NO:212. In some embodiments, the TACI-Fc fusion protein has the sequence set forth in SEQ ID NO:202, and encoded by a sequence set forth in SEQ ID NO:213.

In some embodiments, there is a provided a TACI-Fc fusion protein that is a dimer formed by two identical TACI polypeptides (e.g. variant TACI polypeptide) as described linked to an Fc domain. In some embodiments, identical species (also referred to as copies) of any of the provided TACI-Fc fusion polypeptides, e.g. variant TACI-Fc fusion, will be dimerized to create a homodimer. In some embodiments, the dimer is a homodimer in which the two TACI-Fc polypeptides, e.g. variant TACI-Fc polypeptides, are the same. For generating a homodimeric Fc molecule, the Fc region is one that is capable of forming a homodimer with a matched Fc region by co-expression of the individual Fc regions in a cell. In some embodiments, dimerization is mediated by covalent disulfide bond(s) formed between the Fc regions of the polypeptide fusions.

Also provided are nucleic acid molecules encoding the immunomodulatory protein. In some embodiments, for production of immunomodulatory protein, a nucleic acid molecule encoding the immunomodulatory protein is inserted into an appropriate expression vector. The resulting immunomodulatory protein can be expressed in host cells transformed with the expression where assembly between Fc domains occurs by interchain disulfide bonds formed between the Fc moieties to yield dimeric, such as divalent, immunomodulatory proteins.

Also provided are nucleic acid molecules encoding the TACI-Fc fusion proteins, e.g. variant TACI-Fc fusion protein. In some embodiments, for production of an Fc fusion protein, a nucleic acid molecule encoding a TACI-Fc fusion protein, e.g. variant TACI-Fc fusion protein is inserted into an appropriate expression vector. The resulting TACI-Fc fusion protein, e.g. variant TACI-Fc fusion protein can be expressed in host cells transformed with the expression where assembly between Fc domains occurs by interchain disulfide bonds formed between the Fc moieties to yield dimeric, such as divalent, TACI-Fc fusion proteins. The resulting Fc fusion proteins can be easily purified by affinity chromatography over Protein A or Protein G columns. For the generation of heterodimers, additional steps for purification can be necessary. For example, where two nucleic acids encoding different immunomodulatory proteins are transformed into cells, the formation of heterodimers must be biochemically achieved since immunomodulatory protein carrying the Fc-domain will be expressed as disulfide-linked homodimers as well. Thus, homodimers can be reduced under conditions that favor the disruption of interchain disulfides, but do no effect intra-chain disulfides. In some cases, different immunomodulatory protein monomers are mixed in equimolar amounts and oxidized to form a mixture of homo- and heterodimers. The components of this mixture are separated by chromatographic techniques. Alternatively, the formation of this type of heterodimer can be biased by genetically engineering and expressing immunomodulatory proteins containing Fc fusion molecules that contain one or more TACI variants using knob-into-hole methods as described.

Figure 8A:
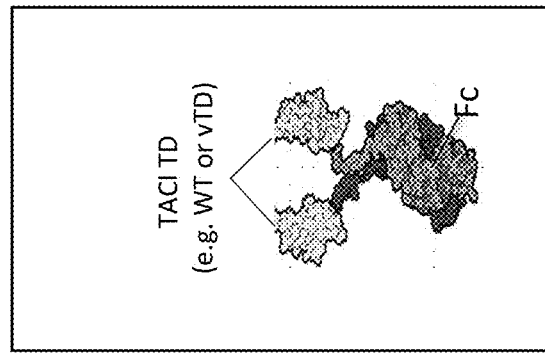
FIG. 8A and FIG. 8B depict schematic representations of exemplary TACI-Fc fusion proteins.
Figure 8B:
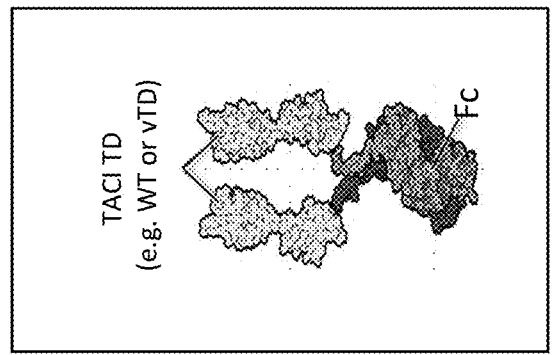

In embodiments, when produced and expressed from a cells, the provided immunomodulatory protein, such as a TACI-Fc (e.g. variant TACI-Fc), is a homodimer containing two identical polypeptide chains. FIG. 8A and FIG. 8B depict the structure of exemplary TACI-Fc fusion proteins provided herein.

Provided herein is a TACI (26)-Fc_73 homodimer of two identical variant TACI-Fc fusion proteins containing a variant of the TACI Cysteine Rich Domain 2 (CRD2) set forth in SEQ ID NO:26 designed to neutralize the B-cell stimulatory activity of APRIL and BAFF. The TACI (26)-Fc_73 homodimer is a dimer consisting of 2 identical receptor Fc-fusion protein chains, each with a variant TACI CRD2 domain human Fc-fusion set forth in SEQ ID NO:167, linked by covalent disulfide bonds.

Provided herein is a TACI (26)-Fc 81 homodimer of two identical variant TACI-Fc fusion proteins containing a variant of the TACI Cysteine Rich Domain 2 (CRD2) set forth in SEQ ID NO:26 designed to neutralize the B-cell stimulatory activity of APRIL and BAFF. The TACI (26)-Fc 81 homodimer is a dimer consisting of 2 identical receptor Fc-fusion protein chains, each with a variant TACI CRD2 domain human Fc-fusion set forth in SEQ ID NO:168, linked by covalent disulfide bonds.

Provided herein is a TACI (27)-Fc_73 homodimer of two identical variant TACI-Fc fusion proteins containing a variant of the TACI Cysteine Rich Domain 2 (CRD2) set forth in SEQ ID NO:27 designed to neutralize the B-cell stimulatory activity of APRIL and BAFF. The TACI (27)-Fc_73 homodimer is a dimer consisting of 2 identical receptor Fc-fusion protein chains, each with a variant TACI CRD2 domain human Fc-fusion set forth in SEQ ID NO:169, linked by covalent disulfide bonds.

Provided herein is a TACI (27)-Fc 81 homodimer of two identical variant TACI-Fc fusion proteins containing a variant of the TACI Cysteine Rich Domain 2 (CRD2) set forth in SEQ ID NO:27 designed to neutralize the B-cell stimulatory activity of APRIL and BAFF. The TACI (27)-Fc 81 homodimer is a dimer consisting of 2 identical receptor Fc-fusion protein chains, each with a variant TACI CRD2 domain human Fc-fusion set forth in SEQ ID NO:170, linked by covalent disulfide bonds.

In some embodiments, provided TACI-Fc (e.g. variant TACI-Fc) fusion proteins, such as homodimers thereof, exhibit an $IC_{50}$ for neutralizing BAFF of less than 400 pM. In some embodiments, the IC50 for neutralizing BAFF is between 1 pM and 400 pM, such as between 10 pM and 300 pM, between 10 pM and 200 pM, between 10 pM and 100 pM, between 10 pM and 50 pM, between 10 pM and 20 pM, between 20 pM and 400 pM, between 20 pM and 300 pM, between 20 pM and 200 pM, between 20 pM and 100 pM, between 20 pM and 50 pM, between 50 pM and 400 pM, between 50 pM and 300 pM, between 50 pM and 200 pM, between 50 pM and 100 pM, between 100 pM and 400 pM, between 100 pM and 300 pM, between 100 pM and 200 pM, between 200 pM and 400 pM, between 200 pM and 300 pM, or between 300 pM and 400 pM. In some embodiments, the $IC_{50}$ for neutralizing BAFF is at or about 10 pM, 15 pM, 20 pM, 25 pM, 30 pM, 35 pM, 40 pM, 45 pM, 50 pM, 55 pM, 60 pM, 65 pM, 70 pM, 75 pM, 80 pM, 85 pM, 90 pM, 95 pM or 100 pM or any value between any of the foregoing.

In some embodiments, provided TACI-Fc (e.g. variant TACI-Fc) fusion proteins, such as homodimers thereof, exhibits an $IC_{50}$ for neutralizing APRIL of less than 400 pM. In some embodiments, the IC50 for neutralizing APRIL is between 0.5 pM and 100 pM, such as between 0.5 pM and 50 pM, between 0.5 pM and 25 pM, between 0.5 pM and 10 pM, between 0.5 pM and 5 pM, between 0.5 pM and 1 pM, between 1 pM and 100 pM, between 1 pM and 50 pM, between 1 pM and 25 pM, between 1 pM and 10 pM, between 1 pM and 5 pM, between 5 pM and 100 pM, between 5 pM and 50 pM, between 5 pM and 25 pM, between 5 pM and 10 pM, between 10 pM and 100 pM, between 10 pM and 50 pM, between 10 pM and 25 pM, or between 25 pM and 100 pM, between 25 pM and 50 pM, or between 50 pM and 100 pM. In some embodiments, the IC50 for neutralizing APRIL is at or about 0.5 pM, 0.75 pM, 1 pM, 2 pM, 3 pM, 4 pM, 5 pM, 6 pM, 7 pM, 8 pM, 9 pM, 10 pM, 11 pM, 12 pM, 13 pM, 14 pM, 15 pM, 20 pM or 25 pM or any value between any of the foregoing.

III. Nucleic Acids, Vectors and Methods for Producing the Polypeptides or Cells Provided herein are isolated or recombinant nucleic acids collectively referred to as "nucleic acids" which encode any of the immunomodulatory proteins provided herein. In some embodiments, nucleic acids provided herein, including all described below, are useful in recombinant production (e.g., expression) of immunomodulatory proteins provided herein. In some embodiments, nucleic acids provided herein, including all described below, are useful in expression of immunomodulatory proteins provided herein, such as TACI fusion proteins provided herein. The nucleic acids provided herein can be in the form of RNA or in the form of DNA, and include mRNA, cRNA, recombinant or synthetic RNA and DNA, and cDNA. The nucleic acids provided herein are typically DNA molecules, and usually double-stranded DNA molecules. However, single-stranded DNA, single-stranded RNA, double-stranded RNA, and hybrid DNA/RNA nucleic acids or combinations thereof comprising any of the nucleotide sequences of the invention also are provided.

In some cases, a heterologous (non-native) signal peptide can be added to the nucleic acid encoding the immunomodulatory protein. This may be desired, for example, in the case of expression of TACI fusion proteins, which do not contain an amino terminal signal sequence. In some embodiments, the signal peptide is a signal peptide from an immunoglobulin (such as IgG heavy chain or IgG-kappa light chain), a cytokine (such as interleukin-2 (IL-2), or CD33), a serum albumin protein (e.g. HSA or albumin), a human azurocidin preprotein signal sequence, a luciferase, a trypsinogen (e.g. chymotrypsinogen or trypsinogen) or other signal peptide able to efficiently express and, in some aspects, secret a protein from a cell. Exemplary signal peptides include any described in the Table 3.

TABLE 3

Exemplary Signal Peptides

| SEQ ID NO | Signal Peptide | Peptide Sequence |
|---|---|---|
| SEQ ID NO: 149 | HSA signal peptide | MKWVTFISLLFLFSSAYS |
| SEQ ID NO: 150 | Ig kappa light chain | MDMRAPAGIFGFLLVLFPGYRS |
| SEQ ID NO: 151 | human azurocidin preprotein signal sequence | MTRLTVLALLAGLLASSRA |
| SEQ ID NO: 152 | IgG heavy chain signal peptide | MELGLSWIFLLAILKGVQC |
| SEQ ID NO: 153 | IgG heavy chain signal peptide | MELGLRWVFLVAILEGVQC |
| SEQ ID NO: 154 | IgG heavy chain signal peptide | MKHLWFFLLLVAAPRWVLS |
| SEQ ID NO: 155 | IgG heavy chain signal peptide | MDWTWRILFLVAAATGAHS |
| SEQ ID NO: 156 | IgG heavy chain signal peptide | MDWTWRFLFVVAAATGVQS |
| SEQ ID NO: 157 | IgG heavy chain signal peptide | MEFGLSWLFLVAILKGVQC |
| SEQ ID NO: 158 | IgG heavy chain signal peptide | MEFGLSWVFLVALFRGVQC |
| SEQ ID NO: 159 | IgG heavy chain signal peptide | MDLLHKNMKHLWFFLLLVAAPRWVLS |
| SEQ ID NO: 160 | IgG Kappa light chain signal sequences: | MDMRVPAQLLGLLLLWLSGARC |
| SEQ ID NO: 161 | IgG Kappa light chain signal sequences: | MKYLLPTAAAGLLLLAAQPAMA |
| SEQ ID NO: 162 | *Gaussia luciferase* | MGVKVLFALICIAVAEA |
| SEQ ID NO: 163 | Human albumin | MKWVTFISLLFLFSSAYS |
| SEQ ID NO: 164 | Human chymotrypsinogen | MAFLWLLSCWALLGTTFG |
| SEQ ID NO: 165 | Human interleukin-2 | MQLLSCIALILALV |
| SEQ ID NO: 166 | Human trypsinogen-2 | MNLLLILTFVAAAVA |

In some embodiments, the immunomodulatory protein comprises a signal peptide when expressed, and the signal peptide (or a portion thereof) is cleaved from the immunomodulatory protein upon secretion.

Also provided herein are recombinant expression vectors and recombinant host cells useful in producing the immunomodulatory proteins, such as TACI fusion proteins provided herein.

In any of the above provided embodiments, the nucleic acids encoding the immunomodulatory polypeptides provided herein can be introduced into cells using recombinant DNA and cloning techniques. To do so, a recombinant DNA molecule encoding an immunomodulatory polypeptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidite method. Also, a combination of these techniques could be used. In some instances, a recombinant or synthetic nucleic acid may be generated through polymerase chain reaction (PCR). A DNA insert encoding an immunomodulatory protein can be cloned into an appropriate transduction/transfection vector as is known to those of skill in the art. Also provided are expression vectors containing the nucleic acid molecules.

In some embodiments, the expression vectors are capable of expressing the immunomodulatory proteins in an appropriate cell under conditions suited to expression of the protein. In some aspects, nucleic acid molecule or an expression vector comprises the DNA molecule that encodes the immunomodulatory protein operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

In some embodiments, expression of the immunomodulatory protein is controlled by a promoter or enhancer to control or regulate expression. The promoter is operably linked to the portion of the nucleic acid molecule encoding the variant polypeptide or immunomodulatory protein.

The resulting recombinant expression vector having the DNA molecule thereon is used to transform an appropriate host. This transformation can be performed using methods well known in the art. In some embodiments, a nucleic acid provided herein further comprises nucleotide sequence that encodes a secretory or signal peptide operably linked to the nucleic acid encoding an immunomodulatory polypeptide such that a resultant soluble immunomodulatory polypeptide is recovered from the culture medium, host cell, or host cell periplasm. In other embodiments, the appropriate expression control signals are chosen to allow for membrane expression of an immunomodulatory polypeptide. Furthermore, commercially available kits as well as contract manufacturing companies can also be utilized to make engineered cells or recombinant host cells provided herein.

In some embodiments, the resulting expression vector having the DNA molecule thereon is used to transform, such as transduce, an appropriate cell. The introduction can be performed using methods well known in the art. Exemplary methods include those for transfer of nucleic acids encoding the receptors, including via viral, e.g., retroviral or lentiviral, transduction, transposons, and electroporation. In some embodiments, the expression vector is a viral vector. In some embodiments, the nucleic acid is transferred into cells by lentiviral or retroviral transduction methods.

Any of a large number of publicly available and well-known mammalian host cells, including mammalian T-cells or APCs, can be used in the preparing the polypeptides or engineered cells. The selection of a cell is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all cells can be equally effective for the expression of a particular DNA sequence.

In some embodiments, the host cell is a mammalian cell. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al, Som. Cell. Molec. Genet. 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

In some embodiments, the host cells can be a variety of eukaryotic cells, such as in yeast cells, or with mammalian cells such as Chinese hamster ovary (CHO) or HEK293 cells. In some embodiments, the host cell is a suspension cell and the polypeptide is engineered or produced in cultured suspension, such as in cultured suspension CHO cells, e.g. CHO—S cells. In some examples, the cell line is a CHO cell line that is deficient in DHFR (DHFR−), such as DG44 and DUXB11. In some embodiments, the cell is deficient in glutamine synthase (GS), e.g. CHO—S cells, CHOK1 SV cells, and CHOZN((R)) GS−/− cells. In some embodiments, the CHO cells, such as suspension CHO cells, may be CHO—S-2H2 cells, CHO—S-clone 14 cells, or ExpiCHO-S cells.

In some embodiments, host cells can also be prokaryotic cells, such as with *E. coli*. The transformed recombinant host is cultured under polypeptide expressing conditions, and then purified to obtain a soluble protein. Recombinant host cells can be cultured under conventional fermentation conditions so that the desired polypeptides are expressed. Such fermentation conditions are well known in the art. Finally, the polypeptides provided herein can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, and affinity chromatography. Protein refolding steps can be used, as desired, in completing configuration of the mature protein. Finally, high performance liquid chromatography (HPLC) can be employed in the final purification steps.

In some embodiments, the recombinant vector is a viral vector. Exemplary recombinant viral vectors include a lentiviral vector genome, poxvirus vector genome, vaccinia virus vector genome, adenovirus vector genome, adenovirus-associated virus vector genome, herpes virus vector genome, and alpha virus vector genome. Viral vectors can be live, attenuated, replication conditional or replication deficient, non-pathogenic (defective), replication competent viral vector, and/or is modified to express a heterologous gene product, e.g., the variant immunomodulatory polypeptides provided herein. Vectors for generation of viruses also can be modified to alter attenuation of the virus, which includes any method of increasing or decreasing the transcriptional or translational load.

Exemplary viral vectors that can be used include modified vaccinia virus vectors (see, e.g., Guerra et al., J. Virol. 80:985-98 (2006); Tartaglia et al., AIDS Research and Human Retroviruses 8: 1445-47 (1992); Gheradi et al., J. Gen. Virol. 86:2925-36 (2005); Mayr et al., Infection 3:6-14 (1975); Hu et al., J. Virol. 75: 10300-308 (2001); U.S. Pat. Nos. 5,698,530, 6,998,252, 5,443,964, 7,247,615 and 7,368, 116); adenovirus vector or adenovirus-associated virus vectors (see, e.g., Molin et al., J. Virol. 72:8358-61 (1998); Narumi et al., Am J. Respir. Cell Mol. Biol. 19:936-41 (1998); Mercier et al., Proc. Natl. Acad. Sci. USA 101:6188-93 (2004); U.S. Pat. Nos. 6,143,290; 6,596,535; 6,855,317; 6,936,257; 7,125,717; 7,378,087; 7,550,296); retroviral vectors including those based upon murine leukemia virus (MuLV), gibbon ape leukemia virus (GaLV), ecotropic retroviruses, simian immunodeficiency virus (SIV), human immunodeficiency virus (HIV), and combinations (see, e.g., Buchscher et al., J. Virol. 66:2731-39 (1992); Johann et al., J. Virol. 66: 1635-40 (1992); Sommerfelt et al., Virology 176:58-59 (1990); Wilson et al., J. Virol. 63:2374-78 (1989); Miller et al., J. Virol. 65:2220-24 (1991); Miller et al., Mol. Cell Biol. 10:4239 (1990); Kolberg, NIH Res. 4:43 1992; Cornetta et al., Hum. Gene Ther. 2:215 (1991)); lentiviral vectors including those based upon Human Immunodeficiency Virus (HIV-1), HIV-2, feline immunodeficiency virus (FIV), equine infectious anemia virus, Simian Immunodeficiency Virus (SIV), and maedi/visna virus (see, e.g., Pfeifer et al., Annu. Rev. Genomics Hum. Genet. 2: 177-211 (2001); Zufferey et al., J. Virol. 72: 9873, 1998; Miyoshi et al., J. Virol. 72:8150, 1998; Philpott and Thrasher, Human Gene Therapy 18:483, 2007; Engelman et al., J. Virol. 69: 2729, 1995; Nightingale et al., Mol. Therapy, 13: 1121, 2006; Brown et al., J. Virol. 73:9011 (1999); WO 2009/076524; WO 2012/141984; WO 2016/011083; McWilliams et al., J. Virol. 77: 11150, 2003; Powell et al., *J. Virol.* 70:5288, 1996) or any, variants thereof, and/or vectors that can be used to generate any of the viruses described above. In some embodiments, the recombinant vector can include regulatory sequences, such as promoter or enhancer sequences, that can regulate the expression of the viral genome, such as in the case for RNA viruses, in the packaging cell line (see, e.g., U.S. Pat. Nos. 5,385,839 and 5,168,062).

In some aspects, nucleic acids or an expression vector comprises a nucleic acid sequence that encodes the immunomodulatory protein operatively linked to appropriate expression control sequences. Methods of effecting this operative linking, either before or after the nucleic acid sequence encoding the immunomodulatory protein is inserted into the vector, are well known. Expression control sequences include promoters, activators, enhancers, operators, ribosomal binding sites, start signals, stop signals, cap signals, polyadenylation signals, and other signals involved with the control of transcription or translation. The promoter can be operably linked to the portion of the nucleic acid sequence encoding the immunomodulatory protein.

Transcriptional regulatory sequences include a promoter region sufficient to direct the initiation of RNA synthesis. Suitable eukaryotic promoters include the promoter of the mouse metallothionein I gene (Hamer et al, J. Molec. Appl Genet. 1:273 (1982)), the TK promoter of Herpes virus (McKnight, Cell 31:355 (1982)), the SV40 early promoter (Benoist et al, Nature 290:304 (1981)), the Rous sarcoma virus promoter (Gorman et al, Proc. Nat'l Acad. Sci. USA 79:6777 (1982)), the cytomegalovirus promoter (Foecking et al, Gene 45:101 (1980)), and the mouse mammary tumor virus promoter (see, generally, Etcheverry, "Expression of Engineered Proteins in Mammalian Cell Culture," in Protein Engineering: Principles and Practice, Cleland et al. (eds.), pages 163-181 (John Wiley & Sons, Inc. 1996)). One useful combination of a promoter and enhancer is provided by a myeloproliferative sarcoma virus promoter and a human cytomegalovirus enhancer.

Alternatively, a prokaryotic promoter, such as the bacteriophage T3 RNA polymerase promoter, can be used to control production of an immunomodulatory protein in mammalian cells if the prokaryotic promoter is regulated by a eukaryotic promoter (Zhou et al, Mol Cell. Biol. 10:4529 (1990), and Kaufman et al, Nucl. Acids Res. 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), Gene Transfer and Expression Protocols (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multidrug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

In some embodiments, polypeptides provided herein can also be made by synthetic methods. Solid phase synthesis is the preferred technique of making individual peptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Peptides can then be assembled into the polypeptides as provided herein.

IV. Pharmaceutical Compositions

Provided herein are compositions containing any of the provided immunomodulatory proteins described herein. The pharmaceutical composition can further comprise a pharmaceutically acceptable excipient. For example, the pharmaceutical composition can contain one or more excipients for modifying, maintaining or preserving, for example, the pH, osmolarity, viscosity, clarity, color, isotonicity, odor, sterility, stability, rate of dissolution or release, adsorption, or penetration of the composition. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

In some embodiments, the pharmaceutical composition is a solid, such as a powder, capsule, or tablet. For example, the components of the pharmaceutical composition can be lyophilized. In some embodiments, the solid pharmaceutical composition is reconstituted or dissolved in a liquid prior to administration.

In some embodiments, the pharmaceutical composition is a liquid, for example immunomodulatory proteins dissolved in an aqueous solution (such as physiological saline or Ringer's solution). In some embodiments, the pH of the pharmaceutical composition is between about 4.0 and about 8.5 (such as between about 4.0 and about 5.0, between about 4.5 and about 5.5, between about 5.0 and about 6.0, between about 5.5 and about 6.5, between about 6.0 and about 7.0, between about 6.5 and about 7.5, between about 7.0 and about 8.0, or between about 7.5 and about 8.5).

In some embodiments, the pharmaceutical composition comprises a pharmaceutically-acceptable excipient, for example a filler, binder, coating, preservative, lubricant, flavoring agent, sweetening agent, coloring agent, a solvent, a buffering agent, a chelating agent, or stabilizer. Examples of pharmaceutically-acceptable fillers include cellulose, dibasic calcium phosphate, calcium carbonate, microcrystalline cellulose, sucrose, lactose, glucose, mannitol, sorbitol, maltol, pregelatinized starch, corn starch, or potato starch. Examples of pharmaceutically-acceptable binders include polyvinylpyrrolidone, starch, lactose, xylitol, sorbitol, maltitol, gelatin, sucrose, polyethylene glycol, methyl cellulose, or cellulose. Examples of pharmaceutically-acceptable coatings include hydroxypropyl methylcellulose (HPMC), shellac, corn protein zein, or gelatin. Examples of pharmaceutically-acceptable disintegrants include polyvinylpyrrolidone, carboxymethyl cellulose, or sodium starch glycolate. Examples of pharmaceutically-acceptable lubricants include polyethylene glycol, magnesium stearate, or stearic acid. Examples of pharmaceutically-acceptable preservatives include methyl parabens, ethyl parabens, propyl paraben, benzoic acid, or sorbic acid. Examples of pharmaceutically-acceptable sweetening agents include sucrose, saccharine, aspartame, or sorbitol. Examples of pharmaceutically-acceptable buffering agents include carbonates, citrates, gluconates, acetates, phosphates, or tartrates.

In some embodiments, the pharmaceutical composition further comprises an agent for the controlled or sustained release of the product, such as injectable microspheres, bio-erodible particles, polymeric compounds (polylactic acid, polyglycolic acid), beads, or liposomes.

In some embodiments, the pharmaceutical composition is sterile. Sterilization may be accomplished by filtration through sterile filtration membranes or radiation. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

A pharmaceutically acceptable carrier may be a pharmaceutically acceptable material, composition, or vehicle. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

In some embodiments, the pharmaceutical composition is administered to a subject. Generally, dosages and routes of administration of the pharmaceutical composition are determined according to the size and condition of the subject, according to standard pharmaceutical practice. For example, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans. The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy.

Long-acting pharmaceutical compositions may be administered every 3 to 4 days, every week, or biweekly depending on the half-life and clearance rate of the particular formulation. The frequency of dosing will depend upon the pharmacokinetic parameters of the molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

In some embodiments, the pharmaceutical composition is administered to a subject through any route, including orally, transdermally, by inhalation, intravenously, intra-arterially, intramuscularly, direct application to a wound site, application to a surgical site, intraperitoneally, by suppository, subcutaneously, intradermally, transcutaneously, by nebulization, intrapleurally, intraventricularly, intra-articularly, intraocularly, or intraspinally.

A provided pharmaceutical formulation may, for example, be in a form suitable for intravenous infusion.

In some embodiments, the dosage of the pharmaceutical composition is a single dose or a repeated dose. In some embodiments, the doses are given to a subject once per day, twice per day, three times per day, or four or more times per day. In some embodiments, about 1 or more (such as about 2 or more, about 3 or more, about 4 or more, about 5 or more, about 6 or more, or about 7 or more) doses are given in a week. In some embodiments, multiple doses are given over the course of days, weeks, months, or years. In some embodiments, a course of treatment is about 1 or more doses (such as about 2 or more does, about 3 or more doses, about 4 or more doses, about 5 or more doses, about 7 or more doses, about 10 or more doses, about 15 or more doses, about 25 or more doses, about 40 or more doses, about 50 or more doses, or about 100 or more doses).

In some embodiments, an administered dose of the pharmaceutical composition is about 1 µg of protein per kg subject body mass or more (such as about 2 µg of protein per kg subject body mass or more, about 5 µg of protein per kg subject body mass or more, about 10 µg of protein per kg subject body mass or more, about 25 µg of protein per kg subject body mass or more, about 50 µg of protein per kg subject body mass or more, about 100 µg of protein per kg subject body mass or more, about 250 µg of protein per kg subject body mass or more, about 500 µg of protein per kg subject body mass or more, about 1 mg of protein per kg subject body mass or more, about 2 mg of protein per kg subject body mass or more, or about 5 mg of protein per kg subject body mass or more).

V. Methods for Assessing Activity and Immune Modulation of Immunomodulatory Proteins In some embodiments, the provided immunomodulatory proteins, such as TACI fusion proteins provided herein exhibit immunomodulatory activity. The provided immunomodulatory proteins, such as TACI fusion protein can modulate B cell activity, such as one or more of B cell proliferation, differentiation or survival.

The function of immunomodulatory proteins can be examined using a variety of approaches to assess the ability of the proteins to bind to cognate binding partners. For example, TACI fusion proteins may be assessed for binding to APRIL or BAFF. A variety of assays are known for assessing binding affinity and/or determining whether a binding molecule (e.g., immunomodulatory protein) specifically binds to a particular binding partner. It is within the level of a skilled artisan to determine the binding affinity of a binding molecule, e.g., immumodulaotry protein, for a binding partner, e.g., APRIL or BAFF, such as by using any of a number of binding assays that are well known in the art. Various binding assays are known and include, but are not limited to, for example, ELISA KD, KinExA, flow cytometry, and/or surface plasmon resonance devices), including those described herein. Such methods include, but are not limited to, methods involving BIAcore®, Octet®, or flow cytometry. For example, in some embodiments, a BIAcore® instrument can be used to determine the binding kinetics and constants of a complex between two proteins using surface plasmon resonance (SPR) analysis (see, e.g., Scatchard et al., *Ann. N.Y. Acad. Sci.* 51:660, 1949; Wilson, Science 295:2103, 2002; Wolff et al., *Cancer Res.* 53:2560, 1993; and U.S. Pat. Nos. 5,283,173, 5,468,614, or the equivalent). SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of expressed polynucleotides or binding of proteins.

Provided immunomodulatory proteins also can be assessed in any of a variety of assess to assess modulation of B cell activity. One such assay is a cell proliferation assay. Cells are cultured in the presence or absence of a test compound (e.g. immunomodulatory protein), and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, J. Immunol. Meth. 65: 55-63, 1983). An alternative assay format uses cells that are further engineered to express a reporter gene. The reporter gene is linked to a promoter element that is responsive to the receptor-linked pathway, and the assay detects activation of transcription of the reporter gene. Numerous reporter genes that are easily assayed for in cell extracts are known in the art, for example, the *E. coli* lacZ, chloroamphenicol acetyl transferase (CAT) and serum response element (SRE) (see, e.g., Shaw et al., Cell 56:563-72, 1989). An exemplary reporter gene is a luciferase gene (de Wet et al., Mol. Cell. Biol. 7:725, 1987). Expression of the luciferase gene is detected by luminescence using methods known in the art (e.g., Baumgartner et al., J. Biol. Chem. 269:29094-101, 1994; Schenborn and Goiffin, Promega Notes 41:11, 1993). Luciferase activity assay kits are commercially available from, for example, Promega Corp., Madison, Wis.

Provided immunomodulatory proteins can be characterized by the ability to inhibit the stimulation of human B cells by soluble APRIL or BAFF, as described by Gross et al, international publication No. WO00/40716. Briefly, human B cells are isolated from peripheral blood mononuclear cells, such as using CD19 magnetic beads separation (e.g. Miltenyi Biotec Auburn, Calif.). The purified B cells can be incubated under conditions of stimulation, e.g. in the presence of soluble APRIL, and further in the presence of titrated concentration of immunomodulatory protein. The B cells can be labeled with a proliferation dye or can be labeled with 1 µCi $^3$H-thymidine to measure proliferation. The number of B cells can be determined over time.

Reporter cell lines that express a reporter gene under the operable control of a transcription factor, such as NF-κB, NFAT-1 and AP-1, can be made that express TACI or BCMA. For example, the reporter cell can include Jurkat and other B Lymphoma cell lines. Incubation of these cells with soluble BAFF or APRIL ligands signal through the reporter genes in these constructs. The effect of provided immunomodulatory proteins to modulate this signaling can be assessed.

Well established animal models are available to test in vivo efficacy of provided immunomodulatory proteins in certain disease states, including those involving autoimmune or inflammatory conditions. For example, animal models of autoimmune disease include, for example, MRL-lpr/lpr or NZB×NZW F1 congenic mouse strains which serve as a model of SLE (systemic lupus erythematosus). Such animal models are known in the art, see for example *Autoimmune Disease Models* A Guidebook, Cohen and Miller eds. Academic Press. Offspring of a cross between New Zealand Black (NZB) and New Zealand White (NZW) mice develop a spontaneous form of SLE that closely resembles SLE in humans. The offspring mice, known as NZBW begin to develop IgM autoantibodies against T-cells at 1 month of age, and by 5-7 months of age, Ig anti-DNA autoantibodies are the dominant immunoglobulin. Polyclonal B-cell hyperactivity leads to overproduction of autoantibodies. The deposition of these autoantibodies, particularly ones directed against single stranded DNA is associated with the development of glomerulonephritis, which manifests clinically as proteinuria, azotemia, and death from renal failure. Kidney failure is the leading cause of death in mice affected with spontaneous SLE, and in the NZBW strain, this process is chronic and obliterative. The disease is more rapid and severe in females than males, with mean survival of only 245 days as compared to 406 days for the males. While many of the female mice will be symptomatic (proteinuria) by 7-9 months of age, some can be much younger or older when they develop symptoms. The fatal immune nephritis seen in the NZBW mice is very similar to the glomerulonephritis seen in human SLE, making this spontaneous murine model very attractive for testing of potential SLE therapeutics (Putterman and Naparstek, *Murine Models of Spontaneous Systemic Lupus Erythematosus*, Autoimmune Disease Models: A Guidebook, chapter 14, pp. 217-34, 1994; Mohan et al., *J. Immunol.* 154:1470-80, 1995; and Daikh et al., *J. Immunol.* 159:3104-08, 1997). Administration of provided immunomodulatory proteins to these mice to evaluate the efficacy to ameliorate symptoms and alterations to the course of disease can be assessed.

Another mouse model of inflammation and lupus-like disease is the bm12 inducible mouse model of SLE (Klarquist and Janssen, 2015. J. Vis. Exp. (105), e53319). Splenocyte suspensions from female I-A$^{bm12}$B6(C)H2-Ab1$^{bm12}$/KhEgJ ('bm12') mice are adoptively transferred into female C57BL/6NJ recipient mice. H2-Ab1$^{bm12}$ differs from H2-Ab1$^b$ by 3 nucleotides, resulting in alteration of 3 amino acids in the β-chain of the MHC class II I-A molecule. Alloactivation of donor bm12 CD4+ T cells by recipient antigen presenting cells leads to chronic GVHD with symptoms closely resembling SLE, including autoantibody production, changes in immune cell subsets, and mild kidney disease. Glomerulonephritis with immune complex deposition develops late in the model, largely comprised of autoantigens bound to IgG1, IgG2b, IgG2c, and IgG3 antibodies. Endpoints of this model may include concentrations of anti-dsDNA antibodies, select IgG isotypes, blood urea nitrogen (BUN), and creatinine in serum, immune cell subset composition in the spleen and cervical LN, and kidney histology.

In some embodiments, mouse models for Sjögren's syndrome (SjS) can be used. The SjS disease, as well as an accelerated onset of diabetes, can be induced in female diabetes-prone non-obese diabetic (NOD) mice using repeat dosing with anti-mouse (m) PD-L1 antibody, based on a modified version of a protocol published by Zhou et al., 2016 Sci. Rep. 6, 39105. Starting at 6 weeks of age, mice are injected intraperitoneally (IP) on Study Days 0, 2, 4, and 6 with 100 µg of anti-PD-L1 antibody and are treated on various days with provided immunomodulatory proteins. Naïve mice are included as controls for the endpoint analyses. All mice are typically terminated on Study Day 10 and submandibular glands (SMG) and the pancreas from each mouse are collected for histopathology evaluation to assess for signs and severity of sialadenitis and insulitis. Blood glucose levels can be measured on various days.

In some embodiments, mouse models for experimental allergic encephalomyelitis (EAE) can be used. The models resemble human multiple sclerosis, and produces demyelination as a result of T-cell activation to neuroproteins such as myelin basic protein (MBP), or proteolipid protein (PLP). Inoculation with antigen leads to induction of CD4+, class II MHC-restricted T-cells (Th1). Changes in the protocol for EAE can produce acute, chronic-relapsing, or passive-transfer variants of the model (Weinberg et al., *J. Immunol.* 162:1818-26, 1999; Mijaba et al., *Cell. Immunol.* 186:94-102, 1999; and Glabinski, *Meth. Enzym.* 288:182-90, 1997). Administration of provided immunomodulatory proteins to ameliorate symptoms and alterations to the course of disease can be assessed.

In some embodiments, a collagen-induced arthritis (CIA) model can be used in which mice develop chronic inflammatory arthritis which closely resembles human rheumatoid arthritis (RA). Since CIA shares similar immunological and pathological features with RA, this makes it an ideal model for screening potential human anti-inflammatory compounds. Another advantage in using the CIA model is that the mechanisms of pathogenesis are known. The T and B cell epitopes on type II collagen have been identified, and various immunological (delayed-type hypersensitivity and anti-collagen antibody) and inflammatory (cytokines, chemokines, and matrix-degrading enzymes) parameters relating to immune-mediating arthritis have been determined and can be used to assess test compound efficacy in the models (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995). Administration of provided immunomodulatory proteins to ameliorate symptoms and alterations to the course of disease can be assessed.

In some embodiments, models for bronchial infection, such as asthma, can be created when mice are injected with ovalbumin and restimulated nasally with antigen which produces an asthmatic response in the bronchi similar to asthma. Administration of provided immunomodulatory proteins to ameliorate symptoms and alterations to the course of disease can be assessed.

In some embodiments, myasthenia gravis (MG) is another autoimmune disease for which murine models are available. MG is a disorder of neuromuscular transmission involving the production of autoantibodies directed against the nicotinic acetylcholine receptor (AChR). MG is acquired or inherited with clinical features including abnormal weakness and fatigue on exertion. A mouse model of MG has been established. (Christadoss et al., *Establishment of a Mouse Model of Myasthenia Gravis Which Mimics Human Myasthenia Gravis Pathogenesis for Immune Intervention*, in Immunobiology of Proteins and Peptides VIII, Atassi and Bixler, eds., 1995, pp. 195-99.) Experimental autoimmune myasthenia gravis (EAMG) is an antibody mediated disease characterized by the presence of antibodies to AChR. These antibodies destroy the receptor leading to defective neuromuscular electrical impulses, resulting in muscle weakness. In the EAMG model, mice are immunized with the nicotinic acetylcholine receptor. Clinical signs of MG become evident weeks after the second immunization. EAMG is evaluated by several methods including measuring serum levels of AChR antibodies by radioimmunoassay (Christadoss and Dauphinee, *J. Immunol.* 136:2437-40, 1986; and Lindstrom et al., *Methods Enzymol.* 74:432-60, 1981), measuring muscle AChR, or electromyography (Wu et al. *Protocols in Immunology.* Vol. 3, Eds. Coligen, Kruisbeak, Margulies, Shevach, and Strober. John Wiley and Sons, New York, p. 15.8.1, 1997).

Another use for in vivo models includes delivery of an antigen challenge to the animal followed by administration of immunomodulatory proteins and measuring the T and B cell response. T cell dependent and T cell independent immune response can be measured as described in Perez-Melgosa et al., *J. Immunol.* 163:1123-7, 1999. Immune response in animals subjected to a regular antigen challenge (for example, keyhole limpet hemacyanin (KLH), sheep red blood cells (SRBC), ovalbumin or collagen) followed by administration of provided immunomodulatory proteins can be done to measure effect on B cell response.

Pharmacokinetic studies can be used in association with radiolabeled immunomodulatory proteins to determine the distribution and half life of such polypeptides in vivo.

VI. Therapeutic Applications

The pharmaceutical compositions described herein (including pharmaceutical composition comprising the immunomodulatory protein, e.g. TACI-Fc, described herein) can be used in a variety of therapeutic applications, such as the treatment of a disease. For example, in some embodiments the pharmaceutical composition is used to treat inflammatory or autoimmune disorders, cancer, organ transplantation, viral infections, and/or bacterial infections in a mammal. The pharmaceutical composition can modulate (e.g. decrease) an immune response to treat the disease.

Such methods and uses include therapeutic methods and uses, for example, involving administration of the molecules or compositions containing the same, to a subject having a disease, condition, or disorder. In some cases, such as described, the disease, condition or disorder is an autoimmune or inflammatory disease or disorder. In some embodiments, the molecule or engineered cell is administered in an effective amount to effect treatment of the disease or disorder. Uses include uses of molecules containing an immunomodulatory protein, and in the preparation of a medicament in order to carry out such therapeutic methods. In some embodiments, the methods are carried out by administering a provided immunomodulatory protein, or compositions comprising the same, to the subject having or suspected of having the disease or condition. In some embodiments, the methods thereby treat the disease, disorder or condition or disorder in the subject.

Illustrative subjects include mammalian subjects, such as farm animals, domestic animals, and human patients. In particular embodiments, the subject is a human subject.

The pharmaceutical compositions described herein can be used in a variety of therapeutic applications, such as the treatment of a disease. For example, in some embodiments the pharmaceutical composition is used to treat inflammatory or autoimmune disorders, organ transplantation, viral infections, and/or bacterial infections in a mammal. The pharmaceutical composition can modulate an immune response to treat the disease. In some embodiments, the pharmaceutical composition suppresses an immune response, which can be useful in the treatment of inflammatory or autoimmune disorders, or organ transplantation.

The provided methods are believed to have utility in a variety of applications, including, but not limited to, e.g., in prophylactic or therapeutic methods for treating a variety of immune system diseases or conditions in a mammal in which modulation or regulation of the immune system and immune system responses is beneficial. For example, suppressing an immune response can be beneficial in prophylactic and/or therapeutic methods for inhibiting rejection of a tissue, cell, or organ transplant from a donor by a recipient. In a therapeutic context, the mammalian subject is typically one with an immune system disease or condition, and administration is conducted to prevent further progression of the disease or condition.

The provided immunomodulatory proteins, including TACI fusion proteins, can be used for the treatment of autoimmune diseases, B cell cancers, immunomodulation, EBD and any antibody-mediated pathologies (e.g., ITCP, myasthenia gravis and the like), renal diseases, indirect T cell immune response, graft rejection, and graft versus host disease. Administration of the immunomodulatory proteins (e.g. TACI-Fc) can specifically regulate B cell responses during the immune response. Additionally, administration of provided immunomodulatory proteins can be used to modulate B cell development, development of other cells, antibody production, and cytokine production. Administration or use of provided immunomodulatory proteins can also modulate B cell communication, such as by neutralizing the proliferative effects of BAFF or APRIL.

In some embodiments, the pharmaceutical composition suppresses an immune response, which can be useful in the treatment of inflammatory or autoimmune disorders, or organ transplantation. In some embodiments, the pharmaceutical composition contains an immunomodulatory protein that exhibits antagonist activity of a B cell stimulatory receptor, thereby decreasing or reducing an immune response.

In some embodiments, the compositions can be used to treat an autoimmune disease. In some embodiments, the administration of a therapeutic composition containing an immunomodulatory protein provided herein to a subject suffering from an immune system disease (e.g., autoimmune disease) can result in suppression or inhibition of such immune system attack or biological responses associated therewith. By suppressing this immune system attack on healthy body tissues, the resulting physical symptoms (e.g., pain, joint inflammation, joint swelling or tenderness) resulting from or associated with such attack on healthy tissues can be decreased or alleviated, and the biological and physical damage resulting from or associated with the immune system attack can be decreased, retarded, or stopped. In a prophylactic context, the subject may be one with, susceptible to, or believed to present an immune system disease, disorder or condition, and administration is typically conducted to prevent progression of the disease, disorder or condition, inhibit or alleviate symptoms, signs, or biological responses associated therewith, prevent bodily damage potentially resulting therefrom, and/or maintain or improve the subject's physical functioning.

In some embodiments, the disease or conditions that can be treated by the pharmaceutical composition described herein is any disease mediated by immune complex deposition (e.g. lupus nephritis, vasculitis); direct interference with a pathway (e.g. catastrophic antiphospholipid antibody syndrome, myasthenia gravis crisis; anti-Jo-1 disease); opsonization or direct damage to cells (e.g. Idiopathic thrombocytopenic purpura, autoimmune hemolytic anemia); antibody-mediated rejection of an allograft (e.g. highly-sensitized renal transplant patients); or anti-drug antibodies to biologic replacement factors, vectors (e.g. anti-Factor 8).

In some embodiments, the inflammatory and autoimmune disorders, conditions or diseases that can be treated by the pharmaceutical composition described herein is Systemic lupus erythematosus (SLE), including flare prevention without glucocorticoids; Sjögren's syndrome; Primary biliary cirrhosis (PBC); Systemic scleroderma; Polymyositis; Diabetes prevention; IgA nephropathy; IgA vasculitis; B cell cancers, for example myeloma; Multiple sclerosis or Optic neuritis.

In some embodiments, the provided immunomodulatory proteins can be used to treat pre-B or B-cell leukemias, such as plasma cell leukemia, chronic or acute lymphocytic leukemia, myelomas such as multiple myeloma, plasma cell myeloma, endothelial myeloma and giant cell myeloma, and lymphomas such as non-Hodgkins lymphoma. In some of any embodiments, the type of myeloma includes multiple myeloma, plasmacytoma, multiple solitary plasmacytoma, and/or extramedullary myeloma. In some of any embodiments, the type of myeloma includes light chain myeloma, nonsecretory myeloma, and/or IgD or IgE myeloma.

In some embodiments, the provided immunomodulatory proteins can be used as immunosuppressants to selectively block the action of B-lymphocytes for use in treating disease. For example, certain autoimmune diseases are characterized by production of autoantibodies, which contribute to tissue destruction and exacerbation of disease. Autoantibodies can also lead to the occurrence of immune complex deposition complications and lead to many symptoms of systemic lupus erythematosus, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis. Methods and uses of the provided immunomodulatory proteins to inhibit, block or neutralize action of B cells to thereby suppress antibody production would be beneficial in treatment of autoimmune diseases such as myasthenia gravis, rheumatoid arthritis, polyarticular-course juvenile rheumatoid arthritis, and psoriatic arthritis.

In some embodiments, the provided immunomodulatory proteins can be used to block or neutralize the actions of B-cells in association with end stage renal diseases, which may or may not be associated with autoimmune diseases. Such methods would also be useful for treating immunologic renal diseases. Such methods would be useful for treating glomerulonephritis associated with diseases such as membranous nephropathy, IgA nephropathy or Berger's Disease, IgM nephropathy, IgA Vasculitis, Goodpasture's Disease, post-infectious glomerulonephritis, mesangioproliferative disease, chronic lymphoid leukemia, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HTV-related diseases, amyloidosis or hemolytic uremic syndrome. The provided methods would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis. The methods provided herein also include use of the provided immunomodulatory proteins in the treatment of hypertensive or large vessel diseases, including renal artery stenosis or occlusion and cholesterol emboli or renal emboli. The provided methods and uses also can be used for treatment of renal or urological neoplasms, multiple myelomas, lymphomas, light chain neuropathy or amyloidosis.

In some embodiments, the provided immunomodulatory proteins also can be used for the treatment of asthma and other chronic airway diseases such as bronchitis and emphysema. The provided immunomodulatory proteins can also be used to treat Sjogren's Syndrome.

In some embodiments, methods and uses of the provided immunomodulatory proteins include immunosuppression, in particular for such therapeutic use as for graft-versus-host disease and graft rejection. In some embodiments, methods and uses of the provided immunomodulatory proteins include treatment of such autoimmune diseases as insulin dependent diabetes mellitus (IDDM) and Crohn's Disease. Methods provided herein would have additional therapeutic value for treating chronic inflammatory diseases, in particular to lessen joint pain, swelling, anemia and other associated symptoms as well as treating septic shock.

In some embodiments, the inflammatory and autoimmune disorders that can be treated by a pharmaceutical composition containing an immunomodulatory protein described herein include, but are not limited to, Achalasia; Addison's disease; Adult Still's disease; Agammaglobulinemia; Alopecia areata; Amyloidosis; Ankylosing spondylitis; Anti-GBM/Anti-TBM nephritis; Antiphospholipid syndrome; Autoimmune adrenalitis (Addison's disease); Autoimmune angioedema; Autoimmune dysautonomia; Autoimmune encephalomyelitis; Autoimmune hepatitis; Autoimmune inner ear disease (AIED); Autoimmune myocarditis; Autoimmune oophoritis; Autoimmune orchitis; Autoimmune pancreatitis; Autoimmune polyglandular syndrome type II (APS II); Autoimmune retinopathy; Autoimmune thyroid disease (AITD), i.e. Hashimoto's disease; Autoimmune urticarial; Axonal & neuronal neuropathy (AMAN); Baló disease; Behcet's disease; Benign mucosal pemphigoid; Bullous pemphigoid; Castleman disease (CD); Celiac disease; Chagas disease; Chronic inflammatory demyelinating polyneuropathy (CIDP); Chronic recurrent multifocal osteomyelitis (CRMO); Churg-Strauss Syndrome (CSS) or Eosinophilic Granulomatosis (EGPA); Cicatricial pemphigoid; Cogan's syndrome; Cold agglutinin disease; Congenital heart block; Coxsackie myocarditis; CREST syndrome; Crohn's disease; Dermatitis herpetiformis; Dermatomyositis; Devic's disease (neuromyelitis optica); Discoid lupus; Dressler's syndrome; Endometriosis; Eosinophilic esophagitis (EoE); Eosinophilic fasciitis; Erythema nodosum; Essential mixed cryoglobulinemia; Evans syndrome; Fibromyalgia; Fibrosing alveolitis; Giant cell arteritis (temporal arteritis); Giant cell myocarditis; Glomerulonephritis; Goodpasture's syndrome; Granulomatosis with Polyangiitis; Graves' disease; Guillain-Barre syndrome; Hashimoto's thyroiditis; Hemolytic anemia; Henoch-Schonlein purpura (HSP); Herpes gestationis or pemphigoid gestationis (PG); Hidradenitis Suppurativa (HS) (Acne Inversa); Hypogammalglobulinemia; IgA Nephropathy; IgA Vasculitis; IgG4-related sclerosing disease; Immune thrombocytopenic purpura (ITP); Inclusion body myositis (IBM); Interstitial cystitis (IC); Juvenile arthritis; Juvenile diabetes (Type 1 diabetes); Juvenile myositis (JM); Kawasaki disease; Lambert-Eaton syndrome; Leukocytoclastic vasculitis; Lichen planus; Lichen sclerosus; Ligneous conjunctivitis; Linear IgA disease (LAD); Lupus; Lyme disease chronic; Meniere's disease; Microscopic polyangiitis (MPA); Mixed connective tissue disease (MCTD); Mooren's ulcer; Mucha-Habermann disease; Multifocal Motor Neuropathy (MMN) or MMNCB; Multiple sclerosis; Myasthenia gravis; Myositis; Narcolepsy; Neonatal Lupus; Neuromyelitis optica; Neutropenia; Ocular cicatricial pemphigoid; Optic neuritis; Palindromic rheumatism (PR); PANDAS; Paraneoplastic cerebellar degeneration (PCD); Paroxysmal nocturnal hemoglobinuria (PNH); Parry Romberg syndrome; Pars planitis (peripheral uveitis); Parsonage-Turner syndrome; Pemphigus, Pemphigus vulgaris; Peripheral neuropathy; Perivenous encephalomyelitis; Pernicious anemia (PA); POEMS syndrome; Polyarteritis nodosa; Polyglandular syndromes type I, II, III; Polymyalgia rheumatic; Polymyositis; Postmyocardial infarction syndrome; Postpericardiotomy syndrome; Primary biliary cirrhosis; Primary sclerosing cholangitis; Progesterone dermatitis; Psoriasis; Psoriatic arthritis; Pure red cell aplasia (PRCA); Pyoderma gangrenosum; Raynaud's phenomenon; Reactive Arthritis; Reflex sympathetic dystrophy; Relapsing polychondritis; Restless legs syndrome (RLS); Retroperitoneal fibrosis; Rheumatic fever; Rheumatoid arthritis; Sarcoidosis; Schmidt syndrome; Scleritis; Scleroderma; Sjögren's syndrome; Sperm & testicular autoimmunity; Stiff person syndrome (SPS); Subacute bacterial endocarditis (SBE); Susac's syndrome; Sympathetic ophthalmia (SO); Takayasu's arteritis; Temporal arteritis/Giant cell arteritis; Thrombocytopenic purpura (TTP); Tolosa-Hunt syndrome (THS); Transverse myelitis; Type 1 diabetes; Ulcerative colitis (UC); Undifferentiated connective tissue disease (UCTD); Uveitis; Vasculitis; Vitiligo or Vogt-Koyanagi-Harada Disease.

In some embodiments, the provided immunomodulatory proteins (e.g. TACI-Fc) can be used to treat Scleroderma, Myasthenia gravis, GVHD (including acute GVHD or chronic GVHD), an immune response in connection with transplantation; Antiphospholipid Ab syndrome; Multiple sclerosis; Sjogren's syndrome; IgG4-related disease; Type I diabetes; Rheumatoid arthritis including glucocorticoid therapy (GC) RA or Acute lupus nephritis.

In some embodiments, the provided immunomodulatory proteins (e.g. TACI-Fc) can be used to treat Amyotrophic lateral sclerosis, Neuromyelitis optica, Transverse myelitis, CNS autoimmunity, Guillain-barre syndrome, Neurocystercercosis, Sarcoidosis (T/seroneg), Churg-Strauss Syndrome, Hashimoto's thyroiditis, Grave's disease, immune thrombocytopenia (ITP), Addison's Disease, Polymyositis, or Dermatomyositis.

In some embodiments, the provided immunomodulatory proteins (e.g. TACI-Fc) can be used to treat IgA nephropathy, chronic inflammatory demyelinating polyneuropathy (CIDP), antisynthetase disease such as Jo-1 syndrome, or ANCA vasculitis.

In some embodiments, the provided immunomodulatory proteins (e.g. TACI-Fc) can be used to treat a B cell cancer. In some embodiments, the B cell cancer is a cancer in which BAFF and APRIL are involved or implicated in providing an autocrine survival loop to the B cells. In some embodiments, the cancer is B cell chronic lymphocytic leukemia, non-Hodgkins' lymphoma or myeloma. In some embodiments, the cancer is myeloma.

In some embodiments, a therapeutic amount of the pharmaceutical composition is administered. Typically, precise amount of the compositions of the present invention to be administered can be determined by a physician with consideration of individual differences in age, weight, extent of infection, and condition of the patient (subject). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the therapeutic composition is administered to a patient by intradermal or subcutaneous injection. In another embodiment, the therapeutic composition is administered by i.v. injection.

In some embodiments, the pharmaceutical composition is administered as a monotherapy (i.e., as a single agent) or as a combination therapy (i.e., in combination with one or more additional immunosuppressant agents). In some embodiments, the additional agent is a glucocorticoid (e.g., prednisone, dexamethasone, and hydrocortisone), cytostatic agent, such as a cytostatic agent that affect proliferation of T cells and/or B cells (e.g., purine analogs, alkylating agents, or antimetabolites), an antibody (e.g., anti-CD20, anti-CD25 or anti-CD3 monoclonal antibodies), cyclosporine, tacrolimus, sirolimus, everolimus, an interferon, an opioid, a TNF binding protein, mycophenolate, small biological agent, such as fingolimod or myriocin, cytokine, such as interferon beta-1a, an integrin agonist, or an integrin antagonist.

VII. Articles of Manufacture and Kits

Also provided herein are articles of manufacture that comprise the pharmaceutical compositions described herein in suitable packaging. Suitable packaging for compositions (such as ophthalmic compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

Further provided are kits comprising the pharmaceutical compositions (or articles of manufacture) described herein, which may further comprise instruction(s) on methods of using the composition, such as uses described herein. The kits described herein may also include other materials desirable from a commercial and user standpoint, including other buffers, diluents, filters, needles, syringes, and package inserts with instructions for performing any methods described herein.

VIII. EXEMPLARY EMBODIMENTS

Among the provided embodiments are:

1. An immunomodulatory protein comprising at least one TACI polypeptide that is a truncated wild-type TACI extracellular domain or is a variant thereof, wherein the truncated wild-type TACI extracellular domain contains the cysteine rich domain 2 (CRD2) but lacks the entirety of the cysteine rich domain 1 (CRD1), wherein the variant TACI polypeptide comprises one or more amino acid substitutions in the truncated wild-type TACI extracellular domain.

2. An immunomodulatory protein comprising at least one TACI polypeptide that is a truncated wild-type TACI extracellular domain or is a variant thereof, wherein the truncated wild-type TACI extracellular domain consists of a contiguous sequence contained within amino acid residues 67-118 that consists of amino acid residues 71-104, with reference to positions set forth in SEQ ID NO:122, wherein the variant TACI polypeptide comprises one or more amino acid substitutions in the truncated wild-type TACI extracellular domain.

3. The immunomodulatory protein of embodiment 1 or embodiment 2, wherein the truncated wild-type TACI extracellular domain is 35, 36, 37, 38, 39, 40, 41, 42, 43, 44, 45, 46, 47, 48, 59, 50 or 51 amino acids in length.

4. The immunomodulatory protein of any of embodiments 1-3, wherein the truncated wild-type TACI extracellular domain consists of amino acid residues 68-110 set forth in SEQ ID NO: 122.

5. The immunomodulatory protein of any of embodiments 1-4, wherein the TACI polypeptide consists of the sequence of amino acid set forth in SEQ ID NO:13 or is a variant thereof containing one or more amino acid substitutions in the sequence set forth in SEQ ID NO:13.

6. An immunomodulatory protein comprising at least one TACI polypeptide that is a truncated TACI polypeptide consisting of the sequence of amino acid set forth in SEQ ID NO:13 or a variant thereof containing one or more amino acid substitutions in the sequence set forth in SEQ ID NO:13.

7. The immunomodulatory protein of any of embodiments 1-5, wherein the truncated TACI polypeptide or the variant thereof binds to APRIL, BAFF, or a BAFF/APRIL heterotrimer.

8. The immunomodulatory protein of any of embodiments 1-7, wherein the TACI polypeptide is a truncated wild-type TACI extracellular domain that consists of the sequence set forth in SEQ ID NO: 1.

9. The immunomodulatory protein of any of embodiments 1-7, wherein the TACI polypeptide is a truncated wild-type TACI extracellular domain that consists of the sequence set forth in SEQ ID NO:13.

10. An immunomodulatory protein comprising a truncated TACI polypeptide consisting of the sequence set forth in SEQ ID NO:13.

11. The immunomodulatory protein of any of embodiments 1-7, wherein the TACI polypeptide is the variant TACI polypeptide, wherein the variant TACI polypeptide has increased binding affinity to one or both of APRIL and BAFF compared to the truncated TACI polypeptide.

12. The immunomodulatory protein of any of embodiments 1-7 and 11, wherein the variant TACI polypeptide comprises one or more amino acid substitutions at positions selected from among 74, 75, 76, 77, 78, 79, 82, 83, 84, 85, 86, 87, 88, 92, 95, 97, 98, 99, 101, 102 and 103, corresponding to numbering set forth in SEQ ID NO:122.

13. The immunomodulatory protein of embodiment 12, wherein the one or more amino acid substitutions are selected from E74V, Q75E, Q75R, G76S, K77E, F78Y, Y79F, L82H, L82P, L83S, R84G, R84L, R84Q, D85E, D85V, C86Y, I87L, I87M, S88N, I92V, Q95R, P97S, K98T, Q99E, A101D, Y102D, F103S, F103V, F103Y, or a conservative amino acid substitution thereof.

14. The immunomodulatory protein of embodiment 12 or embodiment 13, wherein the one or more amino acid substitutions comprise at least one of E74V, K77E, Y79F, L82H, L82P, R84G, R84L, R84Q, D85V, or C86Y.

15. The immunomodulatory protein of any of embodiments 12-13, wherein the one or more amino acid substitutions are D85E/K98T, I87L/K98T, L82P/I87L, G76S/P97S, K77E/R84L/F103Y, Y79F/Q99E, L83S/F103S, K77E/R84Q, K77E/A101D, K77E/F78Y/Y102D, Q75E/R84Q, Q75R/R84G/I92V, K77E/A101D/Y102D, R84Q/S88N/A101D, R84Q/F103V, K77E/Q95R/A101D or I87M/A101D.

16. The immunomodulatory protein of any of embodiments 12-15, wherein the one or more amino acid substitutions are K77E/F78Y/Y102D.

17. The immunomodulatory protein of any of embodiments 12-15, wherein the one or more amino acid substitutions are Q75E/R84Q.

18. The immunomodulatory protein of any of embodiments 12-16, wherein the variant TACI polypeptide is set forth in SEQ ID NO: 26.

19. The immunomodulatory protein of any of embodiments 12-15 and 17, wherein the variant TACI polypeptide is set forth in SEQ ID NO:27.

20. The immunomodulatory protein of embodiment 1, wherein the TACI polypeptide is a variant TACI polypeptide that comprises one or more amino acid substitutions in the extracellular domain (ECD) of a reference TACI polypeptide or a specific binding fragment thereof at positions selected from among 40, 59, 60, 61, 74, 75, 76, 77, 78, 79, 82, 83, 84, 85, 86, 87, 88, 92, 95, 97, 98, 99, 101, 102 and 103, corresponding to numbering of positions set forth in SEQ ID NO:122.

21. An immunomodulatory protein comprising at least one variant TACI polypeptide, wherein the at least one variant TACI polypeptide comprises one or more amino acid substitutions in the extracellular domain (ECD) of a reference TACI polypeptide or a specific binding fragment thereof at positions selected from among 40, 59, 60, 61, 74, 75, 76, 77, 78, 79, 82, 83, 84, 85, 86, 87, 88, 92, 95, 97, 98, 99, 101, 102 and 103, corresponding to numbering of positions set forth in SEQ ID NO:122.

22. The immunomodulatory protein of embodiment 20 or embodiment 21, wherein the reference TACI polypeptide is a truncated polypeptide consisting of the extracellular domain of TACI or a specific binding portion thereof that binds to APRIL, BAFF, or a BAFF/APRIL heterotrimer.

23. The immunomodulatory protein of any of embodiments 20-22, wherein the reference TACI polypeptide comprises (i) the sequence of amino acids set forth in SEQ ID NO:122, (ii) a sequence of amino acids that has at least 95% sequence identity to SEQ ID NO:122; or (iii) a portion of (i) or (ii) comprising one or both of a CRD1 domain and CRD2 domain that binds to APRIL, BAFF, or a BAFF/APRIL heterotrimer.

24. The immunomodulatory protein of any of embodiments 20-23, wherein the reference TACI polypeptide lacks an N-terminal methionine.

25. The immunomodulatory protein of any of embodiments 20-24, wherein the reference TACI polypeptide comprises the CRD1 domain and the CRD2 domain.

26. The immunomodulatory protein of any of embodiments 20-25, wherein the reference TACI polypeptide comprises the sequence set forth in SEQ ID NO:1.

27. The immunomodulatory protein of any of embodiments 20-25, wherein the reference TACI polypeptide consists of the sequence set forth in SEQ ID NO:1.

28. The immunomodulatory protein of any of embodiments 20-24, wherein the reference TACI polypeptide consists essentially of the CRD2 domain.

29. The immunomodulatory protein of any of embodiments 20-24 and 28, wherein the reference TACI polypeptide comprises the sequence set forth in SEQ ID NO:13.

30. The immunomodulatory protein of any of embodiments 20-24 and 28, wherein the reference TACI polypeptide consists of the sequence set forth in SEQ ID NO:13.

31. The immunomodulatory protein of any of embodiments 20-30, wherein the one or more amino acid substitutions are selected from W40R, Q59R, R60G, T61P E74V, Q75E, Q75R, G76S, K77E, F78Y, Y79F, L82H, L82P, L83S, R84G, R84L, R84Q, D85E, D85V, C86Y, I87L, I87M, S88N, I92V, Q95R, P97S, K98T, Q99E, A101D, Y102D, F103S, F103V, F103Y, or a conservative amino acid substitution thereof.

32. The immunomodulatory protein of any of embodiments 20-31, wherein the one or more amino acid substitutions comprise at least one of E74V, K77E, Y79F, L82H, L82P, R84G, R84L, R84Q, D85V or C86Y.

33. The immunomodulatory protein of any of embodiments 20-32, wherein the one or more amino acid substitution comprise at least the amino acid substitution K77E.

34. The immunomodulatory protein of any of embodiments 20-32, wherein the one or more amino acid substitution comprise at least the amino acid substitution R84G.

35. The immunomodulatory protein of any of embodiments 20-32, wherein the one or more amino acid substitution comprise at least the amino acid substitution R84Q.

36. The immunomodulatory protein of any of embodiments 20-35, wherein the one or more amino acid substitutions are D85E/K98T, I87L/K98T, R60G/Q75E/L82P, R60G/C86Y, W40R/L82P/F103Y, W40R/Q59R/T61P/K98T, L82P/I87L, G76S/P97S, K77E/R84L/F103Y, Y79F/Q99E, L83S/F103S, K77E/R84Q, K77E/A101D, K77E/F78Y/Y102D, Q75E/R84Q, Q75R/R84G/I92V, K77E/A101D/Y102D, R84Q/S88N/A101D, R84Q/F103V, K77E/Q95R/A101D or I87M/A101D.

37. The immunomodulatory protein of any of embodiments 20-32, 33 and 36, wherein the one or more amino acid substitutions are K77E/F78Y/Y102D.

38. The immunomodulatory protein of any of embodiments 20-32, 35 and 36, wherein the one or more amino acid substitutions are Q75E/R84Q.

39. The immunomodulatory protein of any of embodiments 20-38, wherein the variant TACI polypeptide has increased binding affinity to one or both of APRIL and BAFF compared to the reference TACI polypeptide.

40. The immunomodulatory protein of embodiment 11 or embodiment 39, wherein the variant TACI polypeptide has increased binding affinity to APRIL.

41. The immunomodulatory protein of embodiment 11 or embodiment 39, wherein the variant TACI polypeptide has increased binding affinity to BAFF.

42. The immunomodulatory protein of embodiment 11 or embodiment 39, wherein the variant TACI polypeptide has increased binding affinity to APRIL and BAFF.

43. The immunomodulatory protein of any of embodiments 11, and 39-42, wherein the increased binding affinity for BAFF or APRIL is independently increased more than 1.2-fold, 1.5-fold, 2-fold, 3-fold, 4-fold, 5-fold, 6-fold, 7-fold, 8-fold, 9-fold, 10-fold, 20-fold, 30-fold, 40-fold, 50-fold or 60-fold.

44. The immunomodulatory protein of any of embodiments 1-7 and 11-43, wherein: the variant TACI polypeptide comprises the sequence set forth in any one of SEQ ID NOS: 2-12, 21, 22, 101-120; or the variant TACI polypeptide comprises the sequence set forth in any one of SEQ ID NOS: 14-20, 23-35, 92-100.

45. The immunomodulatory protein of any of embodiments 1-7 and 11-43, wherein: the variant TACI polypeptide consists or consists essentially of the sequence set forth in any one of SEQ ID NOS: 2-12, 21, 22, 101-120; or the variant TACI polypeptide consists or consists essentially of the sequence set forth in any one of SEQ ID NOS: 14-20, 23-35, 92-100.

46. The immunomodulatory protein of any of embodiments 1-7, 11-43 and 45, wherein the variant TACI polypeptide consists or consists essentially of the sequence set forth in SEQ ID NO: 26

47. The immunomodulatory protein of any of embodiments 1-7, 11-43 and 45, wherein the variant TACI polypeptide consists or consists essentially of the sequence set forth in SEQ ID NO:27.

48. The immunomodulatory protein of any of embodiments 1-7, 11-43 and 45, wherein the variant TACI polypeptide consists or consists essentially of the sequence set forth in SEQ ID NO:107.

49. The immunomodulatory protein of any of embodiments 1-7, 11-43 and 45, wherein the variant TACI polypeptide consists or consists essentially of the sequence set forth in SEQ ID NO:20.

50. The immunomodulatory protein of any of embodiments 1-7 and 11-49, comprising a heterologous moiety that is linked to the at least one TACI polypeptide.

51. The immunomodulatory protein of embodiment 50, wherein the heterologous moiety is a half-life extending moiety, a multimerization domain, a targeting moiety that binds to a molecule on the surface of a cell, or a detectable label.

52. The immunomodulatory protein of embodiment 51, wherein the half-life extending moiety comprises a multimerization domain, albumin, an albumin-binding polypeptide, Pro/Ala/Ser (PAS), a C-terminal peptide (CTP) of the beta subunit of human chorionic gonadotropin, polyethylene glycol (PEG), long unstructured hydrophilic sequences of amino acids (XTEN), hydroxyethyl starch (HES), an albumin-binding small molecule, or a combination thereof.

53. The immunomodulatory protein of any of embodiments 1-7 and 11-52, that is a TACI-Fc fusion protein, wherein the at least one TACI polypeptide is linked to an Fc region of an immunoglobulin.

54. The immunomodulatory protein of any of embodiments, 3-5, 7-9, 11-20, and 22-53, wherein the immunomodulatory protein is a dimer.

55. The immunomodulatory protein of embodiment 53, wherein the immunoglobulin Fc region is a homodimeric Fc region.

56. The immunomodulatory protein of embodiment 53, wherein the immunoglobulin Fc region is a heterodimeric Fc region 57. The immunomodulatory protein of embodiment, 3-5, 7-9, 11-20, 22-53, and 54-55, wherein the immunomodulatory protein is a homodimer, wherein each polypeptide of the dimer is the same.

58. The immunomodulatory protein of any of embodiments 53, 54-55, and 57, wherein the immunoglobulin Fc is an IgG1 Fc domain, or is a variant Fc that exhibits reduced binding affinity to an Fc receptor and/or reduced effector function, optionally as compared to a wild-type IgG1 Fc domain.

59. The immunomodulatory protein of any of embodiments 53, 54-55, and 57-58, wherein the immunoglobulin Fc is an IgG1 Fc domain and the Fc comprises the amino acid sequence set forth in SEQ ID NO: 81.

60. The immunomodulatory protein of any of embodiments 53, 54-55, and 57-58, wherein the immunoglobulin Fc is a variant IgG1 Fc domain comprising one or more amino acid substitutions selected from L234A, L234V, L235A, L235E, G237A, S267K, R292C, N297G, and V302C, by EU numbering.

61. The immunomodulatory protein of embodiment 60, wherein the immunoglobulin Fc region contains the amino acid substitutions L234A, L235E an G237A by EU numbering or the amino acid substitutions R292C, N297G and V302C by EU numbering.

62. The immunomodulatory protein of any of embodiments 53, 54-55, 57-58 and 60-61, wherein the Fc is a variant Fc comprising the amino acid sequence set forth in SEQ ID NO:73.

63. The immunomodulatory protein of any of embodiments 1-62, wherein:
the immunomodulatory protein blocks binding of APRIL, BAFF, or an APRIL/BAFF heterotrimer to BCMA or TACI; and/or
the immunomodulatory protein reduces the levels of circulating APRIL, BAFF, or an APRIL/BAFF in the blood following administration to a subject.

64. The immunomodulatory protein of any of embodiments 1-62, wherein the immunomodulatory protein reduces or inhibits B cell maturation, differentiation and/or proliferation.

65. A nucleic acid molecule(s) encoding the immunomodulatory protein of any of embodiments 1-64.

66. The nucleic acid molecule of embodiment 65 that is a synthetic nucleic acid.

67. The nucleic acid molecule of embodiment 65 or embodiment 66 that is a cDNA.

68. A vector, comprising the nucleic acid molecule of any of embodiments 65-67.

69. The vector of embodiment 68 that is an expression vector.

70. The vector of embodiment 68 or embodiment 69, wherein the vector is a mammalian expression vector or a viral vector.

71. A cell, comprising the nucleic acid of any of embodiments 65-67 or the vector of any of any of embodiments 68-70.

72. The cell of embodiment 71 that is a mammalian cell.

73. The cell of embodiment 71 or embodiment 72 that is a human cell.

74. A method of producing an immunomodulatory protein, comprising introducing the nucleic acid molecule of any of embodiments 65-67 or vector of any of embodiments 68-70 into a host cell under conditions to express the protein in the cell.

75. The method of embodiment 74, further comprising isolating or purifying the immunomodulatory protein from the cell.

76. An immunomodulatory protein produced by the method of embodiment 74 or embodiment 75.

77. A pharmaceutical composition, comprising the immunomodulatory protein of any of embodiments 1-64 and 76.

78. A variant TACI-Fc fusion protein comprising a variant TACI polypeptide, an Fc region, and a linker between the TACI polypeptide and Fc region, wherein the variant TACI polypeptide comprises one or more amino acid substitutions in the extracellular domain (ECD) of a reference TACI polypeptide or a specific binding fragment thereof at positions selected from among 40, 59, 60, 61, 74, 75, 76, 77, 78, 79, 82, 83, 84, 85, 86, 87, 88, 92, 95, 97, 98, 99, 101, 102 and 103, corresponding to numbering of positions set forth in SEQ ID NO:122.

79. The variant TACI-Fc fusion protein of embodiment 78, wherein the reference TACI polypeptide is a truncated polypeptide consisting of the extracellular domain of TACI or a specific binding portion thereof that binds to APRIL, BAFF, or a BAFF/APRIL heterotrimer.

80. The variant TACI-Fc fusion protein of embodiment 78 or embodiment 79, wherein the reference TACI polypeptide comprises (i) the sequence of amino acids set forth in SEQ ID NO:122, (ii) a sequence of amino acids that has at least 95% sequence identity to SEQ ID NO:122; or (iii) a portion of (i) or (ii) comprising one or both of a CRD1 domain and CRD2 domain that binds to APRIL, BAFF, or a BAFF/APRIL heterotrimer.

81. The variant TACI-Fc fusion protein of any of embodiments 78-80, wherein the reference TACI polypeptide lacks an N-terminal methionine.

82. The variant TACI-Fc fusion protein of any of embodiments 78-81, wherein the reference TACI polypeptide comprises the CRD1 domain and the CRD2 domain.

83. The variant TACI-Fc fusion protein of any of embodiments 78-82, wherein the reference TACI polypeptide comprises the sequence set forth in SEQ ID NO:1.

84. The variant TACI-Fc fusion protein of any of embodiments 78-82, wherein the reference TACI polypeptide consists of the sequence set forth in SEQ ID NO:1.

85. The variant TACI-Fc fusion protein of any of embodiments 78-81, wherein the reference TACI polypeptide consists essentially of the CRD2 domain.

86. The variant TACI-Fc fusion protein of any of embodiments 78-81 and 85, wherein the reference TACI polypeptide comprises the sequence set forth in SEQ ID NO:13.

87. The variant TACI-Fc fusion protein of any of embodiments 78-81 and 85, wherein the reference TACI polypeptide consists of the sequence set forth in SEQ ID NO:13.

88. The variant TACI-Fc fusion protein of any of embodiments 78-87, wherein the one or more amino acid substitutions are selected from W40R, Q59R, R60G, T61P E74V, Q75E, Q75R, G76S, K77E, F78Y, Y79F, L82H, L82P, L83S, R84G, R84L, R84Q, D85E, D85V, C86Y, I87L, I87M, S88N, I92V, Q95R, P97S, K98T, Q99E, A101D, Y102D, F103S, F103V, F103Y, or a conservative amino acid substitution thereof.

89. The variant TACI-Fc fusion protein of any of embodiments 78-88, wherein the one or more amino acid substitutions comprise at least one of E74V, K77E, Y79F, L82H, L82P, R84G, R84L, R84Q, D85V or C86Y.

90. The variant TACI-Fc fusion protein of any of embodiments 78-89, wherein the one or more amino acid substitution comprise at least the amino acid substitution K77E.

91. The variant TACI-Fc fusion protein of any of embodiments 78-89, wherein the one or more amino acid substitution comprise at least the amino acid substitution R84G.

92. The variant TACI-Fc fusion protein of any of embodiments 78-92, wherein the one or more amino acid substitution comprise at least the amino acid substitution R84Q.

93. The variant TACI-Fc fusion protein of any of embodiments 78-92, wherein the one or more amino acid substitutions are D85E/K98T, I87L/K98T, R60G/Q75E/L82P, R60G/C86Y, W40R/L82P/F103Y, W40R/Q59R/T61P/K98T, L82P/I87L, G76S/P97S, K77E/R84L/F103Y, Y79F/Q99E, L83S/F103S, K77E/R84Q, K77E/A101D, K77E/F78Y/Y102D, Q75E/R84Q, Q75R/R84G/I92V, K77E/A101D/Y102D, R84Q/S88N/A101D, R84Q/F103V, K77E/Q95R/A101D or I87M/A101D.

94. The variant TACI-Fc fusion protein of any of embodiments 78-90 and 93, wherein the one or more amino acid substitutions are K77E/F78Y/Y102D.

95. The variant TACI-Fc fusion protein of any of embodiments 78-90, 92 and 93, wherein the one or more amino acid substitutions are Q75E/R84Q.

96. The variant TACI-Fc fusion protein of any of embodiments 78-95, wherein the variant TACI polypeptide has increased binding affinity to one or both of APRIL and BAFF compared to the reference TACI polypeptide.

97. The variant TACI-Fc fusion protein of any of embodiments 78-96, wherein the variant TACI polypeptide has increased binding affinity to APRIL.

98. The variant TACI-Fc fusion protein of any of embodiments 78-96, wherein the variant TACI polypeptide has increased binding affinity to BAFF.

99. The variant TACI-Fc fusion protein of any of embodiments 78-96, wherein the variant TACI polypeptide has increased binding affinity to APRIL and BAFF.

100. The variant TACI-Fc fusion protein of any of embodiments 96-99, wherein the increased binding affinity for BAFF or APRIL is independently increased more than 1.2-fold, 1.5-fold, 2-fold, 3-fold, 4-fold, 5-fold, 6-fold, 7-fold, 8-fold, 9-fold, 10-fold, 20-fold, 30-fold, 40-fold, 50-fold or 60-fold.

101. The variant TACI-Fc fusion protein of any of embodiments 96-100, wherein: the variant TACI polypeptide comprises the sequence set forth in any one of SEQ ID NOS: 2-12, 21, 22, 101-120; or the variant TACI polypeptide comprises the sequence set forth in any one of SEQ ID NOS: 14-20, 23-35, 92-100.

102. The variant TACI-Fc fusion protein of any of embodiments 96-100, wherein: the variant TACI polypeptide consists or consists essentially of the sequence set forth in any one of SEQ ID NOS: 2-12, 21, 22, 101-120; or the variant TACI polypeptide consists or consists essentially of the sequence set forth in any one of SEQ ID NOS: 14-20, 23-35, 92-100.

103. The variant TACI-Fc fusion protein of any of embodiments 96-100, wherein the variant TACI polypeptide consists or consists essentially of the sequence set forth in SEQ ID NO: 26

104. The variant TACI-Fc fusion protein of any of embodiments 96-100, wherein the variant TACI polypeptide consists or consists essentially of the sequence set forth in SEQ ID NO:27.

105. The variant TACI-Fc fusion protein of any of embodiments 96-100, wherein the variant TACI polypeptide consists or consists essentially of the sequence set forth in SEQ ID NO:107.

106. The variant TACI-Fc fusion protein of any of embodiments 96-100, wherein the variant TACI polypeptide consists or consists essentially of the sequence set forth in SEQ ID NO:20.

107. The Fc fusion protein of any of embodiments 78-106, wherein the linker comprises a peptide linker and the peptide linker is selected from GSGGS (SEQ ID NO: 76), GGGGS (G45; SEQ ID NO: 77), GSGGGGS (SEQ ID NO: 74), GGGGSGGGGS (2×GGGGS; SEQ ID NO: 78), GGGGSGGGGSGGGGS (3×GGGGS; SEQ ID NO: 79), GGGGSGGGGSGGGGSGGGGS (4×GGGGS, SEQ ID NO:84), GGGGSGGGGSGGGGSGGGGSGGGGS (5×GGGGS, SEQ ID NO: 91), GGGGSSA (SEQ ID NO: 80) or combinations thereof.

108. The Fc fusion protein of any of embodiments 78-107 that is a dimer.

109. The Fc fusion protein of any of embodiments 78-108, wherein the immunoglobulin Fc region is a homodimeric Fc region.

110. The Fc fusion protein of any of embodiments 78-109, wherein the immunoglobulin Fc is an IgG1 Fc domain, or is a variant Fc that exhibits reduced binding affinity to an Fc receptor and/or reduced effector function, optionally as compared to a wild-type IgG1 Fc domain.

111. The Fc fusion protein of any of embodiments 78-110, wherein the immunoglobulin Fc is an IgG1 Fc domain and the Fc comprises the amino acid sequence set forth in SEQ ID NO: 81.

112. The Fc fusion protein of any of embodiments 78-106 and 107-111, wherein the TACI-Fc fusion protein is set forth in SEQ ID NO: 168.

113. The Fc fusion protein of any of embodiments 78-106 and 107-111, wherein the TACI-Fc fusion protein is set forth in SEQ ID NO:170.

114. The Fc fusion protein of any of embodiments 78-110, wherein the immunoglobulin Fc is a variant IgG1 Fc domain comprising one or more amino acid substitutions selected from L234A, L234V, L235A, L235E, G237A, S267K, R292C, N297G, and V302C, by EU numbering.

115. The Fc fusion protein of embodiment 114, wherein the immunoglobulin Fc region contains the amino acid substitutions L234A, L235E an G237A by EU numbering or the amino acid substitutions R292C, N297G and V302C by EU numbering.

116. The Fc fusion protein of any of embodiments 78-115, wherein the immunoglobulin Fc is set forth in SEQ ID NO:71.

117. The Fc fusion protein of any of embodiments 78-113 and 114-116, wherein the Fc is a variant Fc comprising the amino acid sequence set forth in SEQ ID NO:73.

118. The Fc fusion protein of any of embodiments 78-106, 107-110, 114, 115 and 117, wherein the TACI-Fc fusion protein is set forth in SEQ ID NO: 167.

119. The Fc fusion protein of any of embodiments 78-106, 107-110, 114, 115 and 117, wherein the TACI-Fc fusion protein is set forth in SEQ ID NO:169.

120. The Fc fusion protein of any of embodiments 78-119 that is a dimer.

121. The Fc fusion protein of any of embodiments 78-120 that is a homodimer.

122. The Fc fusion protein of any of embodiments 78-121, wherein the Fc fusion protein neutralizes APRIL and BAFF.

123. The Fc fusion protein of embodiment 122, wherein:
the IC50 for neutralizing APRIL is less than 100 pM, less than 50 pM, less than 40 pM, less than 30 pM, less than 20 pM, less than 10 pM, less than 5 pM or less than 1 pM, or is any value between any of the foregoing; and/or
the IC50 for neutralizing BAFF is less than 400 pM, less than 300 pM, less than 200 pM, less than 100 pM, less than 75 pM, less than 50 pM, less than 25 pm, or less than 10 pM, or is any value between any of the foregoing.

124. The Fc fusion protein of any of embodiments 78-122, wherein:
the Fc fusion protein blocks binding of APRIL, BAFF, or an APRIL/BAFF heterotrimer to BCMA or TACI; and/or
the Fc fusion protein reduces the levels of circulating APRIL, BAFF, or an APRIL/BAFF in the blood following administration to a subject.

125. The Fc fusion protein of any of embodiments 78-124, wherein the immunomodulatory protein reduces or inhibits B cell maturation, differentiation and/or proliferation.

126. A nucleic acid molecule(s) encoding the Fc fusion protein of any of embodiments 78-125.

127. The nucleic acid molecule of embodiment 126 that is a synthetic nucleic acid.

128. The nucleic acid molecule of embodiment 126 or embodiment 127 that is a cDNA.

129. A vector, comprising the nucleic acid molecule of any of embodiments 126-128.

130. The vector of embodiment 129 that is an expression vector.

131. The vector of embodiment 129 or embodiment 130, wherein the vector is a mammalian expression vector or a viral vector.

132. A cell, comprising the nucleic acid of any of embodiments 126-128 or the vector of any of any of embodiments 129-131.

133. The cell of embodiment 132 that is a mammalian cell.

134. The cell of embodiment 132 or embodiment 133 that is a human cell.

135. A method of producing an Fc fusion protein, comprising introducing the nucleic acid molecule of any of embodiments 126-128 or vector of any of embodiments 129-131 into a host cell under conditions to express the protein in the cell.

136. The method of embodiment 135, further comprising isolating or purifying the Fc fusion protein from the cell.

137. An Fc fusion protein produced by the method of embodiment 135 or embodiment 136.

138. A pharmaceutical composition, comprising the Fc fusion protein of any of embodiments 78-125 and 137.

139. The pharmaceutical composition of embodiment 77 or embodiment 138, comprising a pharmaceutically acceptable excipient.

140. The pharmaceutical composition of any of embodiments 77, 138 and 139, wherein the pharmaceutical composition is sterile.

141. An article of manufacture comprising the pharmaceutical composition of any of embodiments 77 and 138-140 in a vial or container.

142. The article of manufacture of embodiment 141, wherein the vial or container is sealed.

143. A kit comprising the pharmaceutical composition of any of embodiments 77 and 138-140, and instructions for use.

144. A kit comprising the article of manufacture of embodiment 141 or embodiment 142, and instructions for use.

145. A method of reducing an immune response in a subject, comprising administering the immunomodulatory protein of any of embodiments 1-64 or 76 to a subject in need thereof.

146. A method of reducing an immune response in a subject, comprising administering the Fc fusion protein of any of embodiments 78-126 and 137 to a subject in need thereof.

147. A method of reducing an immune response in a subject, comprising administering the pharmaceutical composition of any of embodiments 77 and 137-140 to a subject in need thereof.

148. The method of any of embodiments 145-147, wherein a B cell immune response is reduced in the subject, whereby B cell maturation, differentiation and/or proliferation is reduced or inhibited.

149. The method of any of embodiments 145-148, wherein circulating levels of APRIL, BAFF or an APRIL/BAFF heterotrimer are reduced in the subject.

150. A method of reducing circulating levels of APRIL, BAFF or an APRIL/BAFF heterotrimer in a subject comprising administering the pharmaceutical composition of any of embodiments 77 and 137-140 to the subject.

151. The method of embodiment 57 or embodiment 147, wherein a T cell immune response is reduced in the subject, whereby T cell costimulation is reduced or inhibited.

152. The method of any of embodiments 145-151, wherein reducing the immune response treats a disease or condition in the subject.

153. A method of treating a disease or condition in a subject, comprising administering the immunomodulatory protein of any of embodiments 1-64 or 76 to a subject in need thereof.

154. A method of treating a disease or condition in a subject, comprising administering the Fc fusion protein of any of claims 78-115 and 121 to a subject in need thereof.

155. A method of treating a disease or condition in a subject, comprising administering the pharmaceutical composition of any of embodiments 77 and 137-140 to a subject in need thereof.

156. The method of any of embodiments 150-153, wherein the disease or condition is an autoimmune disease, a B cell cancer, an antibody-mediated pathology, a renal disease, a graft rejection, graft versus host disease, or a viral infection.

157. The method of embodiment 156, wherein the disease or condition is an autoimmune disease selected from the group consisting of Systemic lupus erythematosus (SLE); Sjögren's syndrome, scleroderma, Multiple sclerosis, diabetes, polymyositis, primary biliary cirrhosis, IgA nephropathy, optic neuritis, amyloidosis, antiphospholipid antibody syndrome (APS), autoimmune polyglandular syndrome type II (APS II), autoimmune thyroid disease (AITD), Graves' disease, autoimmune adrenalitis and pemphigus vulgaris.

158. The method of embodiment 156, wherein the disease or condition is a B cell cancer and the cancer is myeloma.

IX. EXAMPLES

The following examples are included for illustrative purposes only and are not intended to limit the scope of the invention.

Example 1. Identification of Affinity Modified TACI

This Example describes the generation of mutant DNA constructs of human TACI TNFR domains (TD) for translation and expression on the surface of yeast as yeast display libraries, introduction of DNA libraries into yeast, and selection of yeast cells expressing affinity-modified variants of the extracellular domain (ECD) of TACI containing at least one TD (TACI vTD). The selected TACI vTD were then formatted as Fc fusion proteins.

A. Generation of Mutant DNA Constructs of TACI TNFR Domains

Libraries containing random substitutions of amino acids were constructed to identify variants of the extracellular domain (ECD) of TACI. Constructs were generated based on a wildtype human TACI sequence containing an ECD portion of TACI that included either (1) both cysteine-rich protein domains (CRD, CRD1/CRD2) as set forth in SEQ ID NO: 1 (corresponding to residues 29-110 as set forth in UniProt Accession No. 014836), or (2) only a single CRD (CRD2) as set forth in SEQ ID NO: 13 (corresponding to residues 68-110 as set forth in UniProt Accession No. 014836).

TACI ECD (29-110) (SEQ ID NO: 1):
VAMRSCPEEQYWDPLLGTCMSCKTICNHQSQRT-CAAFCRSLSCRKEQGKFYDHLLR DCISCA-SICGQHPKQCAYFCENKLRS

TACI ECD (68-110) (SEQ ID NO: 13):
SLSCRKEQGKFYDHLLRDCISCASICGQHPKQCAY-FCENKLRS

DNA encoding the wild-type TACI ECD domain was cloned between the BamHI and KpnI sites of the modified yeast expression vector PBYDS03 (Life Technologies USA) which placed the TACI ECD N-terminal to the yeast surface anchoring domain Sag1 (the C-terminal domain of yeast α-agglutinin) with an in-frame HA fusion tag N-terminal to the TACI ECD sequence and a c-Myc fusion tag C-terminal to the TACI ECD sequence. Expression in this vector is controlled through the inducible GAL1 promoter. After verification of the correct DNA sequence, the wild-type TACI ECD DNA construct was used as template for error-prone PCR to introduce random mutations across the TACI ECD sequence at a frequency of 2-5 mutations per gene copy. The Genemorph II Kit (Agilent, USA) was used in combination with titrating amounts of MnCl2 from 0.0 to 0.6 mM to achieve the desired error rate. After error-prone PCR, the mutagenized DNA was gel purified using the NucleoSpin® Gel and PCR Clean-up kit (Macherey-Nagel, Germany). This isolated DNA fragment was then PCR amplified with OneTaq 2× PCR master mix (New England Biolabs, USA) using primers containing 48 bp overlap regions homologous to pBYDS03 for preparation for large scale yeast electroporation. The TACI ECD DNA insert was gel-purified and resuspended in sterile, deionized water at a nominal concentration of 500 ng/μL.

To prepare the vector for transformation, pBYDS03 was digested with BamHI-HF and KpnI-HF restriction enzymes (New England Biolabs, USA) and the large vector fragment (expected size: 7671 bp) was gel-purified and dissolved in sterile, deionized water at a nominal concentration of 500 ng/µL. To prepare for yeast transformation, 12 µg of library DNA insert was mixed with 4 µg of linearized vector for each electroporation.

To introduce random DNA libraries into yeast, the *Saccharomyces cerevisiae* strain BJ5464 (ATCC.org; ATCC number 208288) was prepared immediately prior to electroporation as detailed in Benatuil, L. et. al., Protein Eng Des Sel. 2010 April; 23(4):155-159. Briefly, an overnight stationary-phase culture of BJ5464 was passaged to $OD_{600}$ 0.3 in 100 mL YPD medium (10 g/L yeast nitrogen base, 20 g/L Peptone and 20 g/L D-(+)-Glucose) and placed in a platform shaker at 30° C. and 300 rpm until the inoculated cultures reached $OD_{600}$ 1.6. After ~5 hours, cells were harvested by centrifugation and kept on ice for the remainder of the protocol unless otherwise stated. After harvesting, cells were washed twice with 50 mL ice-cold water and once with electroporation buffer (1 M Sorbitol, 1 mM CaCl2). Collected cells were conditioned by re-suspending in 20 mL 0.1 M LiAc/10 mM DTT and shaking at 225 rpm in a culture flask for 30 minutes at 30° C. Conditioned cells were immediately centrifuged, washed twice with electroporation buffer, and resuspended with ~100-200 µl of electroporation buffer to bring the volume to 1 mL. This conditioned cell suspension was sufficient for two electroporation reactions in 400 µl cuvettes.

For each electroporation, 12 µg of library DNA insert and 4 µg of linearized pBYDS03 vector (described above) was mixed with 400 µl of electrocompetent BJ5464 and transferred to a pre-chilled BioRad GenePulser cuvette with 2 mm electrode gap. The mixtures were kept on ice for 5 minutes, prior to electroporation using a BTX ECM399 exponential decay wave electroporation system at 2500V. Immediately following electroporation, cells were added to 8 mL of 1:1 mixture of 1 M Sorbitol:1× YPD, and left at room temperature without shaking for 10 min, then placed on platform shaker for 1 hr at 225 rpm and 30° C. Cells were collected by centrifugation and resuspended in 250 mL SCD-Leu medium to accommodate the LEU2 selective marker carried by modified plasmid pBYDS03. One liter of SCD-Leu media was generated with 14.7 gm sodium citrate, 4.29 gm citric acid monohydrate, 20 gm dextrose, 6.7 gm yeast nitrogen base, and 1.6 gm yeast synthetic drop-out media supplement without leucine. The medium was filter sterilized before use using a 0.22 µm vacuum filter device. Library size was estimated by spotting serial dilutions of freshly recovered cells on an SCD-Leu agar plate in the dilution range of $10^{-5}$ to $10^{-10}$ and extrapolating by counting colonies after three days. The remainder of the electroporated culture was grown to saturation and cells from this culture were subcultured 1/100 into the same medium once more and grown to saturation to minimize the fraction of untransformed cells and to allow for segregation of plasmid from cells that may contain two or more library variants. To maintain library diversity, this subculturing step was carried out using an inoculum that contained at least 10× more cells than the calculated library size. Cells from the second saturated culture were resuspended in fresh medium containing sterile 25% (weight/volume) glycerol to a density of $1×10^{10}$/mL and frozen and stored at −80° C. (frozen library stock).

A number of cells equal to at least 10 times the estimated library size were thawed from individual library stocks, suspended to $0.5×10^7$ cells/mL in non-inducing SCD-Leu medium, and grown overnight. The next day, a number of cells equal to 10 times the library size were centrifuged at 2000 RPM for two minutes and resuspended to $0.5×10^7$ cells/mL in inducing SCDG-Leu media. One liter of SCDG-Leu induction media was generated with 5.4 gm $Na_2HPO_4$, 8.56 gm $NaH_2PO_4.H_2O$, 20 gm galactose, 2.0 gm dextrose, 6.7 gm yeast nitrogen base, and 1.6 gm yeast synthetic drop out media supplement without leucine dissolved in water and sterilized through a 0.22 µm membrane filter device. The culture was grown in induction medium overnight at 30° C. to induce expression of library proteins on the yeast cell surface.

Following overnight induction of the TACI ECD libraries, a number of cells equivalent to 10 times the estimated library diversity were sorted by magnetic separation using Dynabeads™ His-Tag magnetic beads preloaded with BAFF-9×His to enrich for TACI ECD variants with the ability to bind their exogenous recombinant counter-structure proteins. The outputs from the magnetic separation were used in a subsequent FACS selection scheme involving four rounds of positive selections alternating between BAFF-9×His and APRIL-FLAG, with simultaneous 10-fold reduction in counter structure concentration each round (e.g., FACS1: 50 nM APRIL-FLAG; FACS4: 0.05 nM BAFF-9×His). The incubation volume was adjusted to maintain at least a 10-fold stoichiometric excess of counter structure over the total number of yeast-displayed TACI ECD variant molecules (assuming 100,000 copies of protein per cell) to avoid ligand depletion artifacts which can reduce library discrimination. Binding of BAFF-9×His and APRIL-FLAG to TACI ECD variants was detected with PE conjugated anti-6×His tag antibody (BioLegend, USA) and PE conjugated anti-FLAG-tag antibody, respectively. Variants from FACS3 and FACS4 outputs were isolated for DNA sequencing and subsequent cloning for recombinant Fc fusion expression.

A second cycle of random mutagenesis was carried out on yeast cell outputs from the FACS4 BAFF-9×His selections described above. The positive selection protocol with alternating counter structures per sort was the same as the first cycle except that the order of counter structures was switched (e.g., FACS1: 50 nM BAFF-9×His; FACS4: 0.05 nM APRIL-FLAG). Additional variants were chosen from FACS3 and FACS4 yeast cell outputs.

B. Reformatting Selection Outputs as Fc-Fusions

TACI ECD variant inserts from FACS3 and FACS4 outputs from both cycle 1 and cycle 2 selections, as described above, were subcloned into an Fc fusion vector for sequence analysis of individual clones To generate recombinant immunomodulatory proteins as Fc fusion proteins containing an ECD of TACI with at least one affinity-modified domain (e.g., variant TACI ECD-Fc), the encoding DNA was generated to encode a protein as follows: variant TACI domain followed by a linker of 7 amino acids (GSGGGGS; SEQ ID NO: 74) followed by a human IgG1 effectorless Fc sequence containing the mutations L234A, L235E and G237A, by the Eu Index numbering system for immunoglobulin proteins. Since the construct does not include any antibody light chains that can form a covalent bond with a cysteine, the human IgG1 Fc also contained replacement of the cysteine residues to a serine residue at position 220 (C220S) by Eu Index numbering system for immunoglobulin proteins (corresponding to position 5 (C5S) with reference to the wild-type or unmodified Fc set forth in SEQ ID NO: 71). The Fc region also lacked the C-terminal lysine at position 447 (designated K447del) normally encoded in the wild type human IgG1 constant region gene (corresponding to position 232 of the wild-type or unmodified Fc set forth in SEQ ID NO: 71). The effectorless (inert) IgG1 Fc in the fusion constructs is set forth in SEQ ID NO:73.

Output cell pools from selected TACI ECD FACS sorts were grown to terminal density in SCD-Leu selection medium and plasmid DNA was isolated using a yeast plasmid DNA isolation kit (Zymoresearch, USA). For generation of Fc fusions, the affinity matured TACI ECD variants were PCR amplified with primers containing 40 bp homologous regions on either end with an AfeI and BamHI digested Fc fusion vector encoding and in-frame with the Fc region to carry out in vitro recombination using Gibson Assembly Master Mix (New England Biolabs). The Gibson Assembly reaction was added to the *E. coli* strain NEB5alpha (New England Biolabs, USA) for heat shock transformation following the manufacturer's instructions.

Dilutions of transformation reactions were plated onto LB-agar containing 100 μg/mL carbenicillin (Teknova, USA) to isolate single colonies for selection. Generally, up to 96 colonies from each transformation were then grown in 96 well plates to saturation overnight at 37° C. in LB-broth containing 100 μg/mL carbenicillin (Teknova cat #L8112) and a small aliquot from each well was submitted for DNA sequencing to identify mutation(s) in all clones.

After sequence analysis and identification of clones of interest, plasmid DNA was prepared using the MidiPlus kit (Qiagen).

Recombinant variant Fc fusion proteins were produced from suspension-adapted human embryonic kidney (HEK) 293 cells using the Expi293 expression system (Invitrogen, USA). Supernatant was harvested and the Fc protein was captured on Mab SelectSure (GE Healthcare cat. no. 17543801). Protein was eluted from the column using 50 mM Acetate pH3.6. The MabSelect Sure eluate was pooled and the pH was adjusted to above pH5.0. This material was then polished on a Preparative SEC column, to generate highly purified monomeric material. This material was buffer exchanged into 10 mM Acetate, 9% Sucrose pH 5.0. The protein purity was assessed by analytic SEC. Material was vialed and stored at −80.

Amino acid substitutions in selected TACI vTDs that were identified and generated by the selection are set forth in Table 1. Selected vTDs, formatted as Fc fusion proteins, were tested for binding and functional activity as described in Example 2.

Example 2. Assessment of Activity of Fc Fusion Proteins

This Example describes characterization of the activity of TACI domain-containing molecules, such as soluble wild-type (WT) or variant TACI vTDs formatted as Fc fusions, using a cell line-based in vitro bioassay.

Jurkat cells with a nuclear factor kappa-light-chain-enhancer of activated B cells (NF-κB) luciferase-based reporter were purchased (BPS Bioscience). Jurkat/NK-κB cells were transduced with lentivirus to yield stable, cell surface expression of mouse TACI (Jurkat/NF-κB/TACI). Cells expressing mouse TACI respond to both human and mouse APRIL or BAFF. Following binding of recombinant human or mouse APRIL or BAFF to TACI, endogenous NK-κB transcription factors in the Jurkat cells bind to the DNA response elements controlling transcription of a firefly luciferase gene. Luciferase production was quantitated through the addition of a luciferin-containing substrate which, when oxidized, generates light that can be measured using a microplate reader. A schematic of the Jurkat/NF-κB/TACI assay is shown in FIG. 1.

Recombinant human and mouse APRIL and BAFF ligands were purchased: human APRIL (Tonbo Biosciences); human BAFF (BioLegend); mouse APRIL (ProSci Incorporated); and mouse BAFF (R & D Systems).

To determine bioactivity of TACI WT or vTD domain-containing molecules, recombinant human or mouse APRIL or BAFF at varying concentrations (ranging 1-10 nM) in 30 μL were incubated with fixed or titrated (ranging 40 nM-66 pM) TACI domain-containing molecules in 30 μL. Ligands and soluble receptors were incubated for 20 minutes with shaking at room temperature (RT). Fifty μL was transferred to a 96-well, white flat-bottomed plated containing $1.5 \times 10^5$ Jurkat/NF-κB/TACI cells/well in 50 μL media (RPMI1640+ 5% fetal bovine serum [FBS]). Wells were mixed and plates incubated for 5 hours at 37° Celsius (C) in a humidified 5% $CO_2$ incubation chamber. Plates were removed from the incubator and 100 μL of cell lysis and luciferase substrate solution (Bio-Glo™ Luciferase Assay System, Promega) was added to each well and the plates were incubated on an orbital shaker for 10 minutes. Relative luminescence values (RLU) were determined for each test sample by measuring luminescence with a 1 second per well integration time using a Cytation 3 (BioTek Instruments) imaging reader. Decreased RLU in the presence of TACI WT or vTDs relative to control proteins represent blockade and inhibition of ligand signaling via the transduced TACI receptor in the Jurkat/NF-κB/TACI cells.

Figure 2:
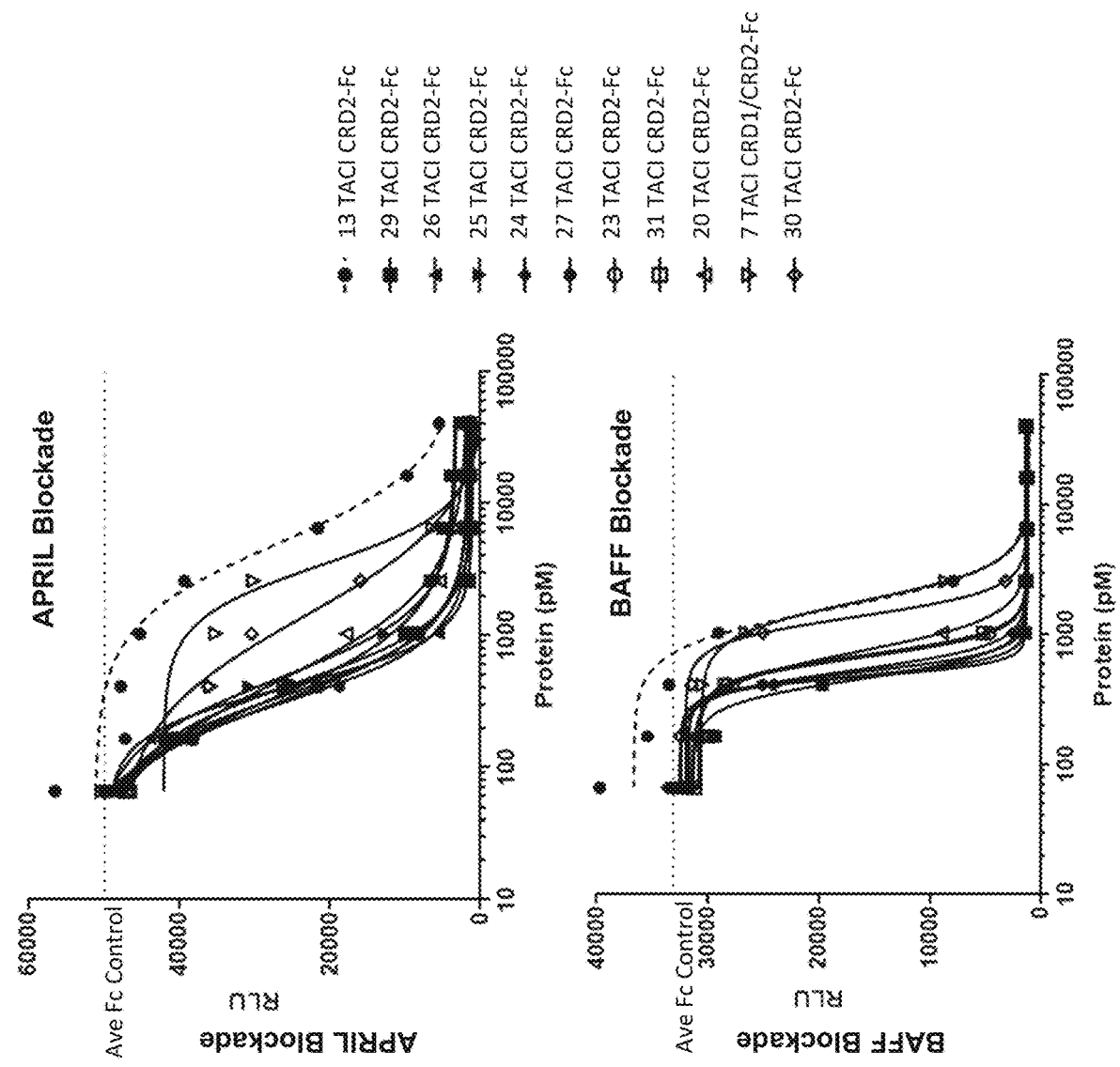
FIG. 2 shows exemplary human TACI TD Fc fusion molecules for blockade of human APRIL (top panel) and BAFF (bottom panel) mediated signaling. TACI TD Fc fusions were incubated with APRIL or BAFF for 20 mins (room temperature with shaking) and then added to wells containing 150,000 Jurkat/TACI/NFκB-luciferase cells for 5 hours.

As shown in FIG. 2, exemplary TACI-Fc vTDs, respectively, inhibit ligand signaling at levels equal to or greater than Fc fusion proteins containing WT TACI domains.

Example 3. Bioactivity Assessment of TACI Blockade of TACI-Mediated Stimulation by TACI-Containing Molecules The cell-line based bioassay described in Example 2 was used to assess the functional characterization of TACI-containing WT or vTD proteins for blockade of APRIL or BAFF-mediated ligand signaling via the TACI receptor in the Jurkat/NF-κB/TACI cells. APRIL or BAFF-mediated ligand signaling was quantitated by monitoring luciferase production in the cells. Binding of a TACI-Fc fusion containing a vTD set forth in SEQ ID NO:26 was assessed (26 TACI CRD2-Fc). For comparison, WT TACI-Fc containing only the CRD2 domain of TACI (13 TACI CRD2-Fc) also was assessed.

Figure 3:
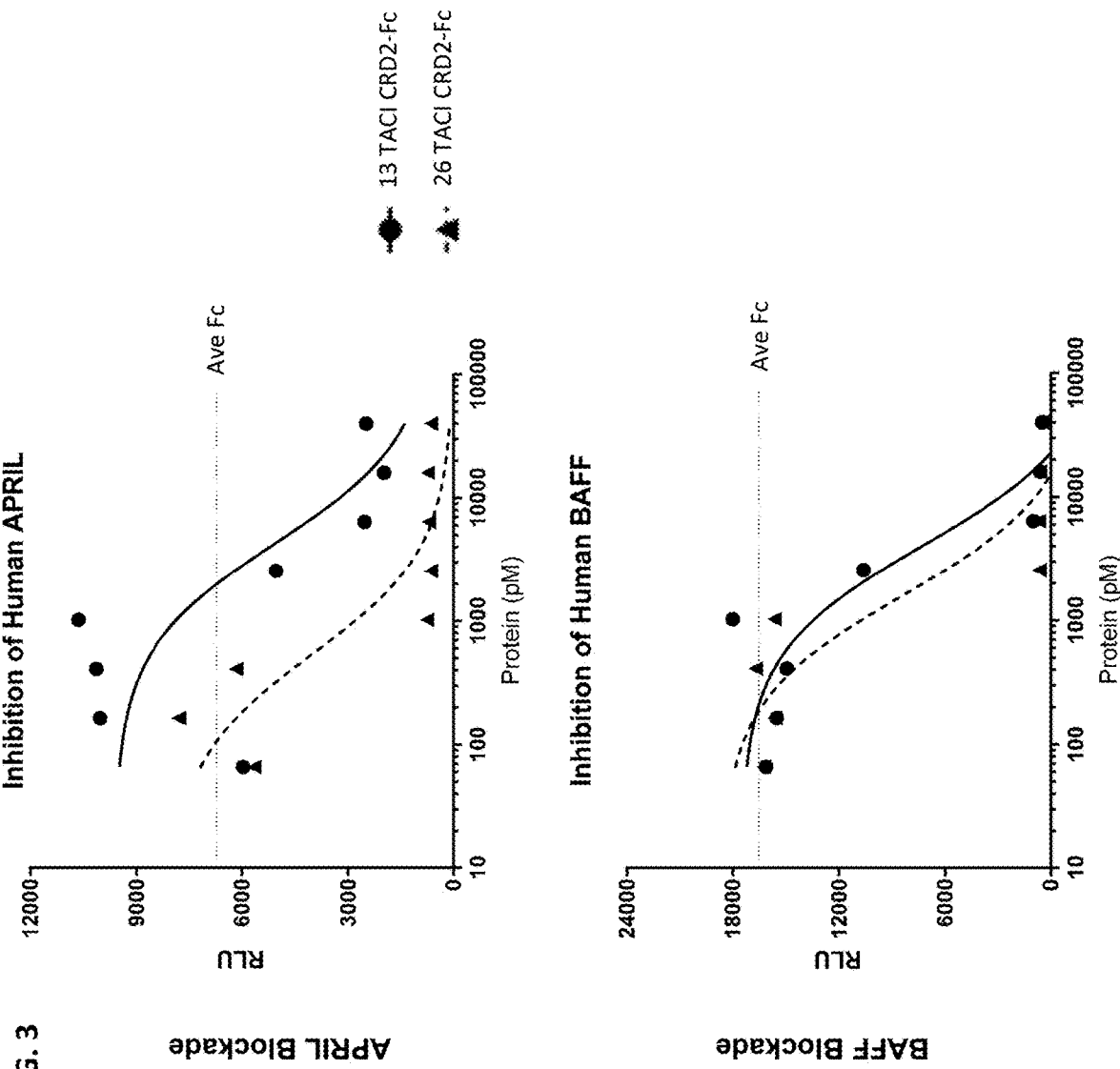
FIG. 3 shows function of exemplary TACI TD Fc fusion molecules for blockade of APRIL (top panel of the FIG) or BAFF (bottom panel of the FIG).
Figure 4:
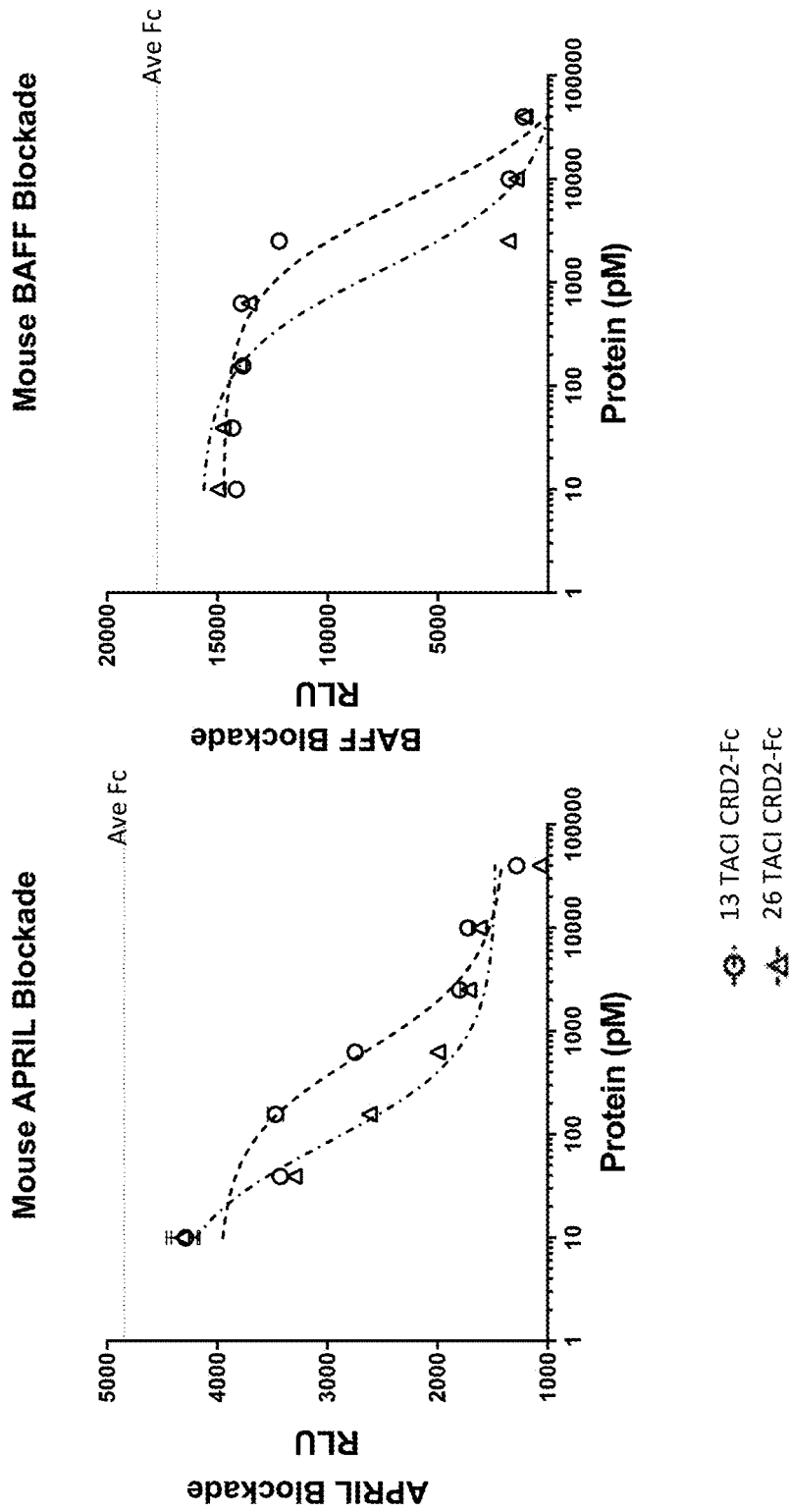
FIG. 4 shows human TACI TD Fc fusion molecules for blockade of mouse APRIL (left panel) and BAFF (right panel) mediated signaling.

As shown in FIG. 3, an exemplary TACI vTD demonstrates increased inhibition of both human APRIL and BAFF. As shown in FIG. 4, exemplary TACI vTD-Fc molecules inhibit mouse APRIL and BAFF ligand signaling. Together, the results show the ability of TACI vTD molecules to block APRIL and BAFF TACI-mediated ligand signaling.

In another similar study, exemplary generated molecules as described in Example 1 were assessed for their ability to block APRIL or BAFF-mediated ligand signaling in Jurkat/NF-κB/TACI cells. For comparison, control molecules were generated containing wild-type TACI ECD fused the Fc sequence set forth in SEQ ID NO: 73. In one control, the fusion protein contained WT TACI (TACI 30-110, SEQ ID NO:130; corresponding to the TACI ECD portion in atacicept, SEQ ID NO:132). In another control, the fusion protein contained WT TACI (TACI 13-118, SEQ ID NO:131), corresponding to the TACI ECD portion in telitacicept).

Activity was compared to the control molecules. Activity also was compared to the anti-BAFF monoclonal antibody belimumab.

Exemplary TACI molecules, either WT or variant TACI vTDs, were titrated (between 100,000 pM-32 pM), added to 2 nM recombinant human APRIL or BAFF and assayed as described above for the Jurkat/NF-κB assay. As shown in FIG. 5, the exemplary molecules containing TACI vTDs exhibited enhanced APRIL and BAFF blockade greater than TACI 30-100-Fc, TACI 13-118-Fc and belimumab. WT TACI-Fc containing only the CRD2 domain of TACI (13 TACI CRD2-Fc) also exhibited enhanced APRIL blockade greater than TACI 30-100-Fc and TACI 13-118-Fc.

These results are consistent with a finding that the minimal CRD2 domain (containing amino acids residues 68-110) exhibits improved blockade of APRIL compared to TACI ECD molecules also containing portions of the CRD1 domain as present in atacicept and telitacicept. Table E1 provides the values for half maximal inhibitory concentration (IC50) for inhibition of APRIL- and BAFF-mediated TACI signaling for the exemplary molecules described in FIG. 5. Also shown in parentheses is the relative blockage compared to atacicept (A atacicept) for each tested molecule.

TABLE E1

Bioactivity of TACI vTDs vs atacicept

| Description | SEQ ID NO | IC50 (nM) APRIL | IC50 (nM) APRIL (Δ TACI 30-110-Fc) | IC50 (nM) BAFF (Δ TACI 30-110-Fc) |
|---|---|---|---|---|
| 26 TACI CRD2-Fc | 26 | 179 | 179 (0.05) | 1216 (0.21) |
| 27 TACI CRD2-Fc | 27 | 262 | 262 (0.07) | 1387 (0.24) |
| 29 TACI CRD2-Fc | 29 | 339 | 339 (0.09) | 1336 (0.23) |
| 13 TACI CRD2-Fc | 13 | 369 | 369 (0.10) | 1328 (0.23) |
| TACI 13-118-Fc | | 9103 | 9103 (2.37) | 7699 (1.33) |
| Belimumab | | 214911 | 214911 (55.84) | 2496 (0.43) |
| TACI 30-110-Fc | | 3849 | 3849 (1.00) | 5771 (1.00) |

Example 4. Assessment of the Activity of TACI vTD-Fcs in an In Vivo Mouse Lupus Model This Example describes the assessment of exemplary TACI vTD-Fc molecules, to affect immune responses in an in vivo murine (NZB/NZW)F1 spontaneous lupus model. (NZB×NZW)F1 mice spontaneously develop an autoimmune disease very similar to human SLE and are regarded as one of the best mouse models of this disease. (NZB/NZW)F1 mice have high circulating concentrations of anti-dsDNA antibodies starting around 20 weeks of age, with the first clinical signs of disease detectable around 23 weeks of age. The mice develop hemolytic anemia, proteinuria, and progressive glomerulonephritis mediated by immune complex deposition in the glomerular basement membrane.

(NZB/NZW)F1 mice were dosed twice weekly via intraperitoneal (IP) injection with 14 mg/kg Fc control, or molar-matched amounts of TACI vTD-Fc (26 TACI CRD2-Fc) (17 mg/kg). Treatment started at group assignment (Week 22 of age) and continued through the end of the study. The study ended when mice reached Week 43 of age, though some animals were euthanized earlier in the study when they became moribund.

Figure 6A:
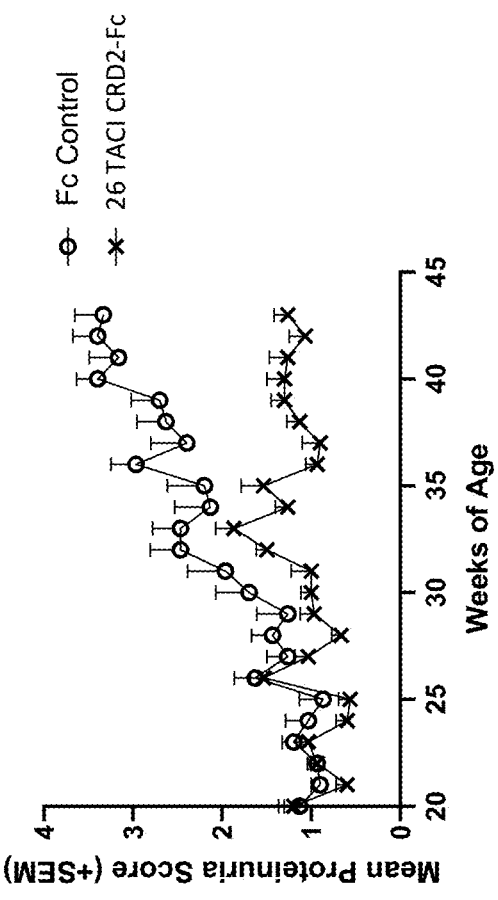
FIGS. 6A-6I show analysis of parameters assessed in an NZB/NZW murine model of human SLE. Proteinuria scores (FIG. 6A), mean percent change in body weight (FIG. 6B), and percent survival (FIG. 6C) were assessed starting at 20 weeks of age. Serum was analyzed for anti-double stranded DNA IgG titers (FIG. 6D) and blood urea nitrogen (BUN) (FIG. 6E) (** vs Fc by Student's t-test, p<0.0001 for anti-dsDNA IgG; * vs Fc by Student's t-test, p=0.0008 for BUN-4). Kidneys were processed and analyzed by histology in replicate Periodic acid-Schiff (PAS)-stained sections, with individual component and total histology scores depicted in FIG. 6F. Frozen kidneys were also sectioned and stained for immunohistochemical analysis of mouse IgG and complement C3 glomerular deposition, as shown in FIG. 6G and FIG. 6H, respectively.
Figure 6B:
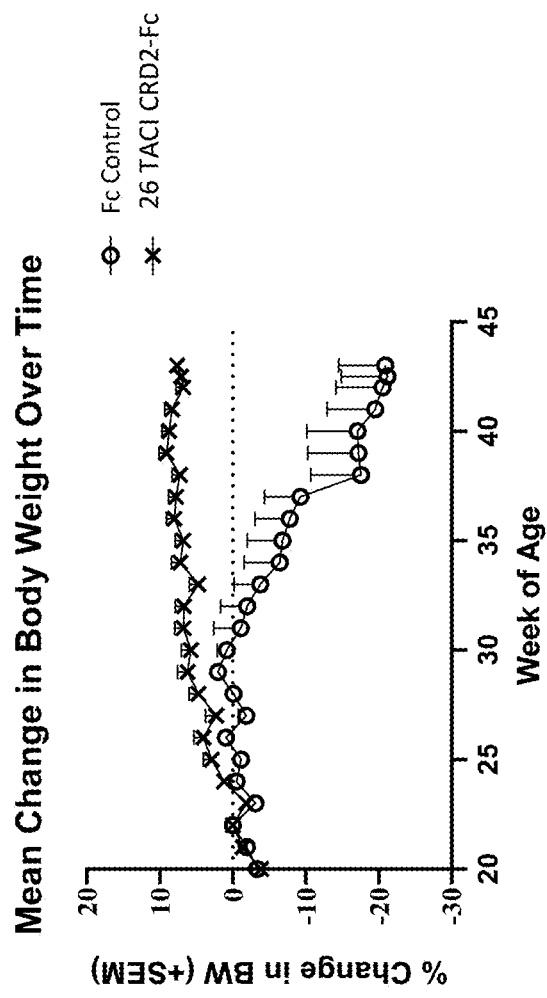
Figure 6C:
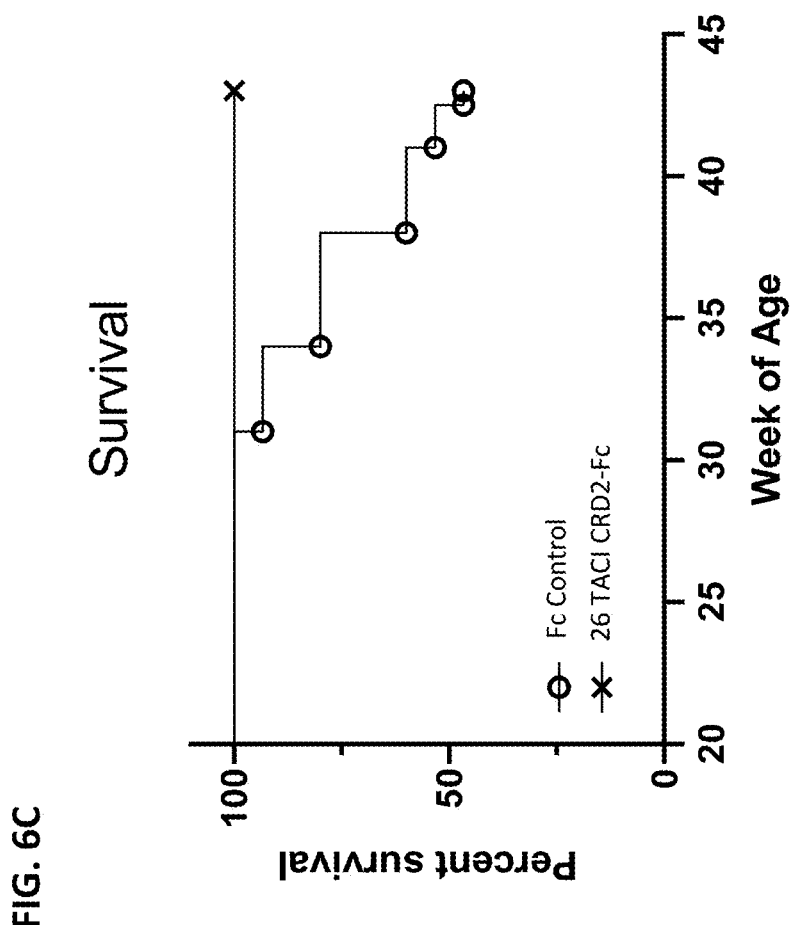
Figure 6E:
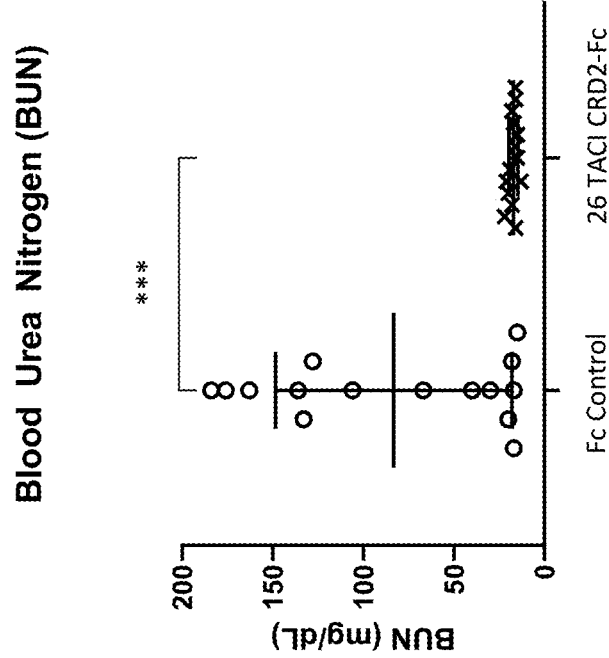
Figure 6D:
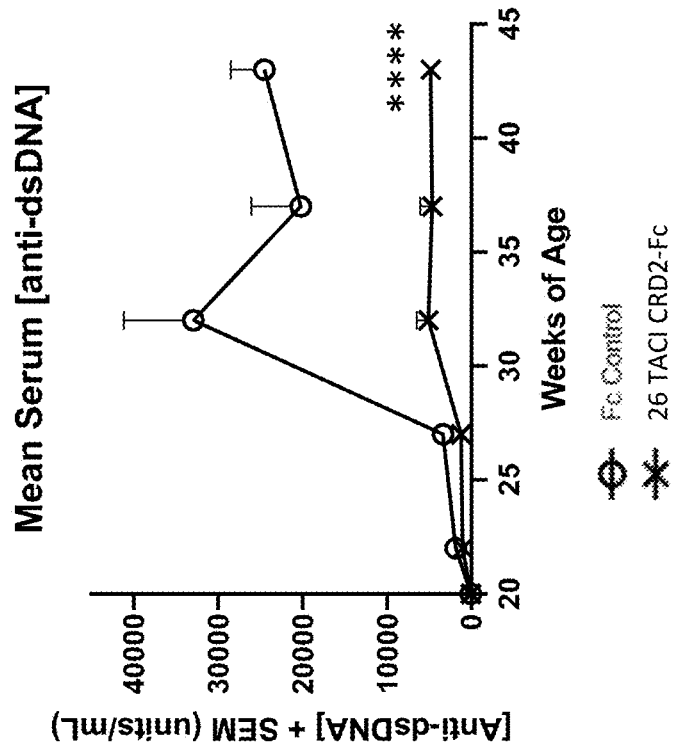

At various time points between 20 and 40 weeks of age, urine and serum samples were collected. Starting when mice were 20 weeks old, the concentration of protein in the urine from all mice on study was determined weekly with urinalysis test strips (Roche Chemstrip 2 GP, cat. 11895397160). Mean proteinuria scores over time in each treatment group are presented in FIG. 6A, and the mean percent change in body weight (weight loss is associated with advancing disease) in each group in plotted in FIG. 6B. The percent survival of mice in each treatment group is plotted in FIG. 6C. Anti-double stranded (ds) DNA IgG serum titers were measured by Hooke Laboratories, Inc. (Lawrence, Mass.) using their in-house kit, and the results are presented in FIG. 6D. Blood urea nitrogen (BUN) levels increase in these mice with advancing disease. BUN levels at termination of the study (or at sacrifice of mice that succumbed early) for each treatment group are shown in FIG. 6E. Statistical analysis was performed using Student's t-test; ** denotes p<0.0001 and * denotes p=0.0008).

Figure 6F:
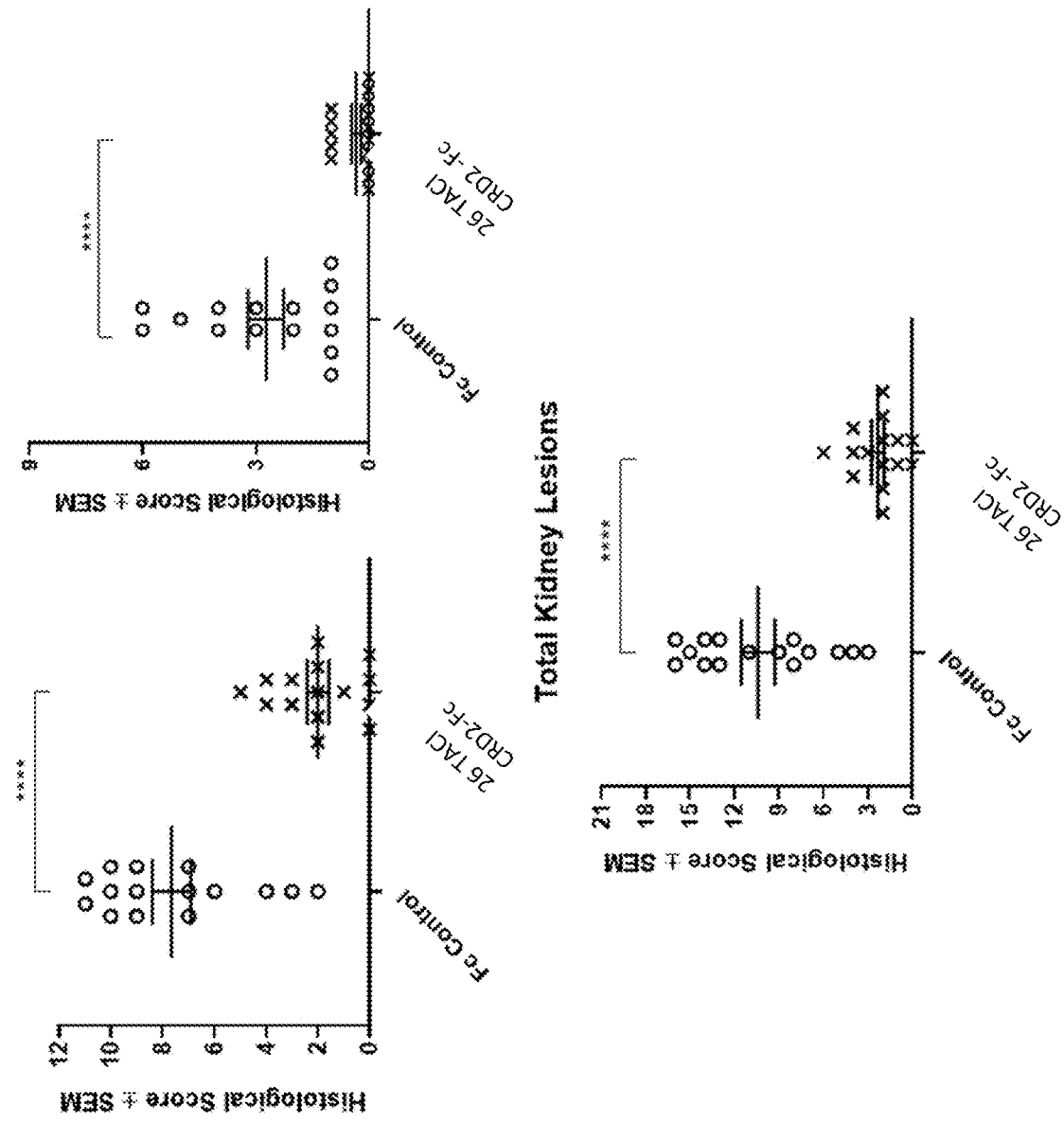

Kidneys were collected at termination from each mouse and analyzed histologically in replicate Periodic acid-Schiff (PAS)-stained sections using the criteria described in Alperovich G et al, 2007. Lupus 16:18-24. All kidney sections were analyzed blind, by a pathologist unaware of the treatments and clinical scores. Glomerular lesions (mesangial expansion, endocapillary proliferation, glomerular deposits, and extracapillary proliferation) and tubular/interstitial lesions (interstitial infiltrates, tubular atrophy, and interstitial fibrosis) were analyzed and graded semi-quantitatively using a scoring system from 0 to 3, with 0=no changes, 1=mild changes, 2=moderate changes, and 3=severe changes. A total histological score for each mouse was calculated as the sum of the individual scores (maximum total score is 21). Kidney scores for total glomerular lesions, total tubular and interstitial lesions, and total kidney lesions are shown in FIG. 6F; as compared to Fc control treated mice, significantly improved renal histopathology was observed in animals treated with TACI vTD-Fc (p<0.0001 vs. Fc group).

Figure 6H:
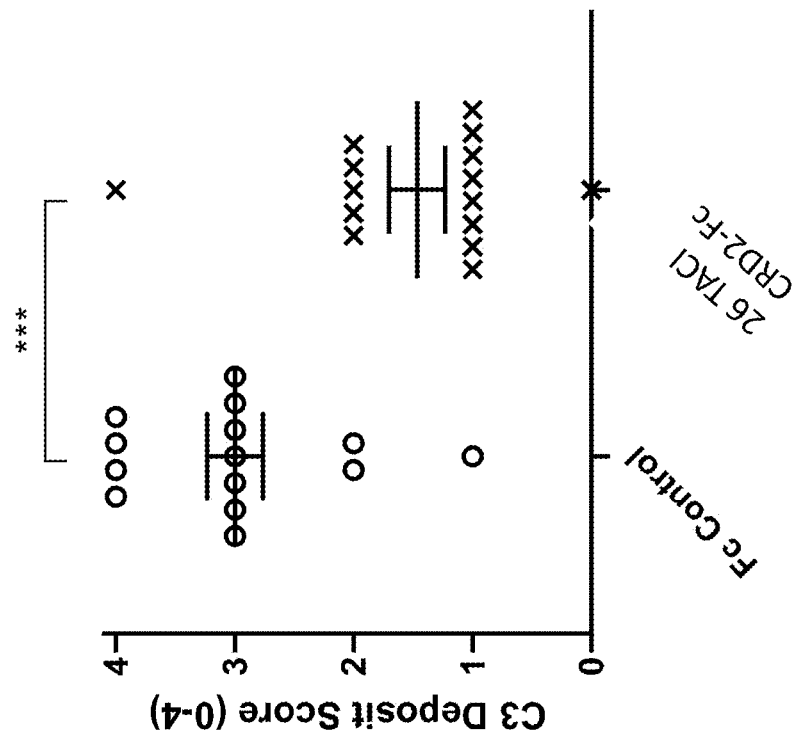
Figure 6G:
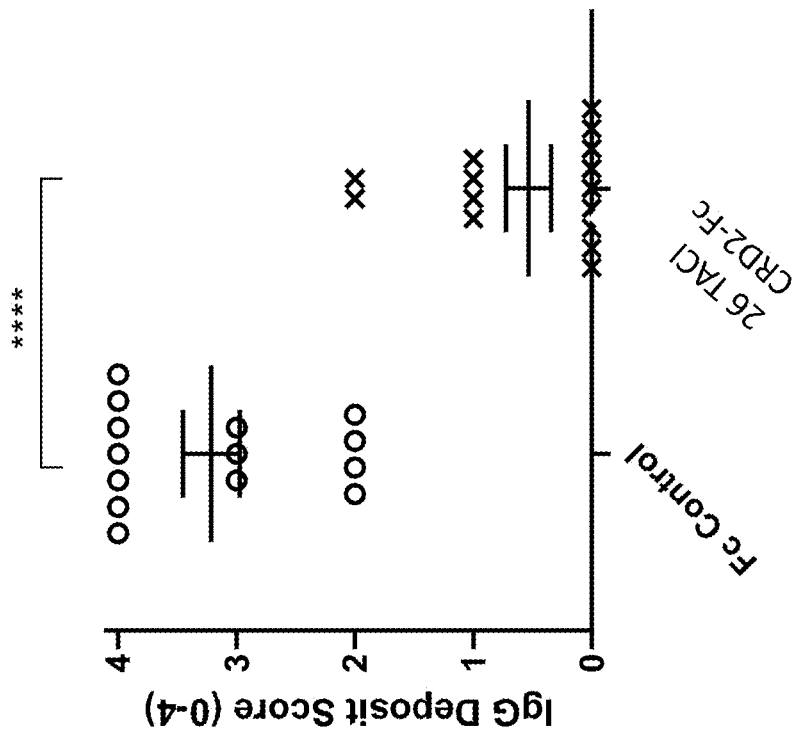
Figure 6I:
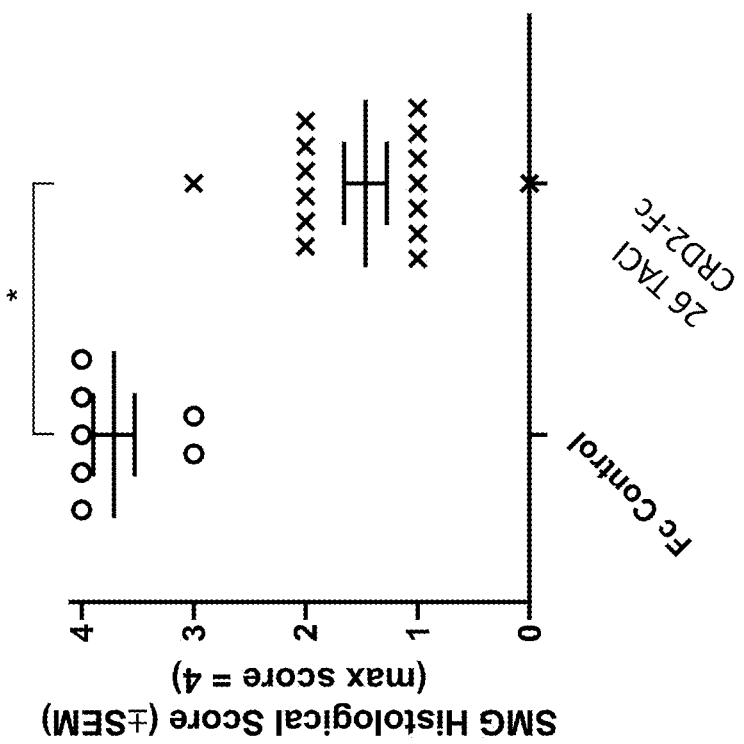

For FIG. 6G-6I, the right kidney was collected from each mouse at study termination, weighed, dissected transversally, and frozen in a single optimal cutting temperature compound (OCT) block. before sectioning and immunohistochemical (IHC) staining of mouse IgG and mouse complement C3 to assess glomerular IgG and C3 deposition, respectively. The kidney sections were permeabilized with acetone and stained with FITC-conjugated rat monoclonal anti-mouse complement component C3 (Cedarlane) diluted 1:25 in Primary Antibody Diluent (Leica Biosystems), or AF594-conjugated goat anti-mouse IgG (Thermo Fisher Scientific) diluted 1:200 in Primary Antibody Diluent. Glomerular depositions of IgG and C3 were analyzed by a pathologist using a semiquantitative scoring system from 0 to 4, with 0=no deposits, 1=mild mesangial deposition, 2=marked mesangial deposition, 3=mesangial and slight capillary deposition, and 4=intense mesangial and mesangiocapillary deposition, based on the method described in Kelkka et al. (2014) Antioxid Redox Signal. 21:2231-45. As compared to Fc control treated mice, significantly reduced glomerular IgG and C3 were observed in animals treated with 26 TACI CRD2-Fc (p<0.0001 vs. Fc control group for IgG, and p=0.0005 for C3); data were analyzed for statistically significant differences using Student's t-test.

Results demonstrate that the TACI vTD-Fc were able to significantly suppress proteinuria, preserve body weight, enhance overall survival, reduce anti-dsDNA autoantibodies and BUN, reduce IgG and C3 renal deposits, and prevent or improve kidney disease in the (NZB/NZW)F1 mouse model of SLE. Exemplary molecules were also capable of potently reducing B and T cell subsets including plasma cells, follicular T helper cells, germinal center cells, and memory T cells in the spleens and lymph nodes of these mice (data not shown).

Example 5: Assessment of Activity of TACI 13-118-Fc with the Addition of Identified Mutations The impact of TACI mutations identified in Example 1 (see Table 1) were assessed to determine their ability to modulate the activity of Fc fusion proteins containing a longer TACI ECD sequence (containing both the CRD1 and CRD2 domain). In this example, the exemplary mutations K77E, F78Y and Y102D were introduced into the reference TACI ECD 13-118, which was fused to the exemplary Fc sequence set forth in SEQ ID NO:73. Activity was compared to a TACI vTD-Fc fusion protein containing only the CRD2 domain with the same mutations (set forth in SEQ ID NO:26), or to WT TACI (30-110, SEQ ID NO:130; corresponding to the TACI ECD portion in atacicept, SEQ ID NO:132), each also fused to the Fc sequence set forth in SEQ ID NO:73. The cell line-based bioassay described in Example 2 was used to assess blockade of APRIL or BAFF-mediated ligand signaling via the TACI receptor in the Jurkat/NF-κB/TACI cells. APRIL or BAFF-mediated ligand signaling via the TACI receptor was quantitated by monitoring luciferase production in the cells.

Figure 7:
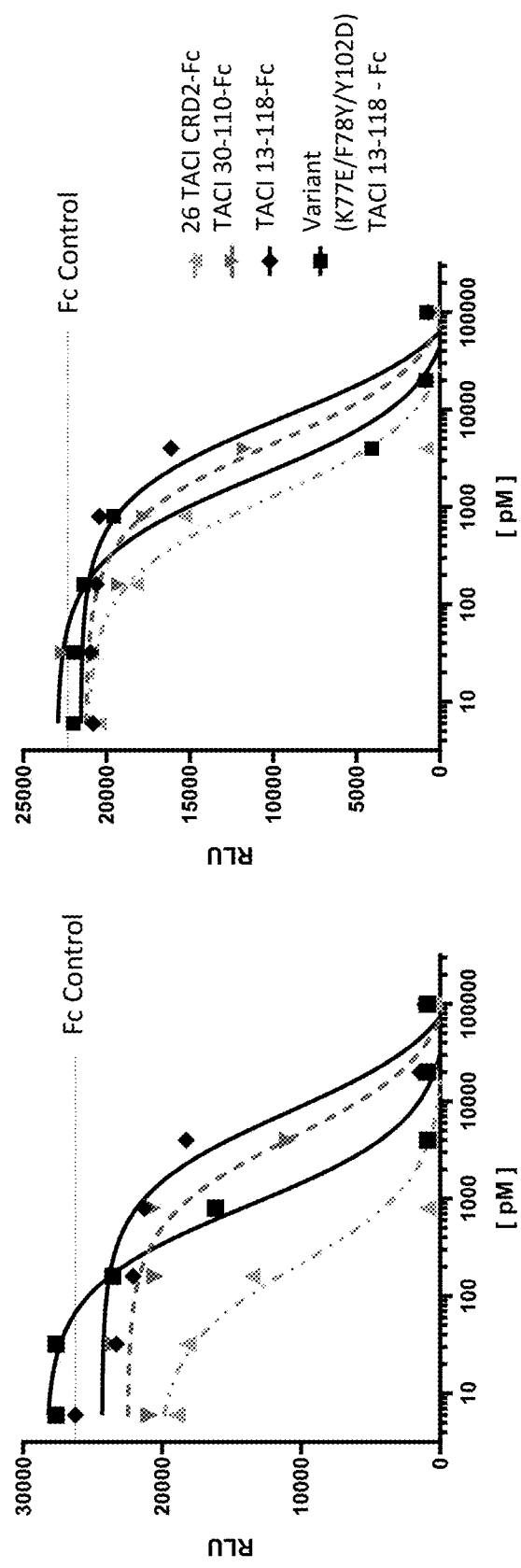
FIG. 7 shows the ability of TACI mutations (K77E/F78Y/Y102D) to inhibit APRIL (left panel) and BAFF (right panel) mediated signaling, quantified by luciferase production in Jurkat/NF-κB/TACI cells.

As shown in FIG. 7, introduction of K77E, F78Y and Y102D mutations into TACI 13-118 ECD to generate variant (K77E/F78Y/T102D) TACI 13-118 improved APRIL and BAFF blockade (respectively) relative to the corresponding WT TACI 13-118ECD (diamonds) or the alternative ECD control WT TACI 30-110 (upward triangles). However, even with the incorporation of the mutations into TACI 13-118 ECD, the shorter variant TACI with the same mutations but containing only the CRD2 domain of TACI (vTD set forth in SEQ ID NO:26) exhibited the greatest APRIL and BAFF blockade in this assay (downward triangles). These results confirm that a minimal CRD2-containing domain confers improved activity to block APRIL and BAFF-mediated TACI signaling, however, the mutations K77E/F78Y/Y102D also further enhance APRIL and BAFF blockade by variant TACI ECDs incorporating the mutations.

Table E2 provides the values for half maximal inhibitory concentration (IC50) for inhibition of APRIL- and BAFF-mediated TACI signaling for the exemplary molecules described in FIG. 7. Also shown is a comparison to WT TACI-Fc controls (Δ atacicept) for each molecule.

TABLE E2

Bioactivity of Multi-Domain Immunomodulatory Proteins vs atacicept

| Description | SEQ ID NO | IC50 (nM) APRIL | IC50 (nM) APRIL (Δ TACI 30-110) | IC50 (nM) BAFF | IC50 (nM) BAFF (Δ TACI 30-110) |
|---|---|---|---|---|---|
| 26 TACI-Fc | 26 | 214 | 214 (0.05) | 1268 | 1268 (0.28) |
| TACI 13-118 | 131 | 7811 | 7811 (1.81) | 8452 | 8452 (1.88) |

TABLE E2-continued

Bioactivity of Multi-Domain Immunomodulatory Proteins vs atacicept

| Description | SEQ ID NO | IC50 (nM) APRIL | IC50 (nM) APRIL (Δ TACI 30-110) | IC50 (nM) BAFF | IC50 (nM) BAFF (Δ TACI 30-110) |
|---|---|---|---|---|---|
| TACI 13-118, with K77E/F78Y/Y102D | | 848 | 848 (0.20) | 2048 | 2048 (0.46) |
| TACI 30-110 | | 4317 | 4317 (1.00) | 4490 | 4490 (1.00) |

Example 6: Comparative Evaluation of TACI vTD-Fcs in an In Vivo KLH Immunization Model This Example describes the assessment of exemplary tested single domain Fc fusion proteins (described in Example 1) to affect immune responses to keyhole limpet hemocyanin (KLH) in vivo in mice. The mouse KLH immunization model can be used to evaluate the effects of the immunomodulatory molecules on antigen-specific responses to the T cell-dependent antigen KLH, following either one or two injections of KLH. Two injections of KLH, each separated by at least 7 days, provides a model that can evaluate both a primary immune response following the $1^{st}$ KLH injection, and a secondary immune response in the period following the $2^{nd}$ injection. This Example describes a study that evaluated the activity of multiple TACI single domain-containing molecules, such as soluble wild-type (WT) or variant TACI vTDs formatted as Fc fusions, in response to two injections of KLH without adjuvant (on Study Day 0 and Day 12). These test articles were compared to administration of molar-matched levels of an Fc isotype control protein. Activity of test articles observed in the mouse KLH model can often predict their immunomodulatory effects in humans.

To begin the KLH study, 10-week old female C57/BL6NJ mice (The Jackson Laboratories, Sacramento, Calif.) were randomized into 12 groups of 5 mice each. Mice were administered 0.25 mg KLH (EMD Millipore, Cat. 374825-25MG) via intraperitoneal (IP) injection on Days 0 and 12; the original commercial stock solution of KLH was diluted to the appropriate concentration with Dulbecco's phosphate-buffered saline (DPBS) prior to injection. Mice were dosed with the test articles as outlined in Table E3 via IP injection (dosed on Days 4 and 11). Six mice remained untreated/uninjected as naïve controls (Group 13). Serum was collected on Day 5 (24 hr post-$1^{st}$ dose), Day 12 (24 hr post-$2^{nd}$ dose/pre-KLH boost), and Day 20 to evaluate drug exposure, ADA, and/or anti-KLH antibody levels. One animal in Group 10 received an incomplete dose of test article and was therefore removed from the study.

TABLE E3

Test Article Descriptions and Dose Regimen

| Group # | # of Mice | Test Article(s) | Dose Level (mg/dose) | (mg/kg) | Dose Schedule (D = Study Day) | Route of Delivery |
|---|---|---|---|---|---|---|
| 1 | 5 | Fc control | 0.225 | 11.3 | D 4 and D 11 | IP |
| 5 | 5 | TACI 30-110 - Fc | 0.306 | 15.3 | D 4 and D 11 | IP |
| 6 | 5 | TACI 13-118 - Fc | 0.327 | 16.4 | D 4 and D 11 | IP |
| 7 | 5 | 26 TACI CRD2-Fc | 0.271 | 13.6 | D 4 and D 11 | IP |
| 8 | 5 | 27 TACI CRD2-Fc | 0.271 | 13.6 | D 4 and D 11 | IP |
| 9 | 5 | 29 TACI CRD2-Fc | 0.272 | 13.6 | D 4 and D 11 | IP |
| 13 | 6 | None (naïve) | N/A | N/A | N/A | N/A |

N/A = not applicable

On Day 20, all mice were anesthetized with isoflurane and blood collected into serum separator tubes. Mice were sacrificed, and their spleens removed, weighed, and placed into DPBS on ice. Whole blood was centrifuged, and the serum removed and stored at −80° C. until analyzed for anti-KLH levels by enzyme-linked immunosorbent assay (ELISA). Spleens were processed to single cell suspensions, the red blood cells (RBC) lysed using RBC Lysis Buffer (Biolegend, Cat. 420301) according to the manufacturer's instructions, and the cells counted in each sample using dual-fluorescence viability, using acridine orange/propidium iodide (AO/PI) staining (Nexcelom, Cat. CS2-0106-5 mL).

Each spleen sample was then stained for flow cytometry analysis of immune cell subsets using the following method: $1 \times 10^6$ live cells were placed into a well of two 96-well plates (Corning, Cat. 3797; one plate for a B cell-specific panel and one for a T cell-specific panel), centrifuged at 1500×g for 10 seconds, the supernatant removed, and the cell pellet washed twice with DPBS. The pellets were resuspended in 100 µL of live-dead stain (LIVE/DEAD Fixable Aqua Dead Cell Stain Kit, Life Technologies Corp., 1:1000 dilution in DPBS) and incubated for 10 min in the dark at room temperature. Following two washes with flow cytometry buffer (175 µL each), tumor pellets were resuspended in Mouse BD Fc Block (diluted 1:50 with flow buffer), and incubated in the dark for an additional 5 min at RT. Without any additional washes, 50 µL of a cocktail of the following flow cytometry antibodies (diluted in flow cytometry buffer) were added to each well of cells for the B or T cell panels. For the B cell panel, the following antibodies were combined for the cocktail: anti-mouse CD19 BUV395 (clone 1D3, Becton-Dickinson; 1:100), anti-mouse CD138 BV421 (clone 281-2, BioLegend Inc.; 1:100, final concentration), anti-mouse CD3E BV510 (clone 17A2, BioLegend Inc.; 1:100, final concentration), anti-mouse IgD BV605 (clone 11-26c.2a, BioLegend Inc.; 1:100, final concentration), anti-mouse B220 BV785 (clone RA3-6B2, BioLegend Inc.; 1:100, final concentration), anti-mouse CD95 FITC (clone SA367H8, BioLegend Inc.; 1:100, final concentration), anti-mouse CD23 PerCP Cy5.5 (clone B3B4, BioLegend Inc.; 1:100, final concentration), anti-mouse GL7 PE (clone GL7, BioLegend Inc.; 1:100, final concentration), anti-mouse Gr1 PE Cy7 (clone RB6-8C5, BioLegend Inc.; 1:100, final concentration), anti-mouse CD21 APC (clone 7E9, BioLegend Inc.; 1:100, final concentration), and anti-mouse IgM APC Cy7 (clone RMM-1, BioLegend Inc.; 1:100, final concentration). For the T cell panel, the following antibodies were combined for the cocktail: anti-mouse PD-1 BV421 (clone 29F.1A12, BioLegend Inc.; 1:100, final concentration), anti-mouse CD11b BV510 (clone M1/70, BioLegend Inc.; 1:100, final concentration), anti-mouse CD3E BV605 (clone 145-2C11, BioLegend Inc.; 1:100, final concentration), anti-mouse CD8 BV785 (clone 53-6.7, BioLegend Inc.; 1:100, final concentration), anti-mouse CD44 FITC (clone IM7, BioLegend Inc.; 1:100, final concentration), anti-mouse CD4 PerCP Cy5.5 (clone GK1.5, BioLegend Inc.; 1:100, final concentration), anti-mouse CD62L PE (clone MEL-14, BioLegend Inc.; 1:100, final concentration), anti-mouse CXCR5 PE Dazzle (clone L138D7, BioLegend Inc.; 1:100, final concentration), anti-mouse CD25 PE Cy7 (clone PC61.5, BioLegend Inc.; 1:100, final concentration), and anti-mouse CD45 AF700 (clone 30-F11, BioLegend Inc.; 1:100, final concentration). The cells were incubated with one of the antibody cocktails in the dark, on ice, with gentle mixing for 45 min, followed by two washes with flow cytometry buffer (175 µL per wash). Cell pellets were resuspended in 200 µL flow cytometry buffer and collected on an LSRII flow cytometer. Data were analyzed using FlowJo software version 10.2 (FlowJo LLC, USA) and graphed using GraphPad Prism software (Version 8.1.2). Key cellular subset identification analysis included: total B cells ($B220^+$ cells), marginal zone (MZ) B cells ($B220^+$, $CD19^+$, $CD23^-$, $CD21^{high}$, $IgM^{high}$ cells), germinal center (GC) B cells ($B220^+$, $CD19^+$, $GL7^+$, $CD95^+$ cells), T follicular helper (Tfh) cells ($CD45^+$, $CD3^+$, $CD4^+$, $PD-1^+$, $CD185^+$ cells), CD4+T effector memory ($T_{em}$) cells ($CD45^+$, $CD3^+$, $CD4^+$, $CD44^+$, $CD62L^-$ cells), and $CD8^+$ $T_{em}$ cells ($CD45^+$, $CD3^+$, $CD8^+$, $CD44^+$, $CD62L^-$ cells).

Statistically significant differences ($p<0.05$) between groups were determined by one-way analysis of variance (ANOVA) and uncorrected Fisher's Least Significant Difference (LSD) multiple comparison test using GraphPad Prism software (Version 8.1.2).

Figures 10A, 10B:
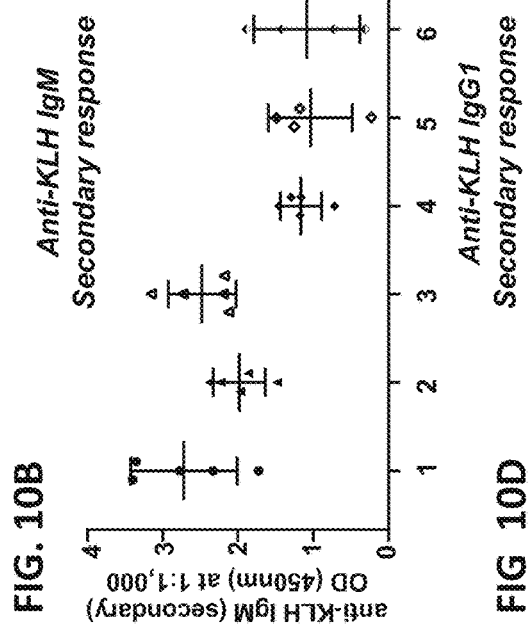
FIGS. 10A-10D show analysis of parameters assessed murine keyhole limpet hemocyanin (KLH) model. Serum-KLH IgM OD levels were assessed as primary response (FIG. 10A) and secondary response (FIG. 10B). Similarly, serum anti-KLH IgG1 OD levels were assessed as both primary response (FIG. 10C) and secondary response (FIG. 10D).
Figures 10C, 10D:
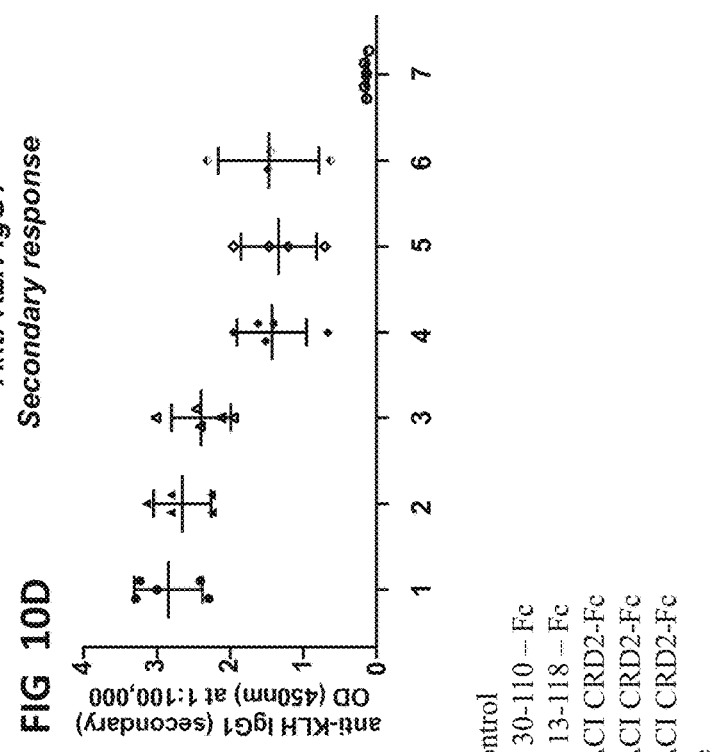

To determine the extent to which the test articles inhibited KLH-mediated antibody immune responses compared to an Fc isotype control (SEQ ID NO:73), serum samples were evaluated for concentrations of anti-KLH antibodies in two ELISA assays. The ELISA assays measured either IgM- or IgG1-specific anti-KLH levels in the serum. Mouse serum samples at numerous dilutions were incubated in plates coated with KLH, followed by washes and detection with 1:2000 goat anti-mouse IgG1:HRP or 1:5000 goat anti-mouse IgM:HRP. Color development was achieved using a TMB Substrate Kit (SeraCare) and the ELISA plates analyzed on a plate reader (SpectraMax® iD3 Microplate Reader, Molecular Devices LLC). There was no standard curve for the assay, thus optical density (OD) was used to compare the levels of anti-KLH antibodies; the higher the OD, the greater the levels of anti-KLH antibodies in the serum sample. For anti-KLH IgM OD levels, data are presented in FIG. 10A (primary response), FIG. 10B (secondary response) and statistical analysis by 1-way ANOVA and uncorrected Fisher's LSD multiple comparison test presented in Table E4 and Table E5, respectively. Anti-KLH IgG1 OD levels are presented in FIG. 10C (primary response), FIG. 10D (secondary response) and statistical analysis by 1-way ANOVA and uncorrected Fisher's LSD multiple comparison test presented in Table E6 and Table E7. Results demonstrate that each of the test articles were able to significantly reduce anti-KLH IgM levels in serum during the primary immune response compared to Fc control treatment, with 29 TACI-CRD2-Fc(SEQ ID NO: 29) demonstrating the largest reductions amongst all test articles, and TACI 30-110-Fc and TACI 13-118-Fc treatment having the most modest effect (FIG. 10A). For the secondary response on Day 20, measured 9 days after the $2^{nd}$ and last dose of test article, all test articles except TACI 13-118-Fc induced significant reductions in anti-KLH IgM levels, with all test articles except TACI 30-110-Fc, TACI 13-118-Fc demonstrating reduction (FIG. 10B). Each of the test articles were also able to significantly reduce anti-KLH IgG1 levels during the primary immune response compared to Fc control, with all test articles except TACI 30-110-Fc, TACI 13-118-Fc again demonstrating the greatest reductions (FIG. 10C). For the secondary response to KLH, all test articles except TACI 30-110-Fc, TACI 13-118-Fc, significantly reduced levels of anti KLH IgG1 (FIG. 10D). These results indicate that most of the molecules containing the TACI vTD were efficacious at reducing the T cell-dependent antibody immune response to KLH, with 26 TACI CRD2-Fc, 27 TACI CRD2-Fc, and 29 TACI CRD2-Fc, exhibiting the most significant effects in this mouse immunization model.

TABLE E4

Statistical Analysis of anti-KLH IgM OD levels (primary response; FIG. 10A)

| Comparison | p-value | Significant? |
|---|---|---|
| Fc Control vs. TACI 30-110 - Fc | <0.0001 | Yes |
| Fc Control vs. TACI 13-118 - Fc | <0.0001 | Yes |
| Fc Control vs. 26 TACI CRD2-Fc | <0.0001 | Yes |
| Fc Control vs. 27 TACI CRD2-Fc | <0.0001 | Yes |
| Fc Control vs. 29 TACI CRD2-Fc | <0.0001 | Yes |
| Fc Control vs. Naive | <0.0001 | Yes |

TABLE E5

Statistical Analysis of anti-KLH IgM OD levels (secondary response; FIG. 10B)

| Comparison | p-value | Significant? |
|---|---|---|
| Fc Control vs. TACI 30-110 - Fc | 0.0283 | Yes |
| Fc Control vs. TACI 13-118 - Fc | 0.4653 | No |
| Fc Control vs. 26 TACI CRD2-Fc | <0.0001 | Yes |
| Fc Control vs. 27 TACI CRD2-Fc | <0.0001 | Yes |
| Fc Control vs. 29 TACI CRD2-Fc | <0.0001 | Yes |
| Fc Control vs. Naive | <0.0001 | Yes |

TABLE E6

Statistical Analysis of anti-KLH IgG1 OD levels (primary response; FIG. 10C)

| Comparison | p-value | Significant? |
|---|---|---|
| Fc Control vs. TACI 30-110 - Fc | 0.0218 | Yes |
| Fc Control vs. TACI 13-118 - Fc | 0.0093 | Yes |
| Fc Control vs. 26 TACI CRD2-Fc | 0.0012 | Yes |
| Fc Control vs. 27 TACI CRD2-Fc | 0.0002 | Yes |
| Fc Control vs. 29 TACI CRD2-Fc | <0.0001 | Yes |
| Fc Control vs. Naive | <0.0001 | Yes |

TABLE E7

Statistical Analysis of anti-KLH IgG1 OD levels (secondary response; FIG. 10D)

| Comparison | p-value | Significant? |
|---|---|---|
| Fc Control vs. TACI 30-110 - Fc | 0.5367 | No |
| Fc Control vs. TACI 13-118 - Fc | 0.1477 | No |
| Fc Control vs. 26 TACI CRD2-Fc | <0.0001 | Yes |
| Fc Control vs. 27 TACI CRD2-Fc | <0.0001 | Yes |
| Fc Control vs. 29 TACI CRD2-Fc | <0.0001 | Yes |
| Fc Control vs. Naive | <0.0001 | Yes |

Figures 11A, 11B:
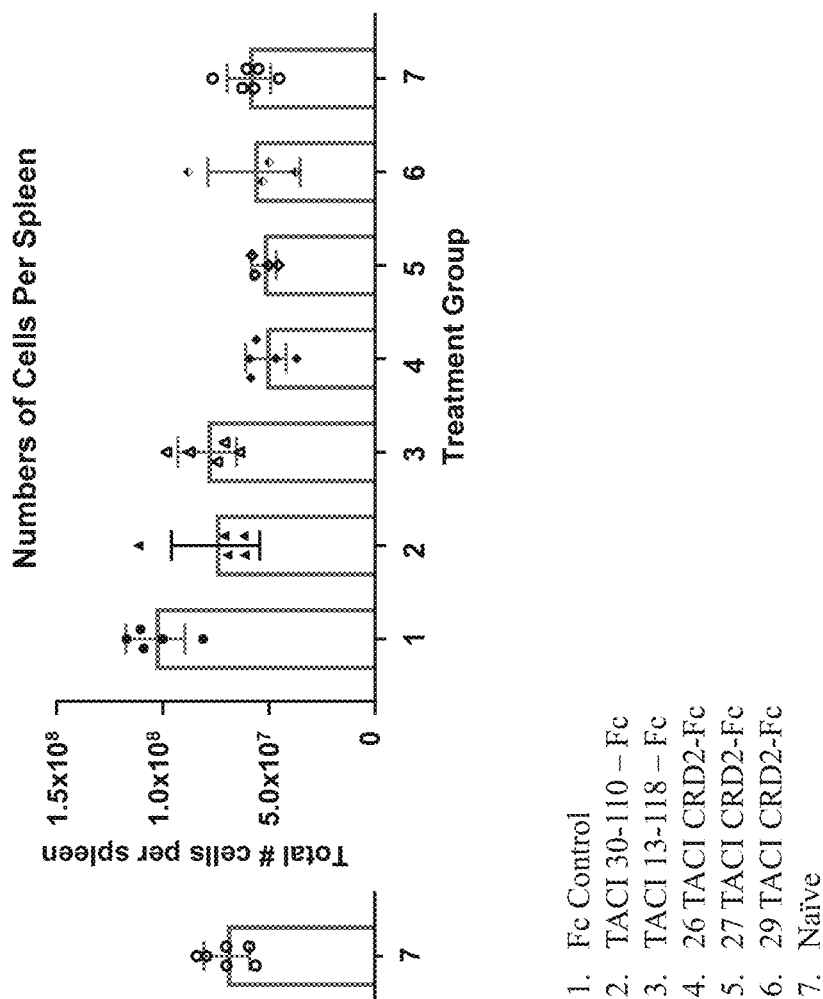
FIGS. 11A-11B shown analysis of harvested spleen assessed from the murine keyhole limpet hemocyanin (KLH) immunization model. Spleens were processed and analyzed by weight (FIG. 11A) as well as total cell number (FIG. 11B).

As shown in FIGS. 11A and 11B, mice treated with all test articles except TACI 30-110-Fc or TACI 13-118-Fc had significantly smaller spleens as assessed by weight and cell number, respectively, at the end of the study (Day 20) compared to Fc control-treated mice (Table E8). Mice treated with each of the test articles also had significantly fewer spleen cells than the Fc control group. The smaller spleens are indicative of reductions in lymphocytes, which can have immunomodulatory effects on the pathogenesis of autoimmune and inflammatory diseases associated with heightened immune responses, particularly those driven by B and/or T cells. Statistical analyses of spleen weights and total cell numbers are shown in Table E8 and Table E9, respectively.

TABLE E8

Statistical Comparisons Across All Treatment Groups for Spleen Weights (FIG. 11A):

| Treatment Group | Fc control | TACI 30-110 - Fc | TACI 13-118 - Fc | 541 TACI CRD2-Fc | 27 TACI CRD2-Fc | 29 TACI CRD2-Fc |
|---|---|---|---|---|---|---|
| TACI 30-110 - Fc | ns | | | | | |
| TACI 13-118 - Fc | ns | ns | | | | |
| 26 TACI CRD2-Fc | 0.0062 | 0.0172 | 0.0319 | | | |
| 27 TACI CRD2-Fc | 0.0097 | 0.0261 | 0.0469 | ns | | |
| 29 TACI CRD2-Fc | 0.0181 | 0.0435 | ns | ns | ns | |
| Naive | 0.041 | ns | ns | ns | ns | ns |

TABLE E9

Statistical Comparisons Across All Treatment Groups for Splenic Cell Numbers (FIG. 11B)

| Treatment Group | Fc control | TACI 30-110 - Fc | TACI 13-118 - Fc | 26 TACI CRD2-Fc | 27 TACI CRD2-Fc | 29 TACI CRD2-Fc |
|---|---|---|---|---|---|---|
| TACI 30-110 - Fc | 0.0022 | | | | | |
| TACI 13-118 - Fc | 0.0079 | ns | | | | |
| 26 TACI CRD2-Fc | <0.0001 | 0.0099 | 0.0029 | | | |
| 27 TACI CRD2-Fc | <0.0001 | 0.004 | 0.0011 | ns | | |
| 29 TACI CRD2-Fc | <0.0001 | ns | 0.0227 | ns | ns | |
| Naive | <0.0001 | ns | 0.0241 | ns | ns | ns |

Figure 12:
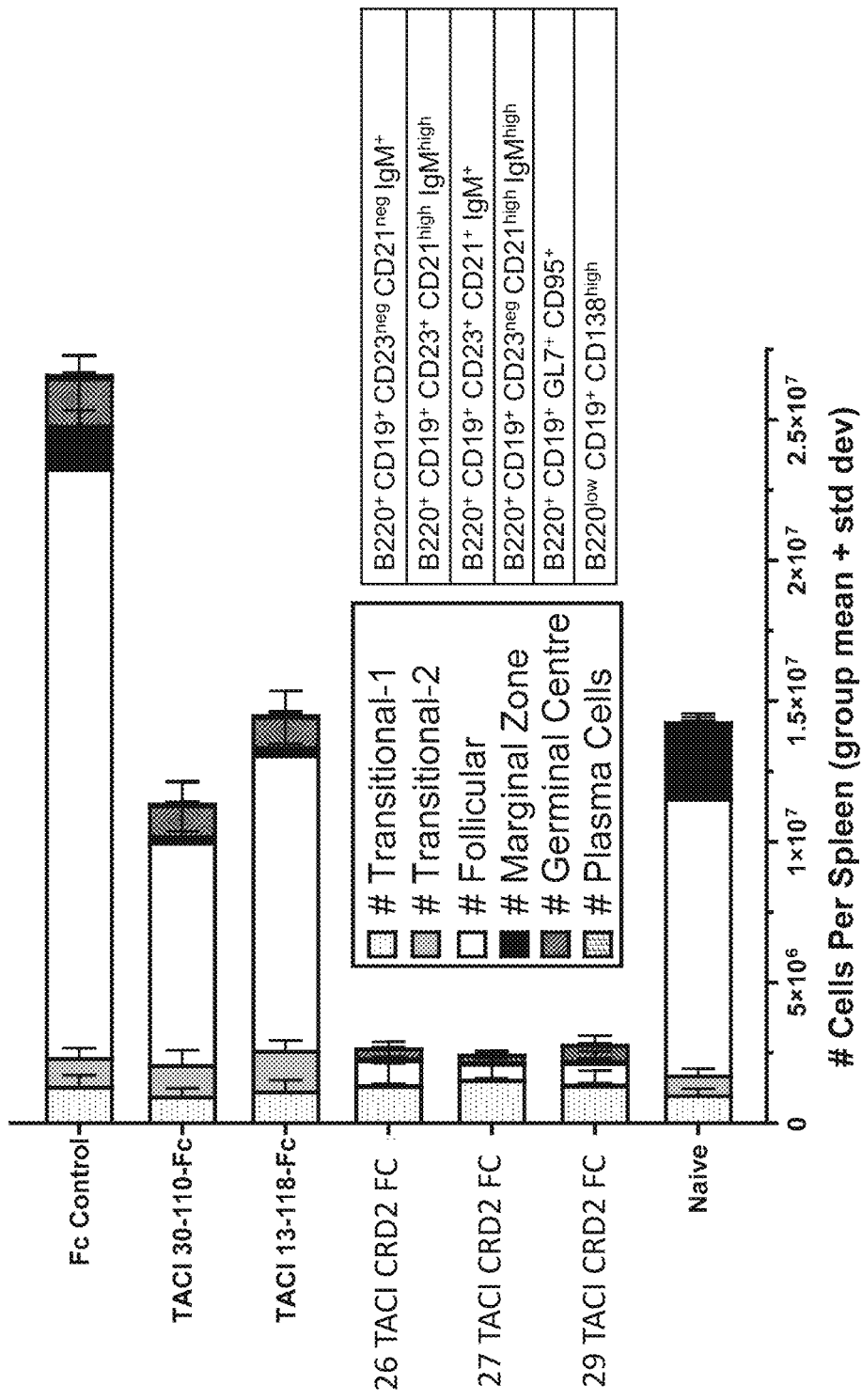
FIG. 12 depicts analysis of spleens assessed for cellular subtype population makeup from the murine keyhole limpet hemocyanin (KLH) model and shows results of B cell subset numbers relative to the group mean.
Figure 13:
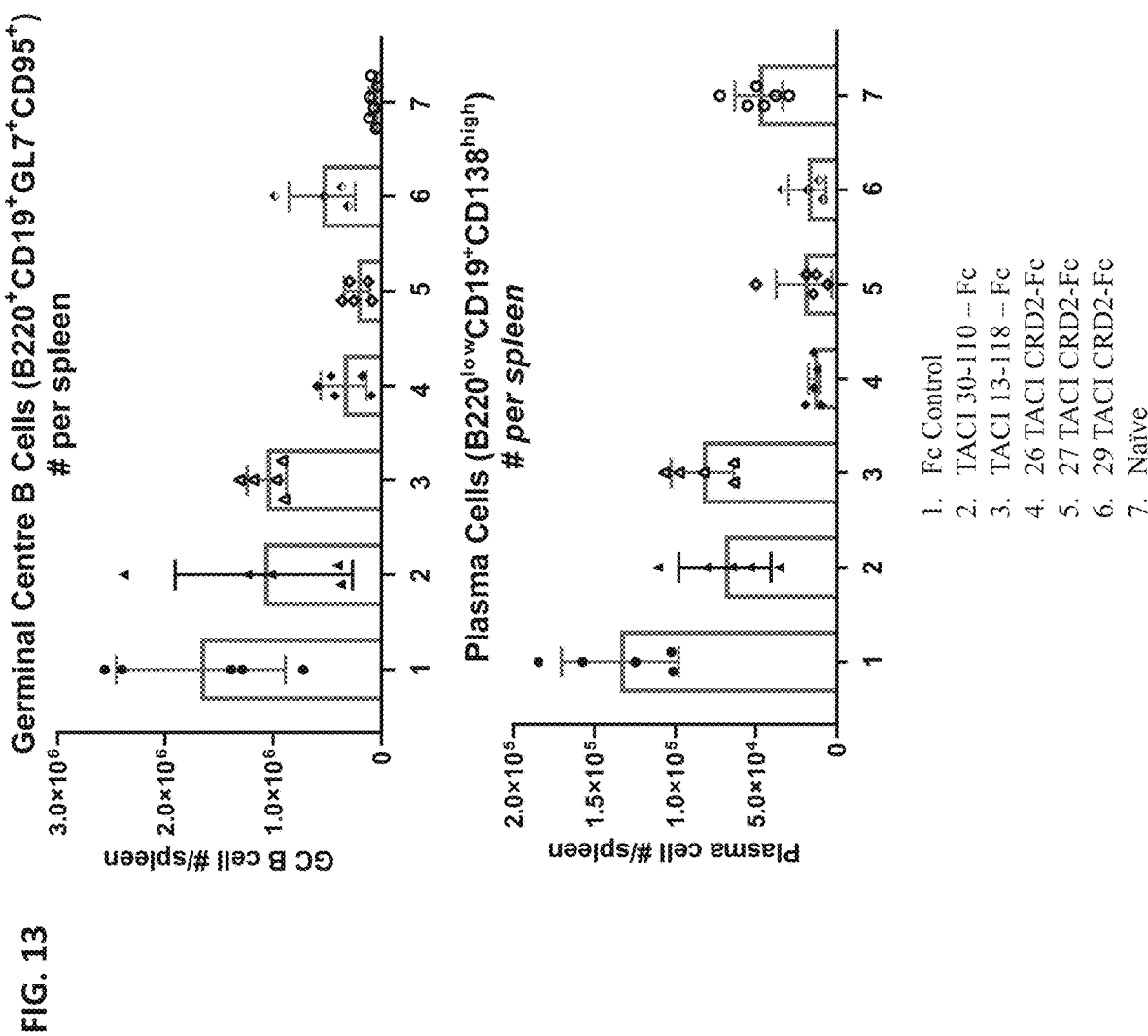
FIG. 13 depicts analysis of spleens assessed for cellular subtype phenotype makeup from the murine keyhole limpet hemocyanin (KLH) model and shows results for numbers of germinal center B cells and plasma cells (FIG. 13).

Of particular importance to the pathogenesis of autoimmune and inflammatory diseases are cell types that promote B cell survival and differentiation, antibody production, and T cell effector memory. These cell types include, but are not limited to, the following: total B cells, marginal zone (MZ) B cells, germinal center (GC) B cells, T follicular helper (Tfh) cells, and CD4$^+$ and CD8+T effector memory (T$_{em}$) cells. Therapeutics whose mechanisms of action include reducing these cell types would be anticipated to be efficacious in the treatment of numerous autoantibody-mediated diseases. Treatment with any of the TACI vTD-Fc test articles substantially reduced the numbers of multiple splenic B cell subsets compared to the remaining treatment groups, including impacts on transitional-2 (B220$^+$ CD19$^+$ CD23$^+$ CD21$^{high}$ IgM$^{high}$), follicular (B220$^+$ CD19$^+$ CD23$^+$ CD21$^+$ IgM$^+$), marginal zone (B220$^+$ CD19$^+$ CD23$^{neg}$ CD21$^{high}$ IgM$^{high}$) germinal centre (B220$^+$ CD19$^+$ GL7$^+$ CD95$^+$), and plasma cells (B220$^{low}$ CD19$^+$ CD138$^{high}$) (FIG. 12 and FIG. 13). These TACI vTD-molecules were as effective or better than the two WT TACI-Fc molecules (TACI 13-188-Fc and TACI 30-110-Fc) in their ability to reduce the percentage (not shown) or numbers of these populations that are important in B cell survival and differentiation and antibody production. Statistical analyses from flow cytometry data of Day 20 splenocytes are shown in Tables E10-E28.

Figure 14A:
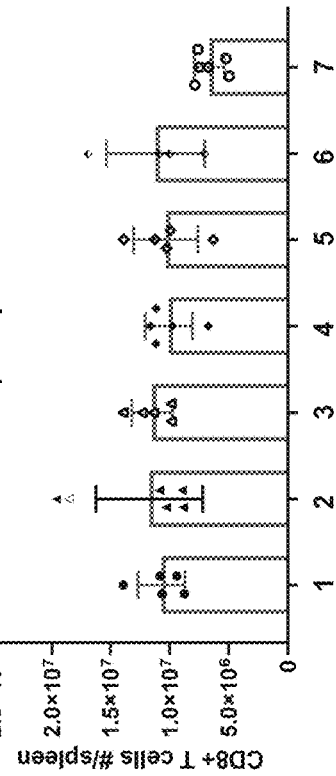
FIGS. 14A-D depict T cell numbers in the murine keyhole limpet hemocyanin (KLH) model. The splenic CD3+, CD8+, CD4+ and Follicular Helper T cells are depicted in FIG. 14A, FIG. 14B, FIG. 14C, and FIG. 14D, respectively.
Figure 14B:
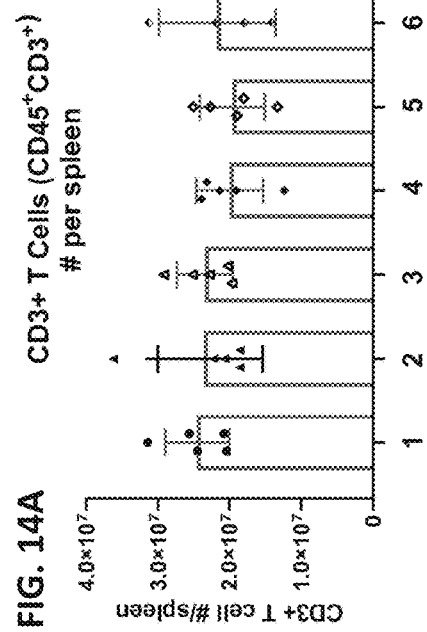
Figure 14C:
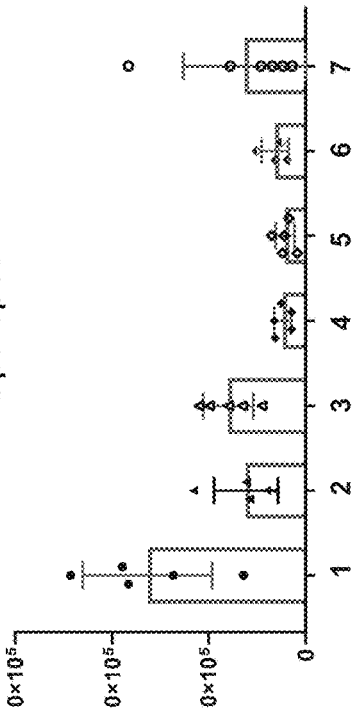
Figure 14D:
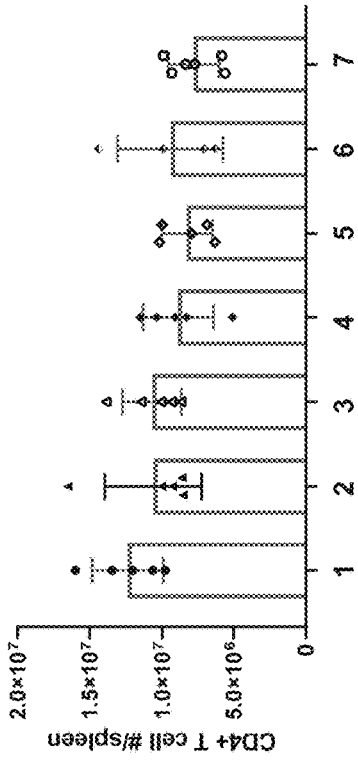
Figure 15:
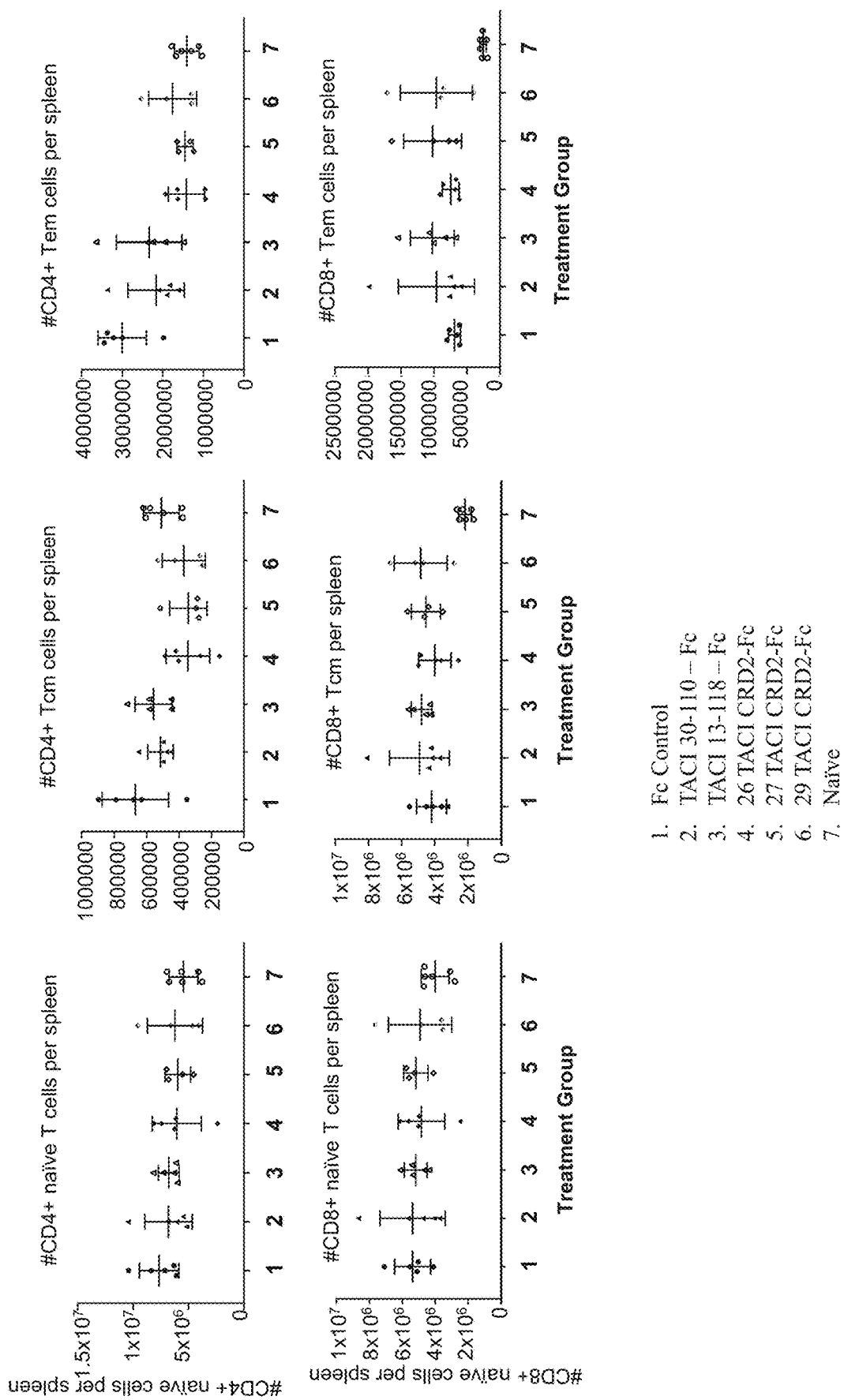
FIG. 15 depicts Tcm and Tem cellular populations in the murine keyhole limpet hemocyanin (KLH) model.

The splenic CD3+, CD4+, or CD8+ T cell populations were largely unaffected by the 6 TACI vTD-containing test articles. compared to the Fc control group (FIG. 14A-C), and Tcm and Tem memory T cells compared to the Fc control group, were unaffected (FIG. 15). As compared to the Fc control, all of the test articles reduced the numbers of follicular helper T cells (CD45$^+$, CD3$^+$, CD4$^+$, PD-1$^+$, CD185$^+$), which interact with B cells in the germinal center and are important contributors to T cell-dependent antibody responses (FIG. 14D).

TABLE E10

Statistical Analysis of Splenic B Cell Subsets-Cell Numbers vs. Fc Control Group (FIG. 12)

| Comparison | T1 B cells | T2 B cells | Follic B cells | Marginal Zone B cells | GC B cells | Plasma Cells |
|---|---|---|---|---|---|---|
| Fc Control vs. TACI 30-110 - Fc | 0.2738 | 0.4820 | <0.0001 | <0.0001 | 0.0152 | <0.0001 |
| Fc Control vs. TACI 13-118 - Fc | 0.5942 | 0.0045 | <0.0001 | <0.0001 | 0.0115 | 0.0012 |
| Fc Control vs. 26 TACI CRD2-Fc | 0.9402 | <0.0001 | <0.0001 | <0.0001 | <0.0001 | <0.0001 |
| Fc Control vs. 27 TACI CRD2-Fc | 0.4679 | <0.0001 | <0.0001 | <0.0001 | <0.0001 | <0.0001 |
| Fc Control vs. 29 TACI CRD2-Fc | 0.9061 | <0.0001 | <0.0001 | <0.0001 | <0.0001 | <0.0001 |
| Fc Control vs. Naive | 0.2333 | 0.0241 | | <0.0001 | <0.0001 | <0.0001 |

TABLE E11

Statistical Analysis of Splenic T Cell Subsets-Cell Numbers vs. Fc Control Group (FIG. 14A-14D)

| Comparison | CD3+ T cells | CD8+ T cells | CD4+ T cells | CD4+ Tfh cells |
|---|---|---|---|---|
| Fc Control vs. TACI 30-110 - Fc | 0.7623 | 0.5177 | 0.2474 | <0.0001 |
| Fc Control vs. TACI 13-118 - Fc | 0.7210 | 0.6151 | 0.2739 | 0.0001 |
| Fc Control vs. 26 TACI CRD2-Fc | 0.1513 | 0.6863 | 0.0261 | <0.0001 |
| Fc Control vs. 27 TACI CRD2-Fc | 0.1209 | 0.8049 | 0.0095 | <0.0001 |
| Fc Control vs. 29 TACI CRD2-Fc | 0.4042 | 0.7596 | 0.0728 | <0.0001 |
| Fc Control vs. Naive | 0.0038 | 0.0086 | 0.0029 | <0.0001 |

TABLE E12

Statistical Analysis of Splenic T Cell Subsets-Cell Numbers vs. Fc Control Group (FIG. 15)

| Comparison | Naïve CD4+ T cells | CD4+ Tcm cells | CD4+ Tem cells | Naïve CD8+ T cells | CD8+ Tcm cells | CD8+ Tem cells |
|---|---|---|---|---|---|---|
| Fc Control vs. TACI 30-110 - Fc | 0.4484 | 0.0695 | 0.0088 | 0.9952 | 0.2531 | 0.1411 |
| Fc Control vs. TACI 13-118 - Fc | 0.4336 | 0.1831 | 0.0355 | 0.8153 | 0.3456 | 0.0729 |
| Fc Control vs. 26 TACI CRD2-Fc | 0.1548 | 0.0003 | <0.0001 | 0.5016 | 0.7516 | 0.7624 |
| Fc Control vs. 27 TACI CRD2-Fc | 0.0824 | <0.0001 | <0.0001 | 0.5055 | 0.8187 | 0.2444 |
| Fc Control vs. 29 TACI CRD2-Fc | 0.2292 | 0.0015 | 0.0004 | 0.5929 | 0.3311 | 0.1632 |
| Fc Control vs. Naive | 0.0433 | 0.0516 | <0.0001 | 0.0782 | 0.0016 | 0.0166 |

TABLE E13

Statistical Comparisons Across All Treatment Groups for Numbers of T1 B Cells

| Treatment Group | Fc control | TACI 30-110 - Fc | TACI 13-118 - Fc | 26 TACI CRD2-Fc | 27 TACI CRD2-Fc | 29 TACI CRD2-Fc |
|---|---|---|---|---|---|---|
| TACI 30-110 - Fc | ns | | | | | |
| TACI 13-118 - Fc | ns | ns | | | | |
| 26 TACI CRD2-Fc | ns | ns | ns | | | |
| 27 TACI CRD2-Fc | ns | ns | ns | ns | | |
| 29 TACI CRD2-Fc | ns | ns | ns | ns | ns | |
| Naive | ns | ns | ns | ns | ns | ns |

TABLE E14

Statistical Comparisons Across All Treatment Groups for Numbers of T2 B cells

| Treatment Group | Fc control | TACI 30-110 - Fc | TACI 13-118 - Fc | 26 TACI CRD2-Fc | 27 TACI CRD2-Fc | 29 TACI CRD2-Fc |
|---|---|---|---|---|---|---|
| TACI 30-110 - Fc | ns | | | | | |
| TACI 13-118 - Fc | 0.0042 | 0.0268 | | | | |
| 26 TACI CRD2-Fc | <0.0001 | <0.0001 | <0.0001 | | | |
| 27 TACI CRD2-Fc | <0.0001 | <0.0001 | <0.0001 | ns | | |
| 29 TACI CRD2-Fc | <0.0001 | <0.0001 | <0.0001 | ns | ns | |
| Naive | 0.0231 | 0.0033 | <0.0001 | <0.0001 | <0.0001 | <0.0001 |

TABLE E15

Statistical Comparisons Across All Treatment Groups for Numbers of Follicular B Cells

| Treatment Group | Fc control | TACI 30-110 - Fc | TACI 13-118 - Fc | 26 TACI CRD2-Fc | 27 TACI CRD2-Fc | 29 TACI CRD2-Fc |
|---|---|---|---|---|---|---|
| TACI 30-110 - Fc | <0.0001 | | | | | |
| TACI 13-118 - Fc | <0.0001 | ns | | | | |
| 26 TACI CRD2-Fc | <0.0001 | <0.0001 | <0.0001 | | | |
| 27 TACI CRD2-Fc | <0.0001 | <0.0001 | <0.0001 | ns | | |
| 29 TACI CRD2-Fc | <0.0001 | <0.0001 | <0.0001 | ns | ns | |
| Naive | <0.0001 | ns | ns | <0.0001 | <0.0001 | <0.0001 |

TABLE E16

Statistical Comparisons Across All Treatment Groups for Numbers of Marginal Zone B Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | <0.0001 | | | | | |
| TACI 13-118-Fc | <0.0001 | ns | | | | |
| 26 TACI CRD2-Fc | <0.0001 | ns | ns | | | |

TABLE E16-continued

Statistical Comparisons Across All Treatment Groups for Numbers of Marginal Zone B Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| 27 TACI CRD2-Fc | <0.0001 | ns | ns | ns | | |
| 29 TACI CRD2-Fc | <0.0001 | ns | ns | ns | ns | |
| Naive | <0.0001 | <0.0001 | <0.0001 | <0.0001 | <0.0001 | <0.0001 |

TABLE E17

Statistical Comparisons Across All Treatment Groups for Numbers of Germinal Centre B Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | 0.0182 | | | | | |
| TACI 13-118-Fc | 0.0139 | ns | | | | |
| 26 TACI CRD2-Fc | <0.0001 | 0.0036 | 0.0049 | | | |
| 27 TACI CRD2-Fc | <0.0001 | 0.0008 | 0.0011 | ns | | |
| 29 TACI CRD2-Fc | <0.0001 | 0.0403 | ns | ns | ns | |
| Naive | <0.0001 | <0.0001 | <0.0001 | ns | ns | 0.0601 |

TABLE E18

Statistical Comparisons Across All Treatment Groups for Numbers of Plasma Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | <0.0001 | | | | | |
| TACI 13-118-Fc | 0.0016 | ns | | | | |
| 26 TACI CRD2-Fc | <0.0001 | 0.0007 | <0.0001 | | | |
| 27 TACI CRD2-Fc | <0.0001 | 0.0024 | 0.0001 | ns | | |
| 29 TACI CRD2-Fc | <0.0001 | 0.0028 | 0.0002 | ns | ns | |
| Naive | <0.0001 | ns | 0.0211 | 0.0236 | ns | ns |

TABLE E19

Statistical Comparisons Across All Treatment Groups for Numbers of CD3+ T Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | ns | ns | ns | | | |
| 27 TACI CRD2-Fc | ns | ns | ns | ns | | |
| 29 TACI CRD2-Fc | ns | ns | ns | ns | ns | |
| Naive | 0.0038 | 0.0089 | 0.0104 | ns | ns | ns |

TABLE E20

Statistical Comparisons Across All Treatment Groups for Numbers of CD4+ T Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | 0.0261 | ns | ns | | | |
| 27 TACI CRD2-Fc | 0.0095 | ns | ns | ns | | |

TABLE E20-continued

Statistical Comparisons Across All Treatment Groups for Numbers of CD4+ T Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| 29 TACI CRD2-Fc | ns | ns | ns | ns | ns | |
| Naive | 0.0029 | 0.062 | ns | ns | ns | ns |

TABLE E21

Statistical Comparisons Across All Treatment Groups for Numbers of CD8+ T Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | ns | ns | ns | | | |
| 27 TACI CRD2-Fc | ns | ns | ns | ns | | |
| 29 TACI CRD2-Fc | ns | ns | ns | ns | ns | |
| Naive | 0.023 | 0.0051 | 0.0072 | ns | 0.0387 | 0.0167 |

TABLE E22

Statistical Comparisons Across All Treatment Groups for Numbers of Follicular Helper T Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | <0.0001 | | | | | |
| TACI 13-118-Fc | 0.0001 | ns | | | | |
| 26 TACI CRD2-Fc | <0.0001 | ns | 0.0078 | | | |
| 27 TACI CRD2-Fc | <0.0001 | ns | 0.0058 | ns | | |
| 29 TACI CRD2-Fc | <0.0001 | ns | 0.0293 | ns | ns | |
| Naive | <0.0001 | ns | ns | 0.0472 | 0.036 | ns |

TABLE E23

Statistical Comparisons Across All Treatment Groups for Numbers of Naïve CD4+ T Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | ns | ns | ns | | | |
| 27 TACI CRD2-Fc | ns | ns | ns | ns | | |
| 29 TACI CRD2-Fc | ns | ns | ns | ns | ns | |
| Naive | 0.0433 | ns | ns | ns | ns | ns |

TABLE E24

Statistical Comparisons Across All Treatment Groups for Numbers of CD4+ Tcm Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | 0.0003 | 0.0488 | 0.0148 | | | |
| 27 TACI CRD2-Fc | <0.0001 | 0.0206 | 0.0056 | ns | | |
| 29 TACI CRD2-Fc | 0.0015 | ns | 0.0415 | ns | ns | |
| Naive | ns | ns | ns | 0.0453 | 0.0183 | ns |

TABLE E25

Statistical Comparisons Across All Treatment Groups for Numbers of CD4+ Tem Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | 0.0088 | | | | | |
| TACI 13-118-Fc | 0.0355 | ns | | | | |
| 26 TACI CRD2-Fc | <0.0001 | 0.0188 | 0.0043 | | | |
| 27 TACI CRD2-Fc | <0.0001 | 0.0094 | 0.002 | ns | | |
| 29 TACI CRD2-Fc | 0.0004 | ns | ns | ns | ns | |
| Naive | <0.0001 | 0.0128 | 0.0026 | ns | ns | ns |

TABLE E26

Statistical Comparisons Across All Treatment Groups for Numbers of Naïve CD8+ T Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | ns | ns | ns | | | |
| 27 TACI CRD2-Fc | ns | ns | ns | ns | | |
| 29 TACI CRD2-Fc | ns | ns | ns | ns | ns | |
| Naive | ns | ns | ns | ns | ns | ns |

TABLE E27

Statistical Comparisons Across All Treatment Groups for Numbers of CD8+ Tcm Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | ns | ns | ns | | | |
| 27 TACI CRD2-Fc | ns | ns | ns | ns | | |
| 29 TACI CRD2-Fc | ns | ns | ns | ns | ns | |
| Naive | 0.0016 | <0.0001 | <0.0001 | 0.0041 | 0.0032 | 0.0001 |

TABLE E28

Statistical Comparisons Across All Treatment Groups for Numbers of CD8+ Tem Cells

| Treatment Group | Fc control | TACI 30-110-Fc | TACI 13-118-Fc | 26 TACI CRD2-Fc | 27 TACI CRD2-Fc | 29 TACI CRD2-Fc |
|---|---|---|---|---|---|---|
| TACI 30-110-Fc | ns | | | | | |
| TACI 13-118-Fc | ns | ns | | | | |
| 26 TACI CRD2-Fc | ns | ns | ns | | | |
| 27 TACI CRD2-Fc | ns | ns | ns | ns | | |
| 29 TACI CRD2-Fc | ns | ns | ns | ns | ns | |
| Naive | 0.0166 | 0.0002 | <0.0001 | 0.0073 | 0.0005 | 0.0004 |

Together, these results indicate that TACI vTD-containing single domain Fc fusion molecules, that inhibit B and/or T cell activity can reduce immune responses and cell subset changes mediated by the T cell-dependent antigen KLH in vivo (i.e. anti-KLH levels in serum and changes in immune cell subsets). These results are consistent with the evaluation of the single TACI domain B cell inhibitory molecules, as clinical therapeutics in the treatment of autoimmune and inflammatory diseases in which hyperactive lymphocytes play a role.

Example 7. Bioactivity Assessment of TACI Blockade of TACI-Mediated Stimulation by TACI-Containing Molecules Additional TACI vTD were generated containing one or more mutations present in exemplary TACI vTDs set forth in SEQ ID NO:26 (K77E, F78Y, Y102D), SEQ ID NO:27 (Q75E, R84Q) or SEQ ID NO: 29 (K77E, A101D, Y102D). Single, double, and triple mutations containing combinations of mutations from Q75E, K77E, F78Y, R84Q, A101D and Y102D were generated. The resulting TACI vTDs were further formatted as a TACI vTD-Fc fusion protein with an Fc domain. The exemplary generated Fc fusion proteins were generated substantially as described in Example 1. Briefly, to generate recombinant immunomodulatory proteins as Fc fusion proteins, the encoding DNA was generated to encode a protein as follows: variant TACI domain followed by a linker of 7 amino acids (GSGGGGS; SEQ ID NO: 74) followed by a human IgG1 effectorless Fc sequence containing the mutations L234A, L235E and G237A, by the Eu Index numbering system for immunoglobulin proteins (SEQ ID NO:73). For comparison, the following molecules also were tested: (1) WT TACI (68-110)-Fc (TACI 68-110, SEQ ID NO: 13, TACI-Fc SEQ ID NO: 171); and (2) a TACI-Fc with exemplary mutations K77E, F78Y and Y102D introduced into the reference TACI ECD 13-118, which was fused to the exemplary Fc sequence set forth in SEQ ID NO:73; see Example 5. Additional controls included: (3) WT TACI (13-118)-Fc (TACI 13-118, SEQ ID NO:131; corresponding to the TACI ECD portion in telitacicept); (4) WT TACI (30-110)-Fc (TACI 30-110, SEQ ID NO:130; corresponding to the TACI ECD portion in atacicept, SEQ ID NO:132); (5) BAFF-R ECD and (6)belimumab The generated molecules were assessed for blockade of APRIL or BAFF-mediated ligand signaling via the TACI receptor in Jurkat/NF-κB/TACI cells substantially as described in Example 2. Exemplary TACI vTD-Fc molecules were titrated from 100,000-6 pM and mixed with 30 nM human APRIL or 10 nM human BAFF, 30 minutes prior to addition of Jurkat/NF-kB/TACI cells. APRIL or BAFF-mediated ligand signaling was quantitated by monitoring luciferase production in the cells.

The results are summarized as the half maximal inhibitory concentration (IC50) of exemplary tested molecules in Table E29. The percent change in IC50 compared to the reference control WT TACI (68-110)-Fc (TACI 68-110, SEQ ID NO: 13, TACI-Fc SEQ ID NO: 171) is indicated in parentheses (ΔWT). Similar to results depicted above, the wild-type minimal CRD2 WT TACI (68-110)-Fc exhibited superior blockade of APRIL and BAFF compared to other tested control molecules, including those with sequences similar to telitacicept and atacicept. As indicated, certain mutations and combinations of mutations were associated with a further substantial increase in the ability to block APRIL or BAFF mediated ligand signaling. Together, the results show the ability of TACI vTD molecules to block APRIL and BAFF TACI-mediated ligand signaling.

TABLE E29

Exemplary TACI vTD-Fc

| SEQ ID NO | Mutations | APRIL IC$_{50}$ (pM) (ΔWT) | BAFF IC$_{50}$ (pM) (ΔWT) |
|---|---|---|---|
| 26 | K77E, F78Y, Y102D | 9209 (0.75) | 1552 (0.84) |
| 27 | Q75E, R84Q | 11832 (0.96) | 1461 (0.79) |
| 29 | K77E, A101D, Y102D | 2914 (0.24) | 1184 (0.64) |
| 177 | Q75E | 1938 (0.16) | 1457 (0.79) |
| 32 | K77E | 159 (0.01) | 1537 (0.83) |
| 183 | F78Y | 176 (0.01) | 1638 (0.88) |
| 30 | R84Q | 566 (0.05) | 5493 (2.96) |
| 23 | A101D | 8382 (0.68) | 1827 (0.99) |
| 190 | Y102D | 11601 (0.94) | 1863 (1.00) |
| 178 | Q75E, K77E | 10709 (0.87) | 1888 (1.02) |
| 179 | Q75E, F78Y | 13431 (1.09) | 1793 (0.97) |
| 180 | Q75E, A101D | 19999 (1.62) | 2357 (1.27) |

TABLE E29-continued

Exemplary TACI vTD-Fc

| SEQ ID NO | Mutations | APRIL IC$_{50}$ (pM) (ΔWT) | BAFF IC$_{50}$ (pM) (ΔWT) |
|---|---|---|---|
| 181 | Q75E, Y102D | 11096 (0.90) | 2147 (1.16) |
| 191 | K77E, F78Y | 10110 (0.82) | 1966 (1.06) |
| 24 | K77E, R84Q | 4256 (0.35) | 2258 (1.22) |
| 25 | K77E, A101D | 2039 (0.17) | 1957 (1.06) |
| 192 | K77E, Y102D | 891 (0.07) | 2178 (1.17) |
| 184 | F78Y, R84Q | 2623 (0.21) | 2260 (1.22) |
| 185 | F78Y, A101D | 2015 (0.16) | 1853 (1.00) |
| 186 | F78Y, Y102D | 8492 (0.69) | 1964 (1.06) |
| 187 | R84Q, A101D | 11200 (0.91) | 2346 (1.27) |
| 188 | R84Q, Y102D | 12300 (1.00) | 1864 (1.01) |
| 189 | A101D, Y102D | 33570 (2.72) | 1953 (1.05) |
| 182 | K77E, F78Y, R84Q | 10058 (0.82) | 2206 (1.19) |
| 13 | WT TACI (68-110) (SEQ ID NO: 171) | 12321 (1.00) | 1854 (1.00) |
| 1 | WT TACI(13-118) Fcl.3 | — | 7905 (4.26) |
| Atacicept | — | — | 7735 (4.17) |
| Telitacicept | — | — | 9172 (4.95) |
| Telitacicept | — | — | 7297 (3.94) |
| Telitacicept+ | K77E, F78Y, Y102D | 13168 (1.07) | 1988 (1.07) |
| BAFF-R | — | — | 53226 (28.7) |
| Belimumab | — | — | 2195 (1.18) |

Example 8. Evaluation in Sjogren's Syndrome Model in Non-Obese Diabetic Mice

This Example describes the assessment of exemplary single domain 26-TACI-vTD Fc fusion proteins (TACI vTD SEQ ID NO:26; Fc fusion SEQ ID NO: 167 in an in vivo short term model of Sjogren's syndrome in NOD mice, including assessment of sialadenitis, serum levels of test molecules and insulitis.

The Sjogren's syndrome model was induced in female diabetes-prone NOD/ShiLtJ mice (about 6 weeks of age) by repeat dosing of an anti-mPD-L1 antibody. Specifically, 0.1 mg of anti-mPD-L1 antibody was administered by intraperitoneal injection on days 0, 2, 4, and 6. Test molecule fusion proteins were dosed on days 0, 2 and 4 according to Table E30 below.

TABLE E30

Treatment Groups and Dosing Regimens

| Group | N | Anti-mPD-L1 Treatment (IP) | Test Article (TA) | TA Dose Level (IP) | mAb Treatment and TA dosing Days |
|---|---|---|---|---|---|
| 1 | 15 | 0.1 mg | Fc control | 0.28 mg | 0, 2, 4, 6 and 0, 2 4 |
| 3 | 15 | 0.1 mg | 26-TACI-CRD2 Fc | 0.34 mg | 0, 2, 4, 6 and 0, 2 4 |
| 6 (naïve) | 5 | 0 | n/a | 0 | n/a |

Abbreviations: IP = intraperitoneal(ly);
mg = milligram;
n/a = not applicable

Blood was obtained from the tail vein of mice (2-5 μL) on days 7, 8, 9, and 10, placed on a ReliOn Prime glucose test strip, and blood glucose (mg/dL) was measured using the ReliOn Prime Glucose Test System. At Day 10 of the experiment, mice were sacrificed and serum, submandibular glands (SMG), and pancreas were collected and analyzed.

The left SMG and pancreas were removed, dissected away from adjacent lymph nodes, and placed into neutral-buffered formalin (NBF) for approximately 72 hours, followed by transfer to 70% ethanol. The fixed tissues were embedded in paraffin, sectioned, and stained on glass slides with hematoxylin and eosin (H&E).

The scoring systems used to evaluate the extent of sialadenitis was scored as per Nandula et al. 2011 (Table 6 therein; reproduced as Table E31), and insulitis per Gutierrez et al 2014 (Table 7 therein; reproduced as Table E32).

TABLE E31

Histological Scoring Used to Evaluate Sialadenitis

| Score | Criteria |
|---|---|
| 0 | No inflammatory foci |
| 1 | 1-5 foci of >50 inflammatory cells |
| 2 | >5 foci without parenchymal destruction |
| 3 | Moderate parenchymal destruction |
| 4 | Extensive parenchymal destruction |

TABLE E32

Histological Scoring Used to Evaluate Insulitis

| Score | Criteria |
|---|---|
| 0 | No insulitis |
| 1 | Peri-islet insulitis |
| 2 | Intermediate insulitis |
| 3 | Intra-islet insulitis |
| 4 | Complete islet insulitis |

Statistically significant differences between groups for histology scores were determined using Student's t-test. GraphPad PRISM® software (Version 8.1.2) was used for statistical analyses and p values<0.05 were considered statistically significant for all statistical tests.

Figure 16B:
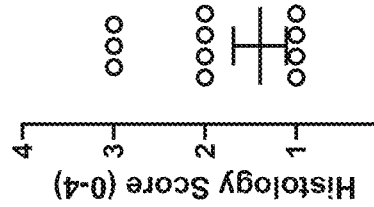
Figure 16A:
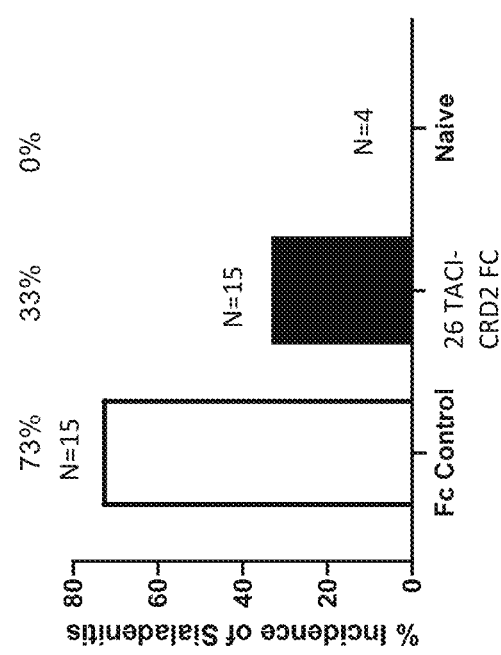

Treatment with the exemplary 26-TACI-CRD2 Fc fusion protein reduced incidence of sialadenitis (FIG. 16A) and resulted in a significantly lower histology score (p<0.01) than the mean scores for Fc control (FIG. 16B). These results are consistent with a finding that treatment of anti-PD-L1 injected NOD mice with the tested molecules reduced both the incidence and severity of sialadenitis in this model of Sjogren's syndrome.

The overall incidence of insulitis in these diabetes-prone mice and the degree of insulitis after treatment with the tested molecules is shown in FIG. 17A and FIG. 17B. 26-TACI-CRD2 Fc fusion proteins significantly reduced the degree of insulitis, as assessed by histological analysis (FIG. 17B).

Together, these results indicate treatment with the tested exemplary TACI-Fc molecule reduced the incidence and severity of sialadenitis in this mouse model of Sjogren's syndrome. These results indicate the potential for TACI molecules in therapeutic use for treating Sjogren's syndrome, and for TACI-CTLA-4 multi-domain stack molecules as therapeutics to impact the onset of type 1 diabetes in humans.

Example 9. Assessment of Exemplary Monomeric and Tetrameric Constructs

Additional TACI-Fc fusion proteins were generated containing one (monomeric) or four (tetrameric barbell and tetrameric tandem) TACI vTD domains using the WT TACI of different lengths: 68-110 (set forth in SEQ ID NO:13), 29-110 (set forth in SEQ ID NO: 1) or 13-118 (set forth in SEQ ID NO: 131), and the TACI vTD set forth in SEQ ID NO:26 (K77E, F78Y, Y102D). The monomeric and tetrameric TACI WT and TACI vTD were formatted as TACI WT and TACI vTD-Fc fusion proteins with an Fc domain. The exemplary generated Fc fusion proteins were generated substantially as described in Example 1 and are described in Tables E33A-E33C.

Briefly, to generate recombinant monomeric immunomodulatory proteins as single chain Fc fusion proteins, the encoding DNA was generated to encode a protein as follows: WT TACI or variant TACI domain followed by a linker of 12 amino acids (GSGGGGSGGGGS; SEQ ID NO: 194) followed by a single chain Fc (scFc) set forth in SEQ ID NO: 218 (composed of a human IgG1 effectorless Fc sequence containing the mutations L234A, L235E and G237A, by the Eu Index numbering system for immunoglobulin proteins (SEQ ID NO:73), followed by a (GGGGS) 13 linker (SEQ ID NO:195) followed by a second human IgG1 effectorless Fc sequence containing the mutations L234A, L235E and G237A, by the Eu Index numbering system for immunoglobulin proteins). The long linker, e.g. set forth in SEQ ID NO:195, connects the C-terminus of the first Fc unity to the N-terminus of the second Fc unit forming the scFc. The generated molecules are summarized in Table E33A.

TABLE E33A

Exemplary Monomeric Immunomodulatory Proteins

| AA SEQ ID NO | NT SEQ ID NO | DESCRIPTION | TACI SEQ ID NO | LINKER SEQ ID NO | FC SEQ ID NO |
|---|---|---|---|---|---|
| 196 | 207 | TACI WT 13 GS(G4S)2 (194) sc_Fc 218 | 13 | 194 | 218 |
| 199 | 210 | TACI 26 GS(G4S)2 (194) scFc_218 | 26 | 194 | 218 |
| 203 | 214 | TACI WT 1 GS(G4S)2 (194) scFc_218 | 1 | 194 | 218 |
| 205 | 216 | TACI WT 131 GS(G4S)2 (194) scFc_218 | 131 | 194 | 218 |

To generate recombinant tetrameric immunomodulatory proteins as Fc fusion proteins, proteins were generated in different formats as follows:

In one format, the encoding DNA was generated to encode three different protein versions as follows: WT TACI (SEQ ID NO NO:198): WT TACI domain SEQ ID NO:13 followed by a linker of (G45)4 SEQ ID NO: 84; followed by a WT TACI domain SEQ ID NO: 13; followed by a linker of GSGGGGS SEQ ID NO: 74; followed by a human IgG1 effectorless Fc sequence containing the mutations L234A, L235E and G237A, by the Eu Index numbering system for immunoglobulin proteins (SEQ ID NO:73).

In one format, the encoding DNA was generated to encode three different protein versions as follows: WT TACI (SEQ ID NO:202): WT TACI domain SEQ ID NO:13 followed by a linker of GSGGGGS SEQ ID NO: 74; followed by a human IgG1 effectorless Fc sequence containing the mutations L234A, L235E and G237A, by the Eu Index numbering system for immunoglobulin proteins (SEQ ID NO:73) followed by a linker of (G4S)4 SEQ ID NO: 84 followed by WT TACI domain SEQ ID NO:13.

In one format, the encoding DNA was generated to encode three different protein versions as follows: TACI vTD Barbell (SEQ ID NO:201): TACI vTD set forth in SEQ ID NO:26 followed by a linker of GSGGGGS SEQ ID NO: 74; followed by a human IgG1 effectorless Fc sequence containing the mutations L234A, L235E and G237A, by the Eu Index numbering system for immunoglobulin proteins (SEQ ID NO:73) followed by a linker of (G4S)4 SEQ ID NO: 84 followed by TACI vTD set forth in SEQ ID NO:26.

TABLE E33B

Exemplary Tetrameric Immunomodulatory Proteins

| AA SEQ ID NO | NT SEQ ID NO | DESCRIPTION | 1$^{ST}$ TACI | LINKER | 2$^{ND}$ TACI | LINKER | Fc |
|---|---|---|---|---|---|---|---|
| 198 | 209 | TACI WT 13 (G4S)4 (84) (TACI WT 13 GSG4S (74) Fc 73 | 13 | 84 | 13 | 74 | 73 |

TABLE E33C

Exemplary Tetrameric Immunomodulatory Proteins

| AA SEQ ID NO | NT SEQ ID NO | DESCRIPTION | 1$^{ST}$ TACI | LINKER | FC | LINKER | 2$^{ND}$ TACI |
|---|---|---|---|---|---|---|---|
| 202 | 213 | TACI WT 13 GSG4S (74) Fc 73(G4S)4 (84) (TACI WT 13 | 13 | 74 | 73 | 84 | 13 |
| 201 | 212 | TACI 26 GSG4S (74) Fc 73 (G45)4 (84) TACI 26 | 26 | 74 | 73 | 84 | 26 |

A. Bioactivity of Exemplary Multi-Domain Molecules

In one experiment, exemplary molecules set forth in Tables E33A-C were assessed using the Jurkat/NF-κB/TACI reporter cells for blockade of APRIL- or BAFF-mediated signaling, substantially as described in Example 1. Activity was assessed for inhibition of the soluble BAFF (3-mer) or for inhibition of an oligomer of twenty BAFF 3-mers (BAFF 60-mer). Table E34 provides the values for half maximal inhibitory concentration (IC50) for inhibition of APRIL- and BAFF-mediated TACI signaling. In some instances, the proteins tested were not compared to their parental of WT controls and appear as (−) in the Table below. The results in Table E34 demonstrate that all generated formats block BAFF and APRIL binding.

TABLE E34

Assessment of Exemplary Monomeric and Tetrameric Immunomodulatory Proteins

| SEQ ID NO | Description | APRIL IC$_{50}$ (pM) | BAFF IC$_{50}$ (pM) | BAFF 60-mer IC$_{50}$ (pM) |
|---|---|---|---|---|
| 196 | TACI WT 13 GS(G4S)2 (194) sc_Fc 218 | | 5695 | 24081 |
| 198 | TACI WT 13 (G4S)4 (84) (TACI WT 13 GSG4S (74) Fc 73 | 34554 | 3287 | 4333 |
| 202 | TACI WT 13 GSG4S (74) Fc 73(G4S)4 (84) (TACI WT 13 | 11910 | 1039 | 2581 |
| 199 | TACI 26 GS(G4S)2 (194) scFc_218 | | 8237 | 106021 |
| 201 | TACI 26 GSG4S (74) Fc 73 (G4S)4 (84) TACI 26 | 3762 | 779 | 778 |
| 203 | TACI WT 1 GS(G4S)2 (194) scFc_218 | | 4422 | 15801 |
| 205 | TACI WT 131 GS(G4S)2 (194) scFc_218 | | 4577 | 14268 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed:

1. An immunomodulatory protein homodimer comprising two identical copies of a TACI-Fc fusion protein, wherein the TACI-Fc fusion protein comprises a variant TACI polypeptide, an Fc region, and a linker between the variant TACI polypeptide and the Fc region, wherein the variant TACI polypeptide comprises the amino acid substitutions K77E, F78Y, and Y102D in the sequence set forth in SEQ ID NO:13, wherein the numbering of positions corresponds to numbering of positions set forth in SEQ ID NO:122.

2. The immunomodulatory protein homodimer of claim 1, wherein the variant TACI polypeptide has increased binding affinity to one or both of APRIL and BAFF compared to the reference TACI polypeptide.

3. The immunomodulatory protein homodimer of claim 1, wherein the variant TACI polypeptide has at least 90% sequence identity to SEQ ID NO:13.

4. The immunomodulatory protein homodimer of claim 1, wherein the variant TACI polypeptide has at least 92% sequence identity to SEQ ID NO:13.

5. The immunomodulatory protein homodimer of claim 1, wherein the variant TACI polypeptide is set forth in SEQ ID NO: 26.

6. The immunomodulatory protein homodimer of claim 1, wherein the linker comprises a peptide linker and the peptide linker is selected from GSGGS (SEQ ID NO: 76), GGGGS (G45; SEQ ID NO: 77), GSGGGGS (SEQ ID NO: 74), GGGGSGGGGS (2×GGGGS; SEQ ID NO: 78), GGGGSGGGGSGGGGS (3×GGGGS; SEQ ID NO: 79), GGGGSGGGGSGGGGSGGGGS (4×GGGGS, SEQ ID NO:84), GGGGSGGGGSGGGGSGGGGSGGGGS (5×GGGGS, SEQ ID NO: 91), GGGGSSA (SEQ ID NO: 80), or GSGGGGSGGGGS (SEQ ID NO:194) or combinations thereof.

7. The immunomodulatory protein homodimer of claim 1, wherein the linker is GSGGGGS (SEQ ID NO: 74).

8. The immunomodulatory protein homodimer of claim 7, wherein the Fc region is an IgG1 Fc domain comprising the amino acid substitutions L234A, L235E an G237A by EU numbering.

9. The immunomodulatory protein homodimer of claim 8, wherein the Fc region is set forth in SEQ ID NO:73.

10. The immunomodulatory protein homodimer of claim 1, wherein the Fc region is an IgG1 Fc domain.

11. The immunomodulatory protein homodimer of claim 10, wherein the Fc region is set forth in SEQ ID NO:81.

12. The immunomodulatory protein homodimer of claim 1, wherein the Fc region is a variant IgG1 Fc domain that exhibits reduced effector function.

13. The immunomodulatory protein homodimer of claim 12, wherein the variant IgG1 Fc domain comprises the amino acid substitutions L234A, L235E, and G237A by EU numbering.

14. The immunomodulatory protein homodimer of claim 13, wherein the Fc region is set forth in SEQ ID NO:73.

15. The immunomodulatory protein homodimer of claim 1, wherein the Fc region is an Fc domain of IgG2.

16. The immunomodulatory protein homodimer of claim 1, wherein the Fc region is an Fc domain of IgG4 or is a variant IgG4 Fc domain containing the S228P mutation.

17. The immunomodulatory protein homodimer of claim 1, wherein the TACI-Fc fusion protein is set forth in SEQ ID NO: 168.

18. The immunomodulatory protein homodimer of claim 1, wherein the TACI-Fc fusion protein is set forth in SEQ ID NO: 167.

19. A pharmaceutical composition comprising the immunomodulatory protein homodimer of claim 1 and a pharmaceutically acceptable excipient.

20. An immunomodulatory protein homodimer comprising two identical copies of a TACI-Fc fusion protein of the formula TACI polypeptide (TACI)-Linker-Fc region, wherein the TACI polypeptide is a variant TACI polypeptide set forth in SEQ ID NO:26.

21. The immunomodulatory protein homodimer of claim 20, wherein the linker comprises a peptide linker and the peptide linker is selected from GSGGS (SEQ ID NO: 76), GGGGS (G45; SEQ ID NO: 77), GSGGGGS (SEQ ID NO: 74), GGGGSGGGGS (2×GGGGS; SEQ ID NO: 78), GGGGSGGGGSGGGGS (3×GGGGS; SEQ ID NO: 79), GGGGSGGGGSGGGGSGGGGS (4×GGGGS, SEQ ID NO:84), GGGGSGGGGSGGGGSGGGGSGGGGS (5×GGGGS, SEQ ID NO: 91), GGGGSSA (SEQ ID NO: 80), or GSGGGGSGGGGS (SEQ ID NO:194) or combinations thereof.

22. The immunomodulatory protein homodimer of claim 20, wherein the linker is GSGGGGS (SEQ ID NO: 74).

23. The immunomodulatory protein homodimer of claim 20, wherein the Fc region is an IgG1 Fc domain.

24. The immunomodulatory protein homodimer of claim 23, wherein the Fc region is set forth in SEQ ID NO:81.

25. The immunomodulatory protein homodimer of claim 20, wherein the Fc region is a variant IgG1 Fc domain that exhibits reduced effector function.

26. The immunomodulatory protein homodimer of claim 25, wherein the Fc region comprises the amino acid substitutions L234A, L235E, and G237A by EU numbering.

27. The immunomodulatory protein homodimer of claim 26, wherein the Fc region is set forth in SEQ ID NO:73.

28. A pharmaceutical composition comprising the immunomodulatory protein homodimer of claim 20 and a pharmaceutically acceptable excipient.

29. An immunomodulatory protein that is a homodimer comprising two identical copies of the TACI-Fc fusion protein set forth in SEQ ID NO:167 or SEQ ID NO: 168 linked by a covalent disulfide bond.

30. A pharmaceutical composition comprising the immunomodulatory protein of claim 29 and a pharmaceutically acceptable excipient.

\* \* \* \* \*